(12) United States Patent
Satsuki et al.

(10) Patent No.: US 7,514,158 B2
(45) Date of Patent: *Apr. 7, 2009

(54) COUMARIN COMPOUND

(75) Inventors: Makoto Satsuki, Okayama (JP);
Makoto Fujiwara, Okayama (JP);
Natsuko Ishida, Okayama (JP);
Sadaharu Suga, Okayama (JP);
Hisayoshi Fujikawa, Aichi (JP); Hisato Takeuchi, Aichi (JP); Yasunori Taga, Aichi (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 221 days.

This patent is subject to a terminal disclaimer.

(21) Appl. No.: 10/498,477

(22) PCT Filed: Dec. 10, 2002

(86) PCT No.: PCT/JP02/12918

§ 371 (c)(1),
(2), (4) Date: Jun. 14, 2004

(87) PCT Pub. No.: WO03/050106

PCT Pub. Date: Jun. 19, 2003

(65) Prior Publication Data

US 2005/0275341 A1    Dec. 15, 2005

(30) Foreign Application Priority Data

| Dec. 13, 2001 | (JP) | ............... 2001-379529 |
| Apr. 19, 2002 | (JP) | ............... 2002-117617 |
| Apr. 22, 2002 | (JP) | ............... 2002-119823 |
| Nov. 27, 2002 | (JP) | ............... 2002-343200 |
| Nov. 27, 2002 | (JP) | ............... 2002-343225 |

(51) Int. Cl.
*H01L 29/08* (2006.01)
*H01L 35/24* (2006.01)
*H01L 51/50* (2006.01)
*C07D 311/02* (2006.01)

(52) U.S. Cl. .................. 428/690; 428/917; 313/504; 313/506; 257/40; 549/284

(58) Field of Classification Search ............ 428/690, 428/917; 257/40; 549/284; 313/504, 506
See application file for complete search history.

(56) References Cited

U.S. PATENT DOCUMENTS 4,985,470 A    1/1991   Nagasaka et al.
5,847,506 A *  12/1998  Nakayama et al. .......... 313/504

FOREIGN PATENT DOCUMENTS

| DE | 22 40 037 A | 4/1973 |
| EP | 1 182 183 A1 | 2/2002 |
| JP | 54-151024 A | 11/1979 |
| JP | 58-29803 A | 2/1983 |
| JP | 59-56403 A | 3/1984 |
| JP | 63-23901 A | 2/1988 |
| JP | 64-33104 A | 2/1989 |
| JP | 03-72898 A | 3/1991 |
| JP | 06-329654 A | 11/1994 |
| JP | 2000-192028 A | 7/2000 |
| JP | 2003-273055 A | 10/2000 |
| JP | 2001-110572 A | 4/2001 |
| WO | WO 01/72673 A1 | 10/2001 |
| WO | WO 01/90098 A1 * | 11/2001 |

OTHER PUBLICATIONS

Meng et al., Science in China: Series B, Chemistry, Life Sciences, and Earth Sciences, 36(5), (1993), p. 540, 541, 543-549.*
O'Callaghan et al., J. Chem. Research (S), 1995, p. 214.*
El-Taweel et al., J. Heterocyclic Chem., 38, (Jul.-Aug. 2001), p. 981-984.*
Fujiwara et al., Journal of Photopolymer Science and Technology, vol. 15, No. 2 (2002), p. 237-238.*
Rao et al., National Academy of Science Letters (India), 13/3, (1991), pp. 85-87.*
Padmanabhan et al., Journal of Heterocyclic Chemistry, 34(1), (1997), p. 301-304.*

Ammar et al., Journal de la Societe Chimique de Tunisie, vol. 4, No. 10, Dec. 2001, p. 1239-1244.*
Meng et al., Synthesis Papers, Aug. 1990, p. 719-721.*
Fujiwara et al., Journal of Photopolymer Science and Technology, vol. 15, No. 2, (2002), p. 237-238.*
Chodankar, N.K., and S. Seshari, "Absorption-emission spectra studies of 3-hetarylcoumarins", Dyes and Pigments. (1985). 6:331-340.
Omar, Ismail, , et al, "Character of electronicabsorption spectra of 4,4'-substituted 2,2'-dihiazolyl with coumarin nucleus" Visnik Kharkivs'kogo Universitetu. (1998) 2: 71-77.
Rao, et al, "Synthesis of some new types of thiazolyl coumarins", Phosphrus, Sulfur, and Silicon. (1996). 113:47-51.
Saito, Yoshinori, Ed. "Organic Light Emitting Diode", The Journal of the Institute of Electronics, Information and Communication Engineers. (2001), 84(11):767-774.
Sasabe, Hiroyuki, Ed. "Organic Photonics" (Mar. 20, 1995). published by Agne Shofusha, Kabushiki Kaisha, Tokyo, Japan, pp. 136-160.
Silin, et al, "Synthesis of 4,4'-disubstituted 2,2'-dethiazolyls", Visnik Kharkivs'kogo Universitetu. (1997) 395: 264-273.
Tabakovic, Ibro, and Zdravko Grujic, "Electrochemical oxidation of 1,5-diphenyl-3-(4-hydroxy-coulmarinyl)-$\Delta^2$-pyrazoline", Glasnik Hemijskog Drustva Beograd. (1982) 47(7): 339-346.

\* cited by examiner

*Primary Examiner*—Dawn Garrett
(74) *Attorney, Agent, or Firm*—Browdy and Neimark, PLLC

(57) ABSTRACT

A method for producing a coumarin compound represented by Formula 1, which comprises a step of reacting a coumarin compound represented by Formula 1 with a compound having an aldehyde group and an activated methylene group; luminous agents for organic EL elements and organic EL elements which all comprise the coumarin compound; and displaying panels and information displaying apparatuses using the organic EL elements:

$$\emptyset(Z)m \qquad \text{Formula 1}$$

wherein in Formula 1, ø is an aromatic ring, heterocycle, or a combination thereof, each Z is the same or a different coumarin group represented by Formula 2; and m is an integer of two or more;

Formula 2:

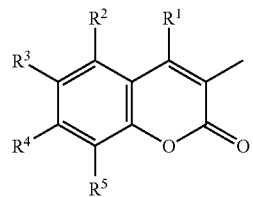

7 Claims, 2 Drawing Sheets

US 7,514,158 B2
COUMARIN COMPOUND

TECHNICAL FIELD

The present invention relates to a novel coumarin compound.

BACKGROUND ART

After coming into this information age, photochemical polymerization has been widely used in various fields beyond that of synthetic resins, and there has been being extensively used even in the fields of information recordings and electronic equipments such as paints, lithographic plates for printing, printing circuits, and integrated circuits. Photochemical polymerization is a technique for polymerizing polymeric compounds by irradiating lights and it is roughly classified into (i) photopolymerization that initiates the polymerization of polymeric compounds by directly irradiating them to be activated, and (ii) photosensitization polymerization that polymerizes polymeric compounds by irradiating them in the presence of photosensitizers to make them into their growth-active forms. In both cases, as characteristic features, the initiation and the suspension of polymerization can be controlled by flashing excited light sources, and the rate and the degree of polymerization can be easily controlled by appropriately selecting the strength and the wavelength of the light sources. The photochemical polymerization can be proceeded even at a relatively low temperature condition because it requires only a lesser beam energy for initiating its polymerization. Due to the above advantageous features of photochemical polymerization, in the field of information recordings such as holography and lithographic plates for printing, and photopolymeric compositions, those which can be polymerized by irradiating visible lights such as those of argon ion lasers, helium ion lasers, and second harmonics of Nd-YAG lasers have been rapidly increased in demand.

However, most of polymeric compounds and polymerization initiators, which are incorporated into photopolymeric compositions, absorb ultraviolet rays only, and this inevitably needs photosensitizes as a technical factor when the photopolymeric compositions are polymerized by visible lights. The properties requisite for polymerization initiators are to have a relatively large molecular absorption coefficient (hereinafter may be abbreviated as "$\epsilon$"), photosensitize various polymeric compounds, have a relatively high sensitization efficiency, have a desired solubility and compatibility with other ingredients, and have a satisfactory stability. Representative examples of such photosensitizes are, for example, melocyanine dyes disclosed in Japanese Patent Kokai No. 151,024/79, cyanine dyes disclosed in Japanese Patent Kokai No. 29,803/83, stilbene dyes disclosed in Japanese Patent Kokai No. 56,403/84, coumarin dyes disclosed in Japanese Patent Kokai No. 23,901/88, methylene blue derivatives disclosed in Japanese Patent Kokai No. 33,104/89, and pyrane derivatives disclosed in Japanese Patent Kokai No. 329,654/94. These compounds have both merit and demerit, and there has not yet been found any photopolymeric compound, comprising a polymeric compound and a binding resin, which does exert the above identified properties. Because of this, in a novel field to which photopolymeric compounds are applicable, for example, in the fields of information recordings and electric equipments, it is usual that, depending on use, materials suitable for polymeric compounds, binders, etc., other than photosensitizes, are firstly selected, and then, among various organic compounds, appropriate ones for such polymeric compounds and polymerization initiators are screened in such a manner of trial and error.

In the field of information displays, electroluminescent elements (hereinafter abbreviated as "EL elements") are now highlighted as a display element for the forthcoming generation. At present, cathode-ray tubes are predominantly used in relatively large-sized information displays such as computer termini and TV receivers. The cathode-ray tubes, however, are relatively large in mass and weight and relatively high in operation voltage, and this hinders their applicability for commonly used equipments and small-sized portable ones whose transportability is highly valued. More required are the information displays for small-sized equipments, which have a thinner and lighter plain-form and operate at a lower operation voltage and wattage. Due to advantageous features of relatively low operation voltage and wattage, liquid crystal elements are now commonly used in many fields. However, the information display equipments equipped with such liquid crystal elements will change in contrast depending on their view angles; information are clearly displayed only when viewed within a specific view angle and usually require blacklight, resulting in a problem that they could not be reduced in wattage as much as they are expected. As a display element to overcome these drawbacks, there appeared an electroluminescent element, i.e., an organic EL element.

Organic EL element is a luminous element which generally comprises an inserted luminous layer containing a luminous compound placed between a cathode and an anode, and which utilizes luminescence such as fluorescence or phosphorescence emitted from the luminous compound in such a manner that a dc voltage is energized between the cathode and the anode to supply both positive holes and electrons to the luminous layer to rebind them together to make the luminous compound into its excited state, and the excited luminous compound returns to its ground state while emitting luminescence. As characteristic features, organic EL element can be appropriately changed its luminous color tint by selecting an appropriate organic compound as a host compound and altering a dopant as a guest compound used with the host compound. Depending on the combination of the host and the guest compounds, the luminescent brightness and the life expectancy of organic EL element can be possibly improved by a large margin. It is said that organic EL element is a theoretically excellent luminous element because it autonomously emits light and has a relatively low operation wattage as disclosed, for example, in "Organic Photonics", edited by Hiroyuki SASABE, pp. 136-160, Mar. 20, 1995, published by Agne Shofusha, Kabushiki Kaisha, Tokyo, Japan, and *The Journal of the Institute of Electronics, Information and Communication Engineers*, Yoshinori SAITO, Vol. 84, No. 11, pp. 767-774, 2001.

Most of the organic EL elements conventionally proposed, however, are relatively low in tolerance and, as a demerit, they have a problem of being easy reduced in brightness within a relatively short period of time when used under severe conditions, for example, when they are used in automobiles that are unavoidable from vibrations and high temperatures.

In view of these circumstances, the object of the present invention is to provide novel organic compounds having an absorption and luminescent maxima in the visible region and widens the variety of selectable light absorption agents and luminous agents in producing polymeric compositions.

Another object of the present invention is to provide organic materials useful in organic EL elements pursuing high durability.

SUMMARY OF THE INVENTION

To attain the above objects, the present inventors focused on coumarin compounds, eagerly screened, and found that coumarin compounds, which comprise a plurality of coumarin groups linked to aromatic rings, heterocycles, or combinations thereof, have an absorption and luminescent maxima in the visible region, effectively absorb the visible light, emit the visible light when excited, have a significantly high thermostability, and have distinct usefulness in the fields that require organic compounds with the above-mentioned advantageous properties. Particularly, they found that these coumarin compounds emit the visible light with a satisfactory light purity when used in organic EL elements, and the emission will be stably continued for a relatively long period of time even at a relatively high temperature.

The present invention solves the above objects by providing the coumarin compounds represented by Formula 1, particularly, those represented by Formula 1 and have a decomposition point of over 330° C.

$$\phi(Z)m \qquad \text{Formula 1}$$

wherein in Formula 1, ø is an aromatic ring, heterocycle, or a combination thereof, with the proviso that the aromatic ring and heterocycle may optionally have a substituent; each Z is the same or different coumarin group represented by Formula 2, with the proviso that each coumarin group may optionally have a substituent; and m is an integer of two or more.

Formula 2:

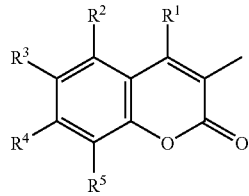

wherein in Formula 2, $R^1$ to $R^5$ independently represent hydrogen or a substituent; $R^3$ and $R^4$ may form a cyclic structure together with the carbon atoms linked to $R^2$, $R^3$, $R^4$ and/or $R^5$, and in this case, $R^2$, $R^3$, $R^4$ and/or $R^5$ do not apparently exist.

The present invention solves the above objects by providing a process for producing coumarin compounds, which comprises a step of reacting a compound, represented by Formula 3 having ø corresponding to that in Formula 1, with a compound represented by Formula 4 having $R^1$ to $R^5$ corresponding to those in Formula 2.

$$\phi(CH_2CN)_m \qquad \text{Formula 3}$$

Formula 4:

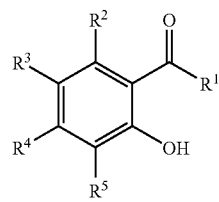

wherein in Formula 4, m is an integer similarly as in Formula 1.

The present invention solves the above objects by providing organic EL compounds comprising the above-identified coumarin compounds.

The present invention solves the above objects by providing a displaying panel with the above-identified organic EL elements.

The present invention solves the above objects by providing an information displaying apparatus with the above-identified organic EL elements.

The present invention solves the above objects by providing a luminescent agent for organic EL elements comprising the above-identified coumarin compounds.

EXPLANATION OF SYMBOLS

Figure 1:
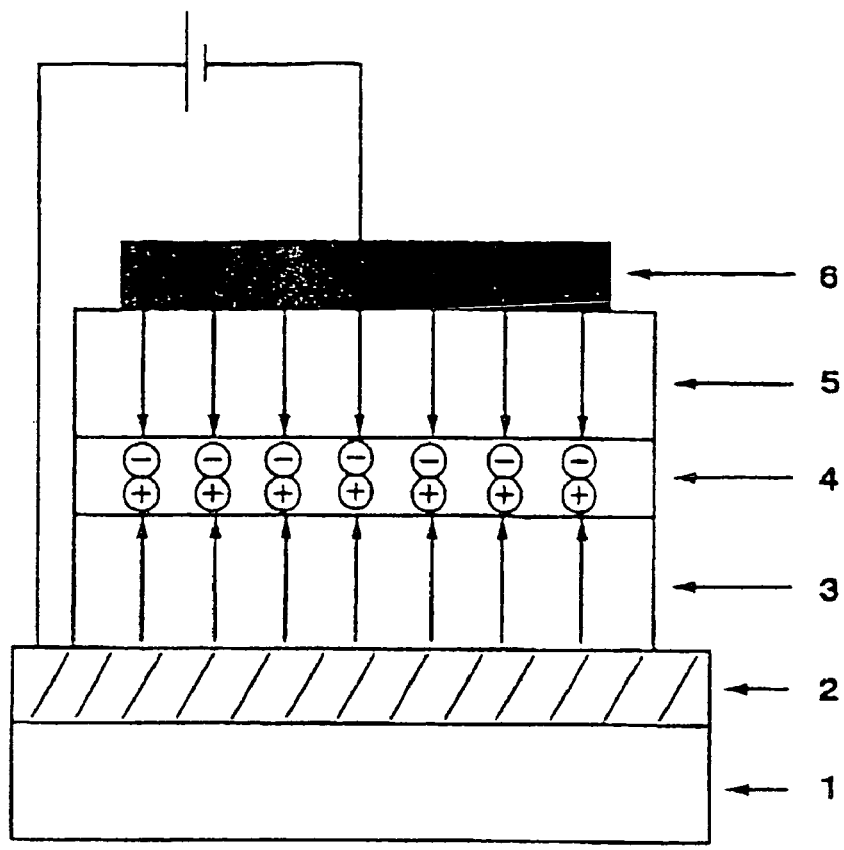
FIG. 1 is a brief drawing of the organic EL element according to the present invention.

1, 10: Substrate
2, 14: Anode
3, 16: Hole injection/transportation layer
4, 18: Luminous layer
5: Electron injection/transporting layer
6, 20: Cathode
30: Direct current (dc)
32, 34: Booster circuit
36, 46: Driving circuit
38: Microcomputer
40: Clock generating circuit
42, 44: Oscillating circuit
48: Displaying panel

BEST MODE FOR CARRYING OUT THE INVENTION

Explaining the preferred embodiments according to the present invention, this present invention relates to the coumarin compounds represented by Formula 1, particularly, those which are represented by Formula 1 and have a decomposition point of over 330° C.; and to processes and uses thereof.

$$\phi(Z)m \qquad \text{Formula 1}$$

In Formula 1, ø represents an aromatic ring, heterocycle, or a combination thereof. Preferred examples of such include monocyclic aromatic or heterocycles such as thiophene, triazine, furan, benzene, pyrazine, and pyridine rings; fused polycyclic aromatic or heterocycles such as naphthalene, anthracene, thieno[3,2-b]thiophene, phenanthrene, fluorene, and furo[3,2-b]furan rings; ring assemblies, for example, aromatic rings and heterocycles such as terphenyl, biphenyl, bithiophene, bifuran rings; combinations of aromatic and heterocycles such as acridine, isoquinoline, indole, carbazole, carboline, quinoline, dibenzofuran, cinnoline, thionaphthene, 1,10-phenanthroline, phenothiazine, purine, and benzofuran rings. One or more of the hydrogen atoms in the above aromatic and heterocycles can be optionally substituted with the following substituents as long as they do not hinder the scope of the object of the present invention: aliphatic hydrocarbon groups such as methyl, ethyl, propyl, isopropyl, butyl, isobutyl, sec-butyl, tert-butyl, and pentyl groups; alicyclic hydrocarbon groups such as cyclopropyl, cyclobutyl, cycloheptyl, cyclohexyl, cyclohexenyl, and cycloheptyl groups; aromatic hydrocarbon groups such as phenyl, o-tolyl, m-tolyl, p-tolyl, xylyl, mesityl, o-cumenyl, m-cumenyl, p-cumenyl and biphenyl groups; ether groups such as methoxy, ethoxy, propoxy, phenoxy, and benzyloxy groups.

In Formula 1, each Z represents the same or a different coumarin group represented by Formula 2, and m is an integer of two or more, meaning the number of Z linked to ø.

Formula 2:

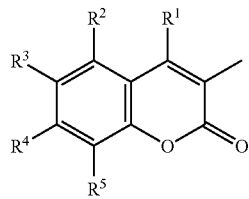

In Formula 2, $R^1$ to $R^5$ independently represent hydrogen or a substituent. Examples of the substituents of $R^1$ to $R^5$ include aliphatic hydrocarbon groups such as methyl, ethyl, propyl, isopropyl, isopropenyl, 1-propenyl, 2-propenyl, 2-propynyl, butyl, isobutyl, sec-butyl, tert-butyl, 2-butenyl, 1,3-butadienyl, pentyl, isopentyl, neopentyl, tert-pentyl, 1-methylpentyl, 2-methylpentyl, 2-pentenyl, 2-pentene-4-inyl, hexyl, isohexyl, heptyl, octyl, nonyl, decyl, undecyl, dodecyl, and octadecyl groups; alicyclic hydrocarbon groups such as cyclopropyl, cyclobutyl, cyclopentyl, cyclohexyl, cyclohexenyl, and cycloheptyl groups; aromatic hydrocarbon groups such as phenyl o-tolyl, m-tolyl, p-tolyl, xylyl, mesityl, o-cumenyl, m-cumenyl, p-cumenyl, and biphenylyl groups; heterocyclic groups such as furyl, thienyl, piperidino, and quinolyl groups; ether groups such as methoxy, ethoxy, propoxy, isopropoxy, butoxy, isobutoxy, sec-butoxy, tert-butoxy, pentyloxy, phenoxy, and benzyloxy groups; ester groups such as methoxycarbonyl ethoxycarbonyl, propoxycarbonyl, acetoxy, and benzoyloxy groups; amino groups such as methyl amino, dimethylamino, ethylamino, diethylamino, propylamino, dipropylamino, butylamino, dibutylamino, isobutylamino, diisobutylamino, sec-butylamino, tert-butylamino, pentylamino, and dipentylamino groups; halogen groups such as fluoro, chloro, bromo, and iodo groups; and combinations thereof. When $R^4$ in Formula 2 is an alkylamino group, it may form a cyclic structure such as a piperazine, piperidine, morpholine, or julolidine ring by combining together with the carbon atoms linked to $R^3$ and/or $R^5$. Alternatively, $R^3$ and $R^4$ may form a cyclic structure such as a benzene ring by combining together with their adjacent carbon atoms linked to $R^2$, $R^3$, $R^4$ or $R^5$. In this case, $R^2$, $R^3$, $R^4$ and/or $R^5$ do not apparently exist. In Formula 1, as described above, the coumarin residues Z represented by Formula 2 may be the same or different, however, the same one would be advantageous in terms of their production cost. Varying depending on use, in the case of using a coumarin group, represented by Formula 2 where any one of $R^1$ to $R^5$ is an ether group, as a luminescent agent which emits light ranging from the ultraviolet region to the blue regions, both $R^2$ and $R^4$ are preferably substantially the same ether groups in terms of their luminous wavelength, thermal stability, production cost, and solubility in organic solvents.

Concrete examples of the coumarin compounds according to the present invention are, for example, those which are represented by Chemical Formulae 1 to 763. All of these compounds have an absorption maximum in the region with wavelengths shorter than 550 nm, more particularly, most of them have an absorption maximum in the region with wavelengths from about 350 nm to about 500 nm, and have a high molecular absorption coefficient of $1\times10^4$ or over, preferably, $3\times10^4$ or over. Because of these, the coumarin compounds efficiently absorb light in the region having substantially the same wavelengths. Most of the coumarin compounds represented by Chemical Formulae 1 to 763 have an emission maximum in the region with wavelengths shorter than 600 nm, more particularly, in the region with wavelengths from about 420 nm to about 570 nm, and they emit a visible light ranging from the ultraviolet region to the green region when excited. In addition, all of these coumarin compounds have a decomposition point of over 330° C., preferably, 400° C. or over. Among which, most of those having a glass transition point have a glass transition point of over 80° C., particularly, those represented by Chemical Formulae 22 and 210 have a glass transition point of over 180° C. As it is well known, there has been said that the decomposition point and the glass transition point in organic compounds are recognized as an index of their thermal stability, i.e., those which have a higher decomposition point and glass transition point have a higher thermal stability. Accordingly, the coumarin compounds of the present invention have various uses in the fields that require organic compounds having a satisfactory light absorbability, emission ability, and thermal stability, and the compounds exert advantageous effects and functions when used, particularly, in organic EL elements. The decomposition points and the glass transition points of the coumarin compounds can be determined by conventional differential thermogravimetry (abbreviated as "DSC" hereinafter).

Chemical Formula 1:
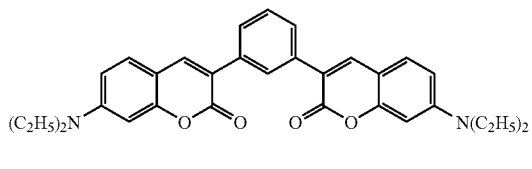
Chemical Formula 2:
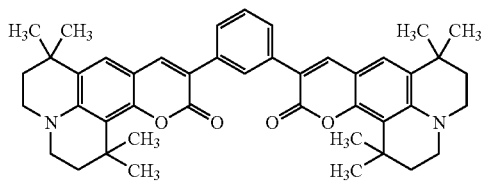
Chemical Formula 3:
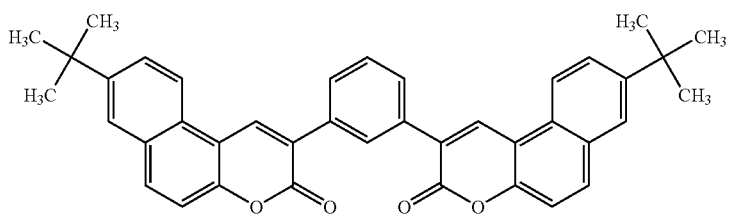
Chemical Formula 4:
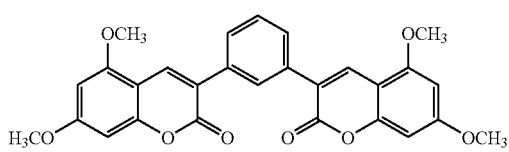
Chemical Formula 5:
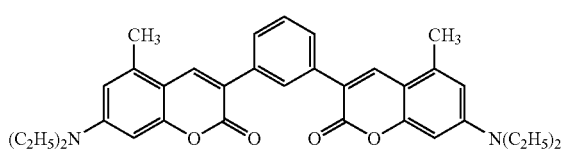
Chemical Formula 6:
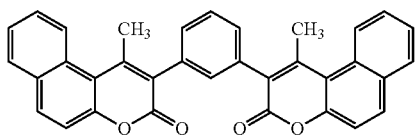
Chemical Formula 7:
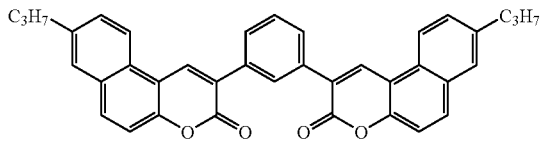
Chemical Formula 8:
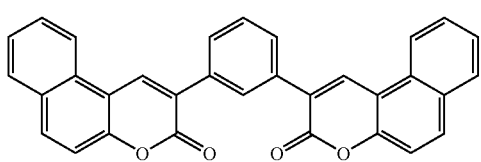
Chemical Formula 9:
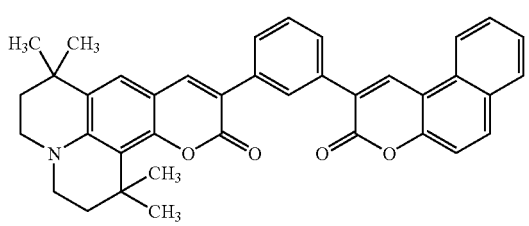
Chemical Formula 10:
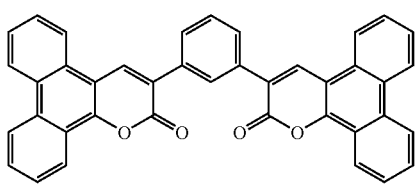
Chemical Formula 11:
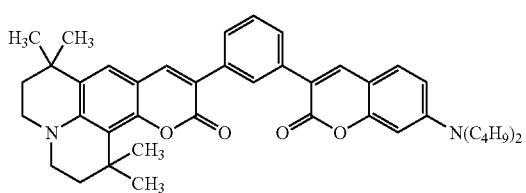
Chemical Formula 12:
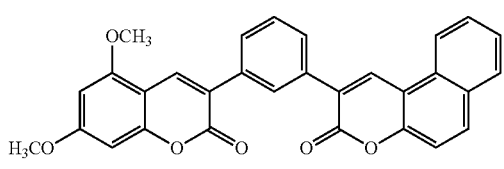
Chemical Formula 13:
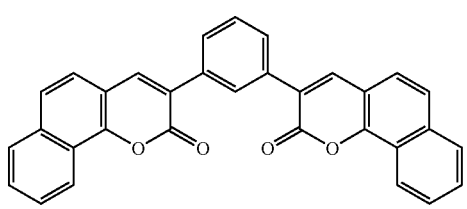

-continued
Chemical Formula 14:
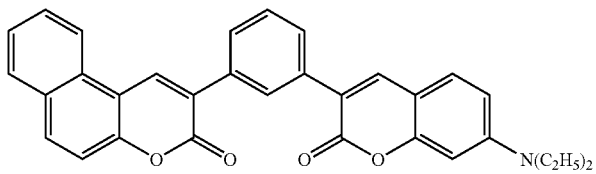
Chemical Formula 15:
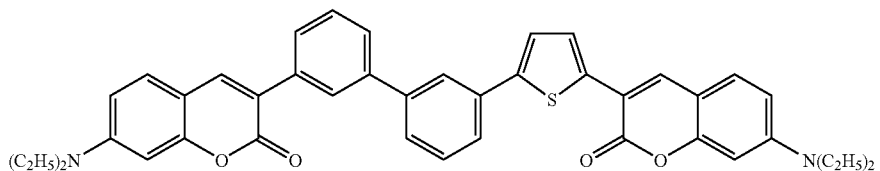
Chemical Formula 16:
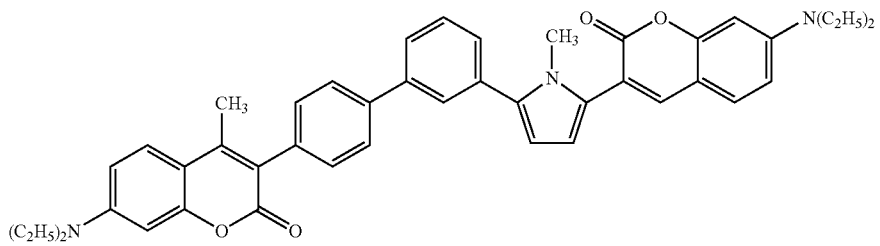
Chemical Formula 17:
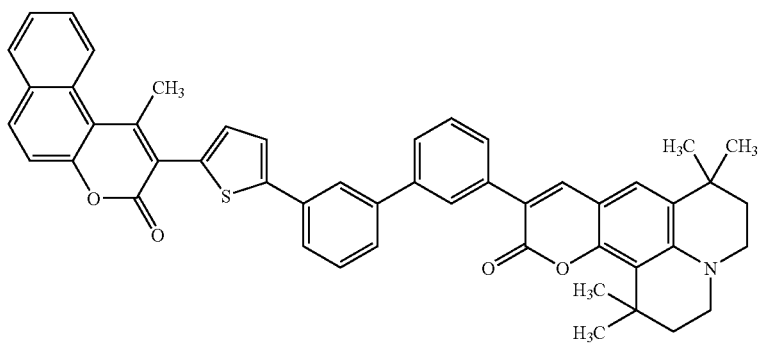
Chemical Formula 18:
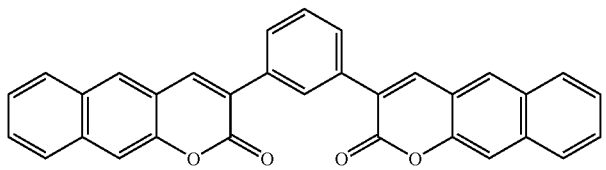
Chemical Formula 19:
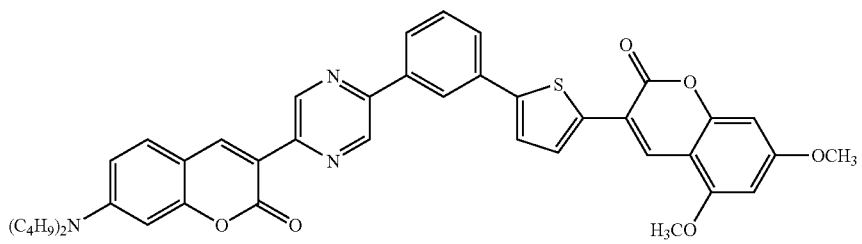

-continued
Chemical Formula 20:
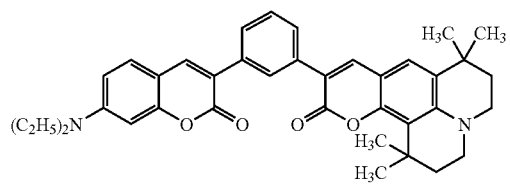
Chemical Formula 21:
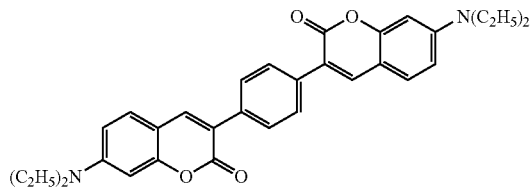
Chemical Formula 22:
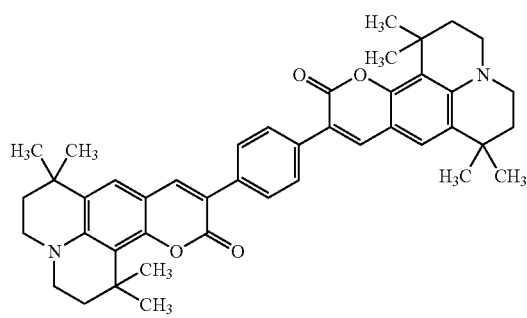
Chemical Formula 23:
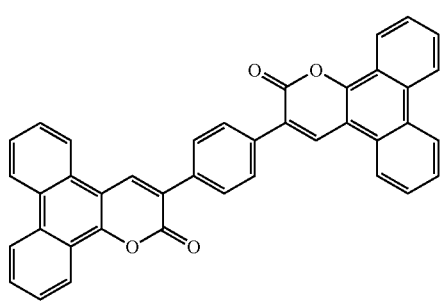
Chemical Formula 24:
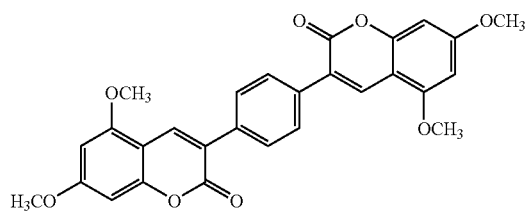
Chemical Formula 25:
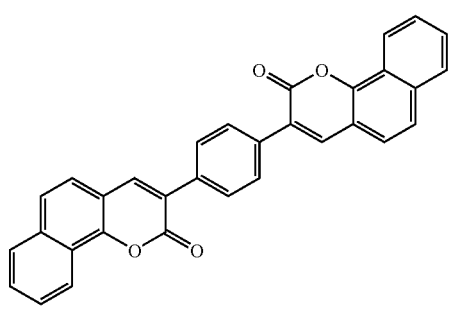
Chemical Formula 26:
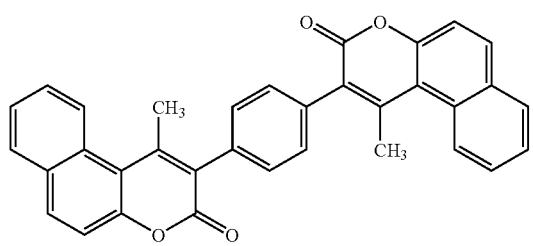
Chemical Formula 27:
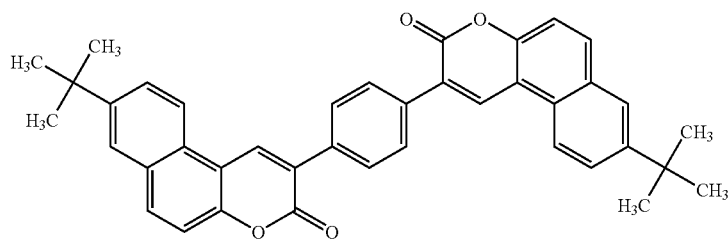

-continued
Chemical Formula 28:
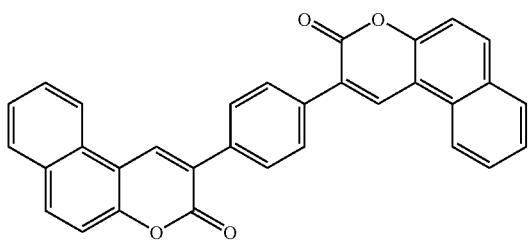
Chemical Formula 29:
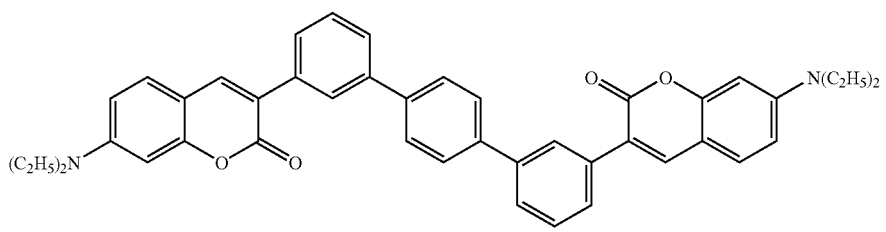
Chemical Formula 30:
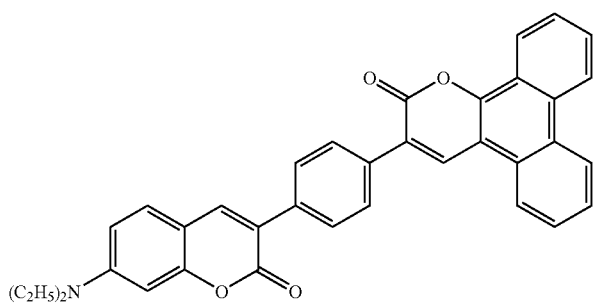
Chemical Formula 31:
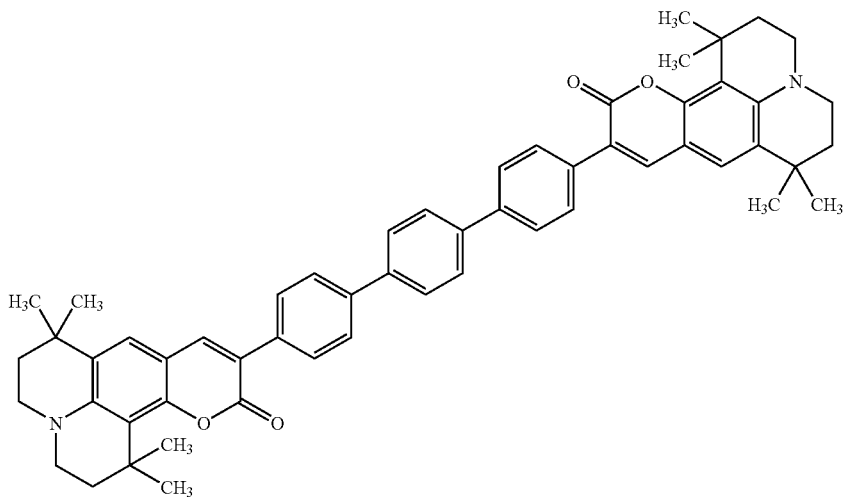
Chemical Formula 32:
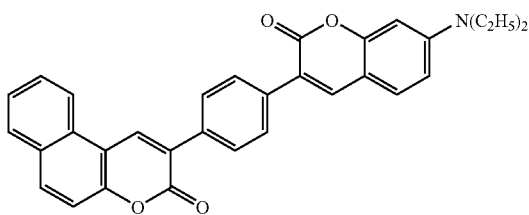
Chemical Formula 33:
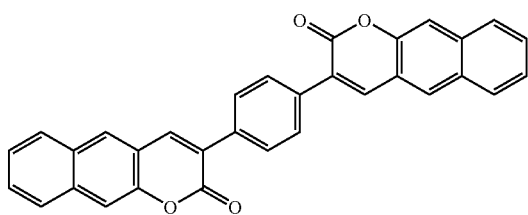

-continued
Chemical Formula 34:
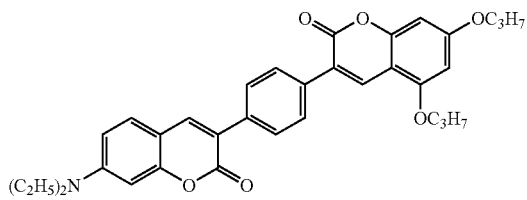
Chemical Formula 35:
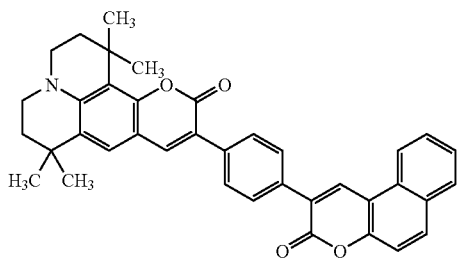
Chemical Formula 36:
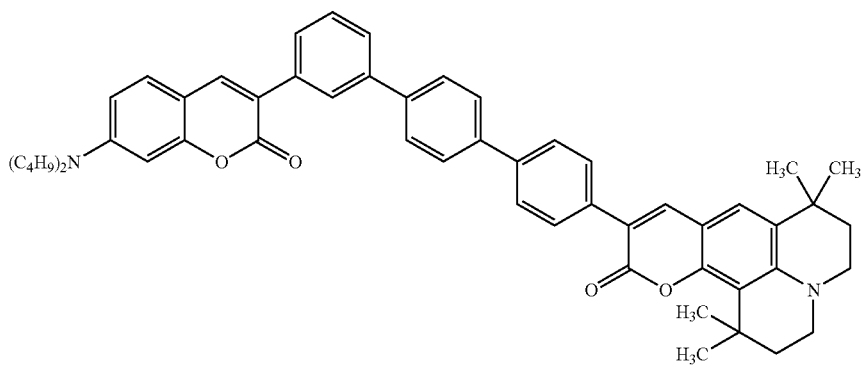
Chemical Formula 37:
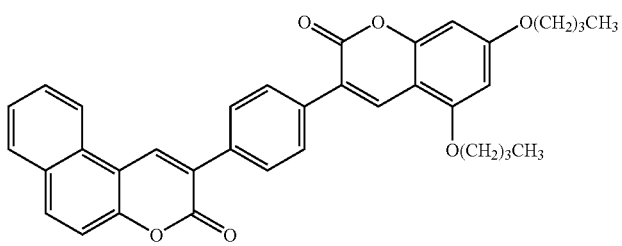
Chemical Formula 38:
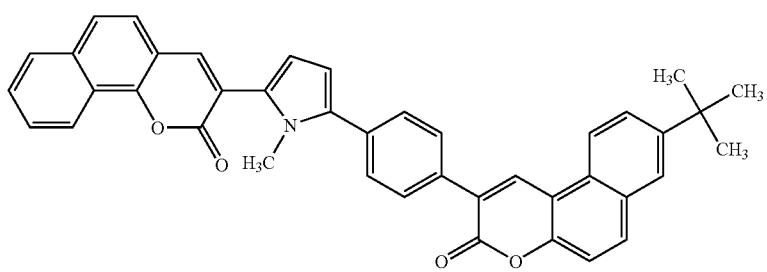
Chemical Formula 39:
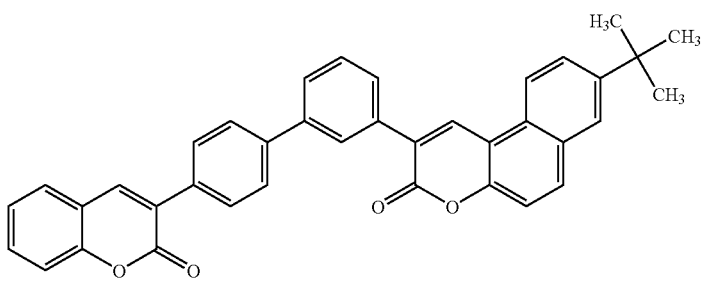

-continued
Chemical Formula 40:
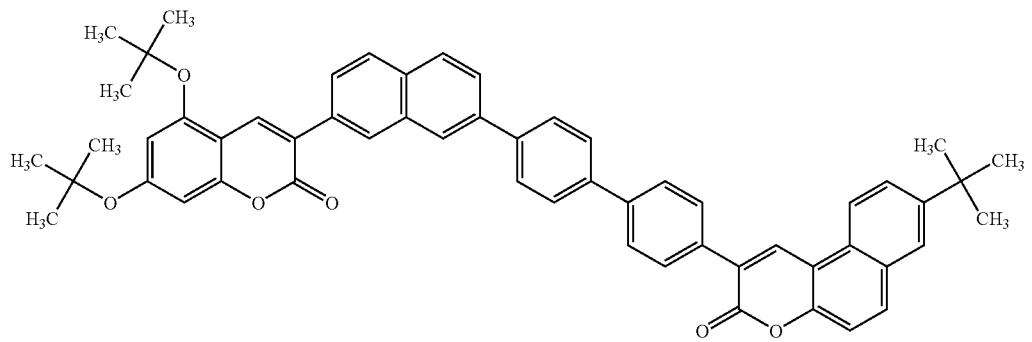
Chemical Formula 41:
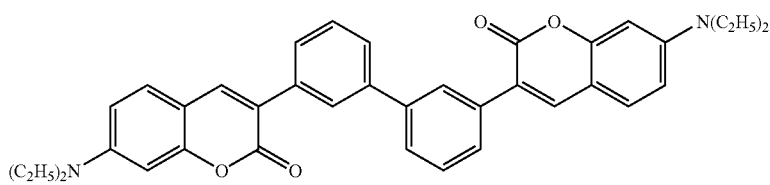
Chemical Formula 42:
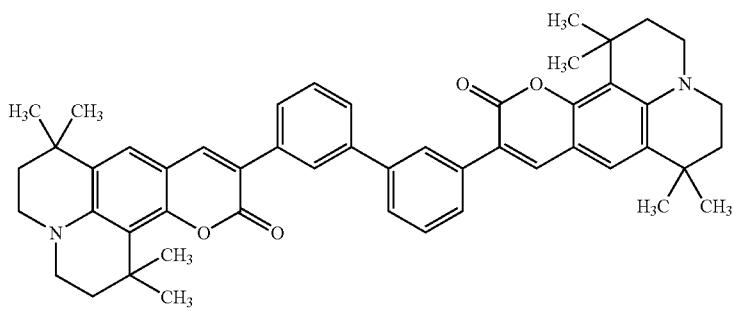
Chemical Formula 43:
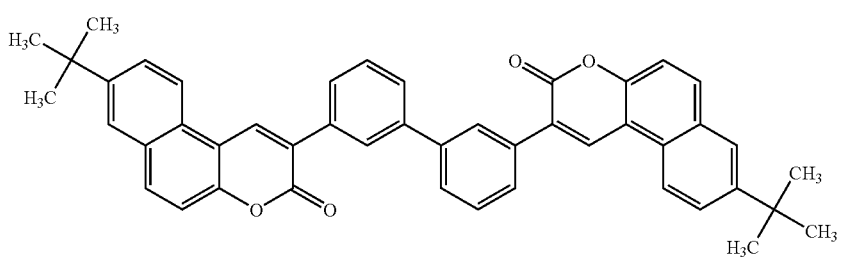
Chemical Formula 44:
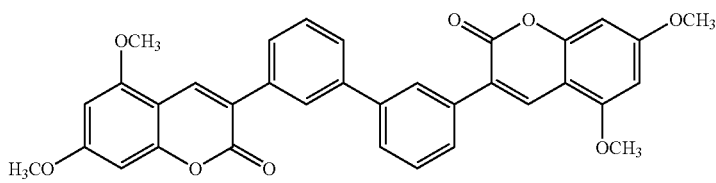
Chemical Formula 45:
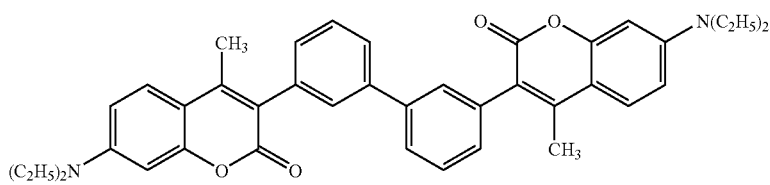

Chemical Formula 46:
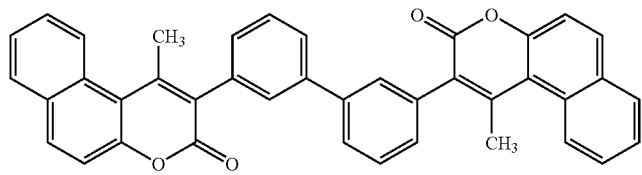
Chemical Formula 47:
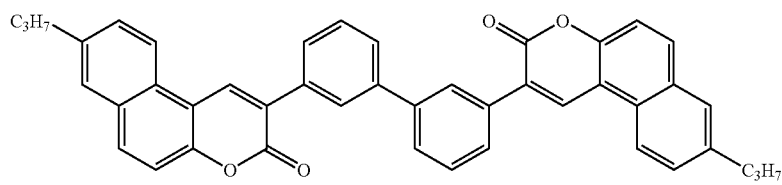
Chemical Formula 48:
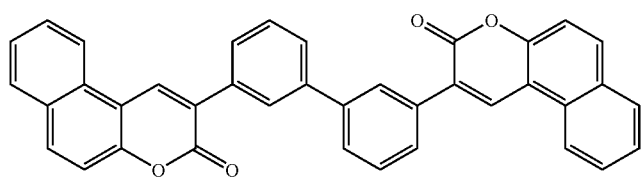
Chemical Formula 49:
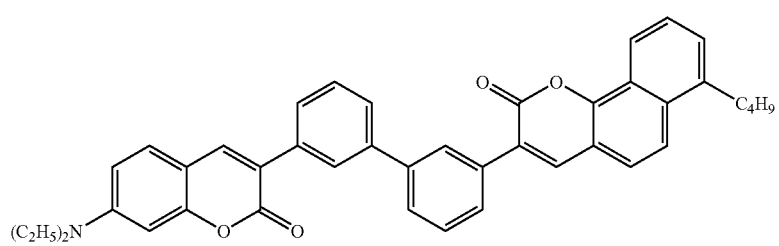
Chemical Formula 50:
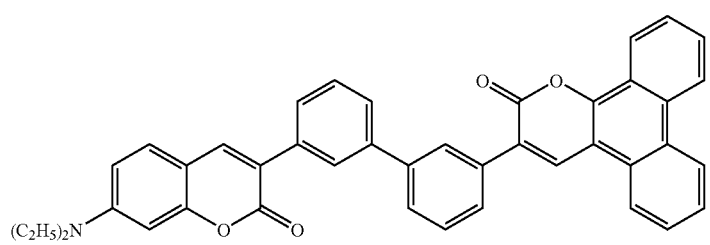
Chemical Formula 51:
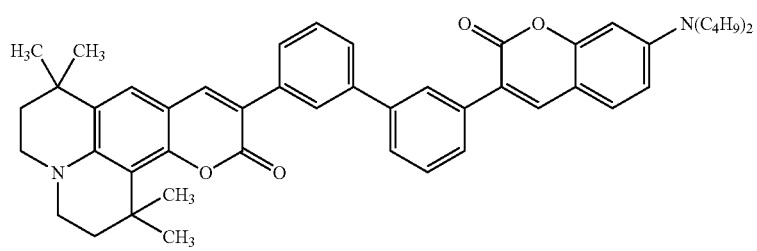

-continued
Chemical Formula 52:
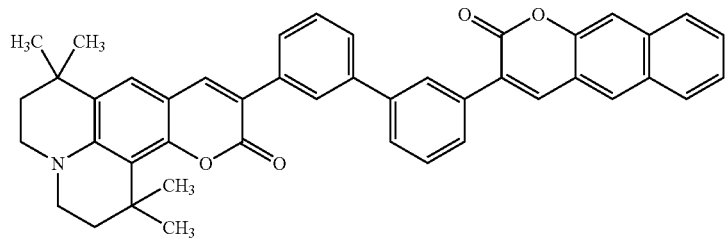
Chemical Formula 53:
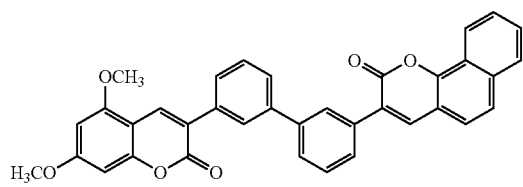
Chemical Formula 54:
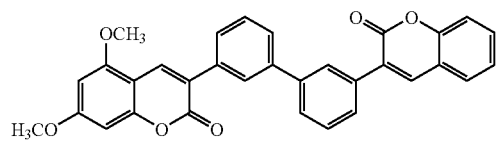
Chemical Formula 55:
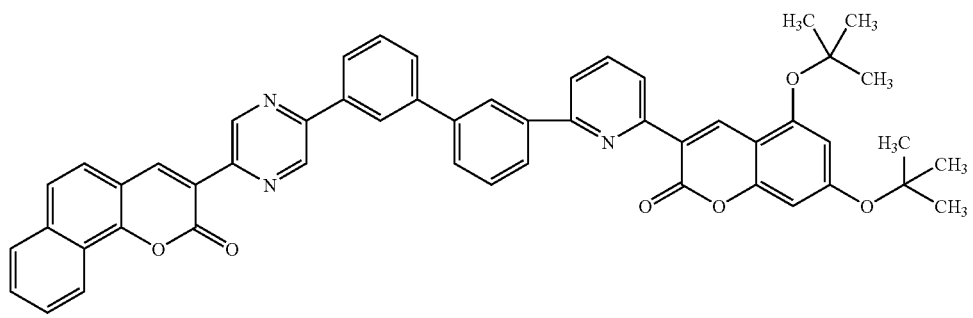
Chemical Formula 56:
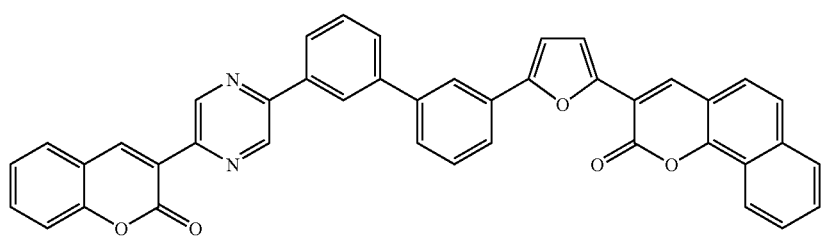
Chemical Formula 57:
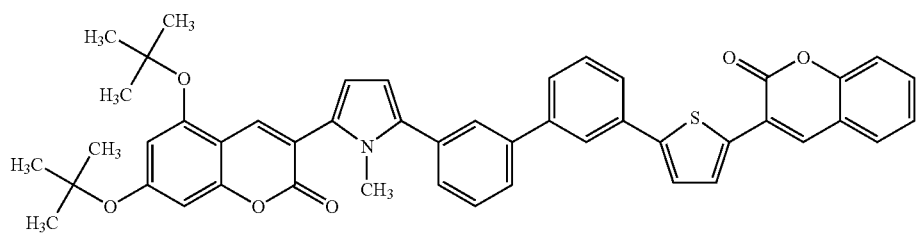
Chemical Formula 58:
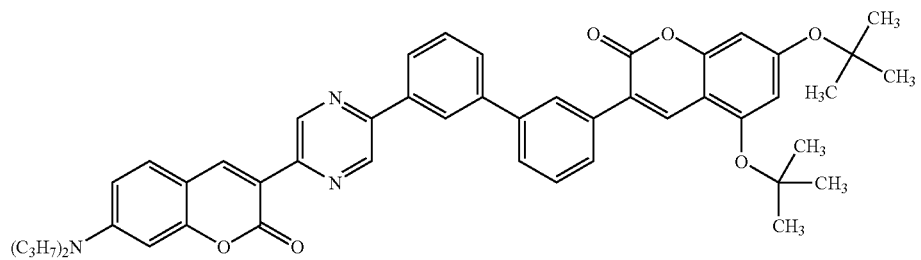

-continued
Chemical Formula 59:
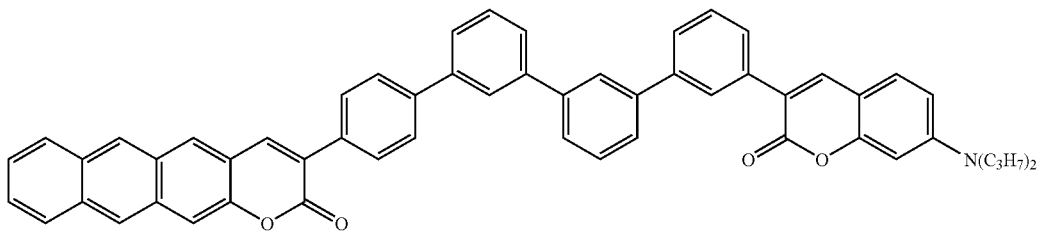
Chemical Formula 60:
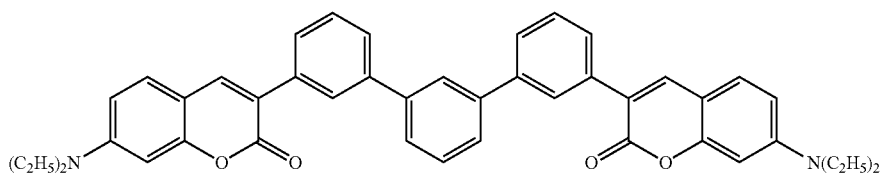
Chemical Formula 61:
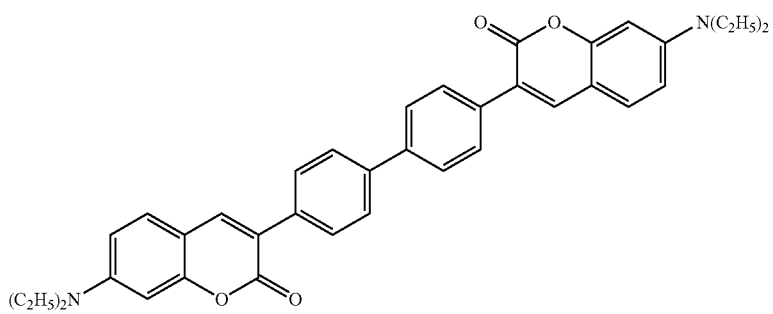
Chemical Formula 62:
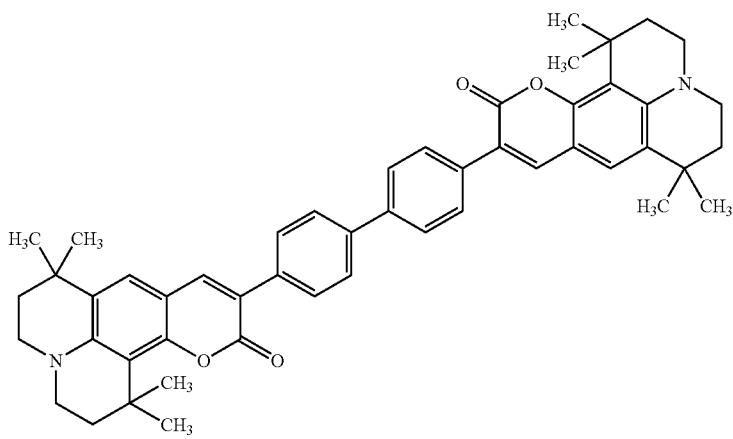
Chemical Formula 63:
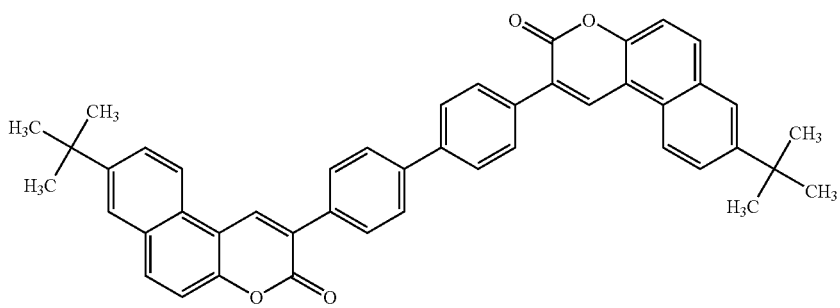

-continued
Chemical Formula 64:
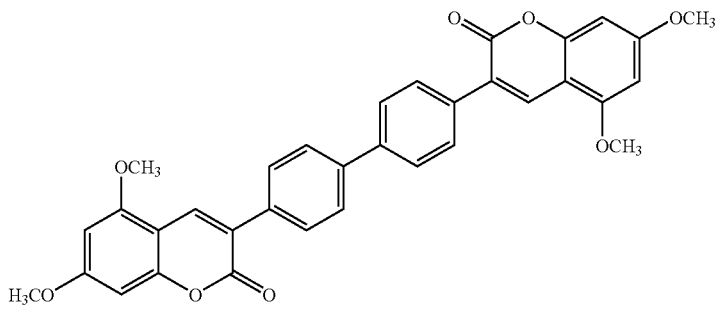
Chemical Formula 65:
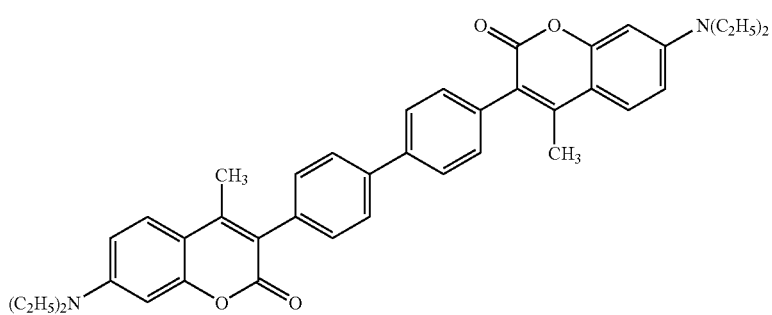
Chemical Formula 66:
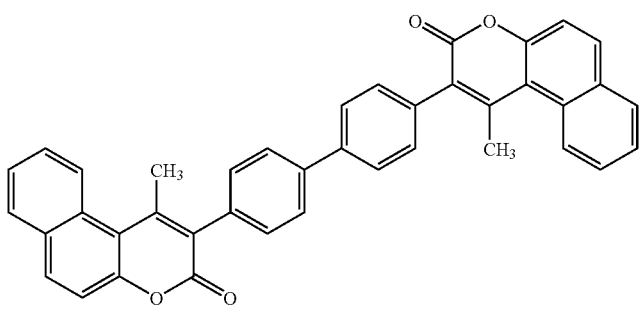
Chemical Formula 67:
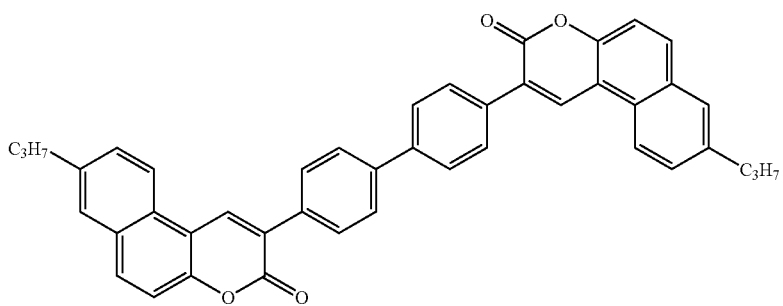
Chemical Formula 68:
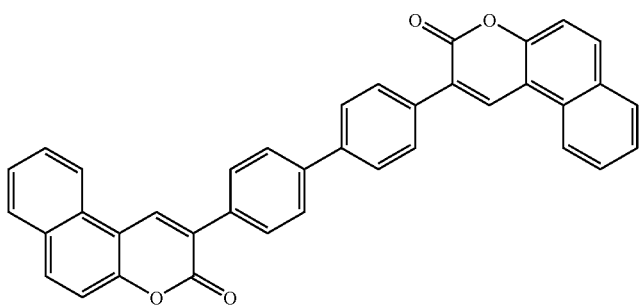

Chemical Formula 69:
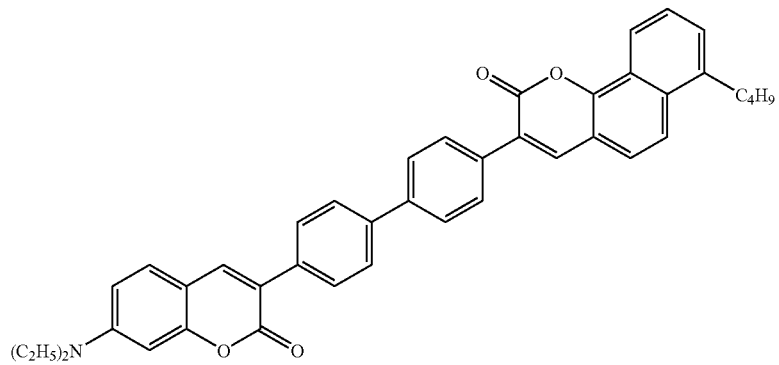
Chemical Formula 70:
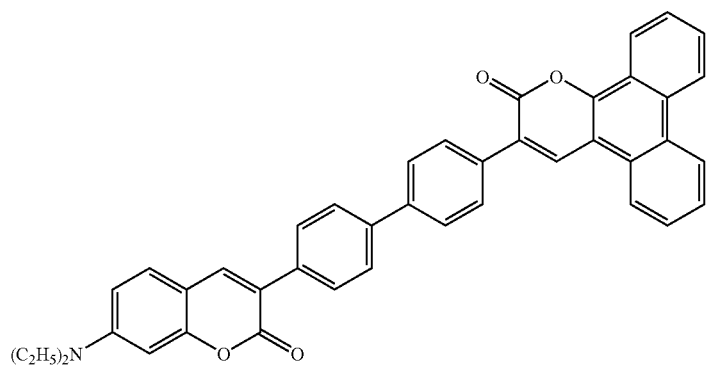
Chemical Formula 71:
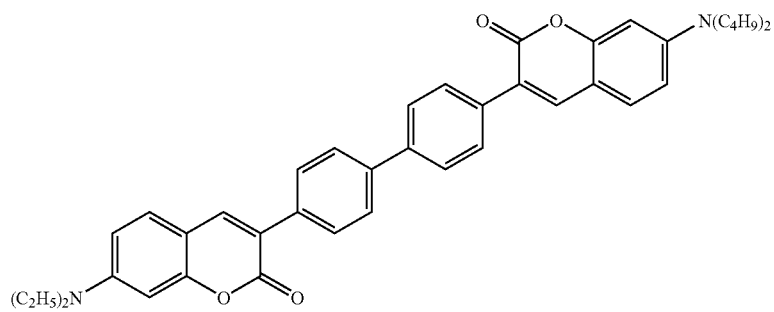
Chemical Formula 72:
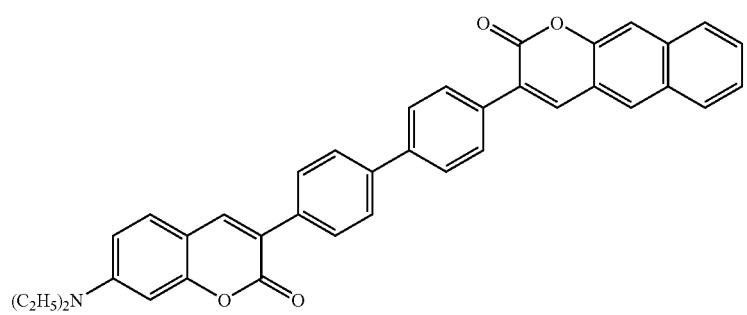

Chemical Formula 73:
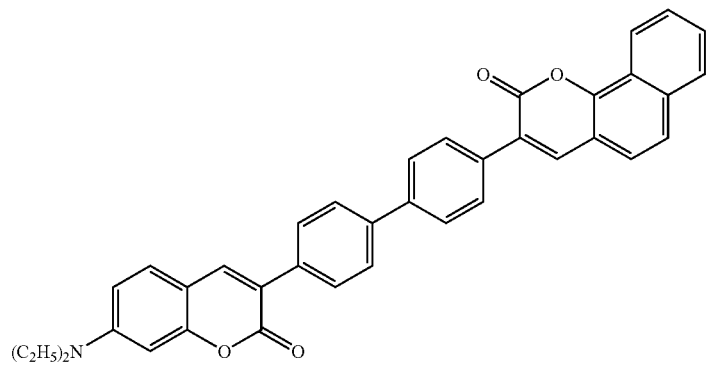
Chemical Formula 74:
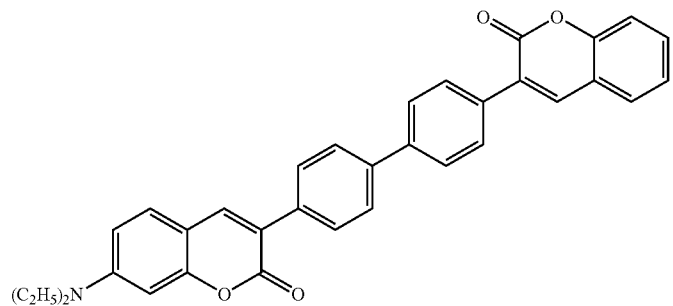
Chemical Formula 75:
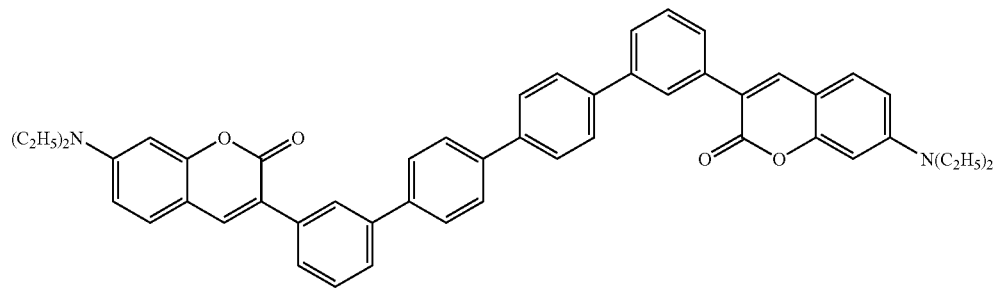
Chemical Formula 76:
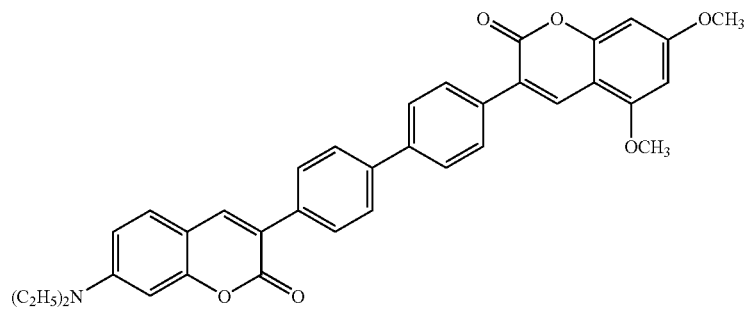

Chemical Formula 77:
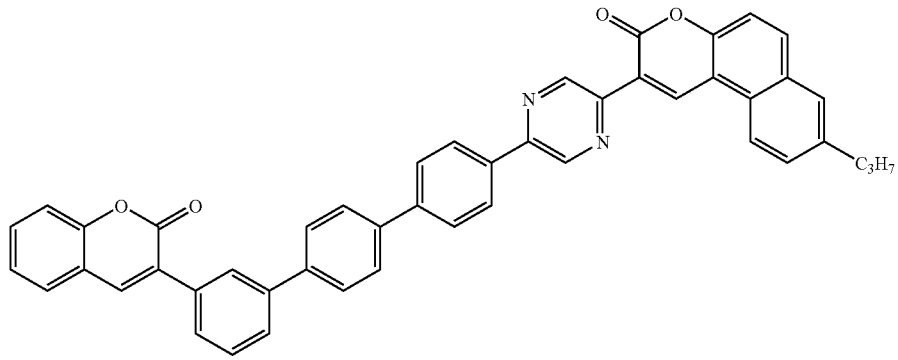
Chemical Formula 78:
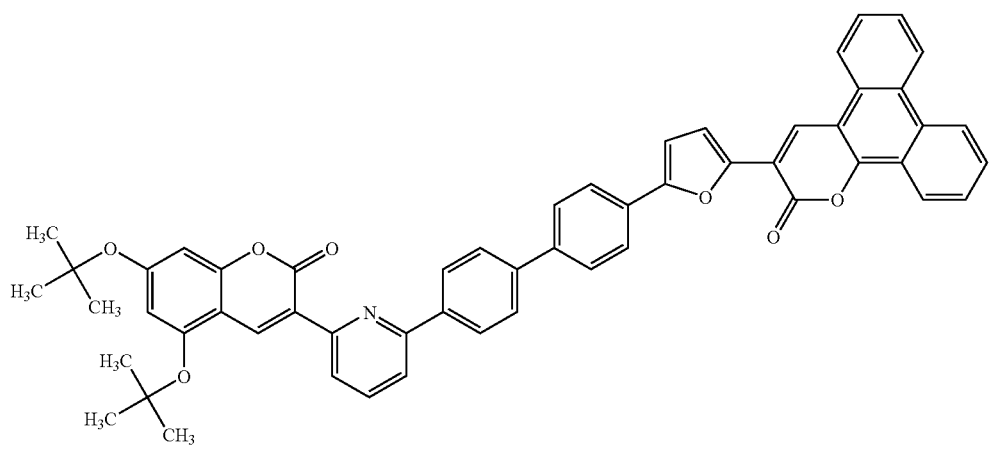
Chemical Formula 79:
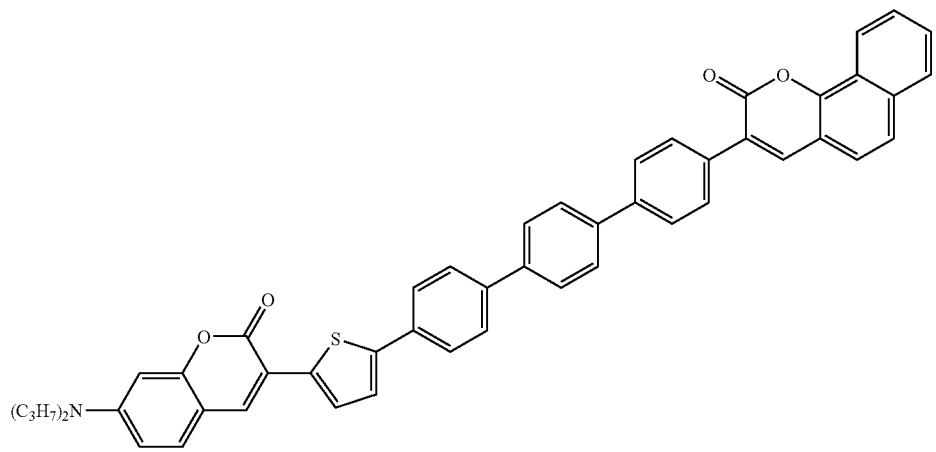

-continued
Chemical Formula 80:
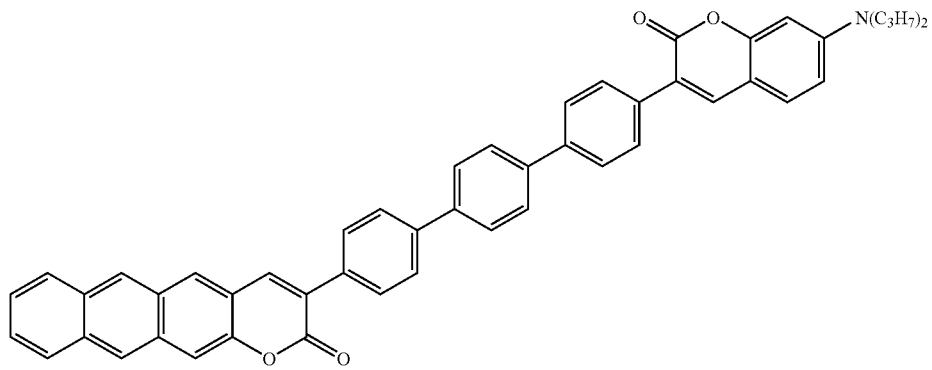
Chemical Formula 81:
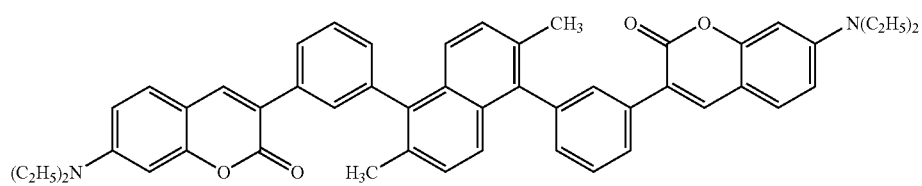
Chemical Formula 82:
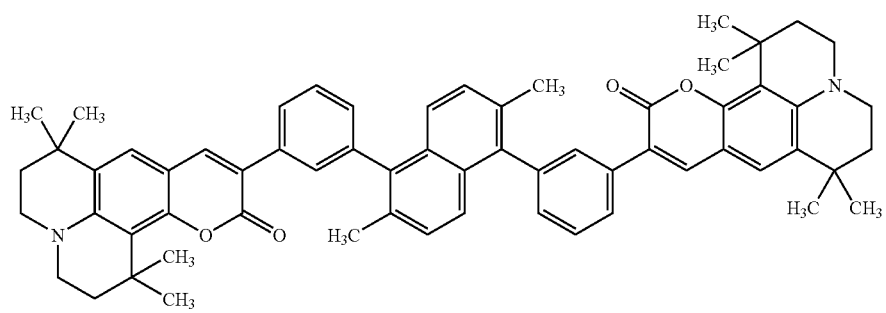
Chemical Formula 83:
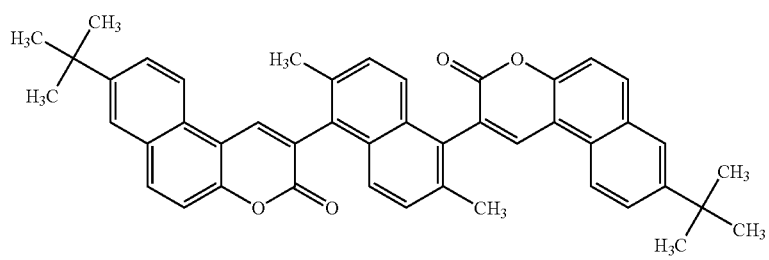
Chemical Formula 84:
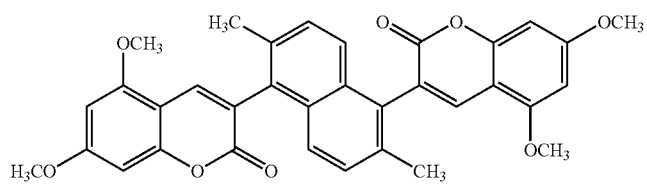
Chemical Formula 85:
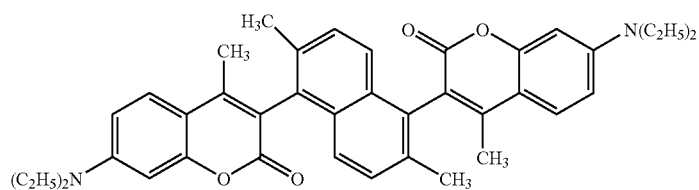

-continued
Chemical Formula 86:
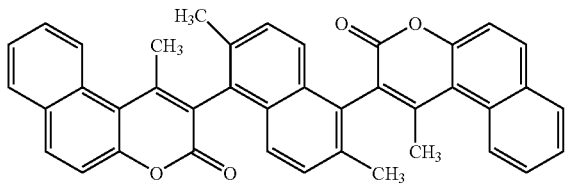
Chemical Formula 87:
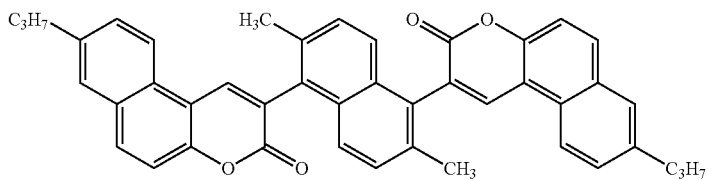
Chemical Formula 88:
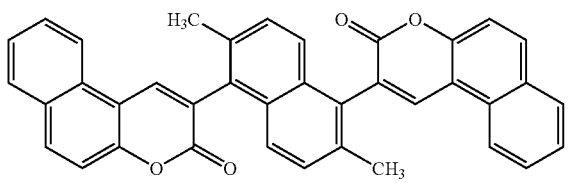
Chemical Formula 89:
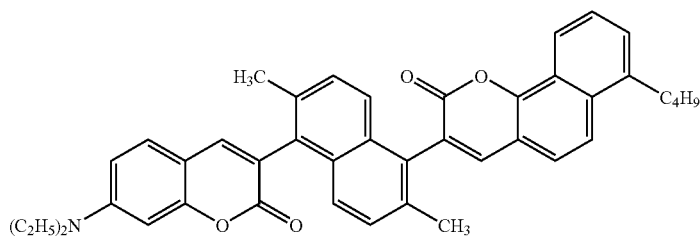
Chemical Formula 90:
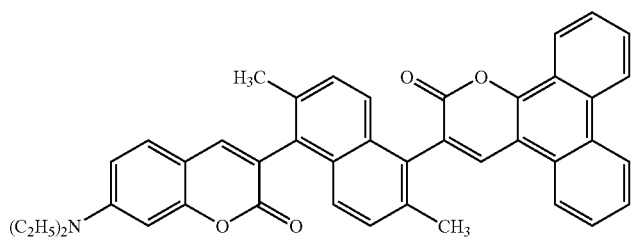
Chemical Formula 91:
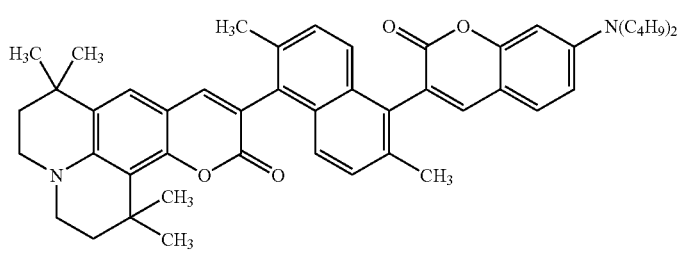
Chemical Formula 92:
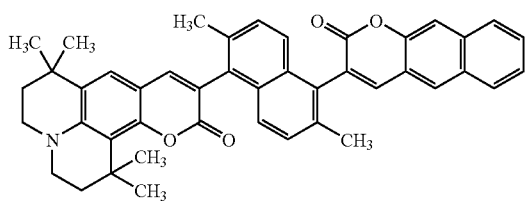
Chemical Formula 93:
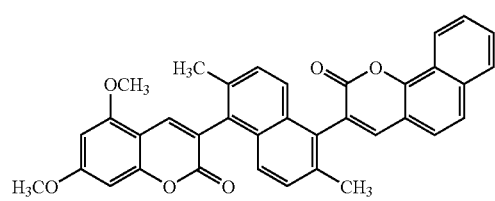

-continued
Chemical Formula 94:
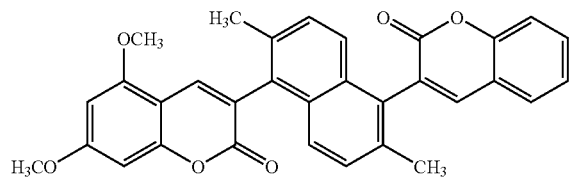
Chemical Formula 95:
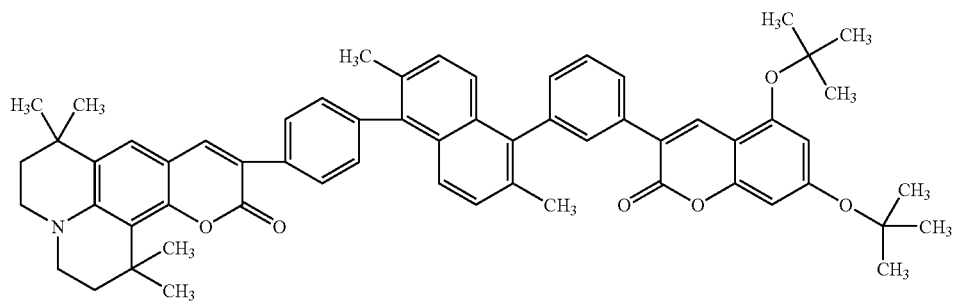
Chemical Formula 96:
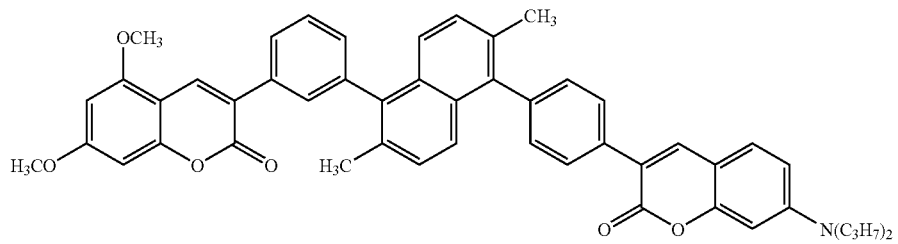
Chemical Formula 97:
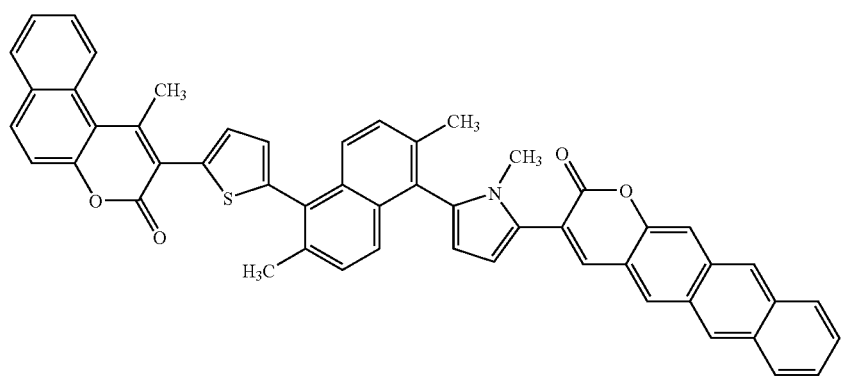
Chemical Formula 98:
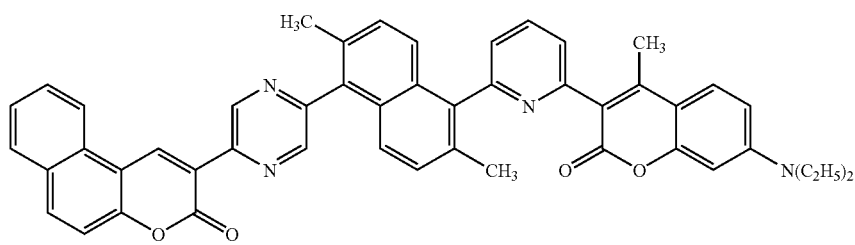

-continued
Chemical Formula 99:
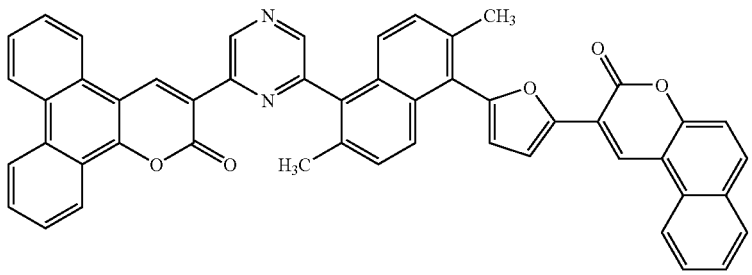
Chemical Formula 100:
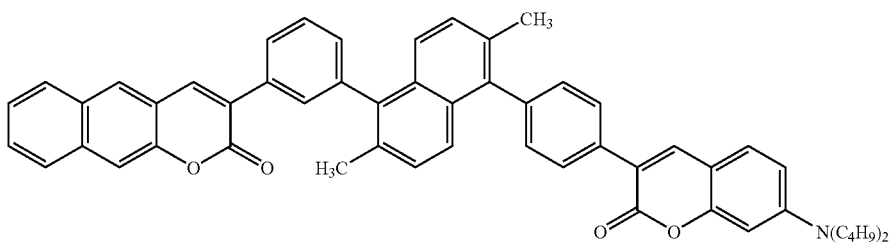
Chemical Formula 101:
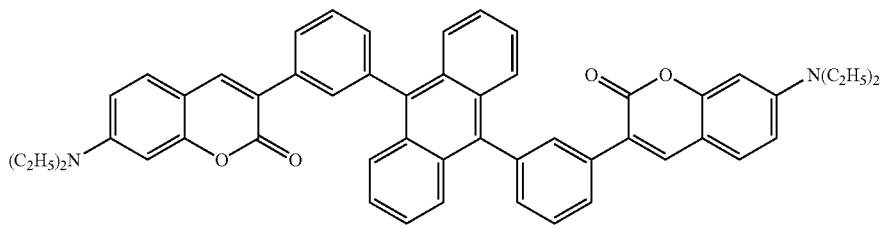
Chemical Formula 102:
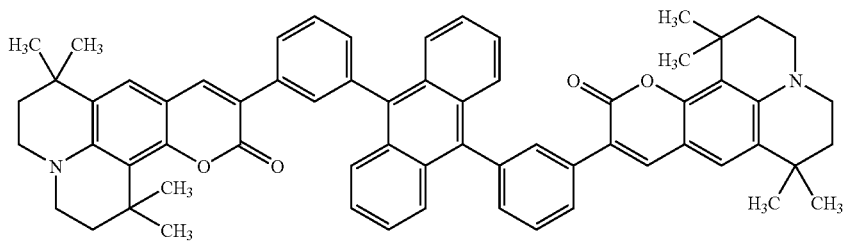
Chemical Formula 103:
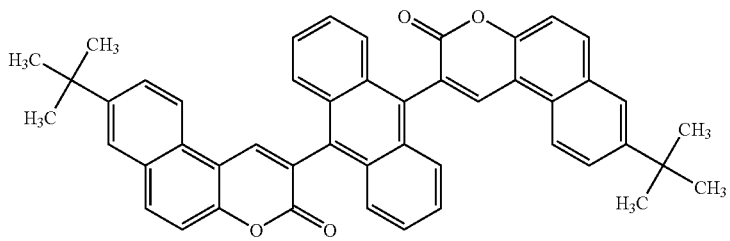
Chemical Formula 104:
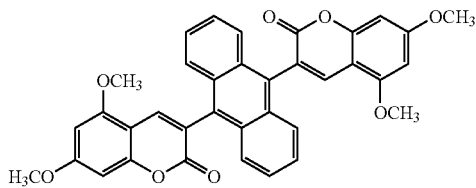
Chemical Formula 105:
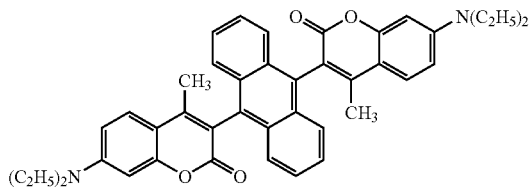

Chemical Formula 106:
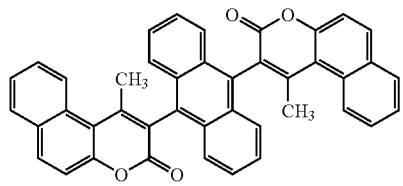
Chemical Formula 107:
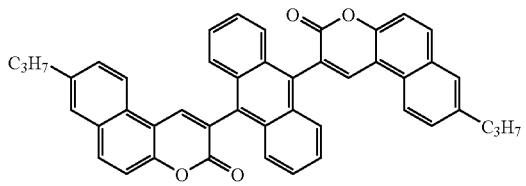
Chemical Formula 108:
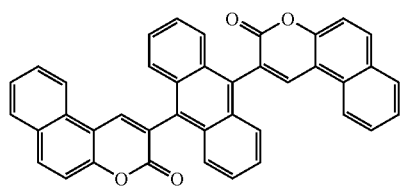
Chemical Formula 109:
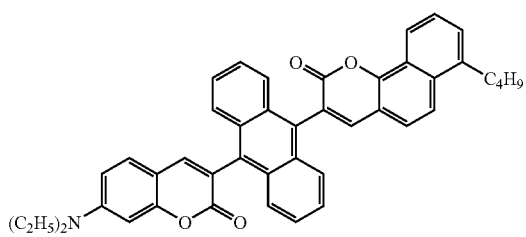
Chemical Formula 110:
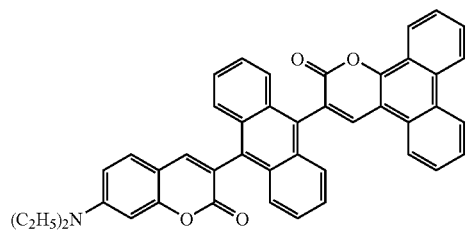
Chemical Formula 111:
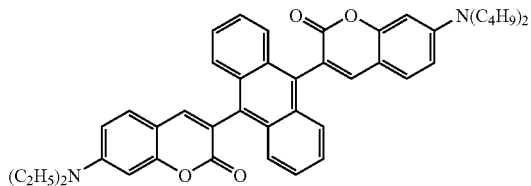
Chemical Formula 112:
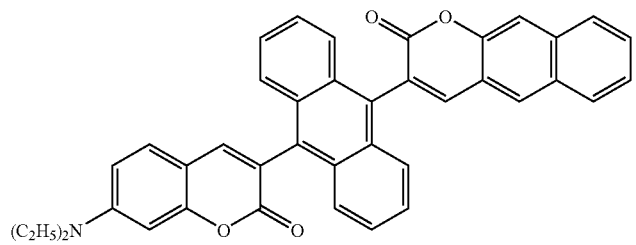
Chemical Formula 113:
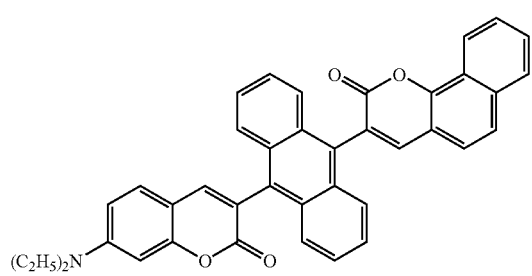
Chemical Formula 114:
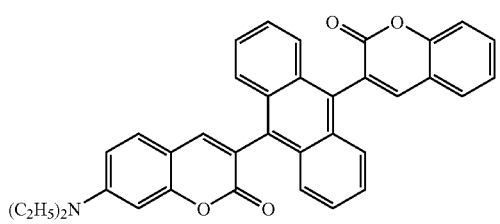

Chemical Formula 115:
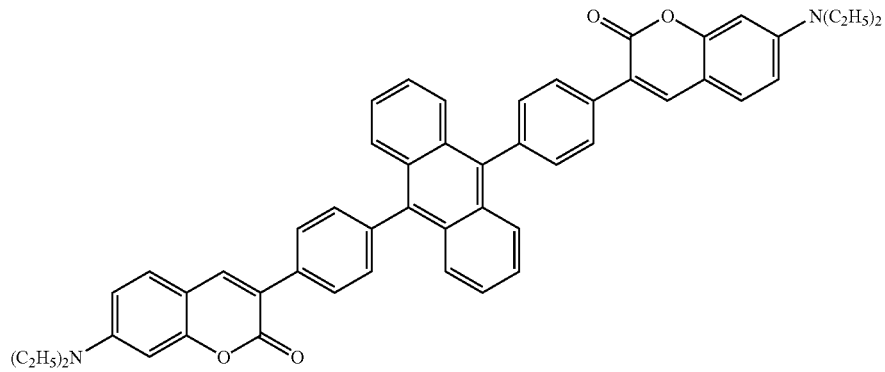
Chemical Formula 116:
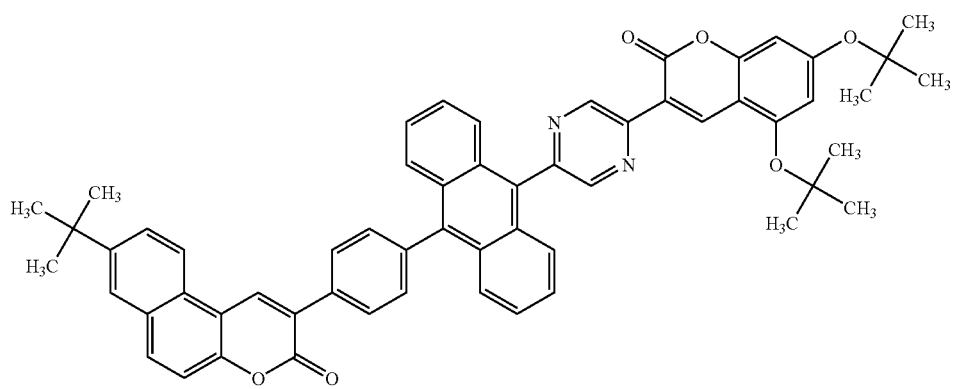
Chemical Formula 117:
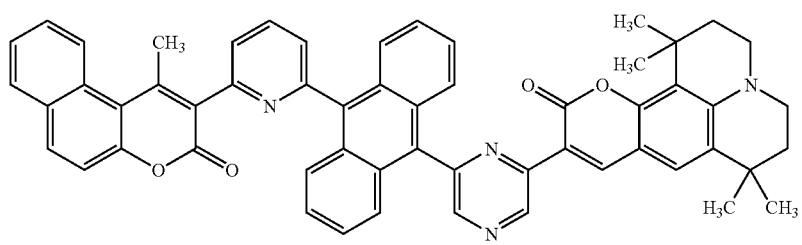
Chemical Formula 118:
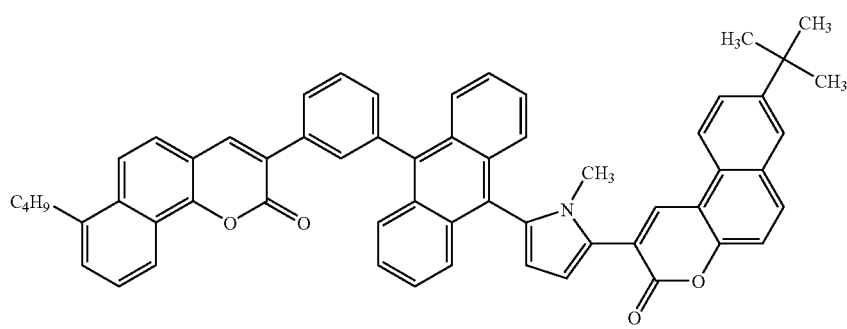
Chemical Formula 119:
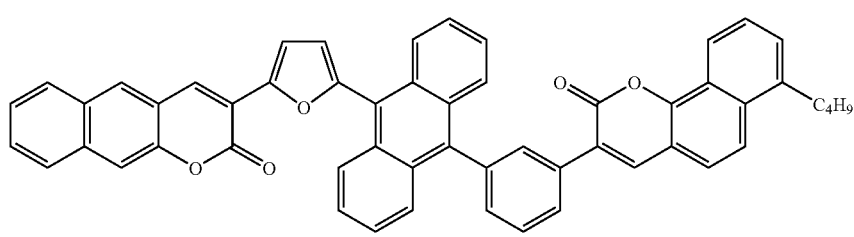

Chemical Formula 120:
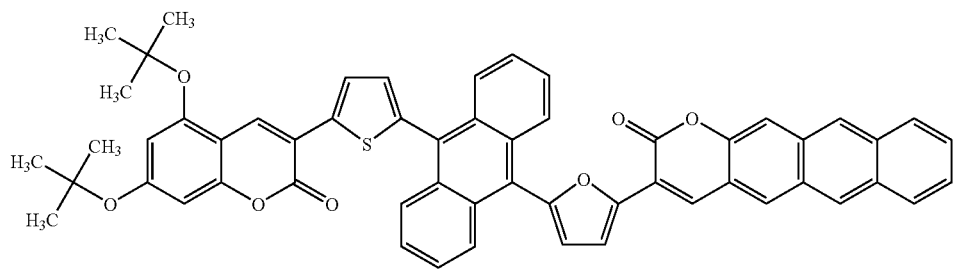
Chemical Formula 121:
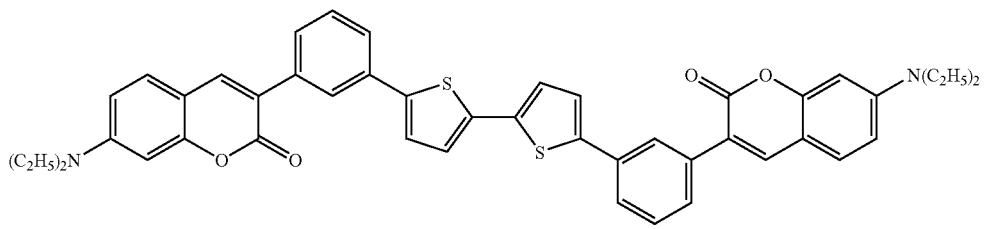
Chemical Formula 122:
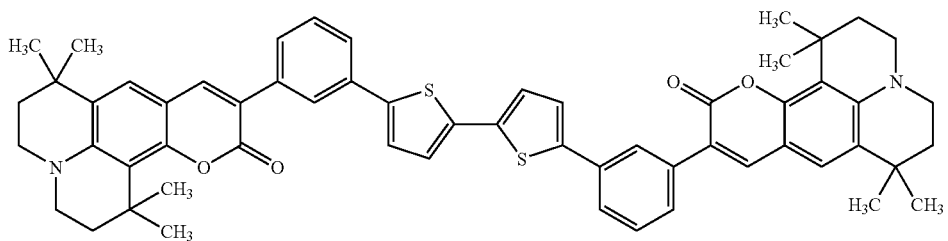
Chemical Formula 123:
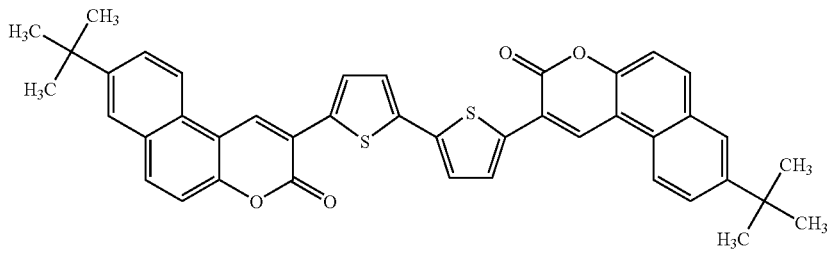
Chemical Formula 124:
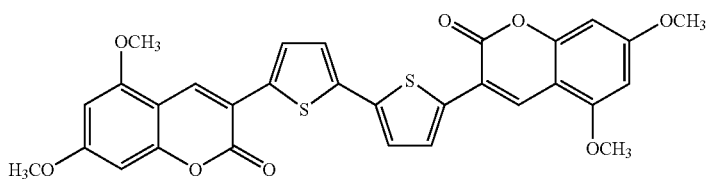
Chemical Formula 125:
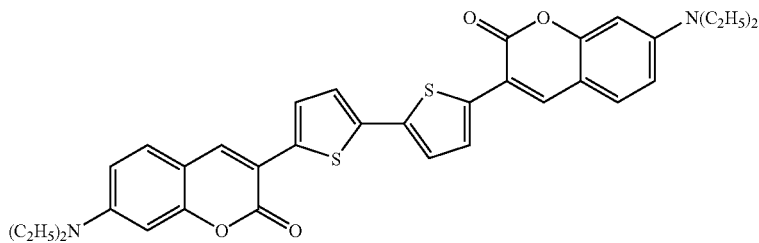

-continued
Chemical Formula 126:
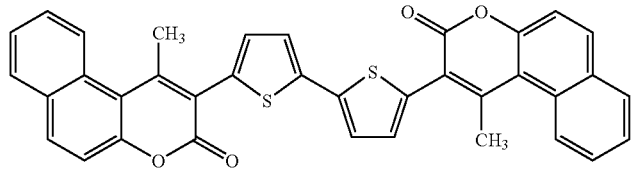
Chemical Formula 127:
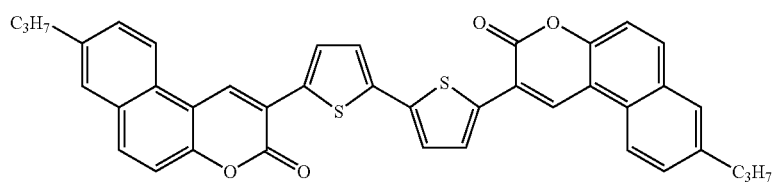
Chemical Formula 128:
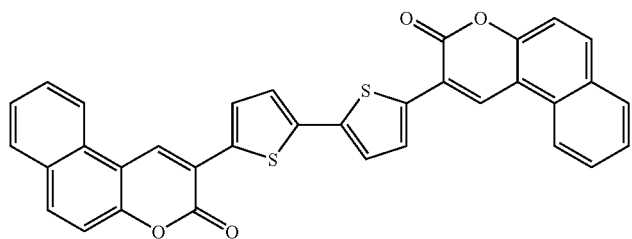
Chemical Formula 129:
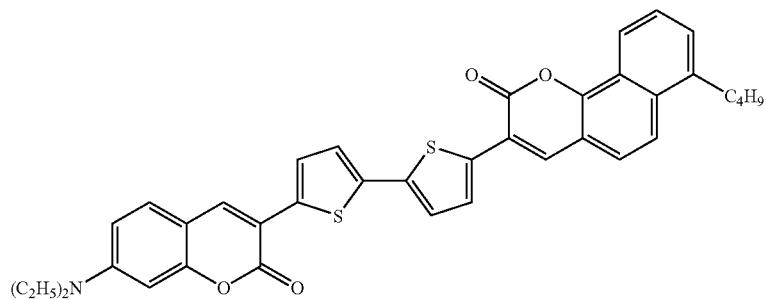
Chemical Formula 130:
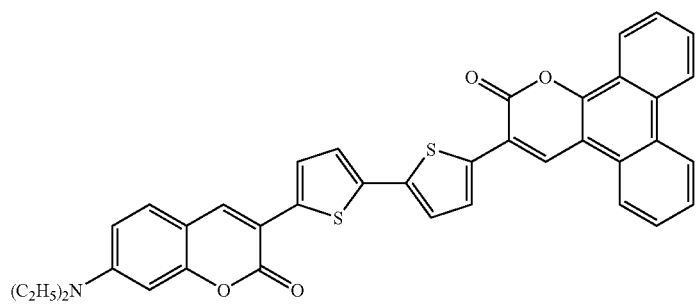
Chemical Formula 131:
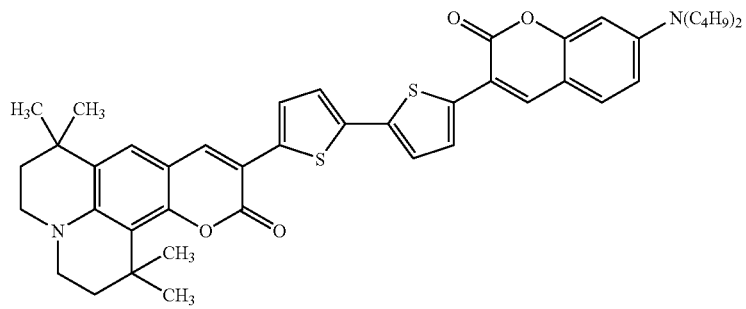

-continued
Chemical Formula 132:
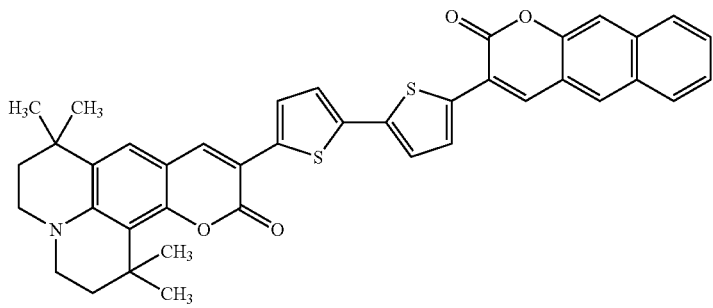
Chemical Formula 133:
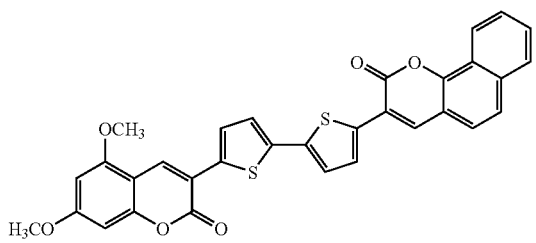
Chemical Formula 134:
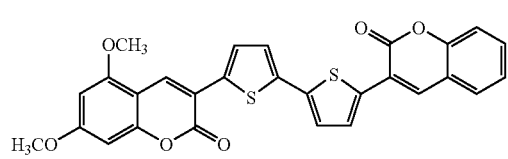
Chemical Formula 135:
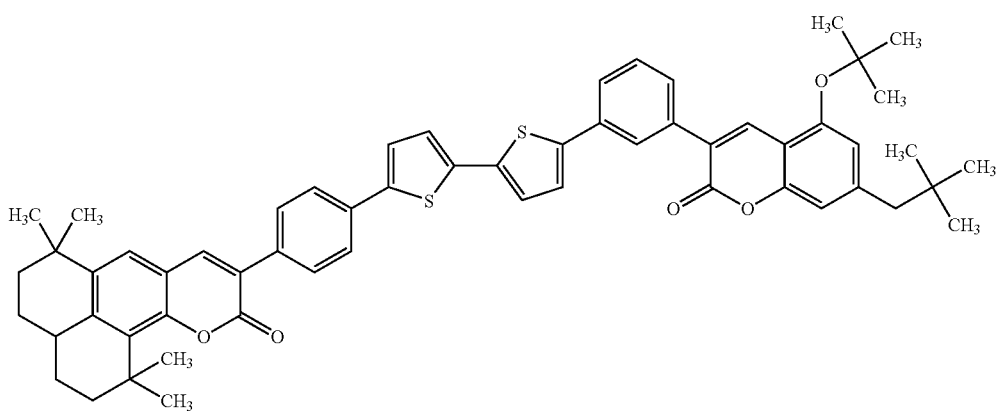
Chemical Formula 136:
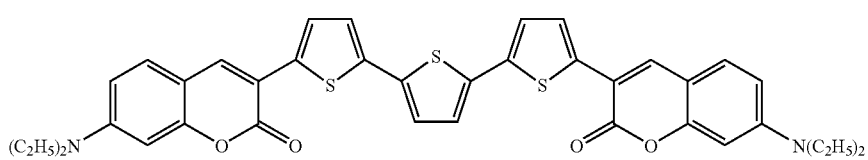
Chemical Formula 137:
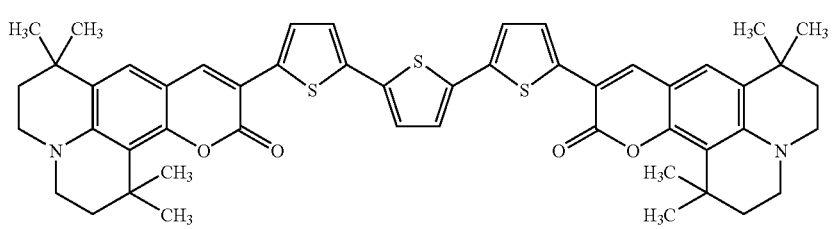

-continued
Chemical Formula 138:
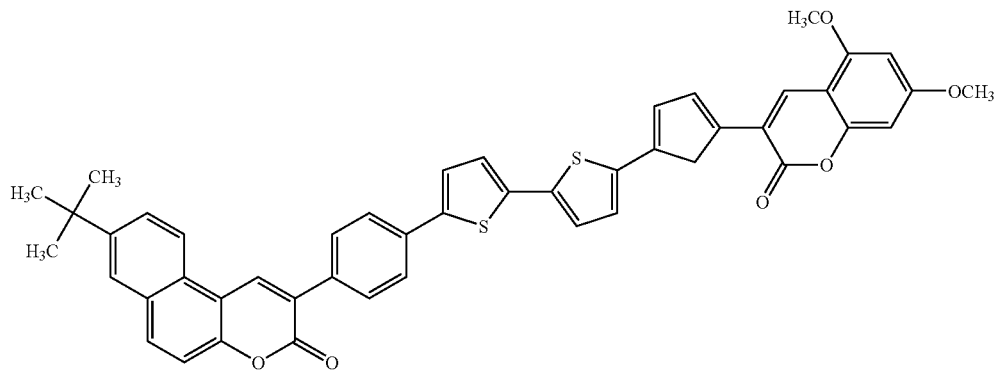
Chemical Formula 139:
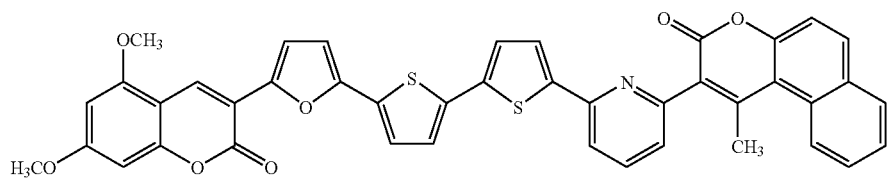
Chemical Formula 140:
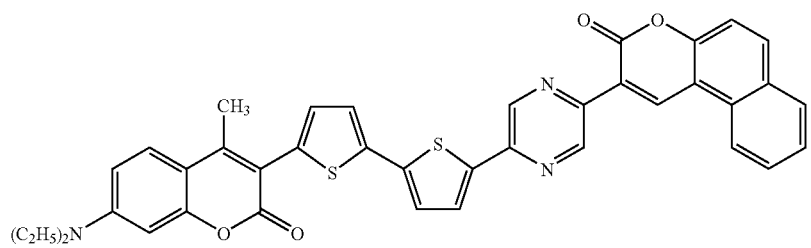
Chemical Formula 141:
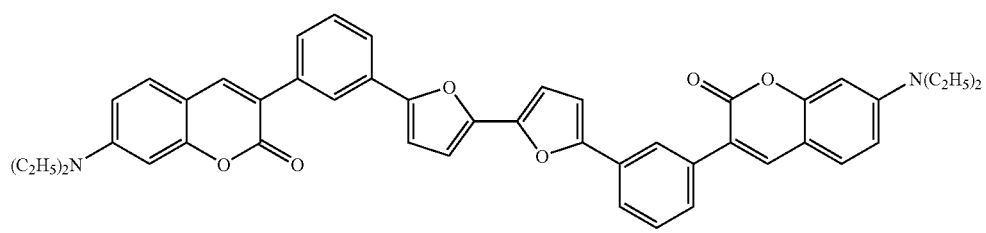
Chemical Formula 142:
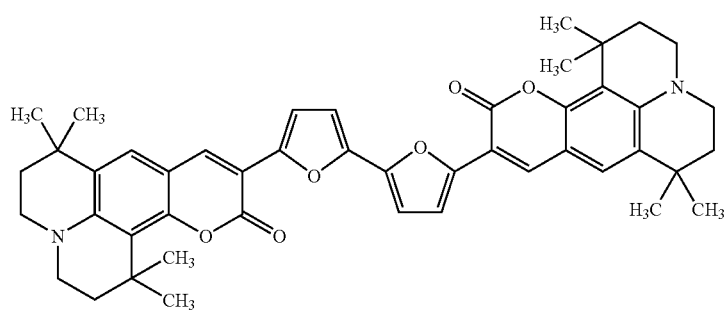

Chemical Formula 143:
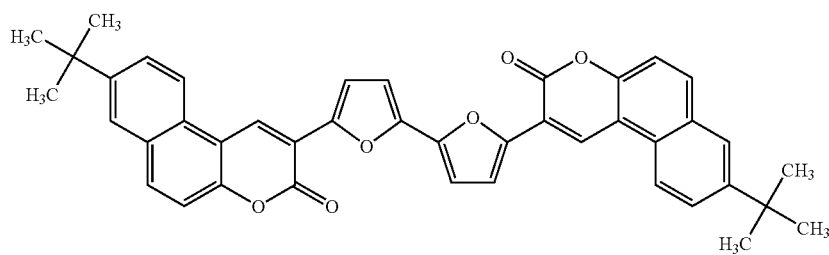
Chemical Formula 144:
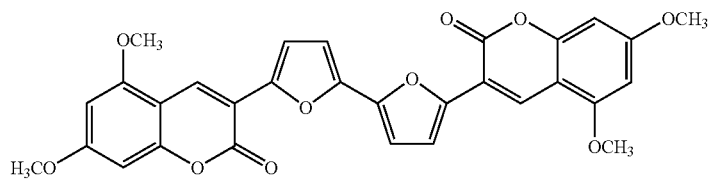
Chemical Formula 145:
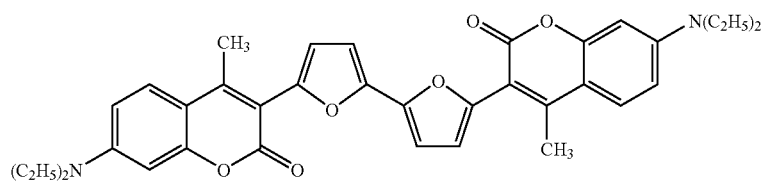
Chemical Formula 146:
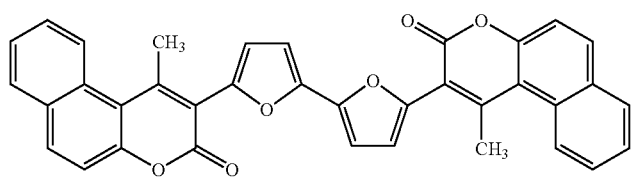
Chemical Formula 147:
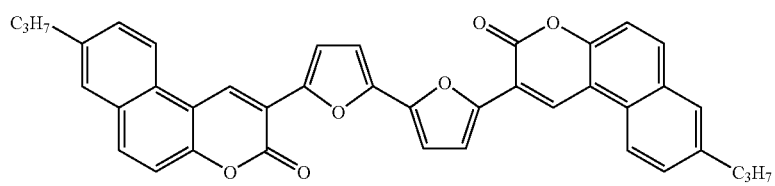
Chemical Formula 148:
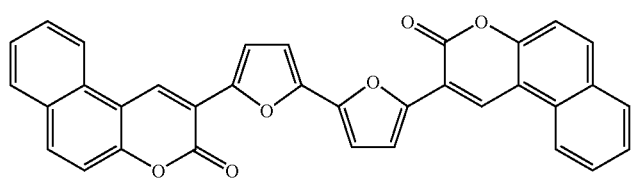
Chemical Formula 149:
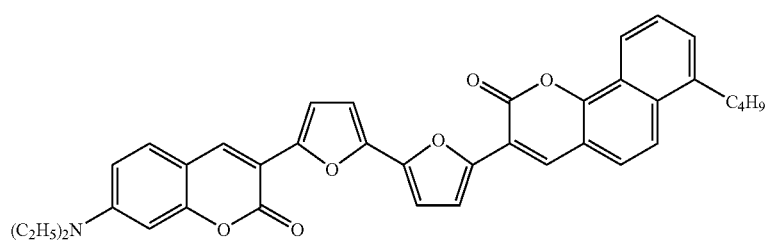

Chemical Formula 150:
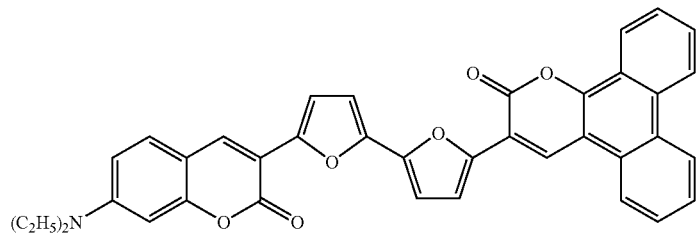
Chemical Formula 151:
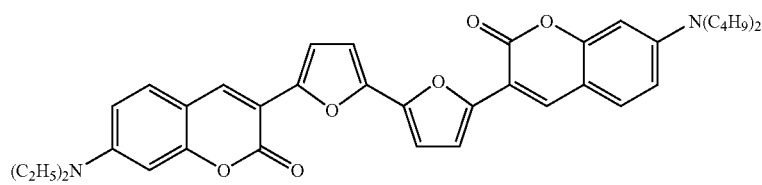
Chemical Formula 152:
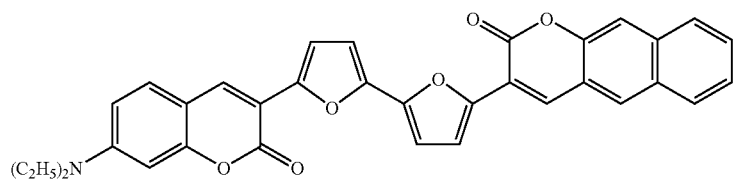
Chemical Formula 153:
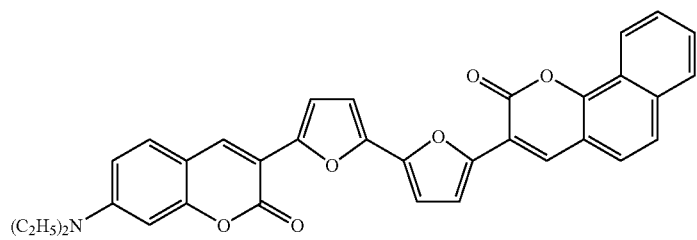
Chemical Formula 154:
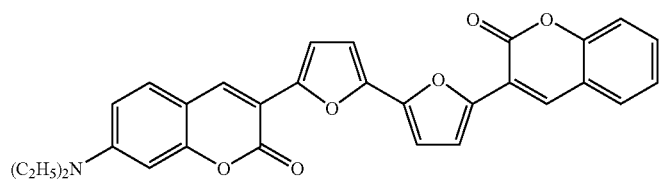
Chemical Formula 155:
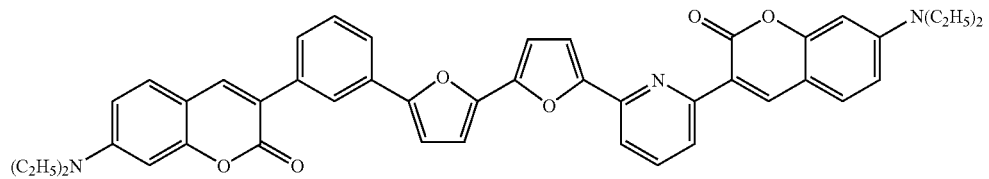

Chemical Formula 156:
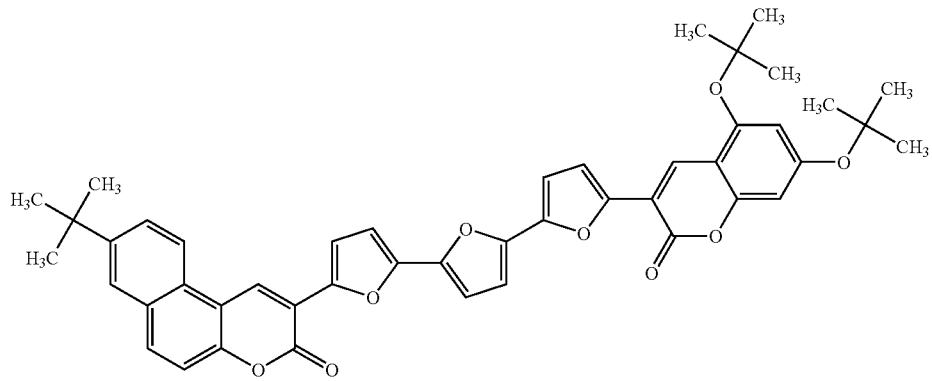
Chemical Formula 157:
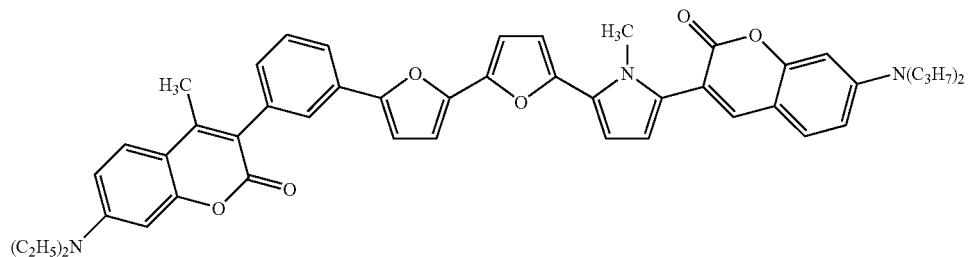
Chemical Formula 158:
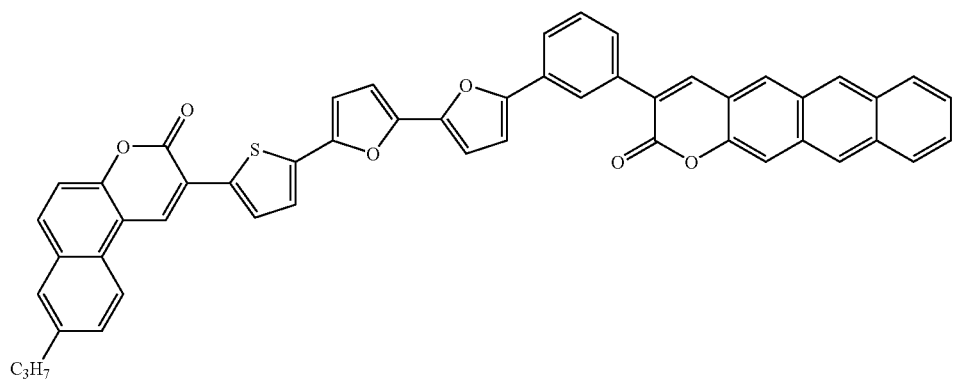
Chemical Formula 159:
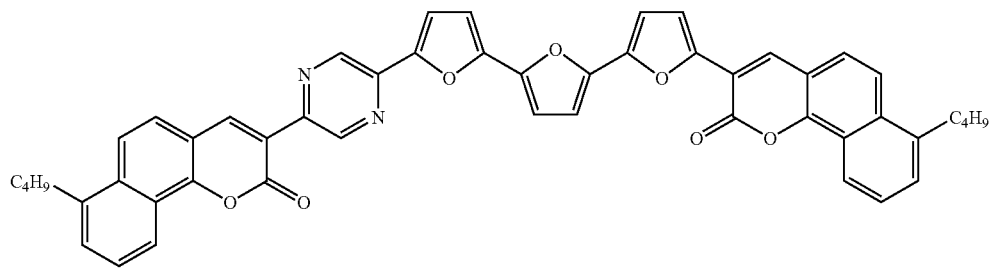

-continued
Chemical Formula 160:
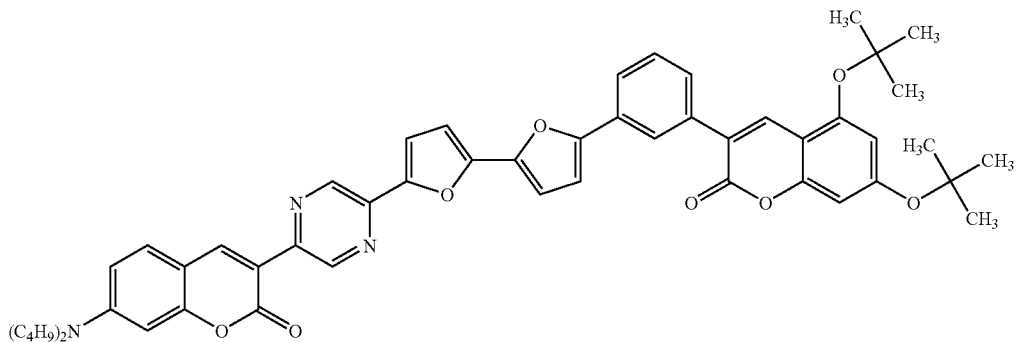
Chemical Formula 161:
Chemical Formula 162:
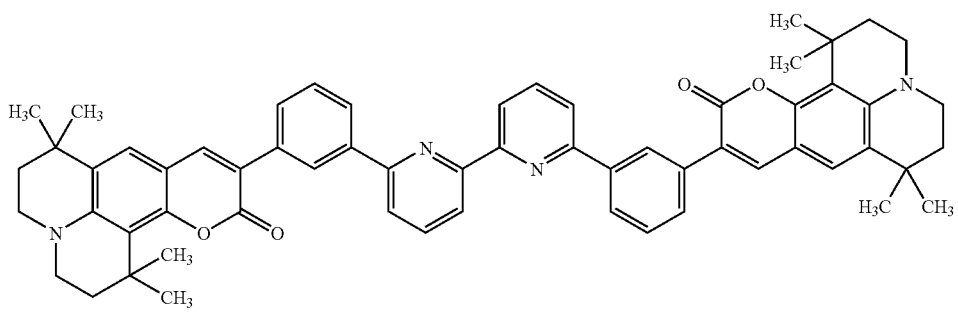
Chemical Formula 163:
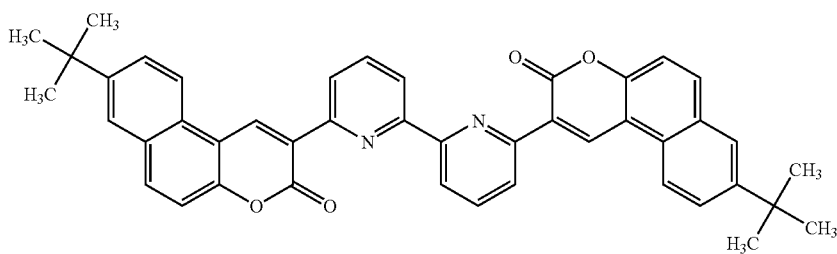
Chemical Formula 164:
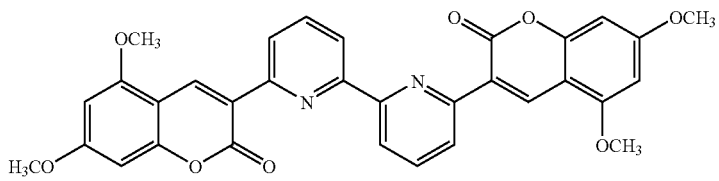
Chemical Formula 165:
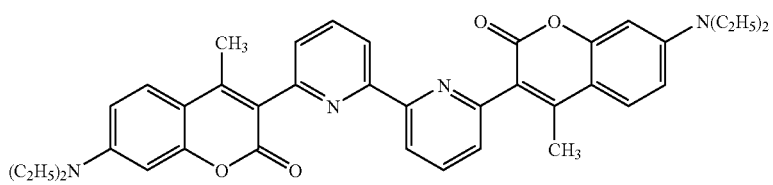

Chemical Formula 166:
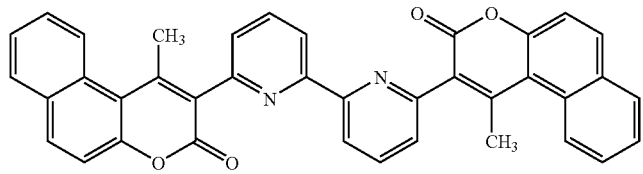
Chemical Formula 167:
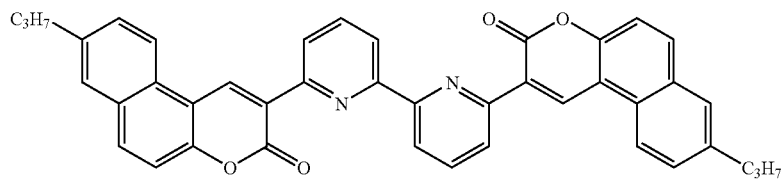
Chemical Formula 168:
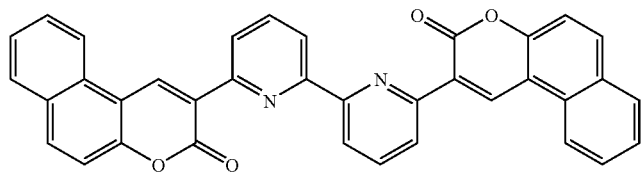
Chemical Formula 169:
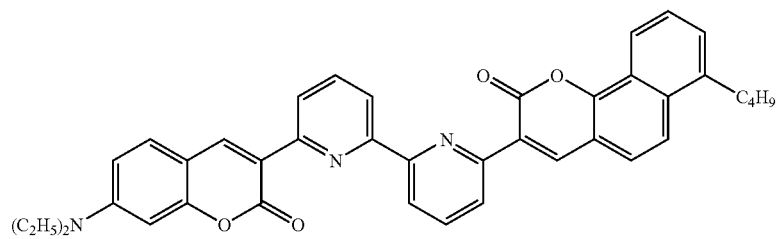
Chemical Formula 170:
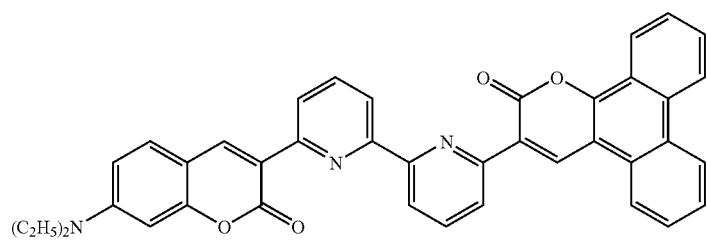
Chemical Formula 171:
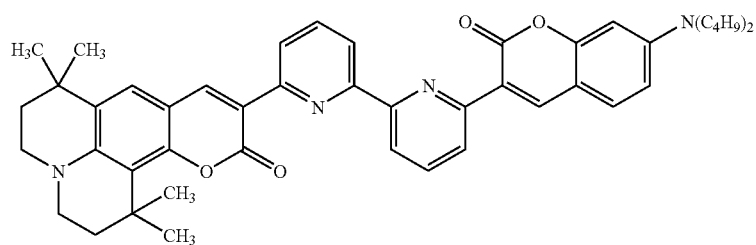

Chemical Formula 172:
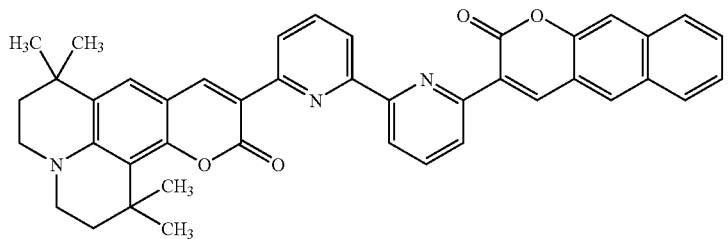
Chemical Formula 173:
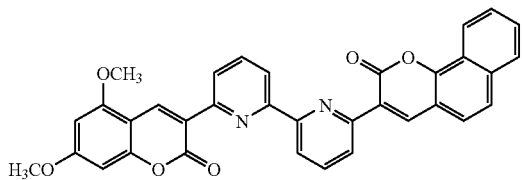
Chemical Formula 174:
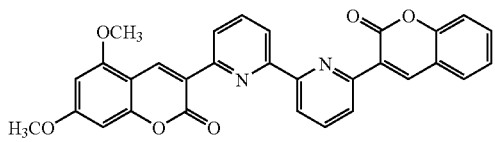
Chemical Formula 175:
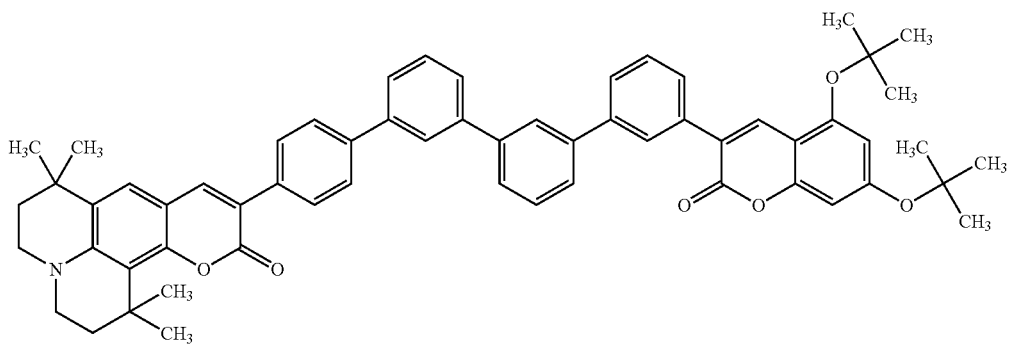
Chemical Formula 176:
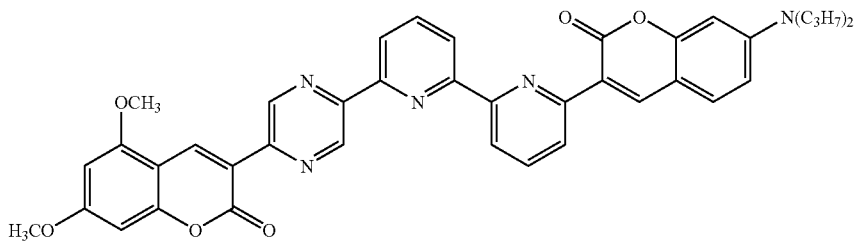
Chemical Formula 177:
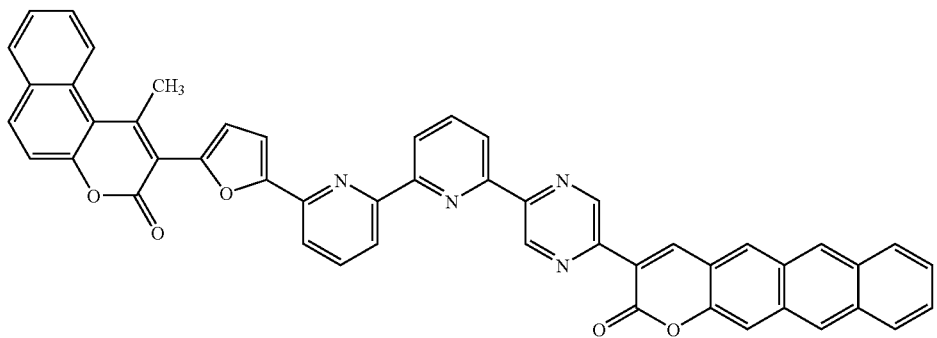

-continued
Chemical Formula 178:
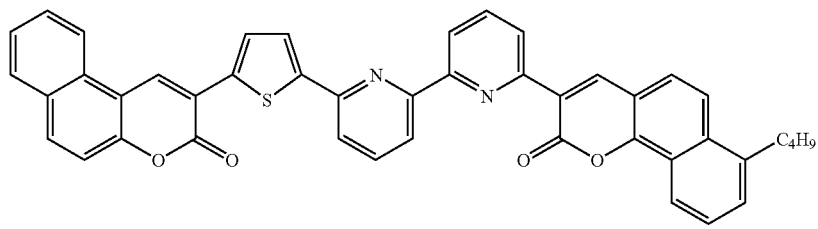
Chemical Formula 179:
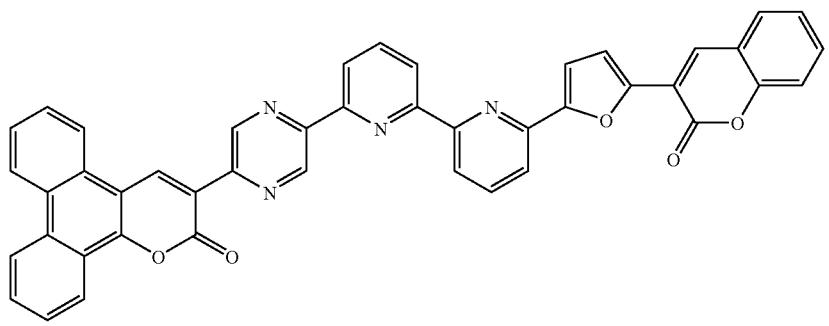
Chemical Formula 180:
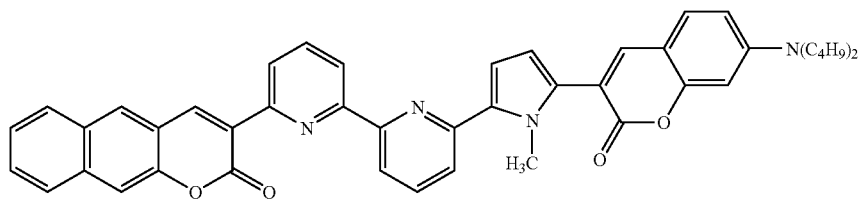
Chemical Formula 181:
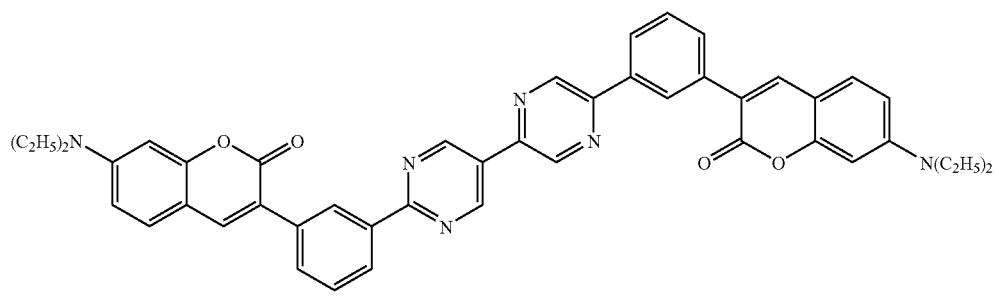
Chemical Formula 182:
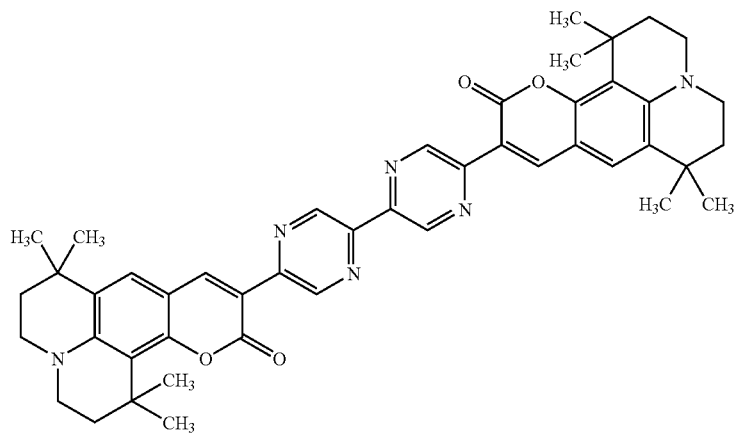

-continued
Chemical Formula 183:
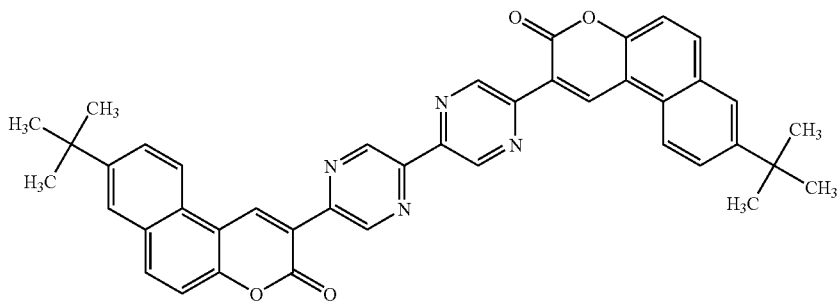
Chemical Formula 184:
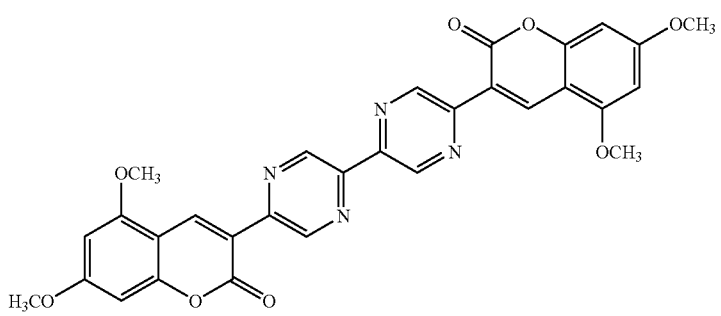
Chemical Formula 185:
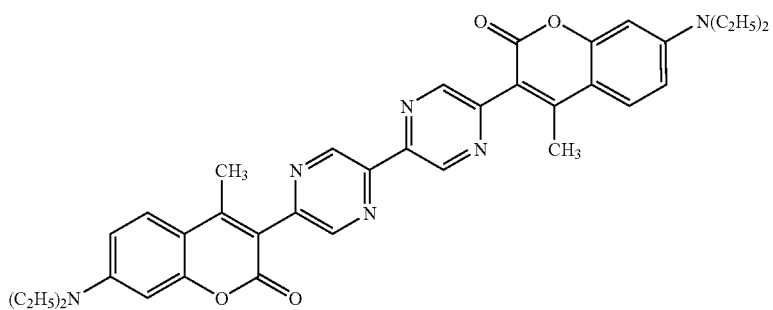
Chemical Formula 186:
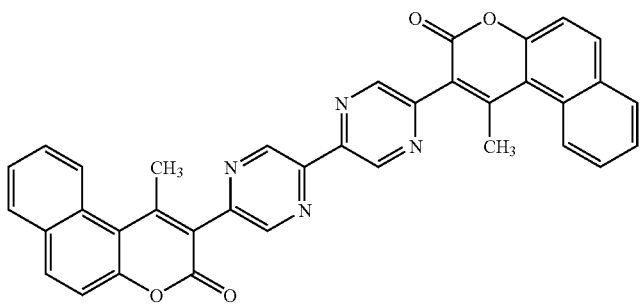
Chemical Formula 187:
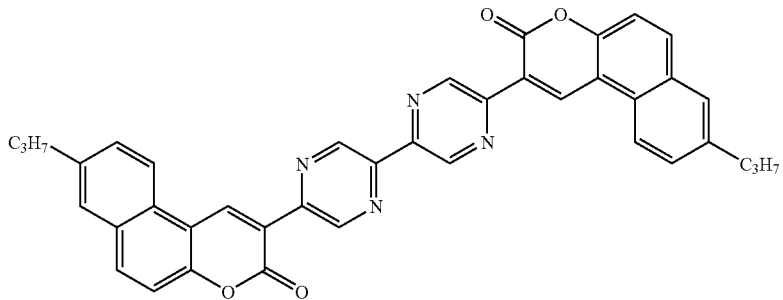

Chemical Formula 188:
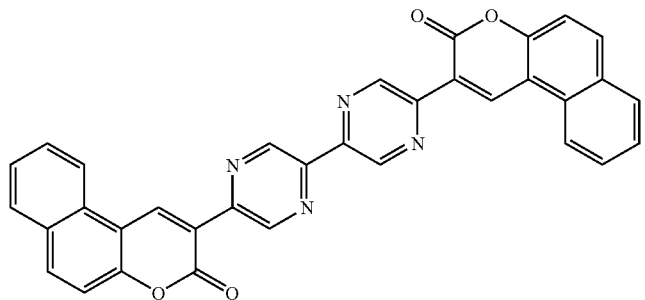
Chemical Formula 189:
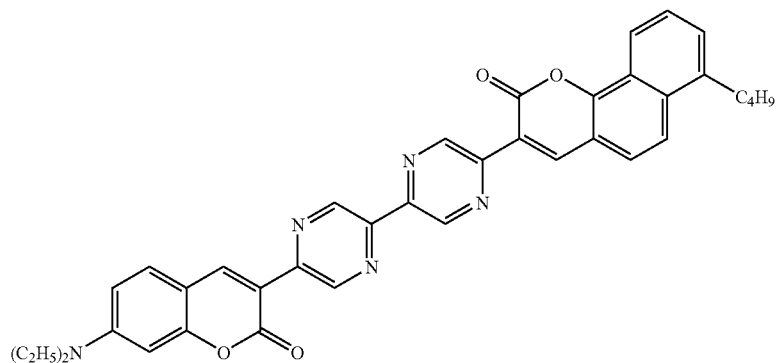
Chemical Formula 190:
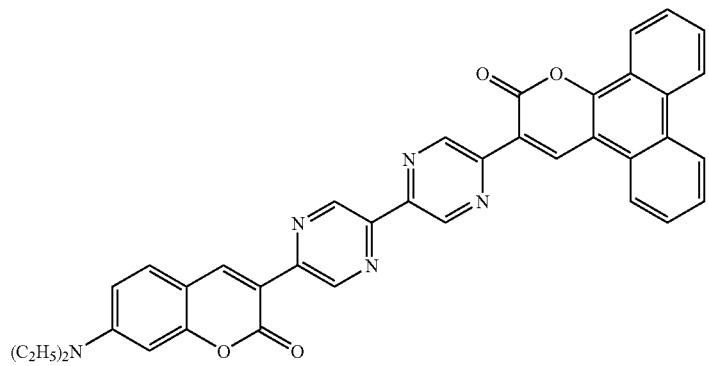
Chemical Formula 191:
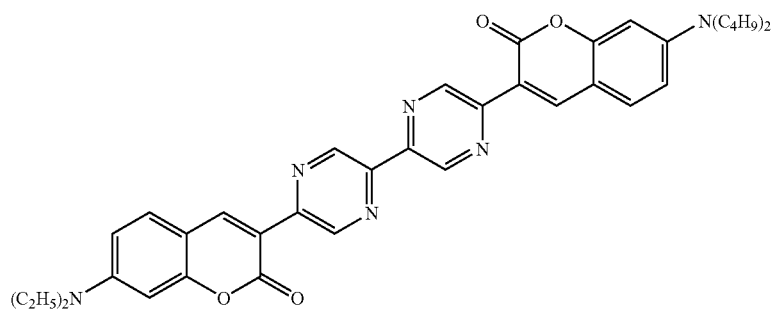

Chemical Formula 192:
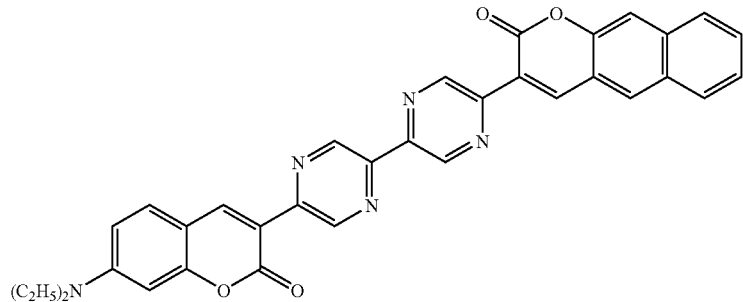
Chemical Formula 193:
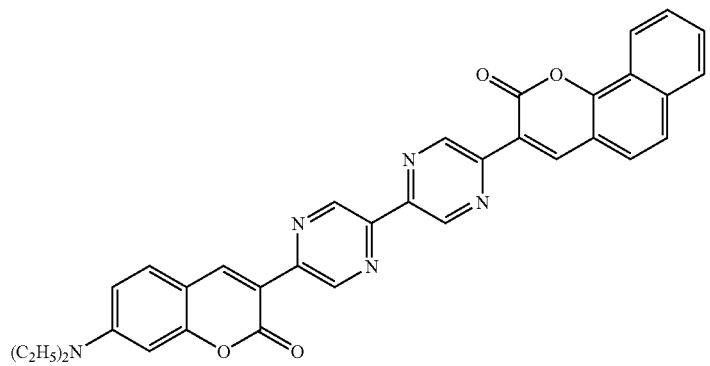
Chemical Formula 194:
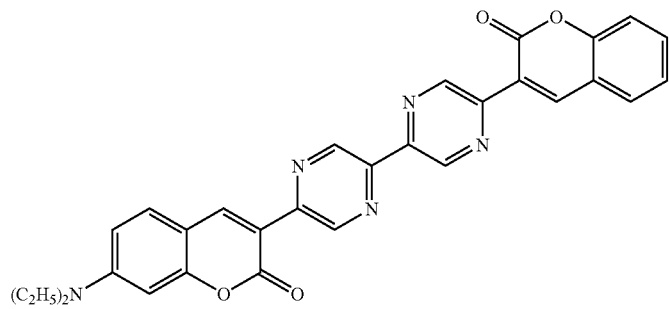
Chemical Formula 195:
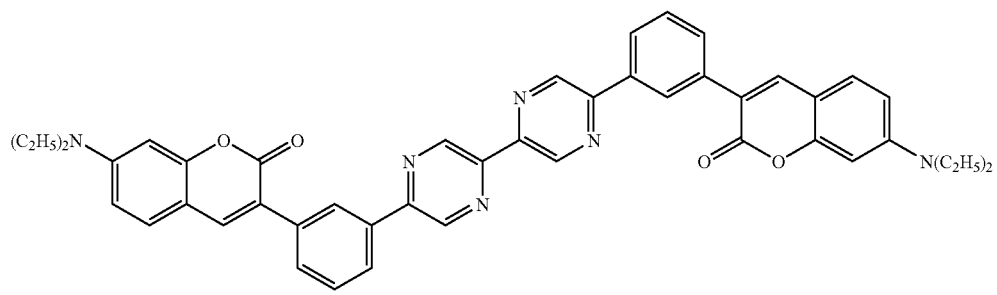

Chemical Formula 196:
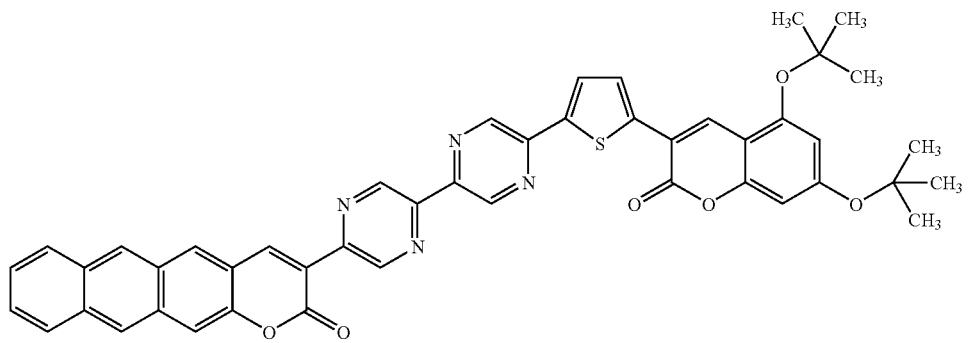
Chemical Formula 197:
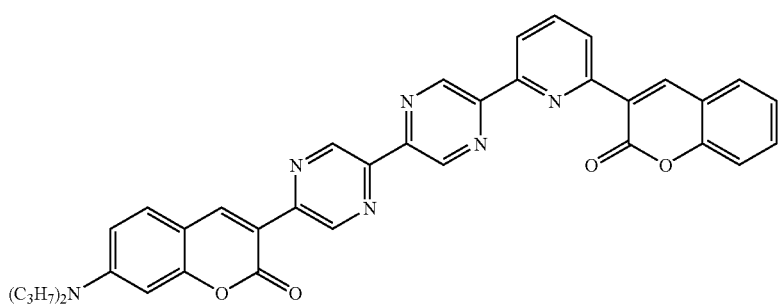
Chemical Formula 198:
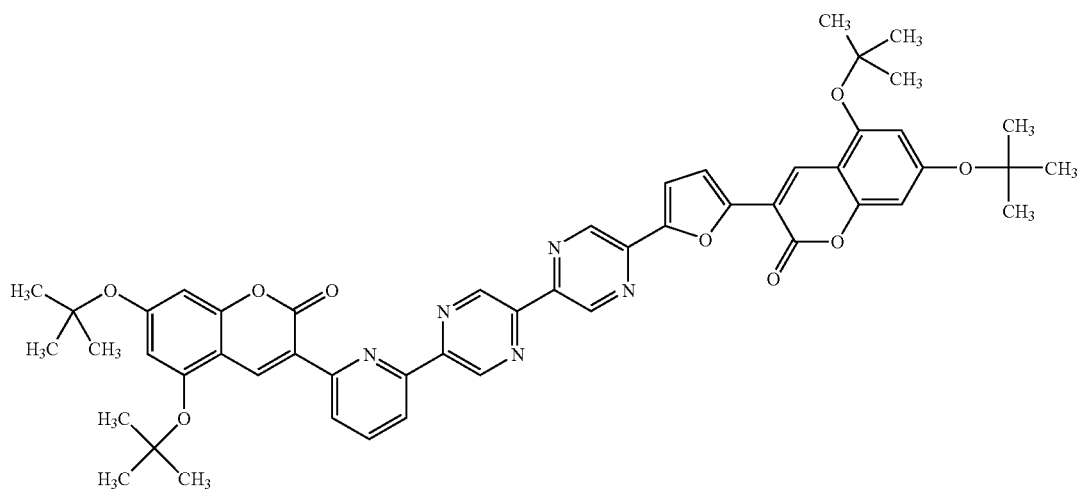
Chemical Formula 199:
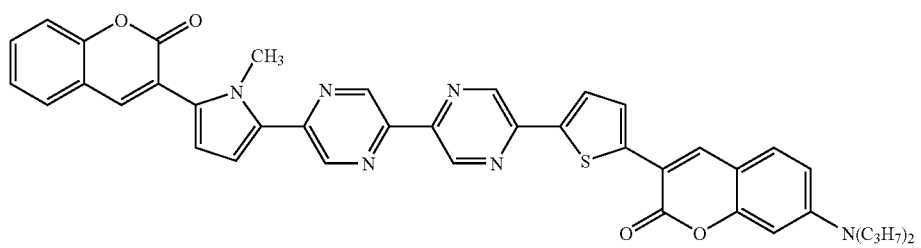

-continued
Chemical Formula 200:
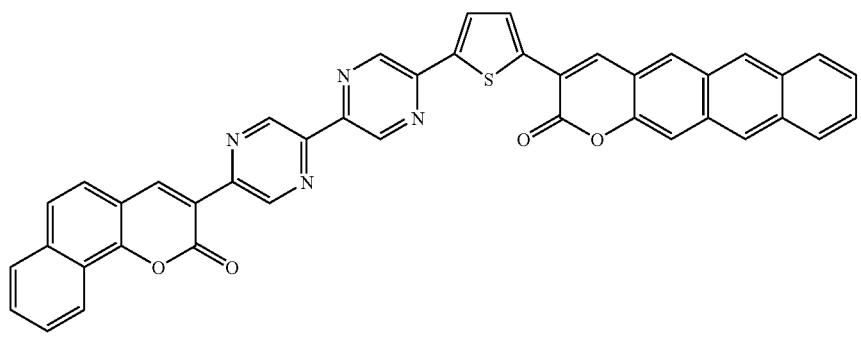
Chemical Formula 201:
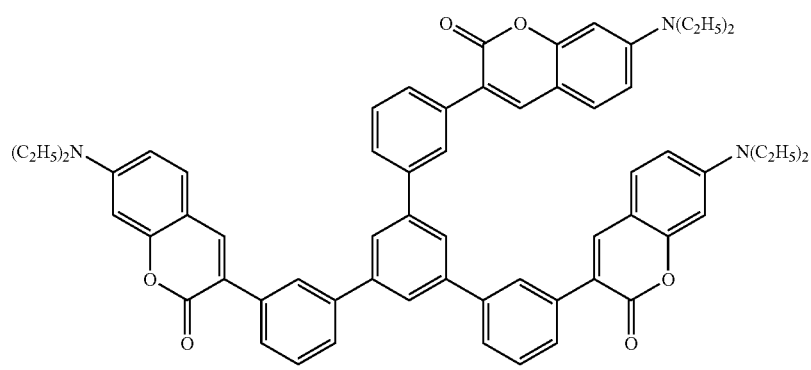
Chemical Formula 202:
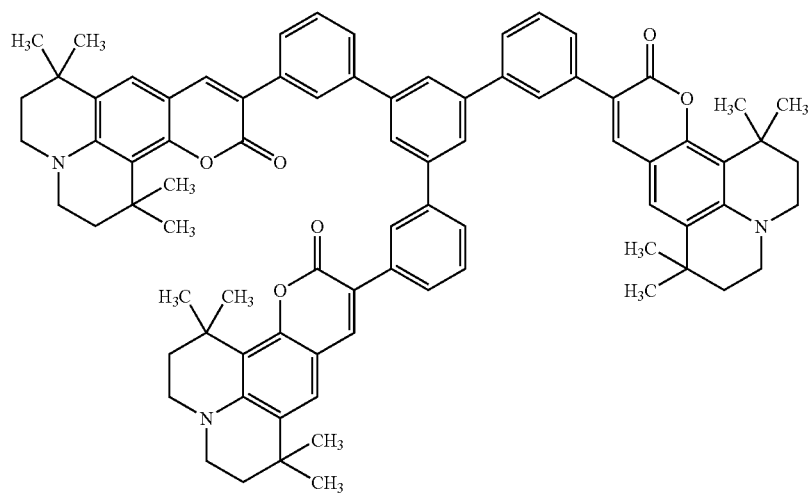

Chemical Formula 203:
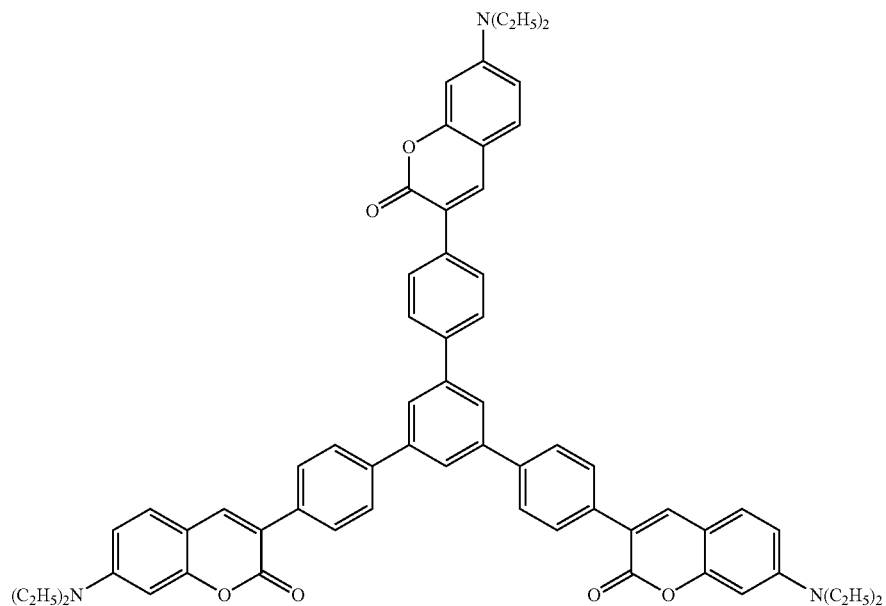
Chemical Formula 204:
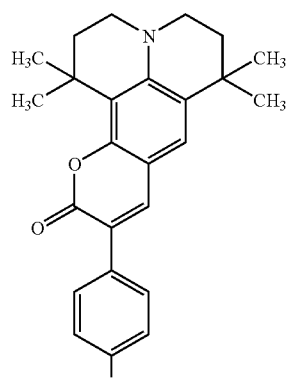
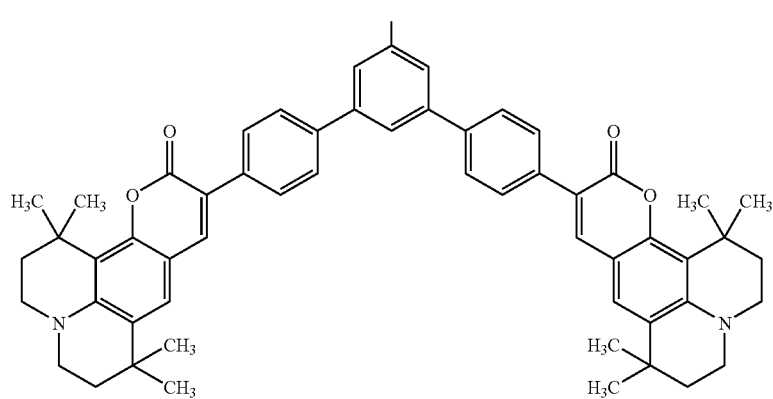

-continued
Chemical Formula 205:
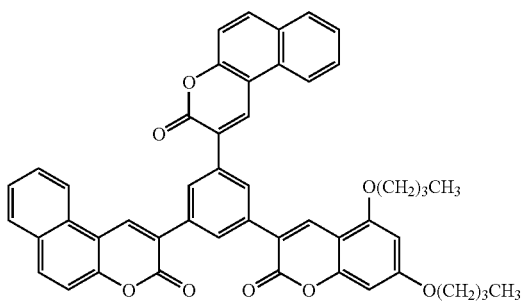
Chemical Formula 206:
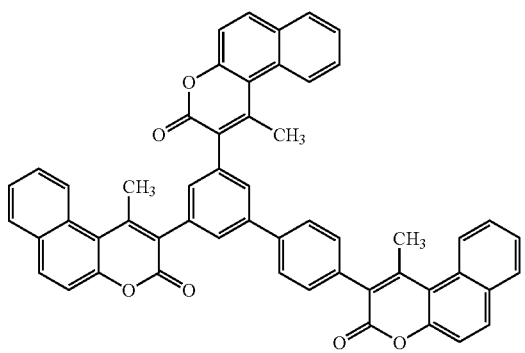
Chemical Formula 207:
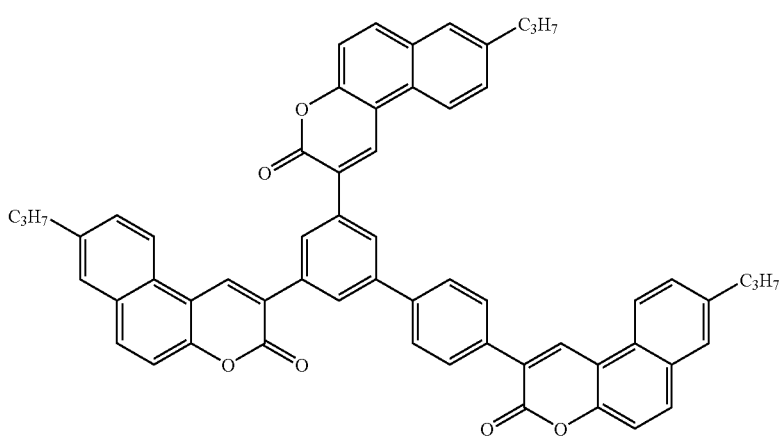
Chemical Formula 208:
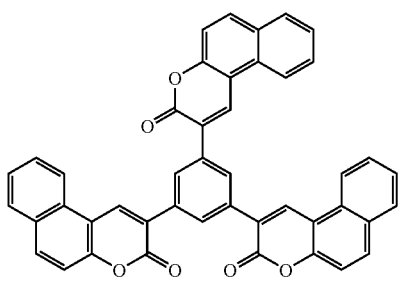
Chemical Formula 209:
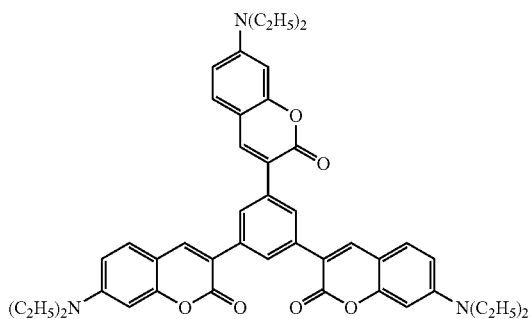
Chemical Formula 210:
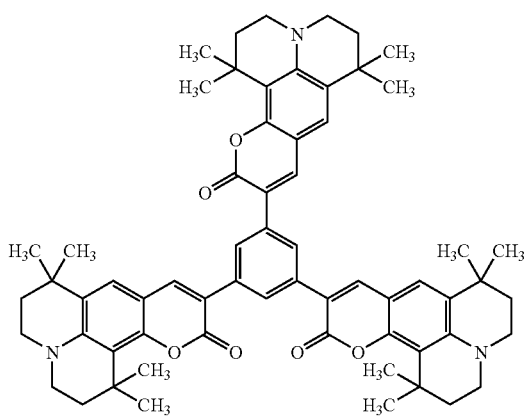
Chemical Formula 211:
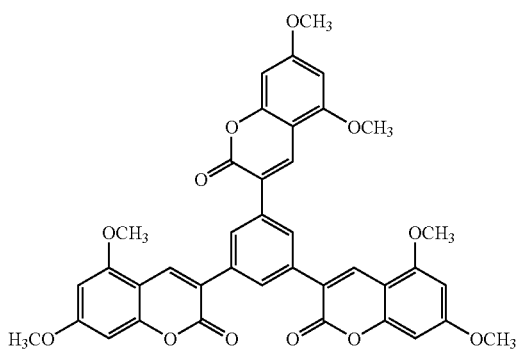

Chemical Formula 212:
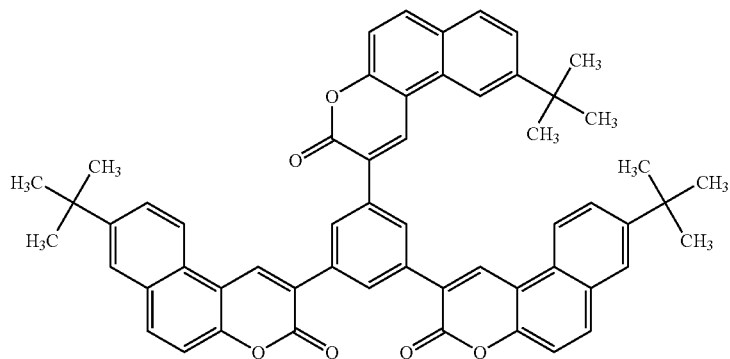
Chemical Formula 213:
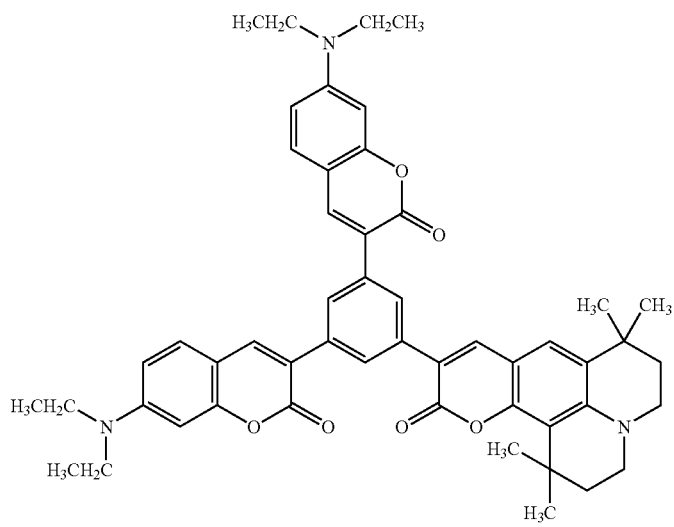
Chemical Formula 214:
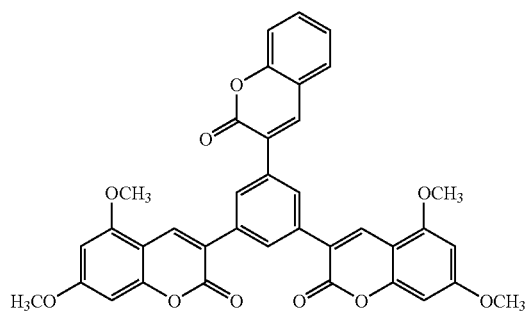
Chemical Formula 215:
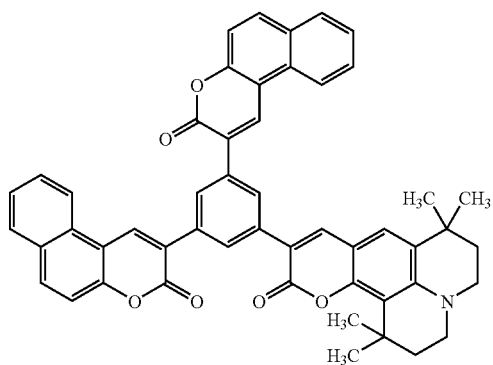

Chemical Formula 216:
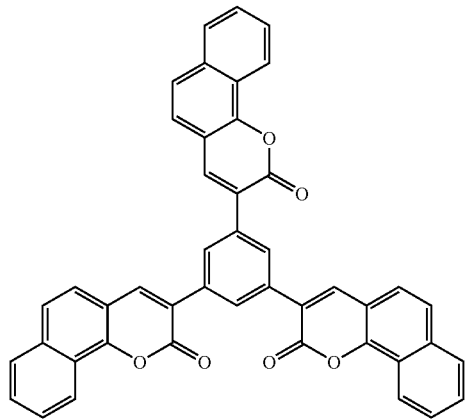
Chemical Formula 217:
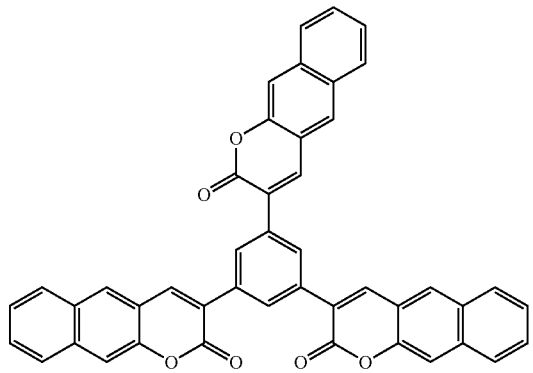
Chemical Formula 218:
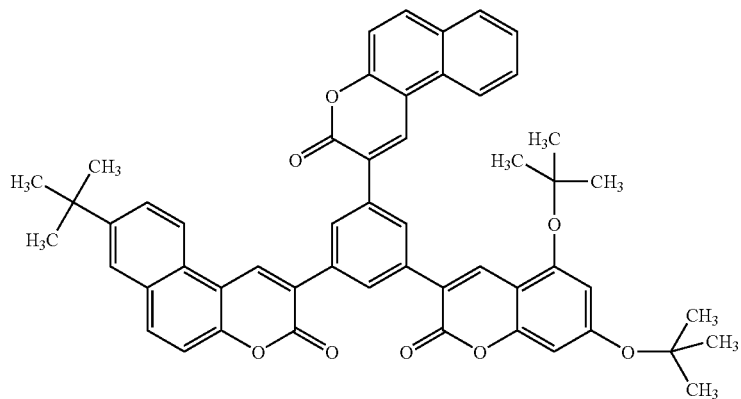
Chemical Formula 219:
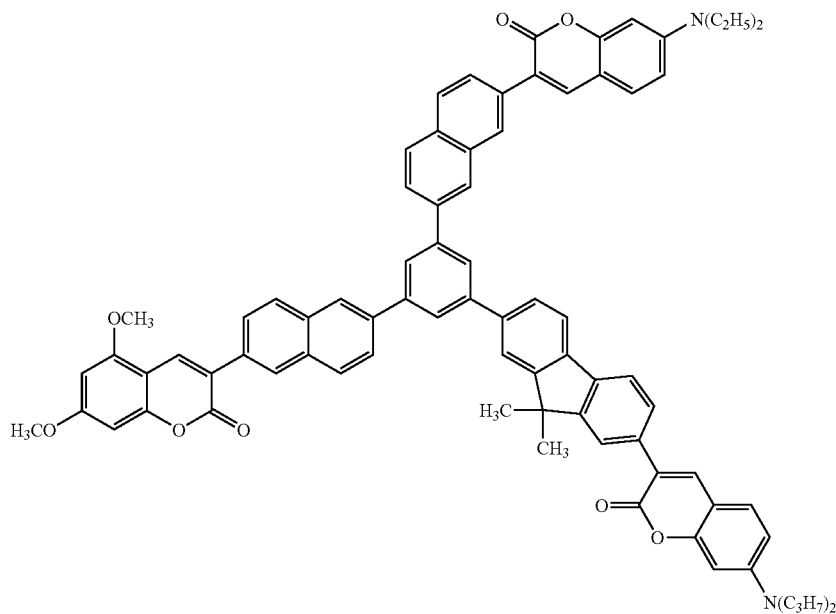

Chemical Formula 220:
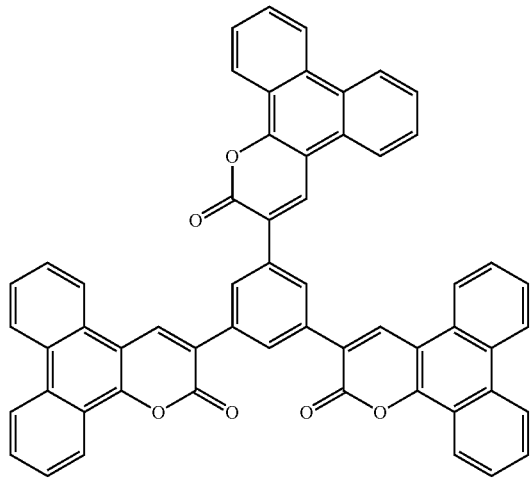
Chemical Formula 221:
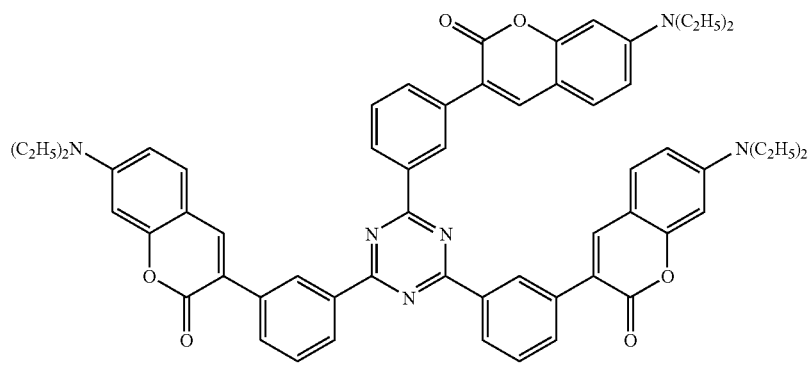
Chemical Formula 222:
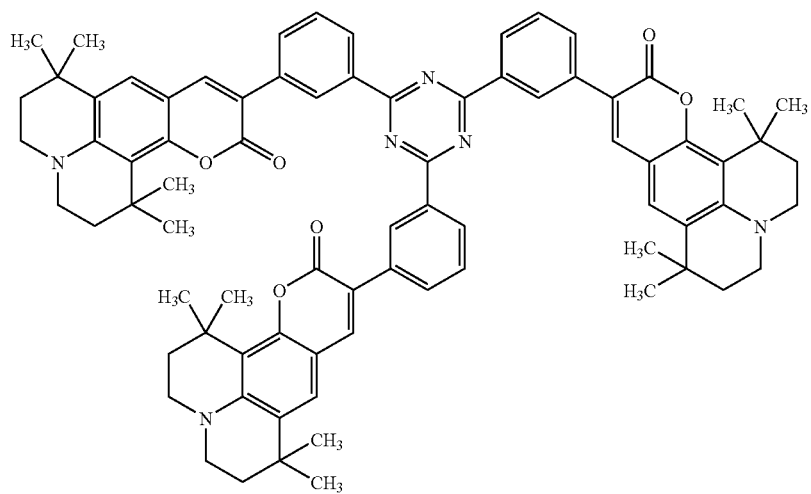

Chemical Formula 223:
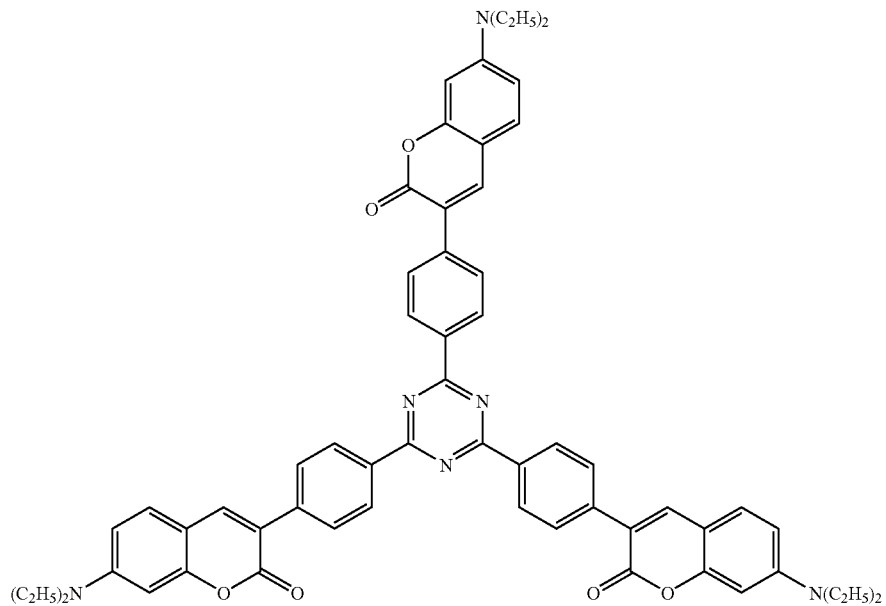
Chemical Formula 224:
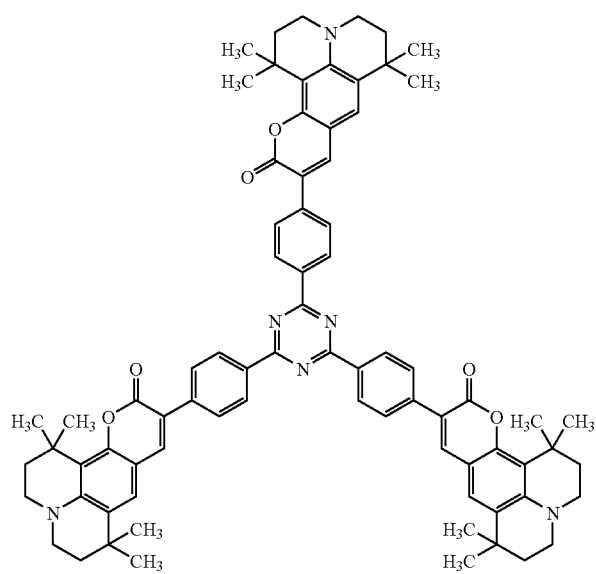

-continued
Chemical Formula 225:
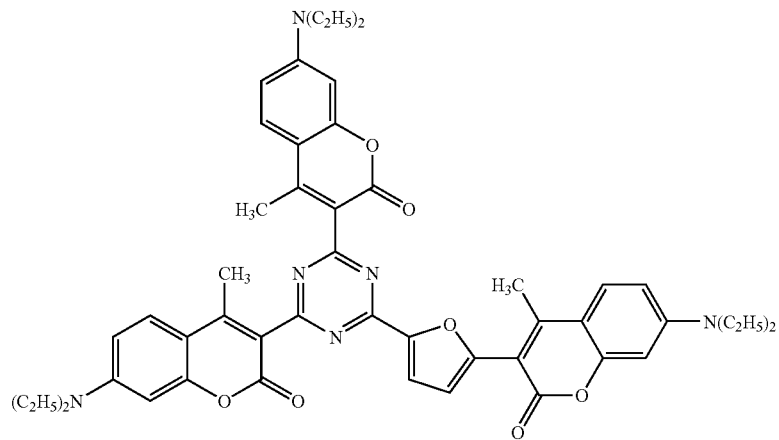
Chemical Formula 226:
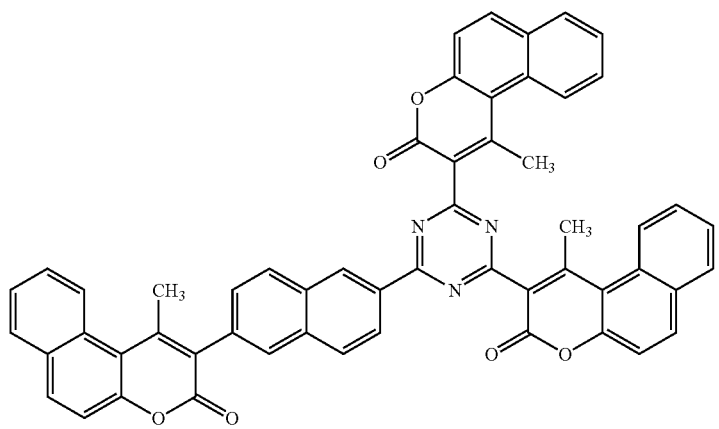
Chemical Formula 227:
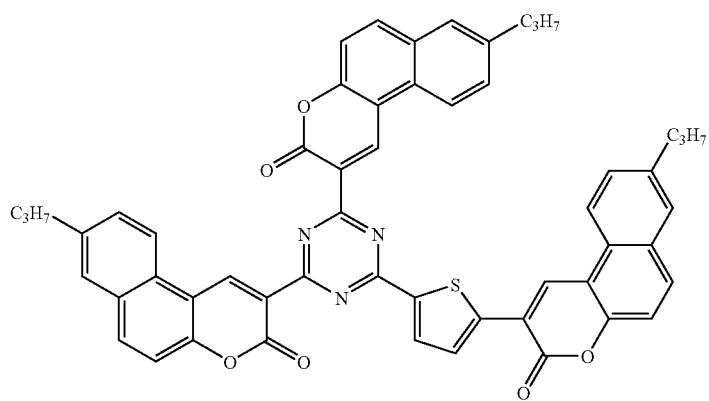

Chemical Formula 228:
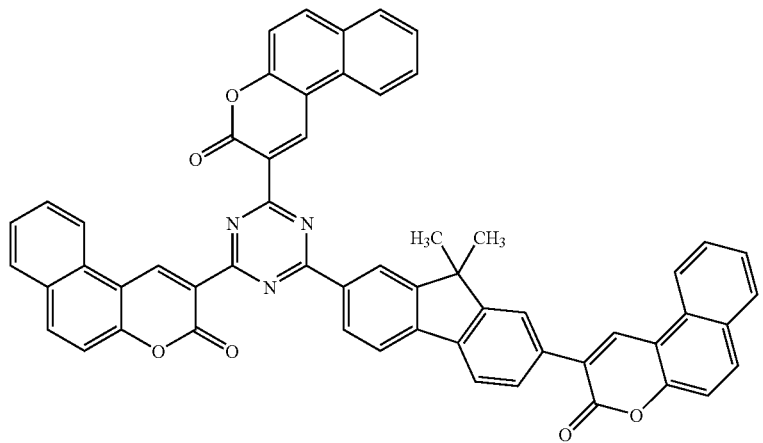
Chemical Formula 229:
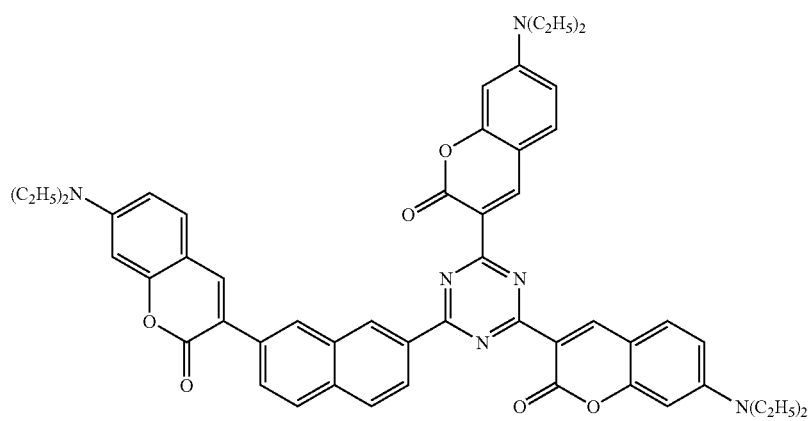
Chemical Formula 230:
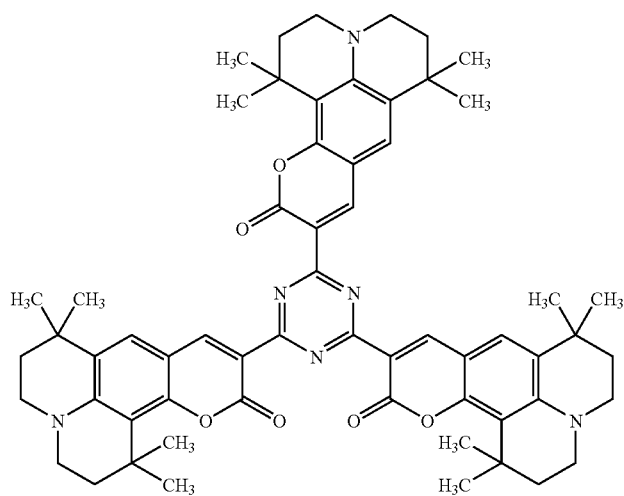

-continued
Chemical Formula 231:
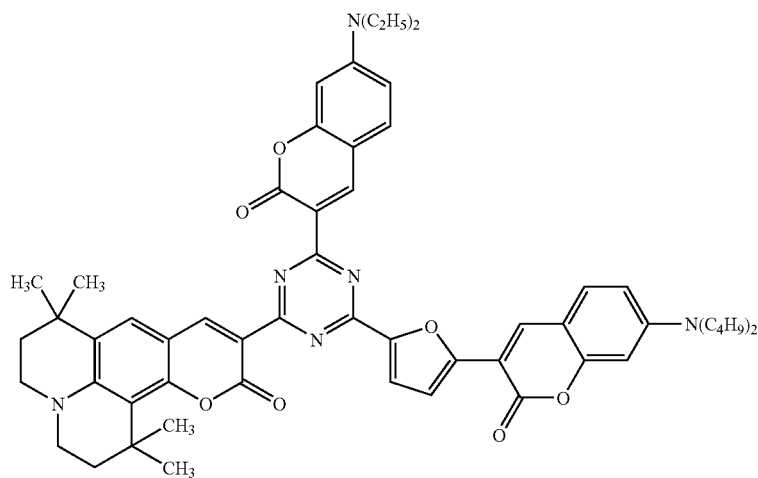
Chemical Formula 232:
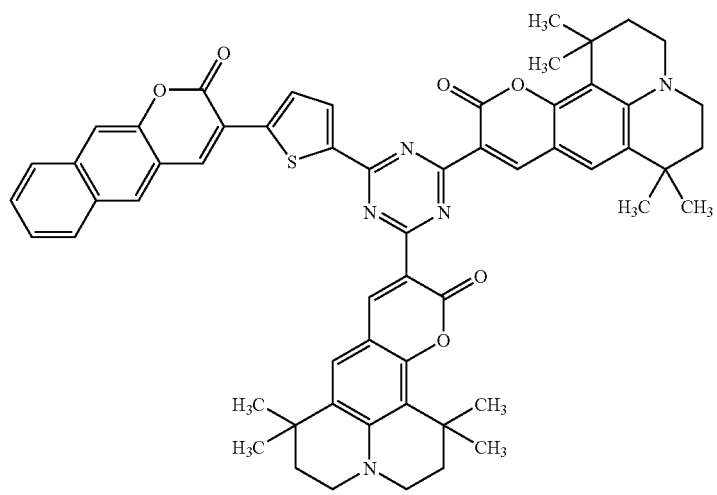
Chemical Formula 233:
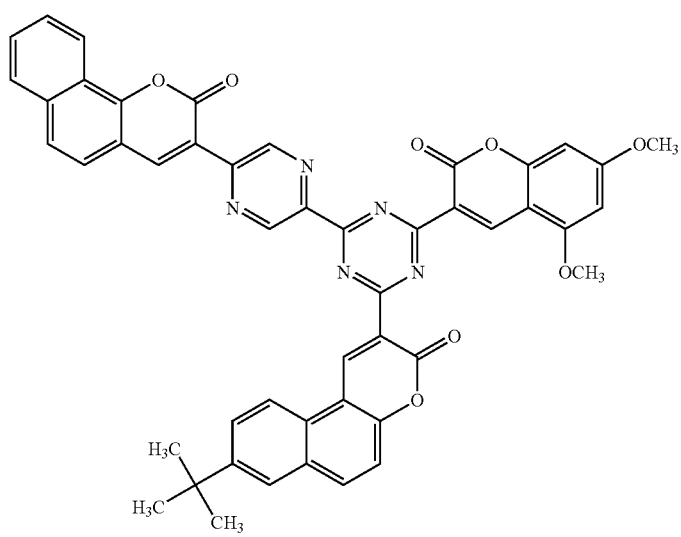

Chemical Formula 234:
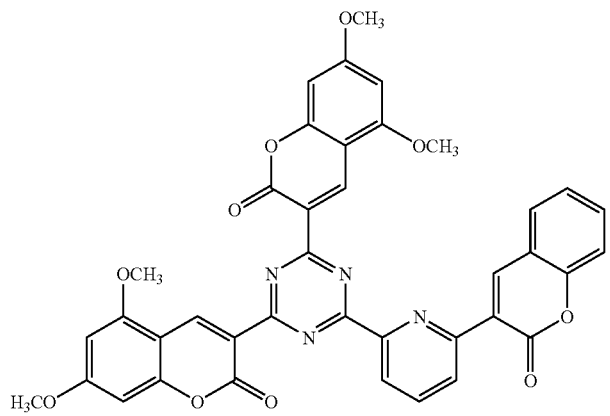
Chemical Formula 235:
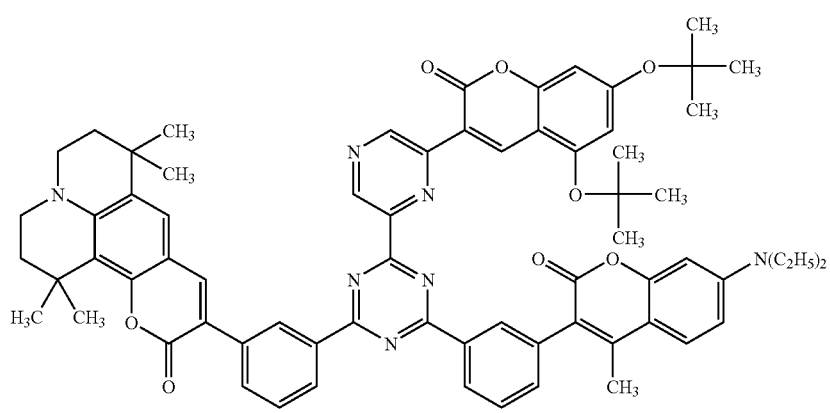
Chemical Formula 236:
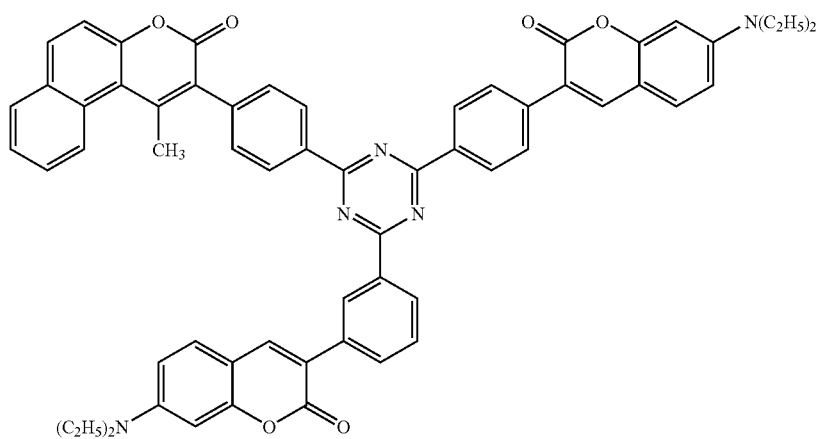

-continued
Chemical Formula 237:
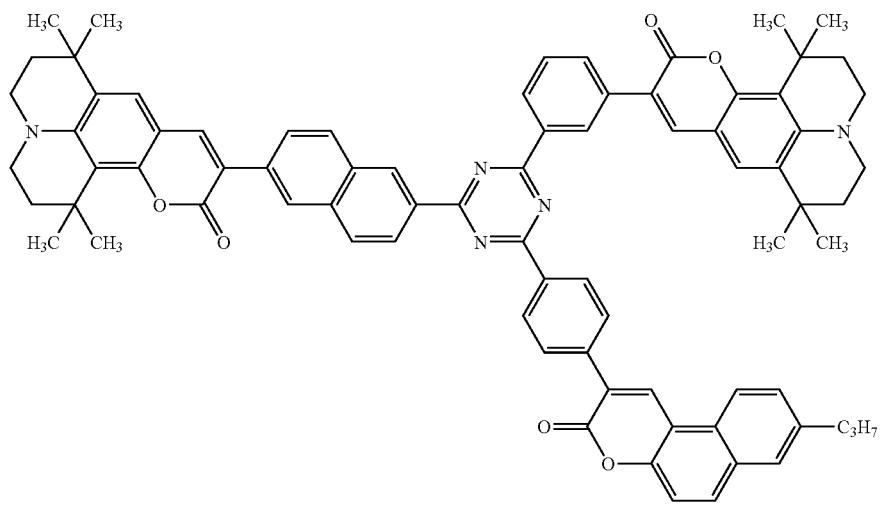
Chemical Formula 238:
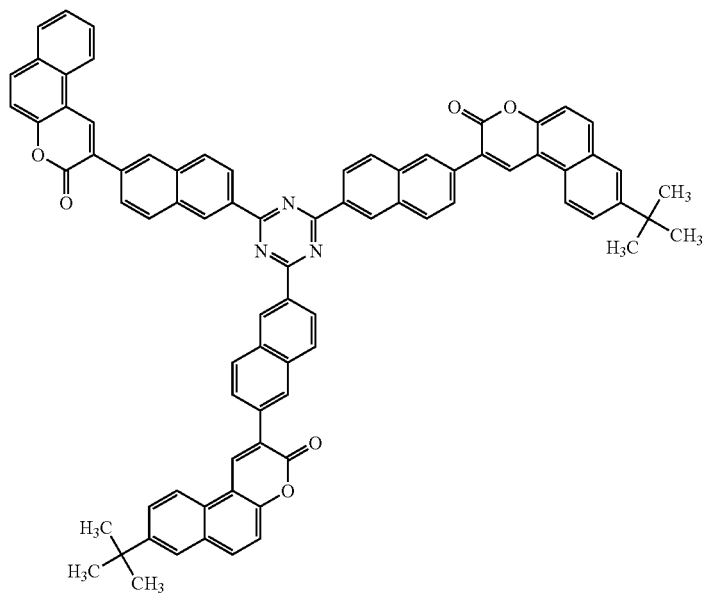
Chemical Formula 239:
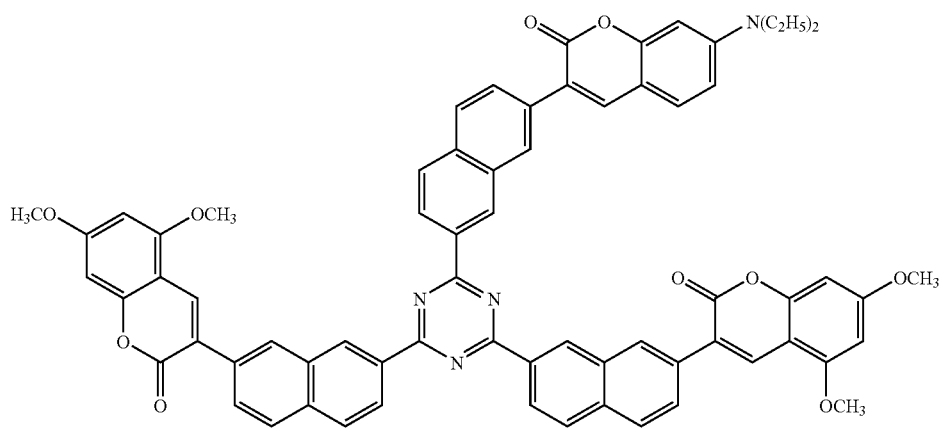

Chemical Formula 240:
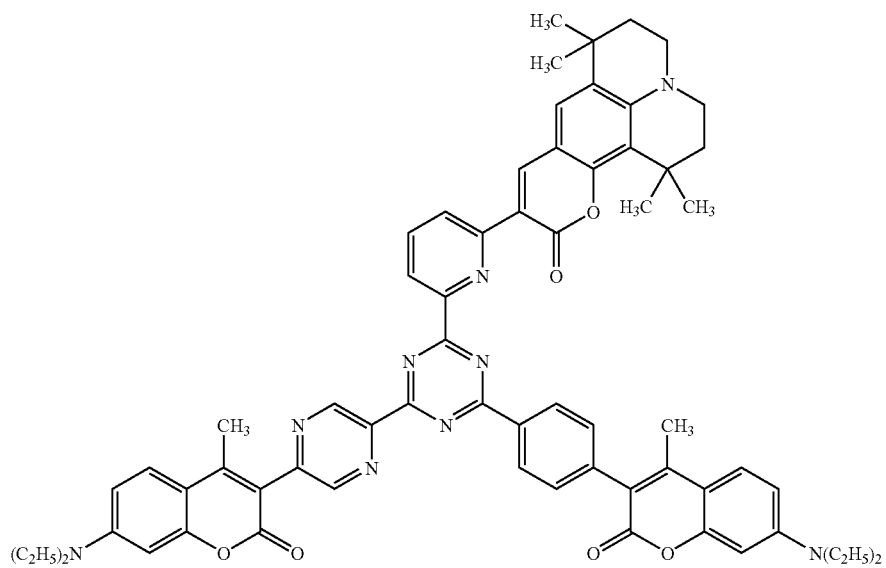
Chemical Formula 241:
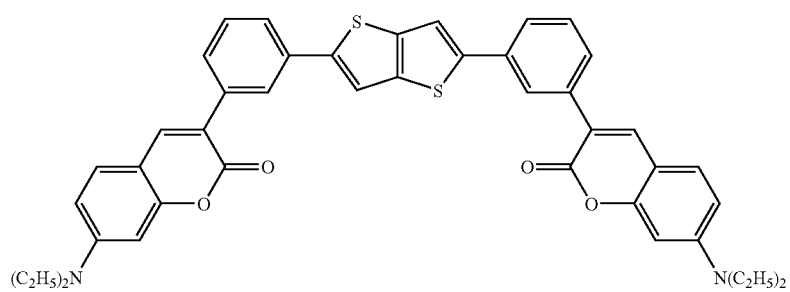
Chemical Formula 242:
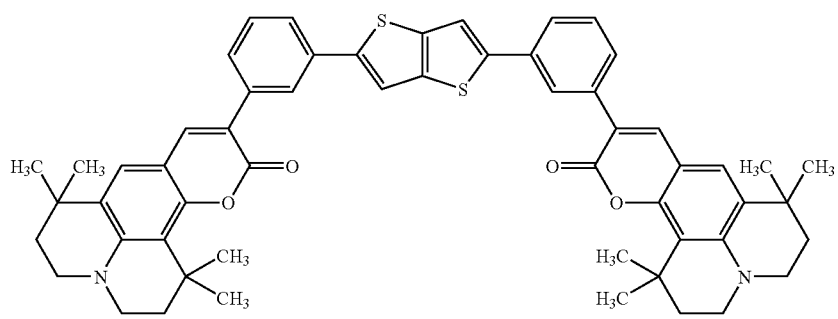
Chemical Formula 243:
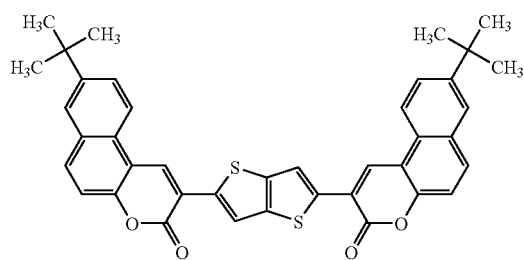
Chemical Formula 244:
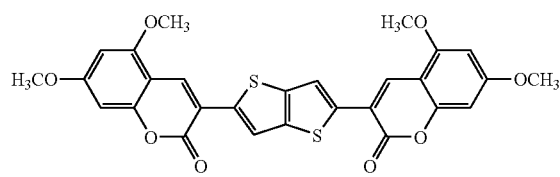

Chemical Formula 245:
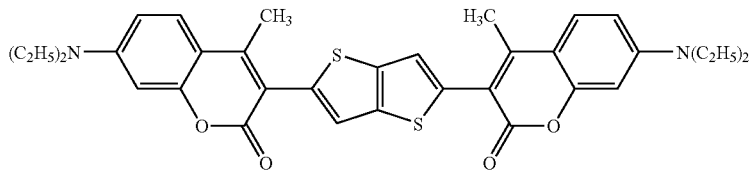
Chemical Formula 246:
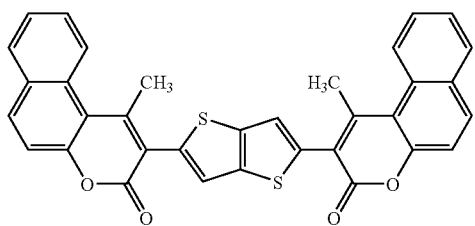
Chemical Formula 247:
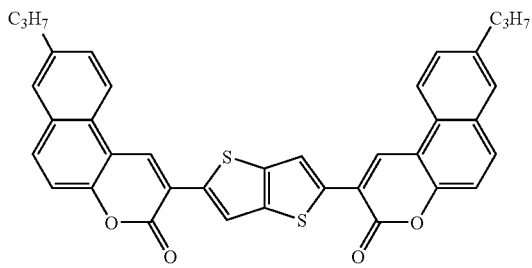
Chemical Formula 248:
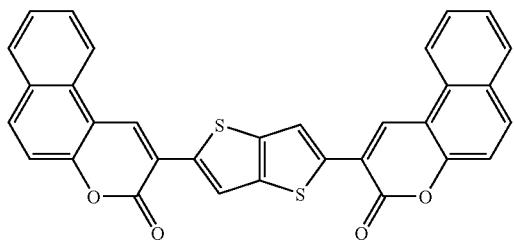
Chemical Formula 249:
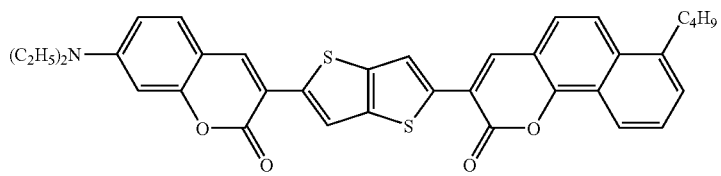
Chemical Formula 250:
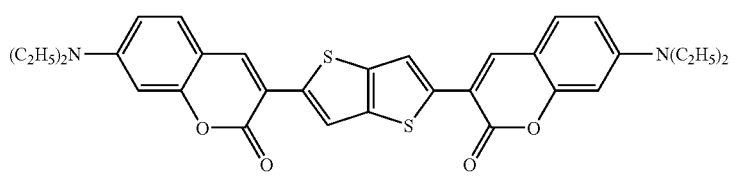
Chemical Formula 251:
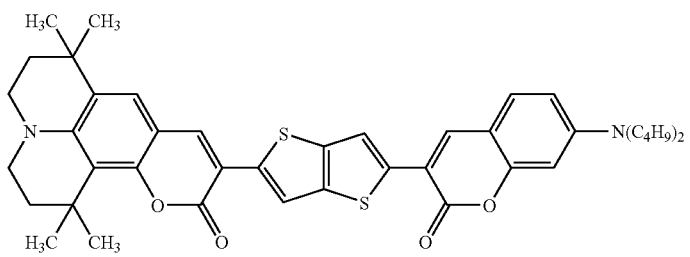
Chemical Formula 252:
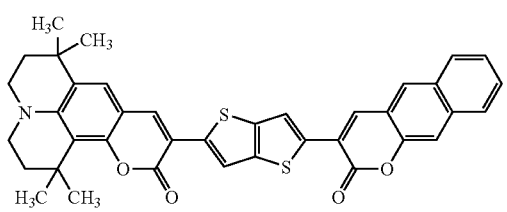
Chemical Formula 253:
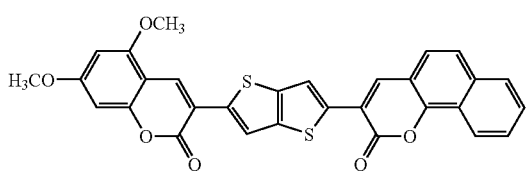

Chemical Formula 254:
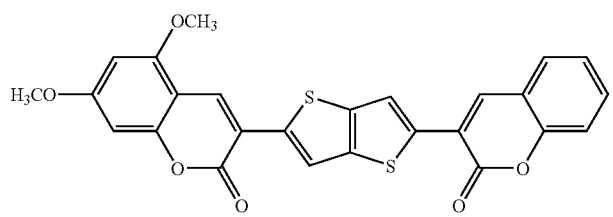
Chemical Formula 255:
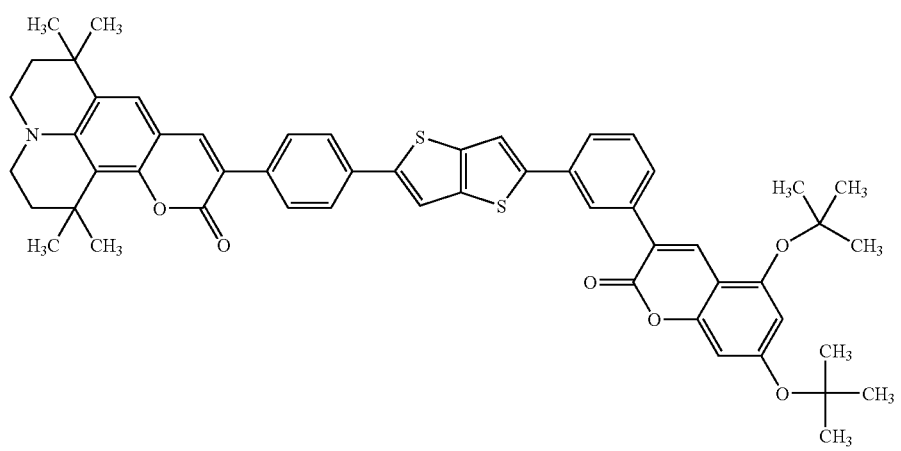
Chemical Formula 256:
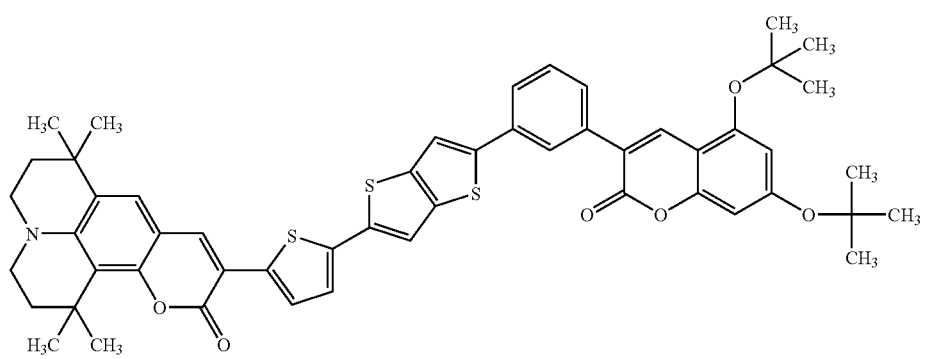
Chemical Formula 257:
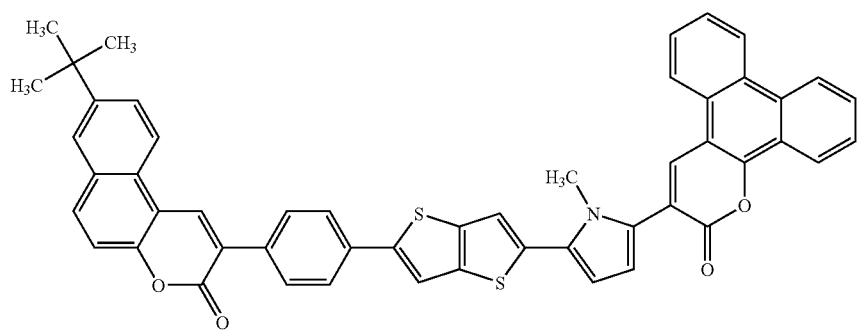

-continued
Chemical Formula 258:
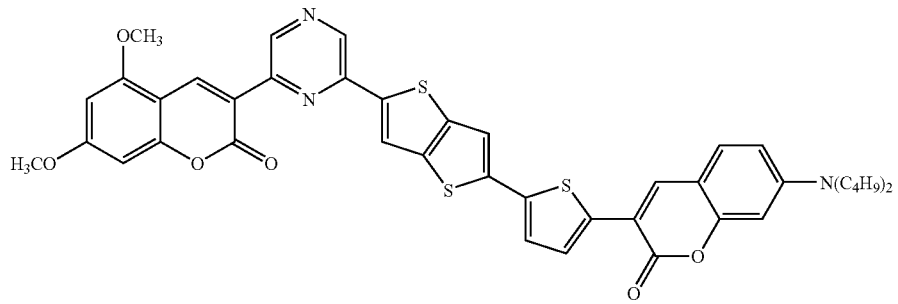
Chemical Formula 259:
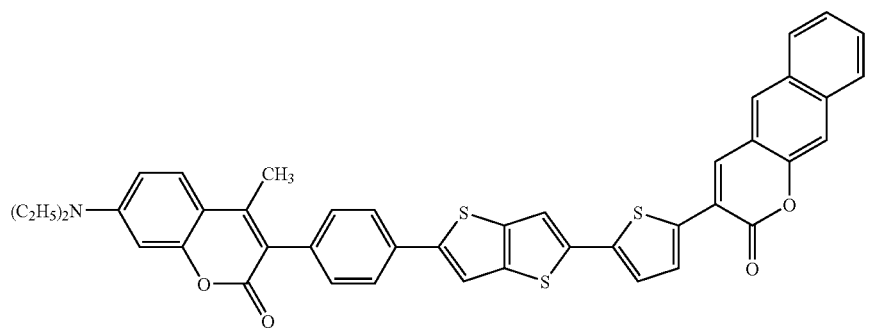
Chemical Formula 260:
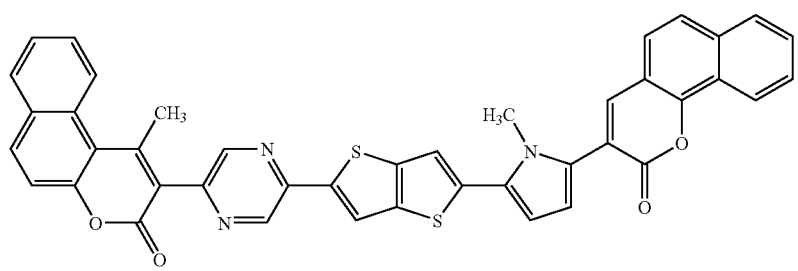
Chemical Formula 261:
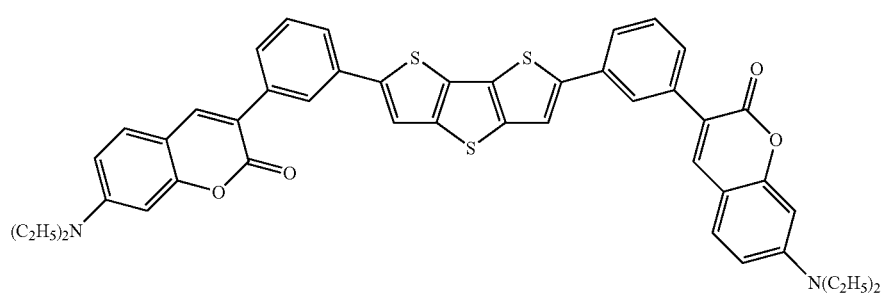
Chemical Formula 262:
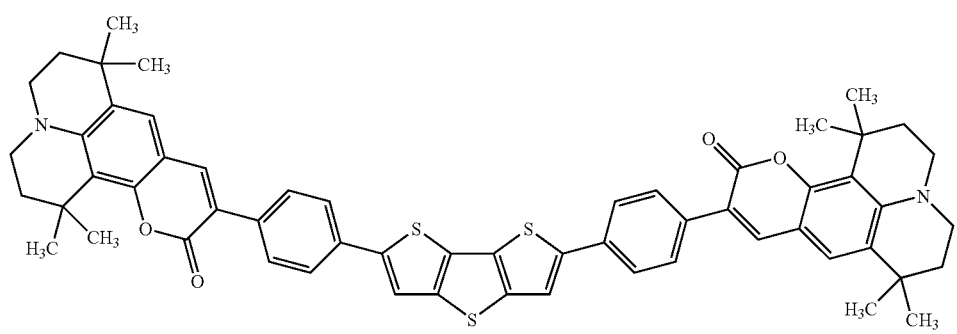

Chemical Formula 263:
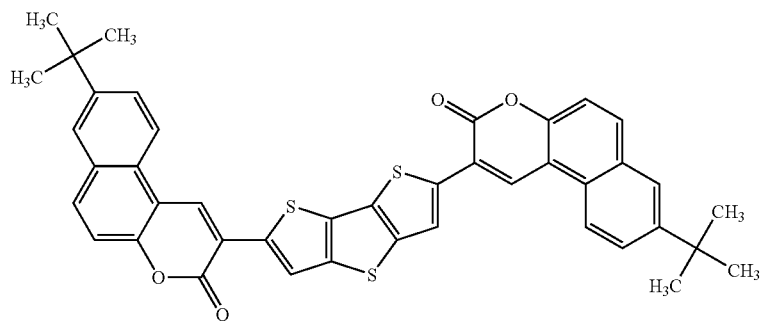
Chemical Formula 264:
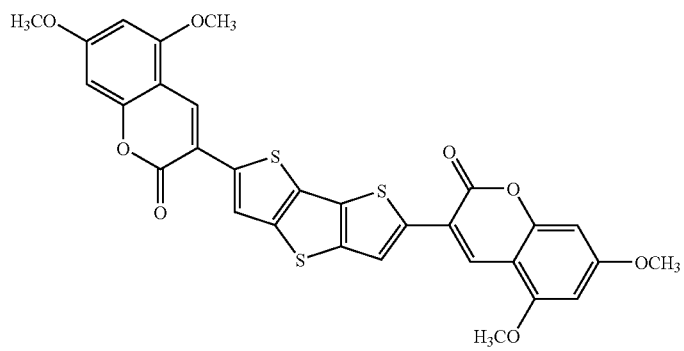
Chemical Formula 265:
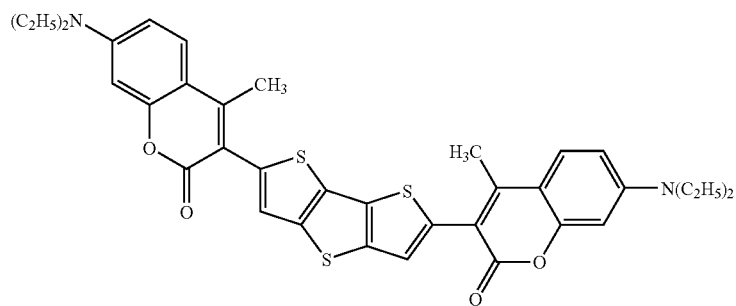
Chemical Formula 266:
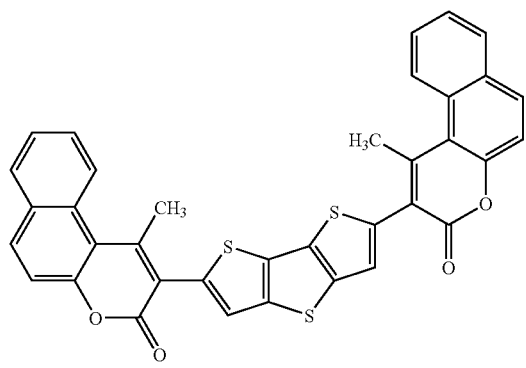
Chemical Formula 267:
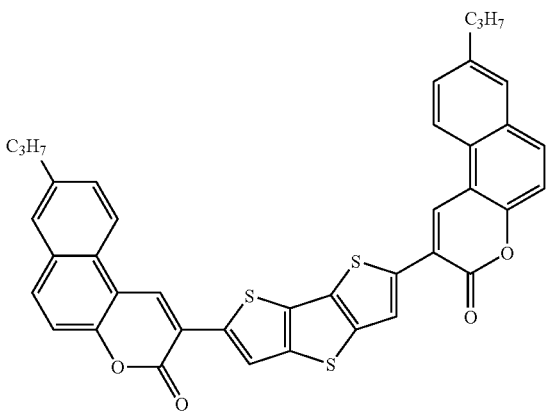

Chemical Formula 268:
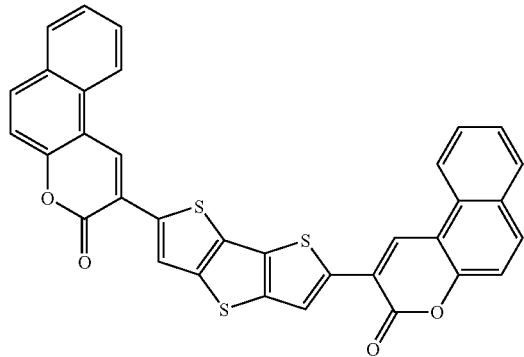
Chemical Formula 269:
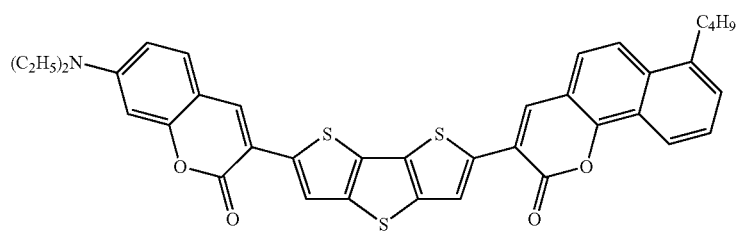
Chemical Formula 270:
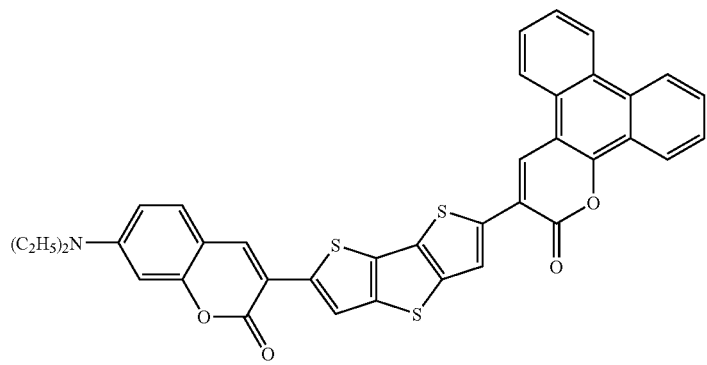
Chemical Formula 271:
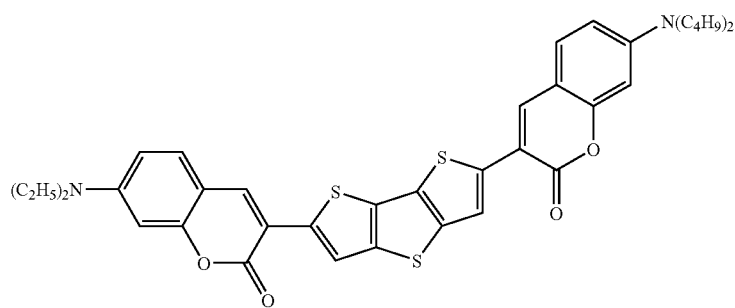

Chemical Formula 272:
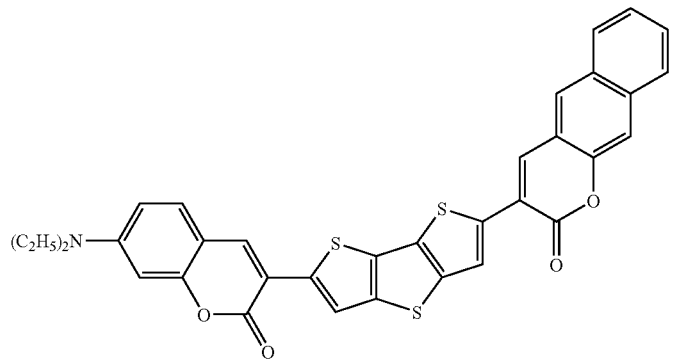
Chemical Formula 273:
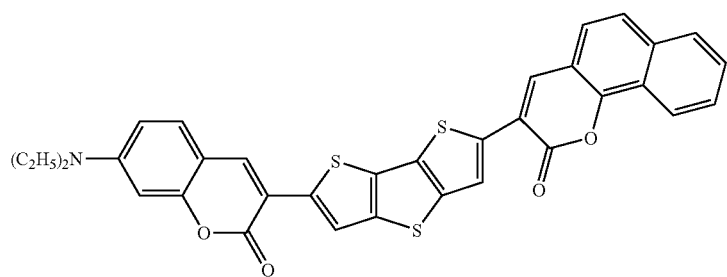
Chemical Formula 274:
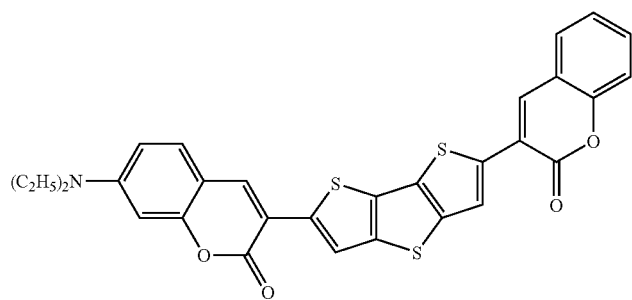
Chemical Formula 275:
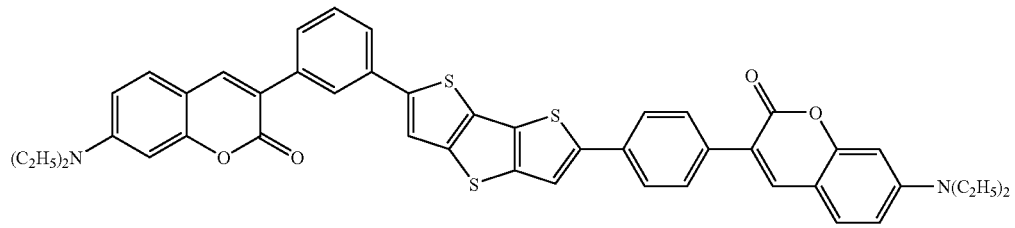

Chemical Formula 276:
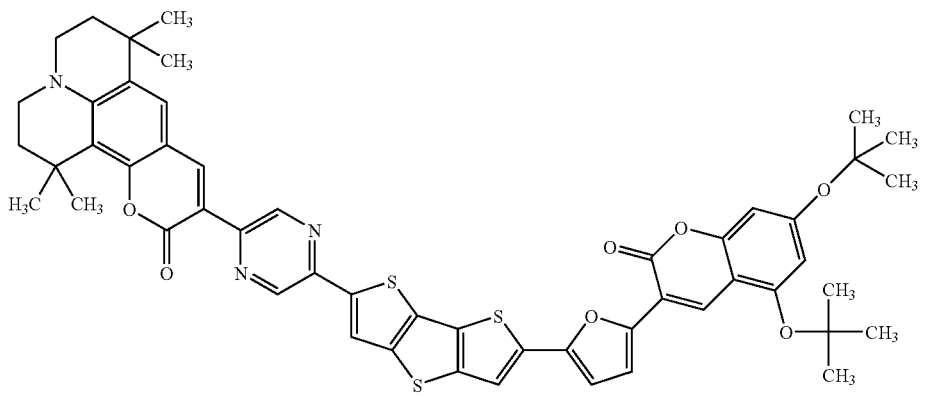
Chemical Formula 277:
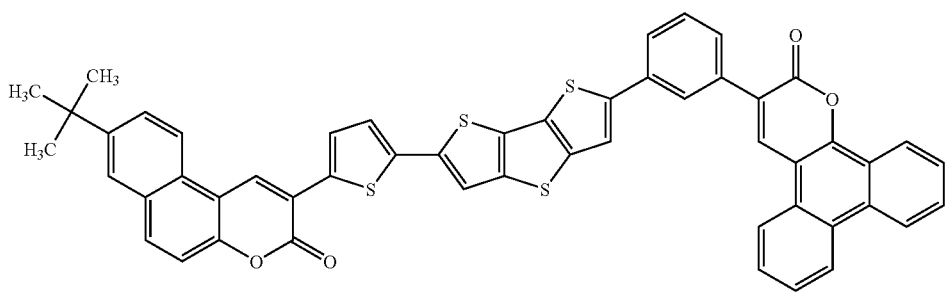
Chemical Formula 278:
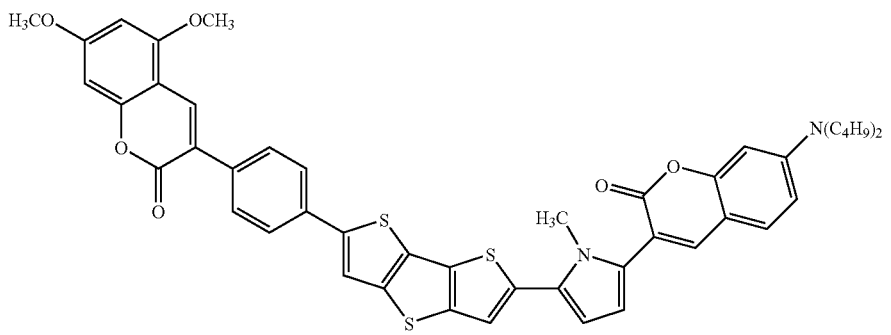
Chemical Formula 279:
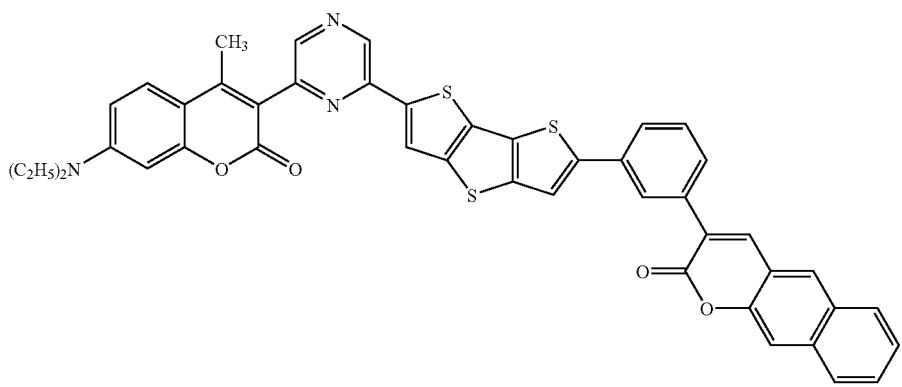

-continued
Chemical Formula 280:
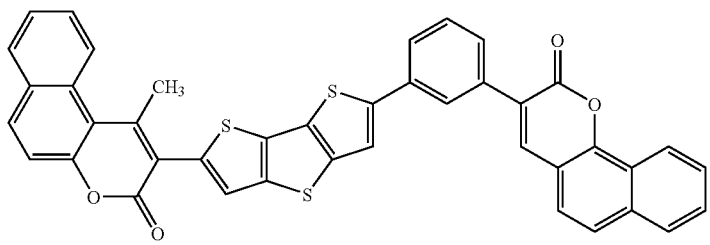
Chemical Formula 281:
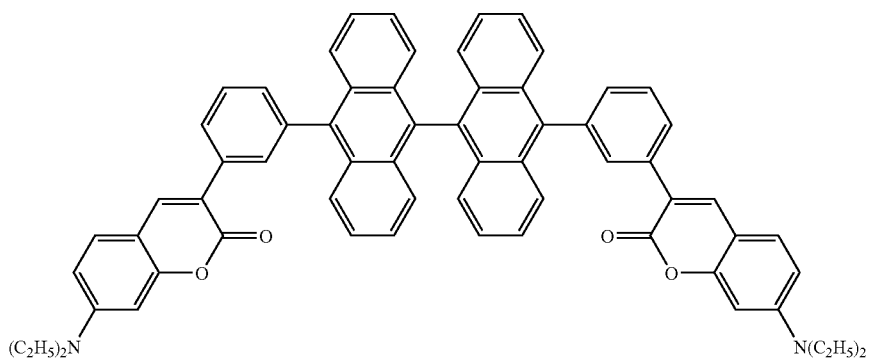
Chemical Formula 282:
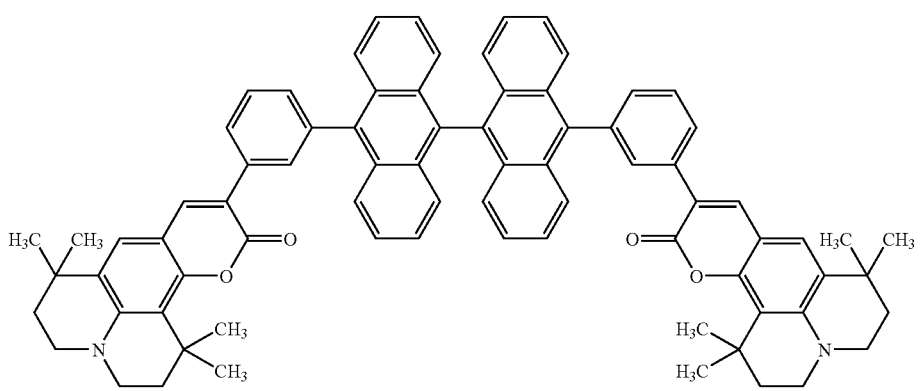
Chemical Formula 283:
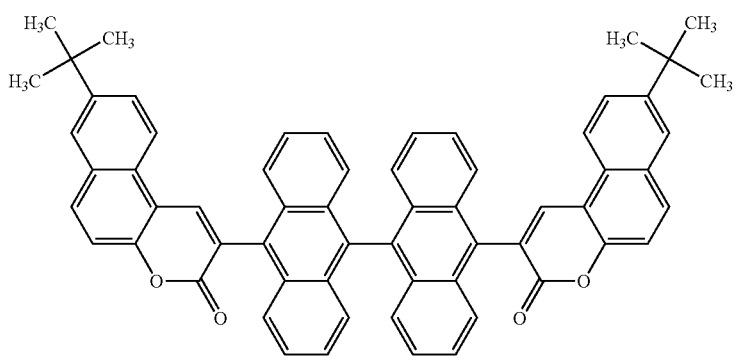

Chemical Formula 284:
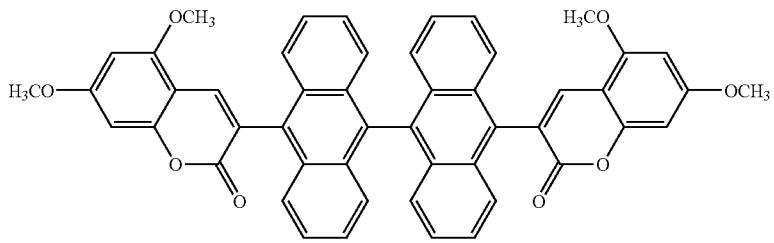
Chemical Formula 285:
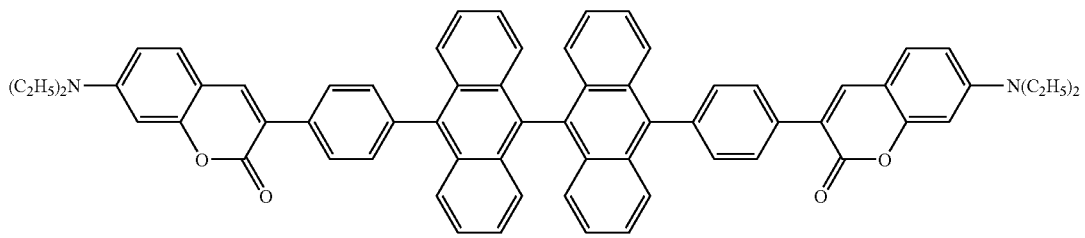
Chemical Formula 286:
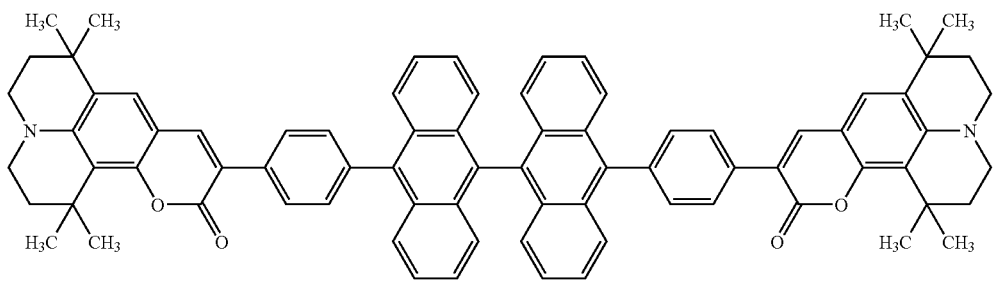
Chemical Formula 287:
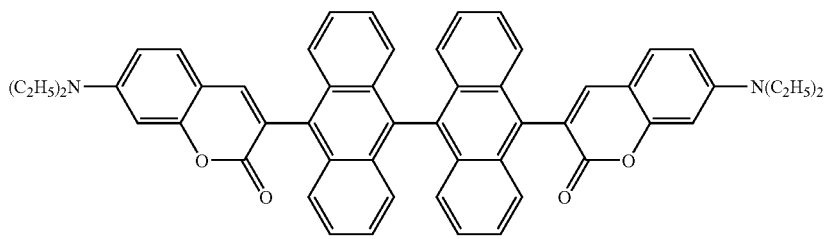
Chemical Formula 288:
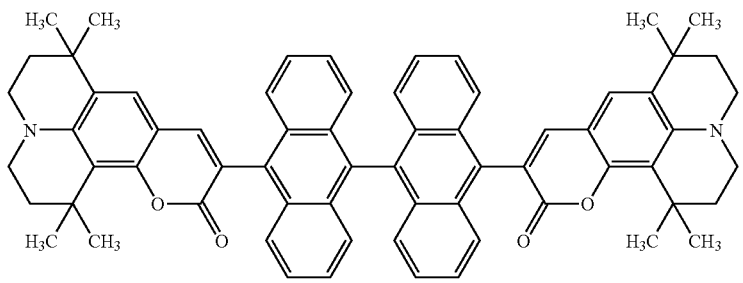
Chemical Formula 289:
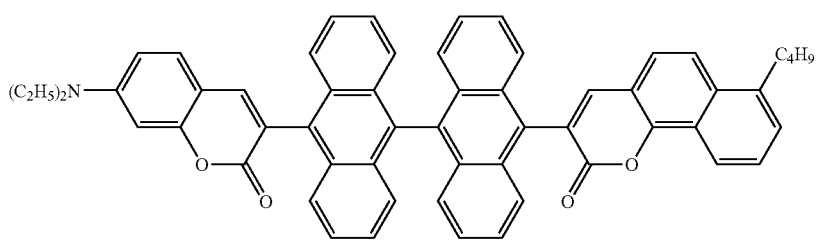

Chemical Formula 290:
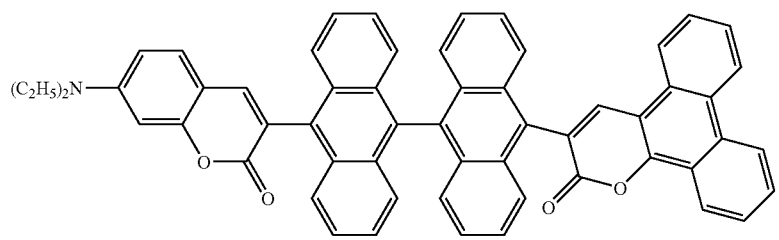
Chemical Formula 291:
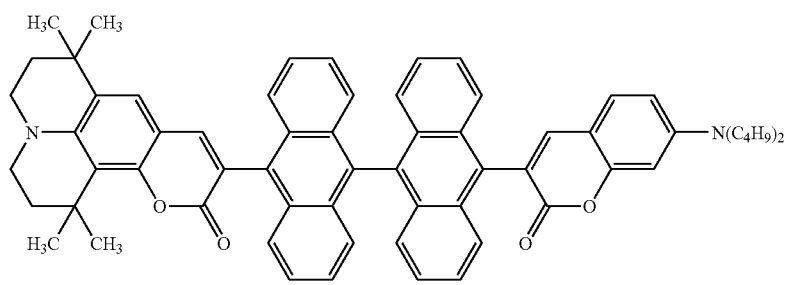
Chemical Formula 292:
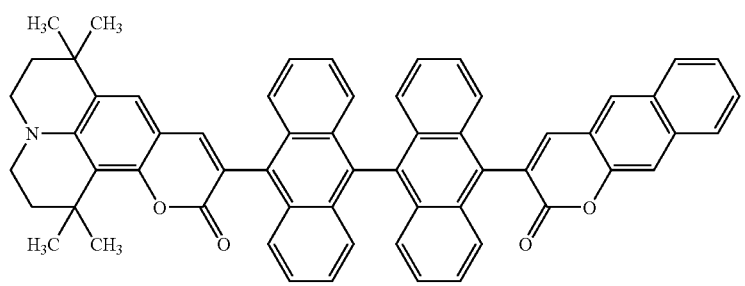
Chemical Formula 293:
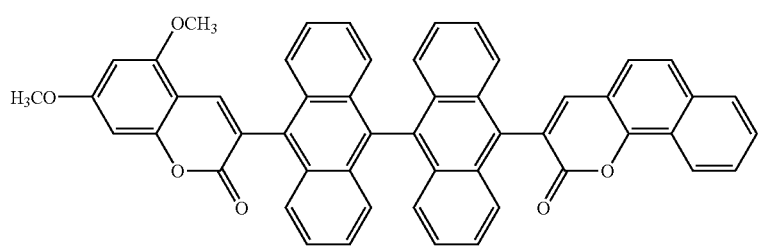
Chemical Formula 294:
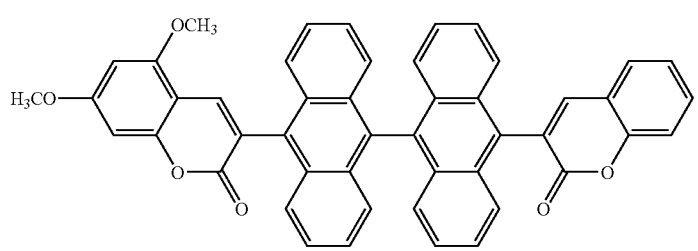

Chemical Formula 295:
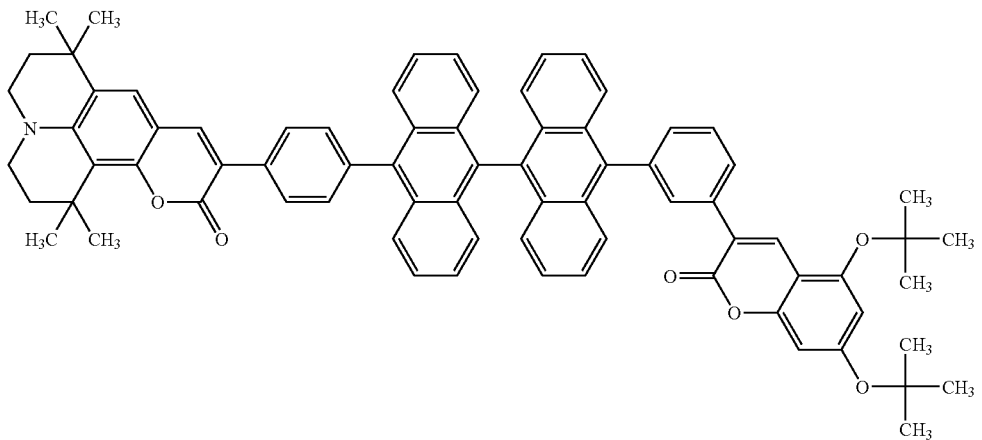
Chemical Formula 296:
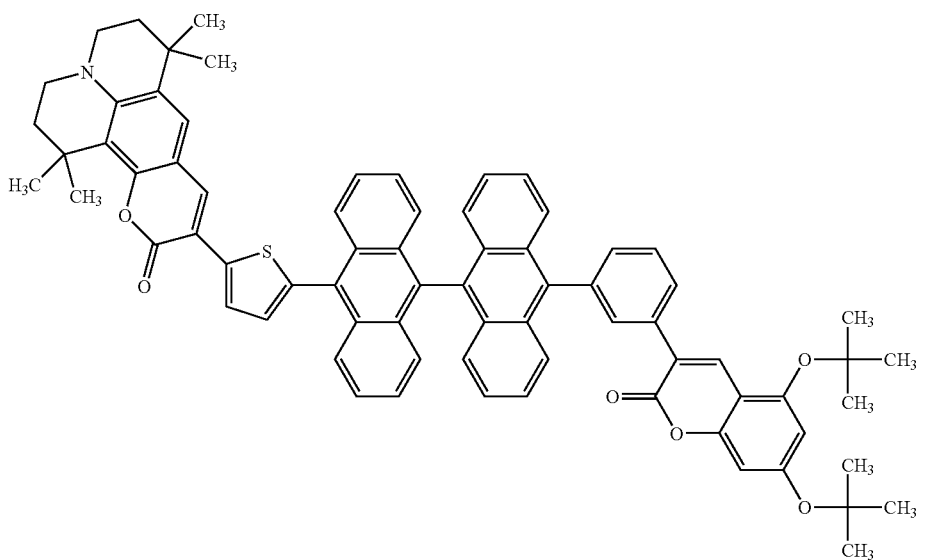
Chemical Formula 297:
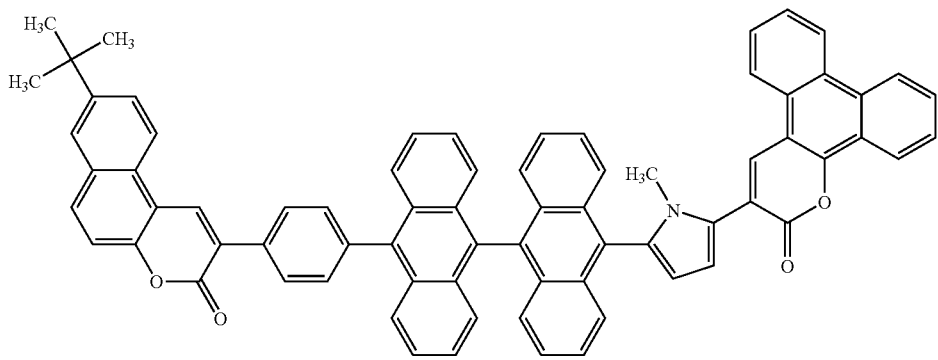

Chemical Formula 298:
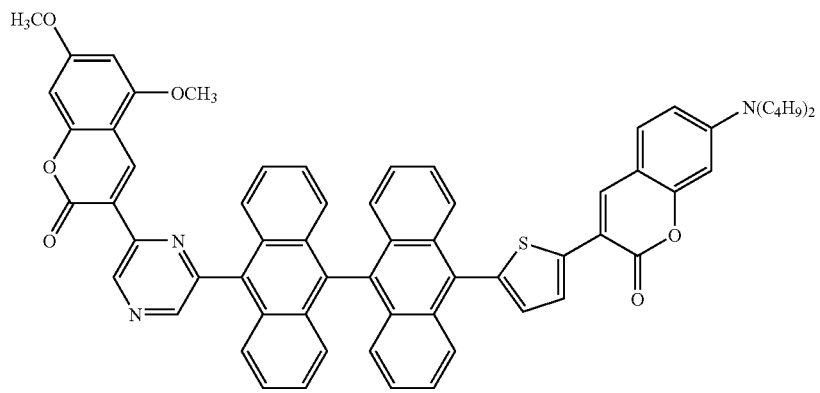
Chemical Formula 299:
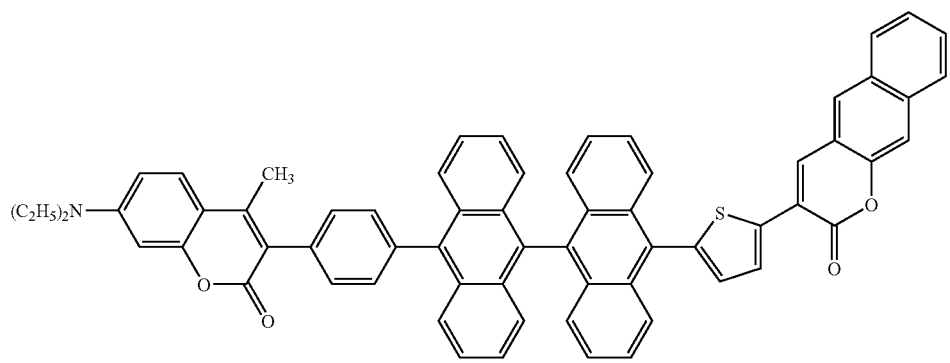
Chemical Formula 300:
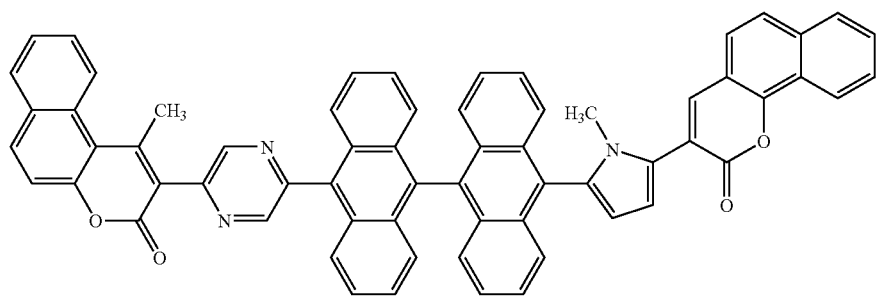
Chemical Formula 301:
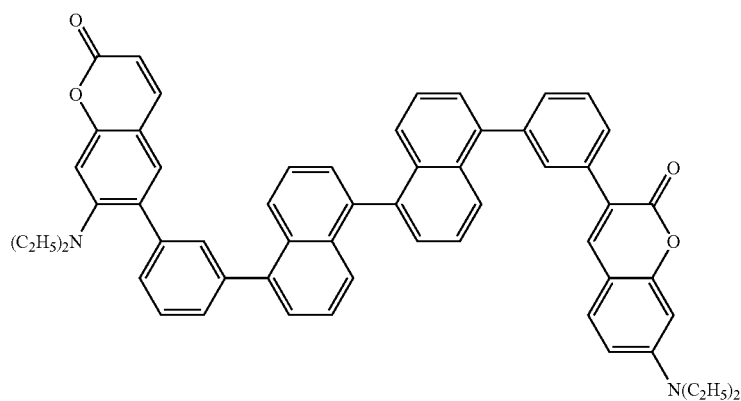

Chemical Formula 302:
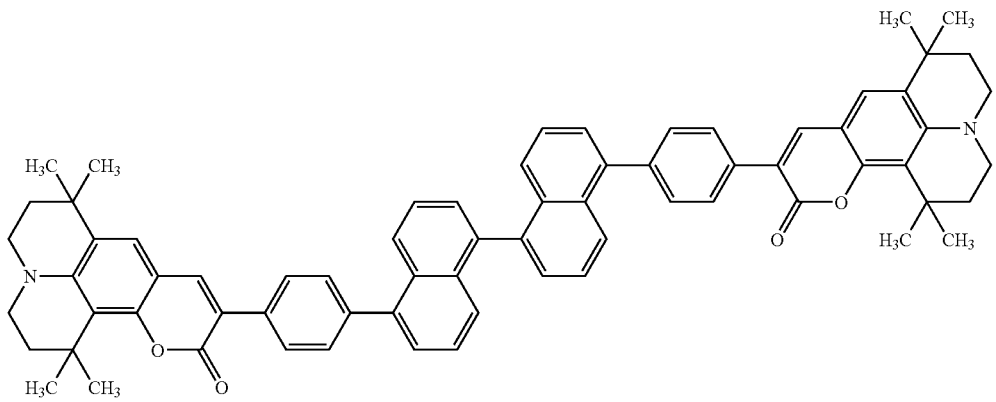
Chemical Formula 303:
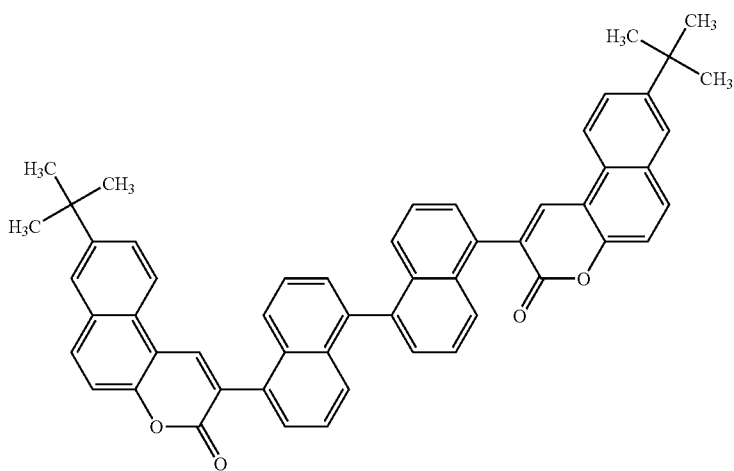
Chemical Formula 304:
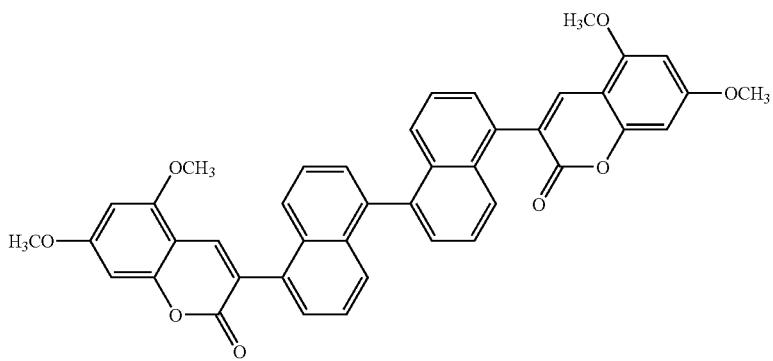
Chemical Formula 305:
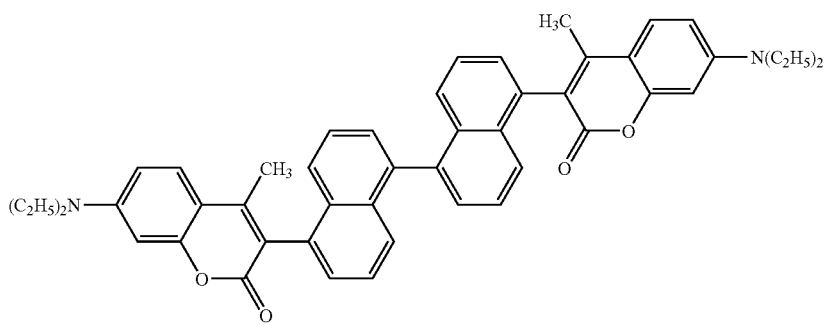

Chemical Formula 306:
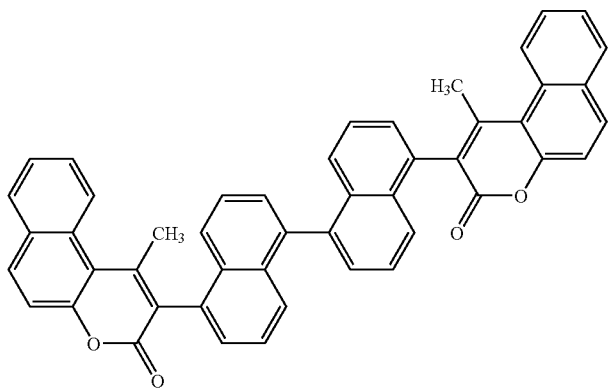
Chemical Formula 307:
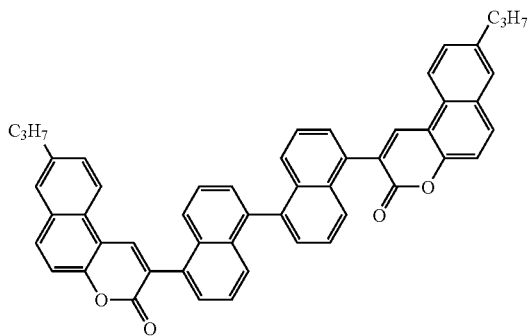
Chemical Formula 308:
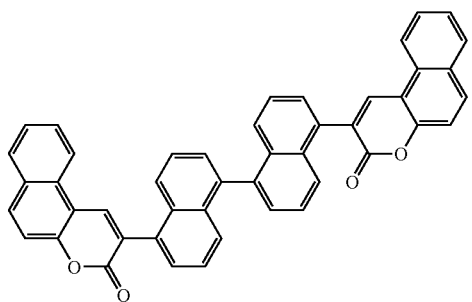
Chemical Formula 309:
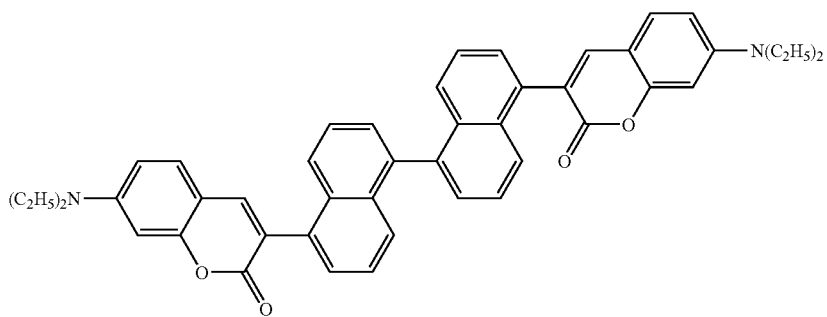
Chemical Formula 310:
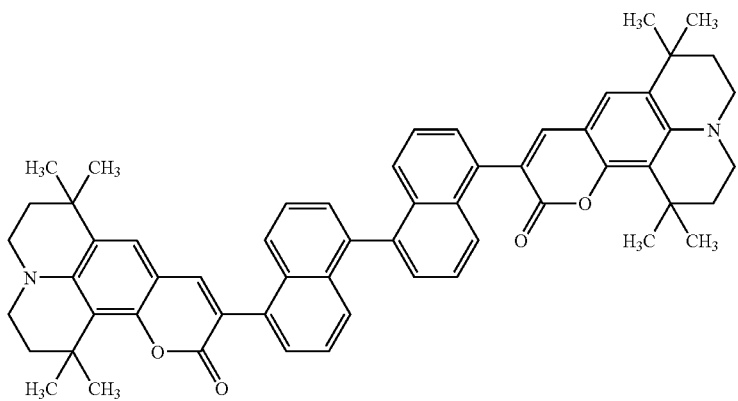

Chemical Formula 311:
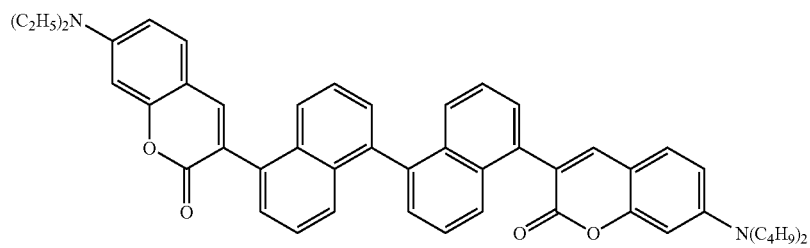
Chemical Formula 312:
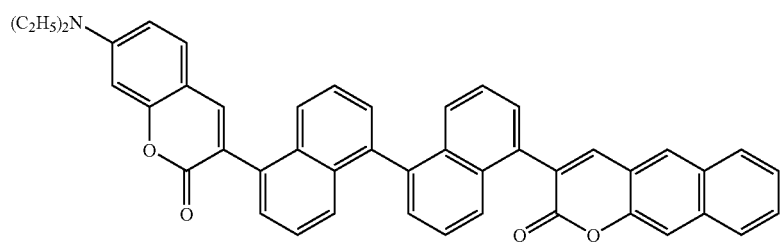
Chemical Formula 313:
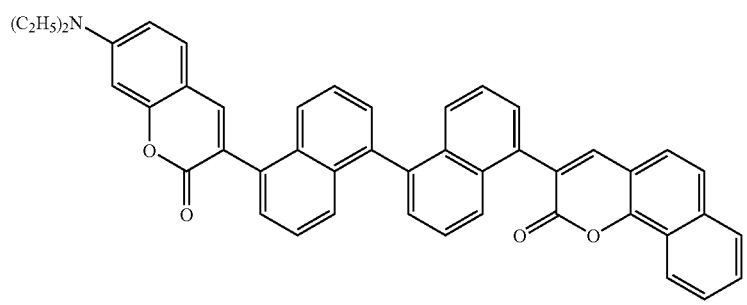
Chemical Formula 314:
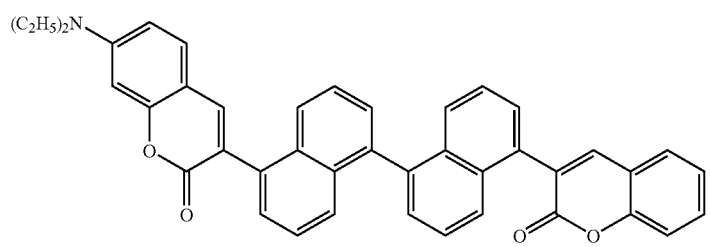
Chemical Formula 315:
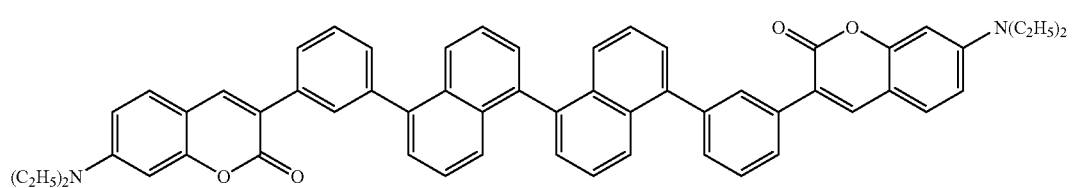

Chemical Formula 316:
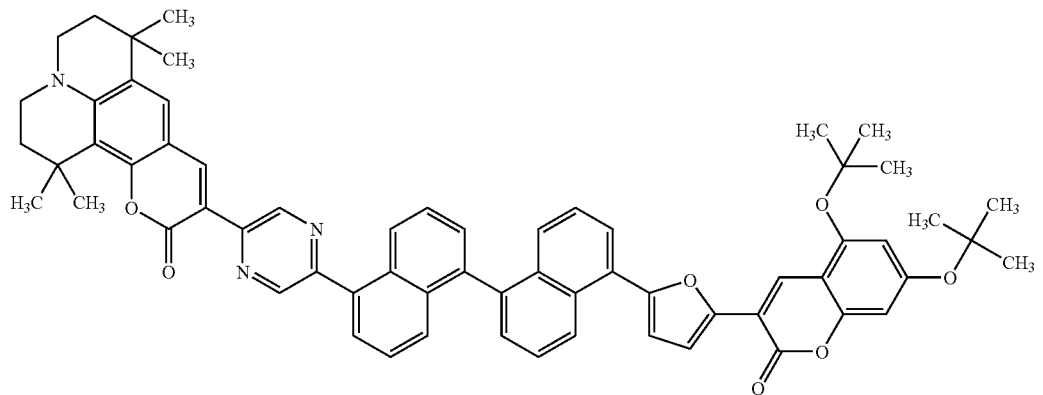
Chemical Formula 317:
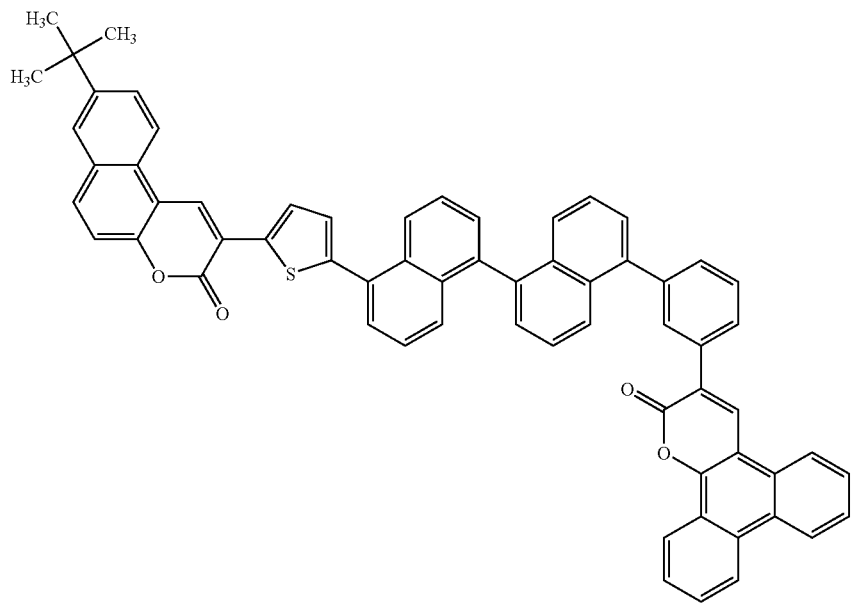
Chemical Formula 318:
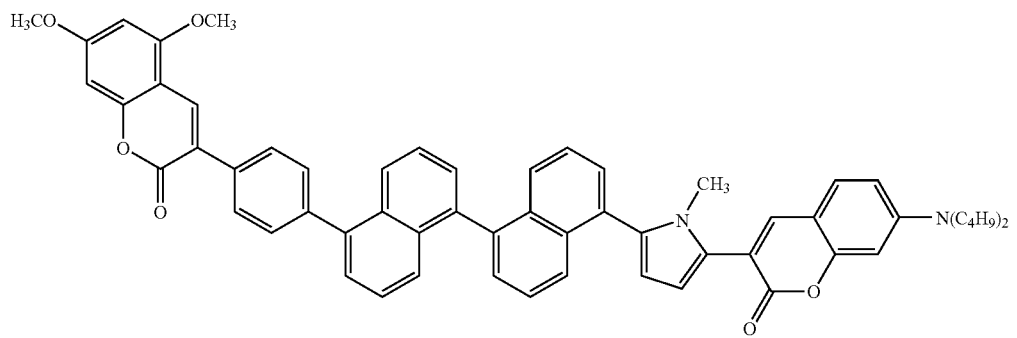

-continued
Chemical Formula 319:
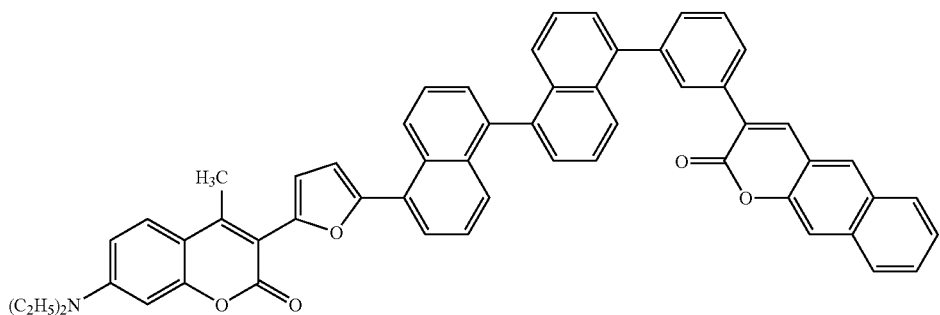
Chemical Formula 320:
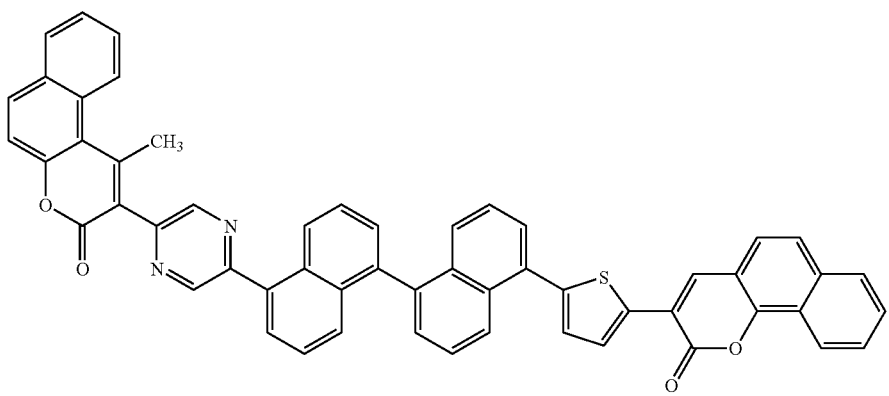
Chemical Formula 321:
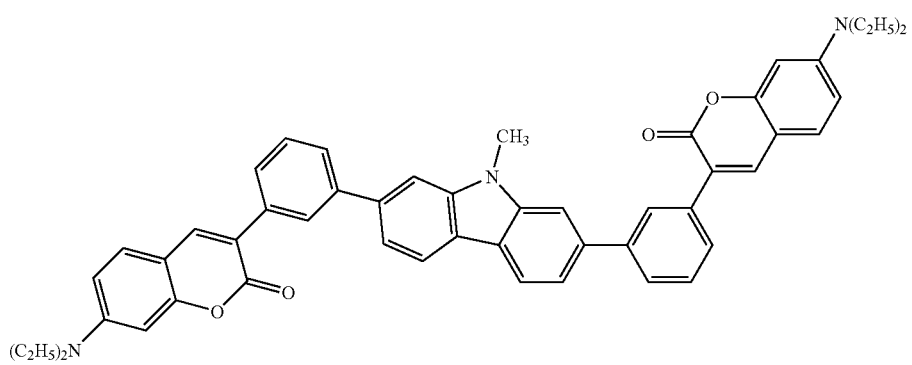
Chemical Formula 322:
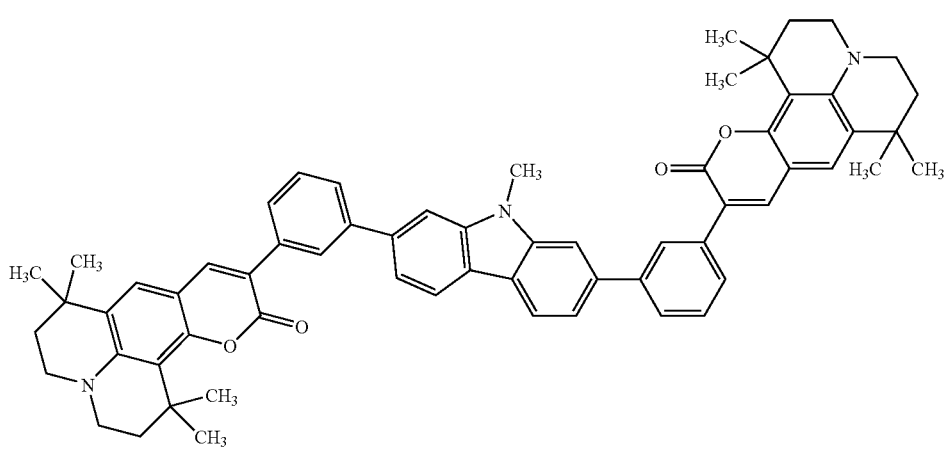

Chemical Formula 323:
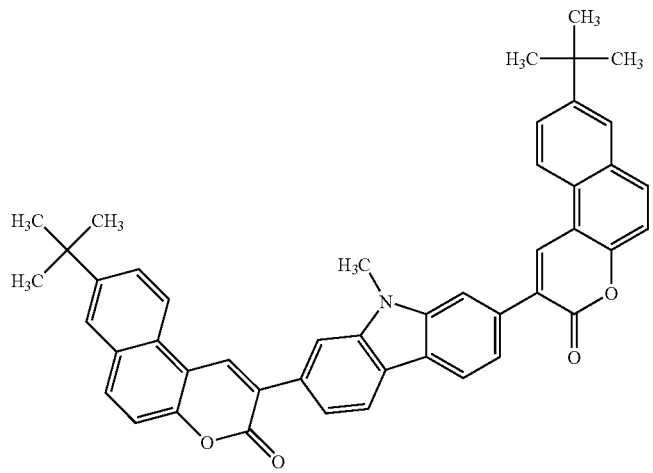
Chemical Formula 324:
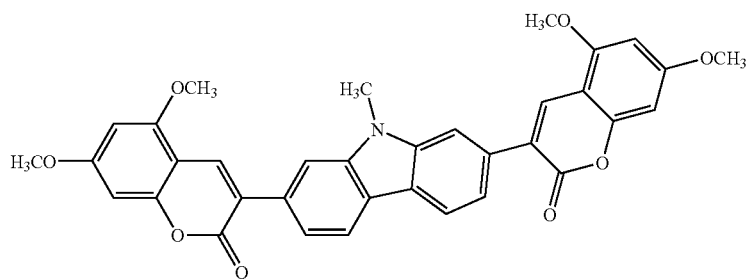
Chemical Formula 325:
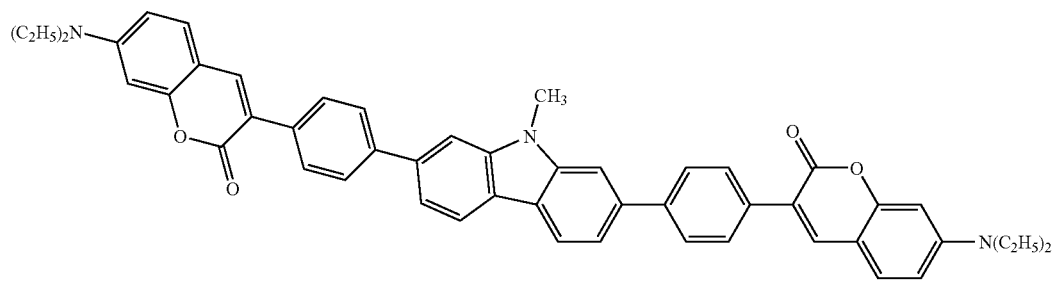
Chemical Formula 326:
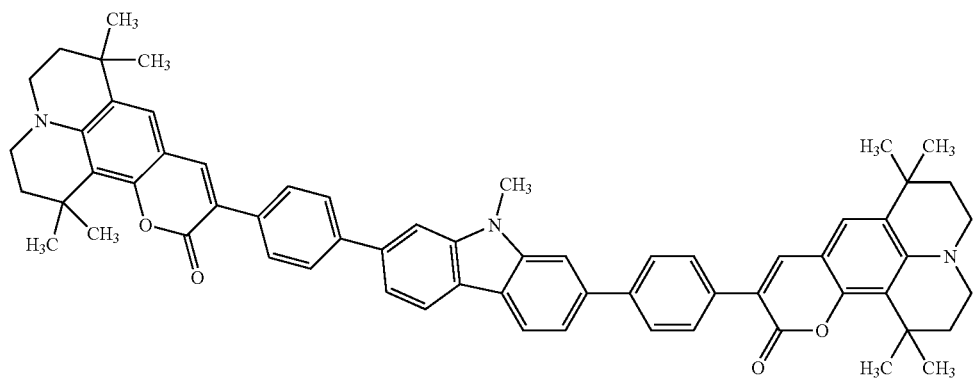

Chemical Formula 327:
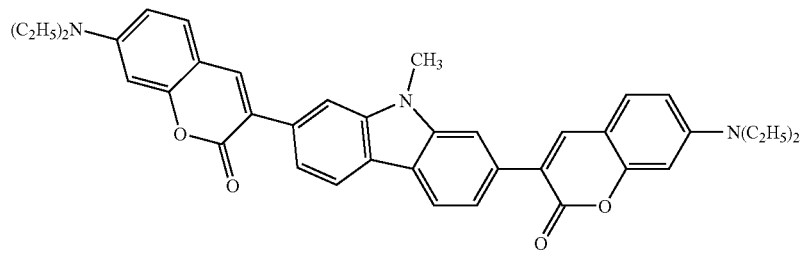
Chemical Formula 328:
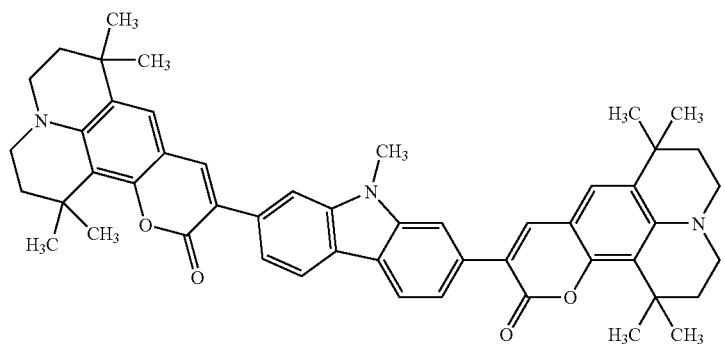
Chemical Formula 329:
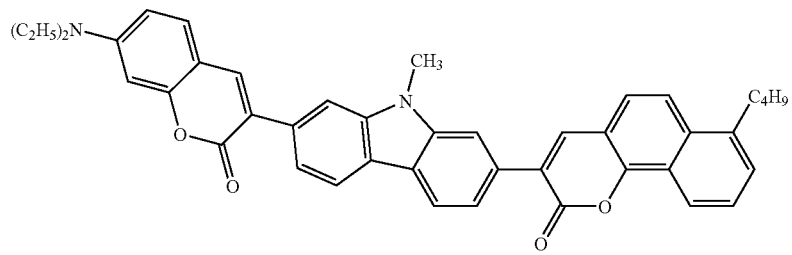
Chemical Formula 330:
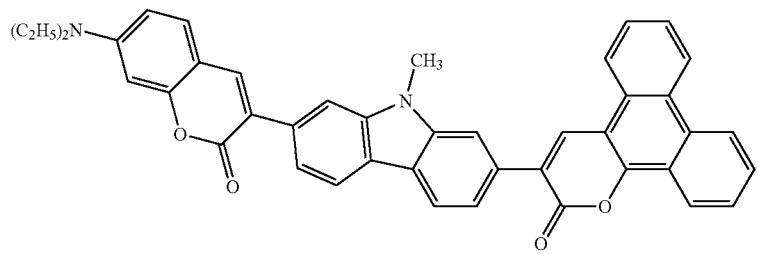
Chemical Formula 331:
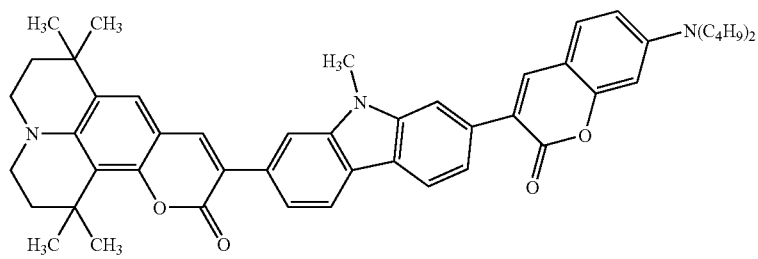

-continued
Chemical Formula 332:
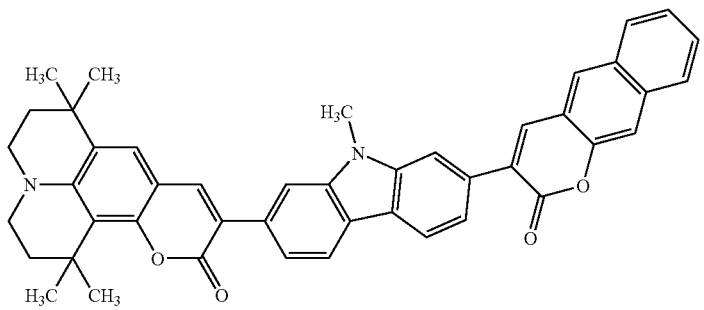
Chemical Formula 333:
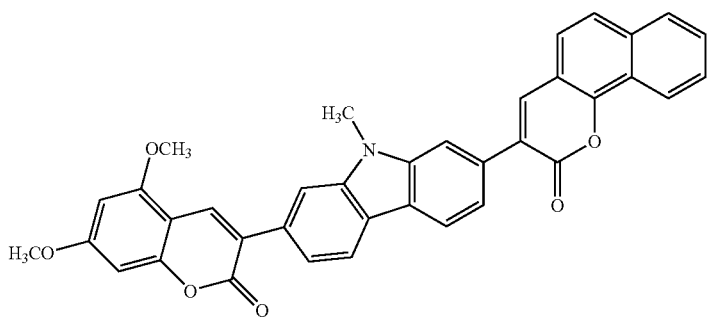
Chemical Formula 334:
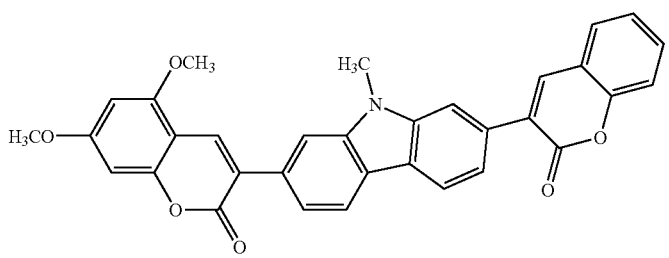
Chemical Formula 335:
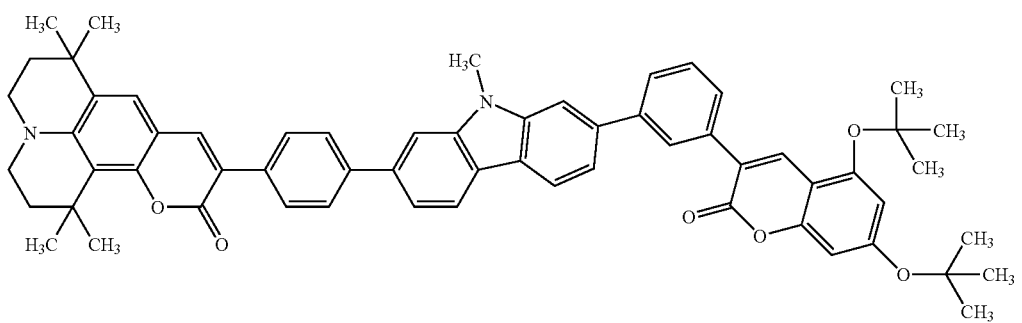
Chemical Formula 336:
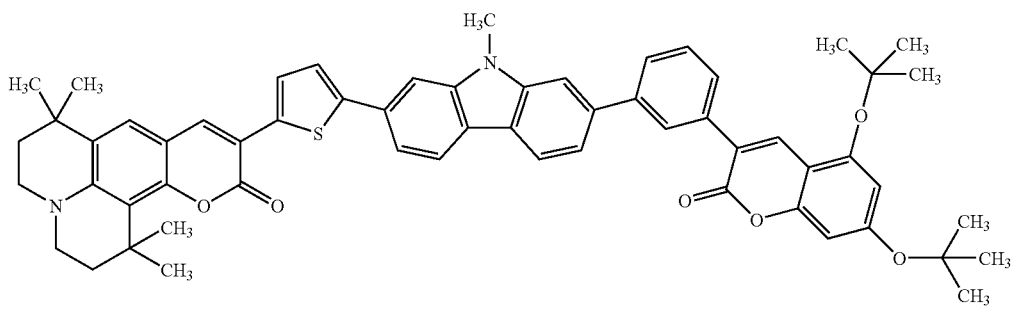

Chemical Formula 337:
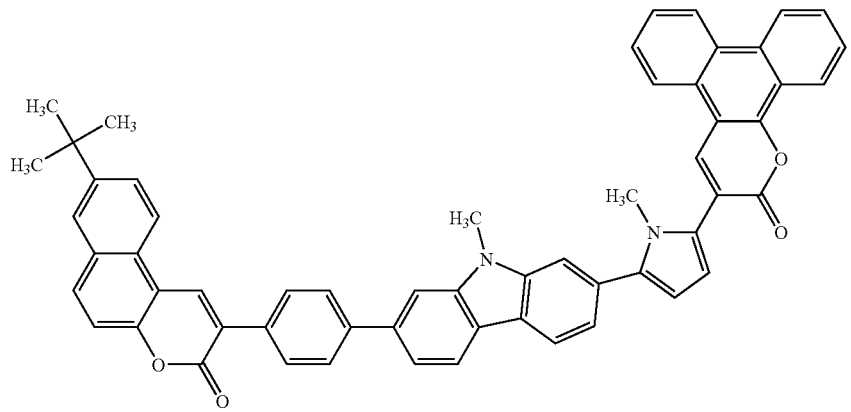
Chemical Formula 338:
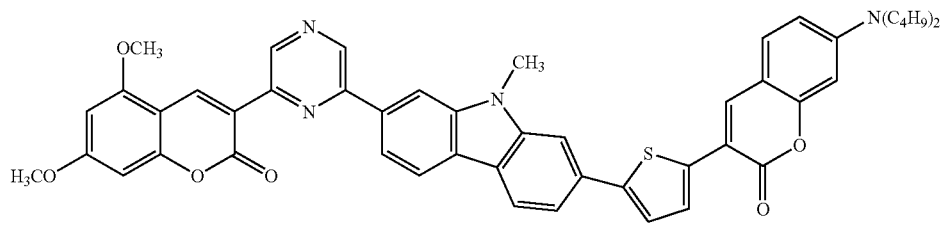
Chemical Formula 339:
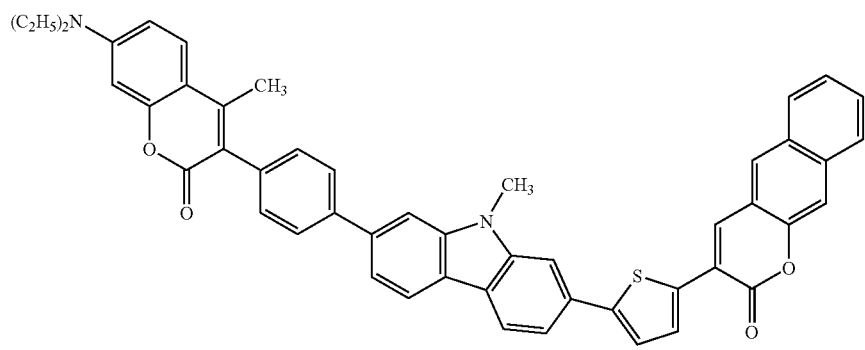
Chemical Formula 340:
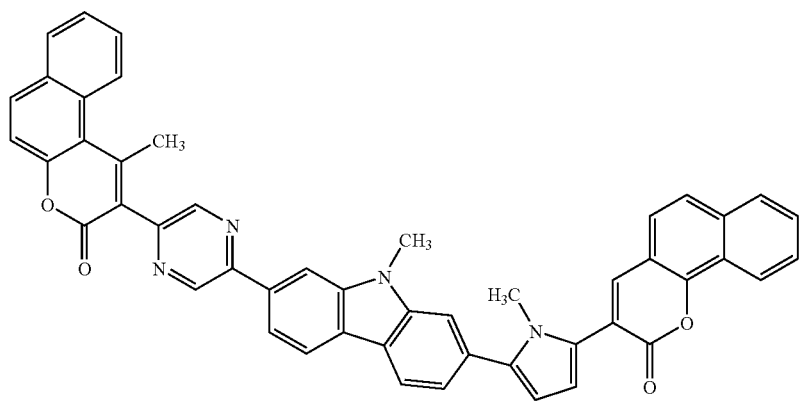

-continued
Chemical Formula 341:
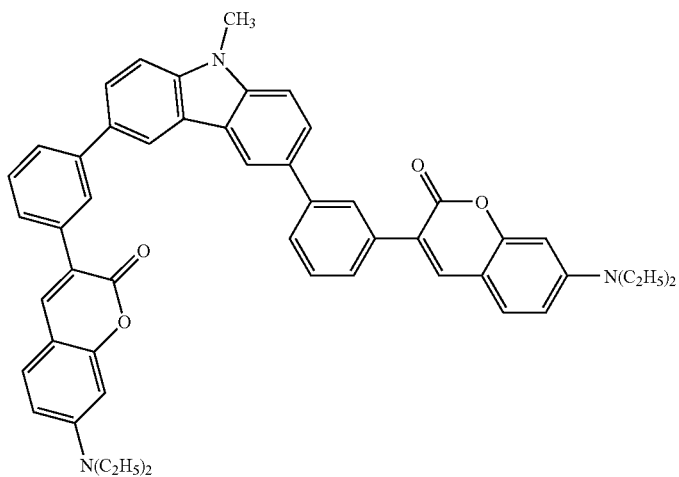
Chemical Formula 342:
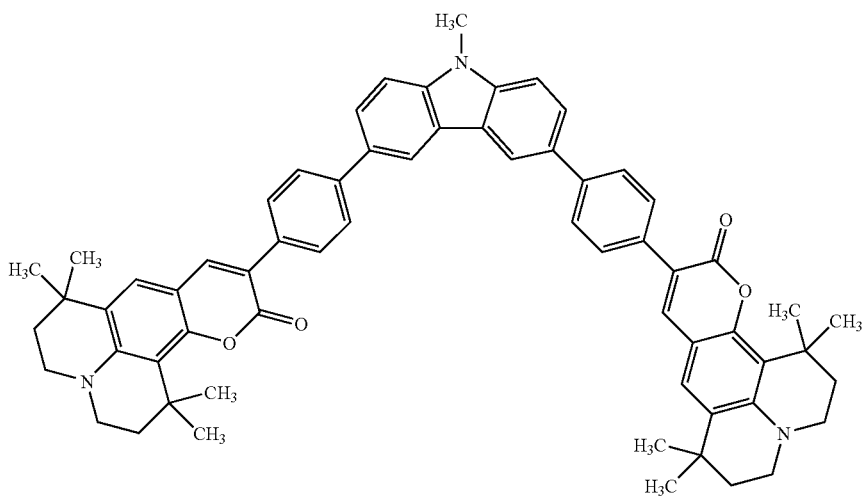
Chemical Formula 343:
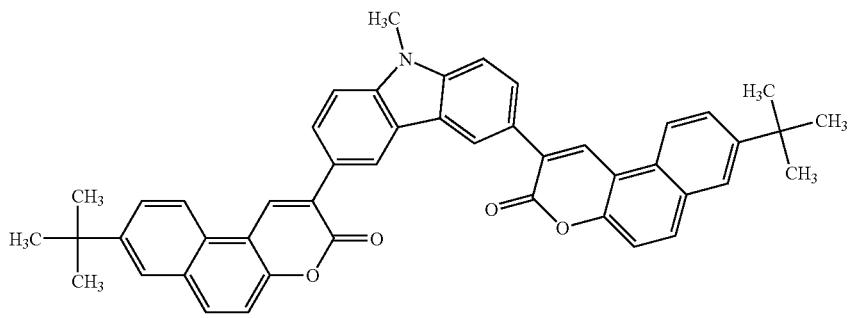
Chemical Formula 344:
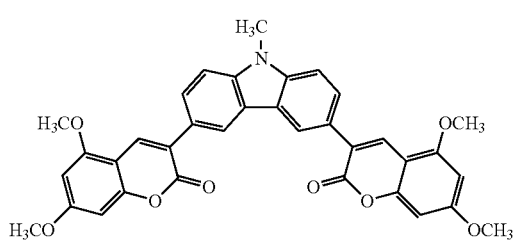
Chemical Formula 345:
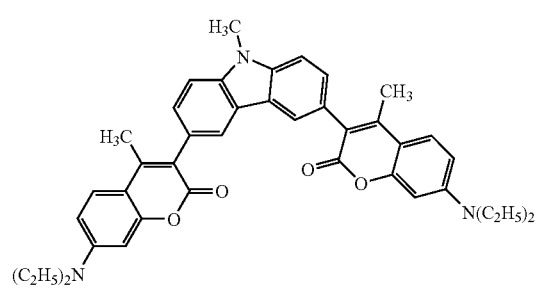

-continued
Chemical Formula 346:
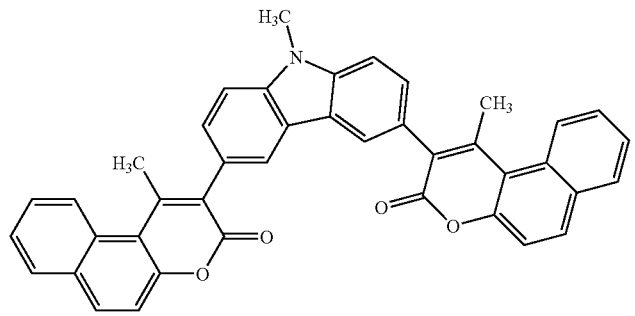
Chemical Formula 347:
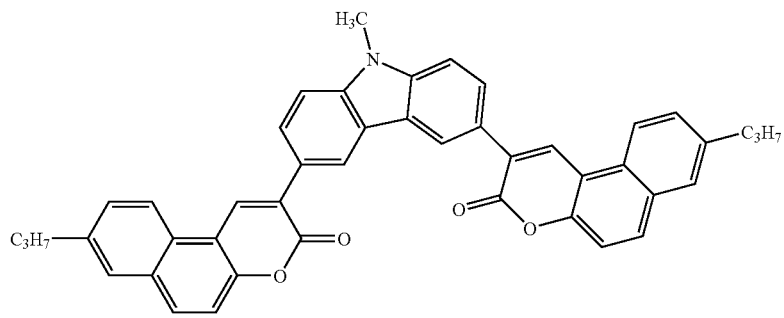
Chemical Formula 348:
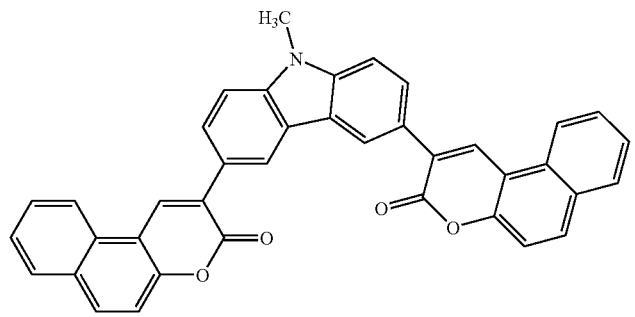
Chemical Formula 349:
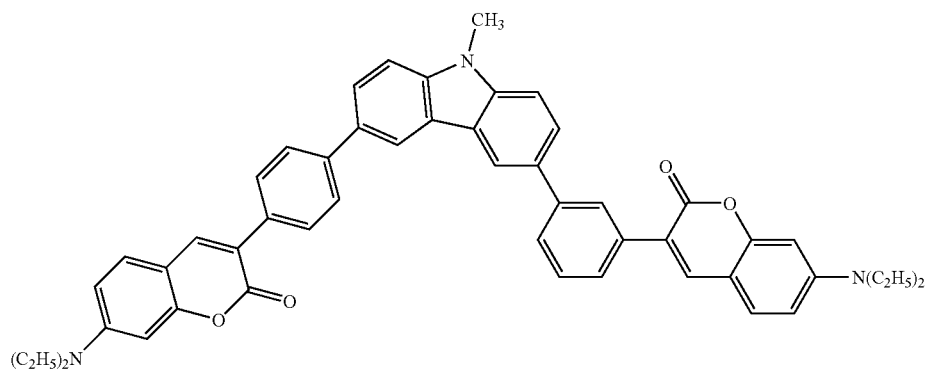

-continued
Chemical Formula 350:
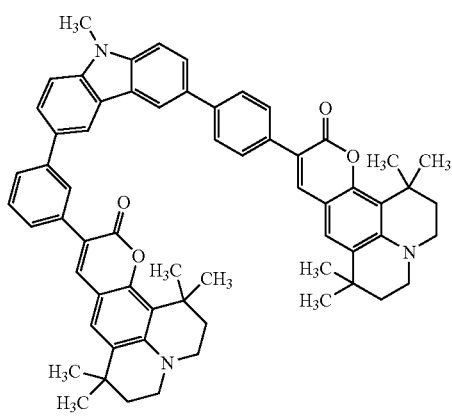
Chemical Formula 351:
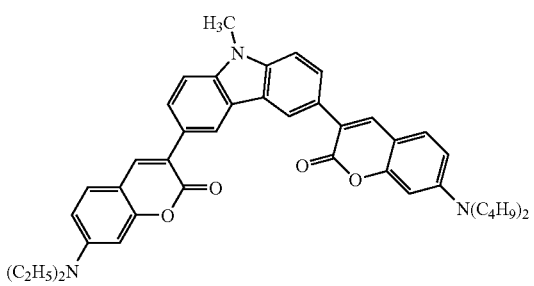
Chemical Formula 352:
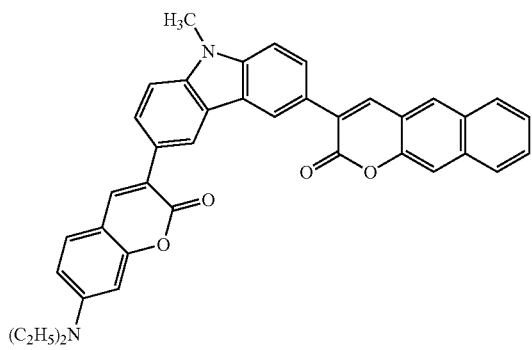
Chemical Formula 353:
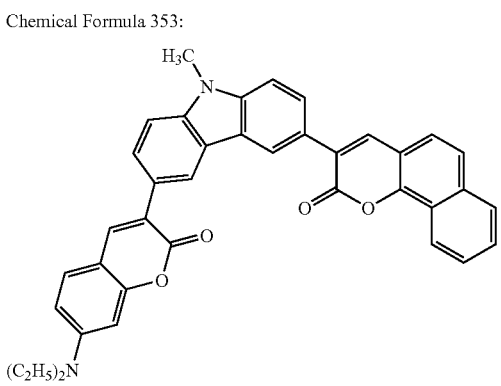
Chemical Formula 354:
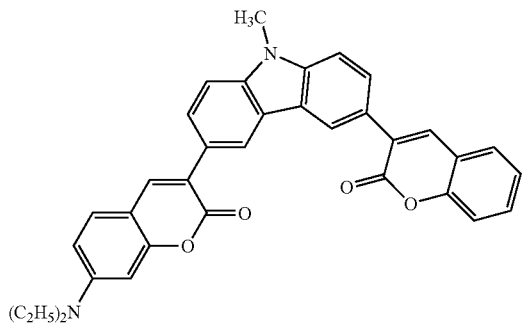
Chemical Formula 355:
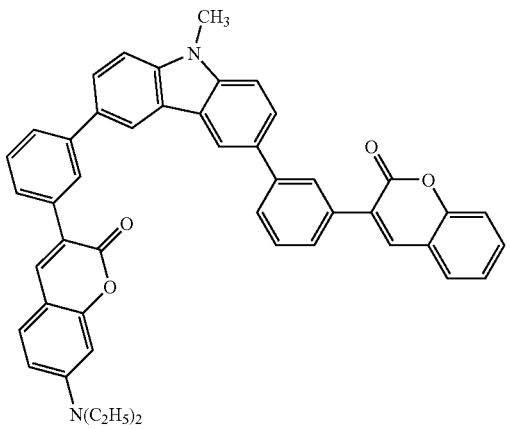
Chemical Formula 356:
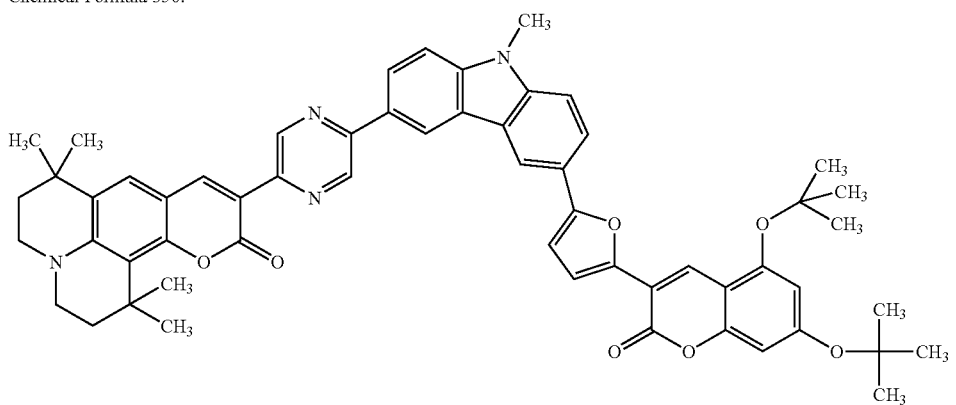

Chemical Formula 357:
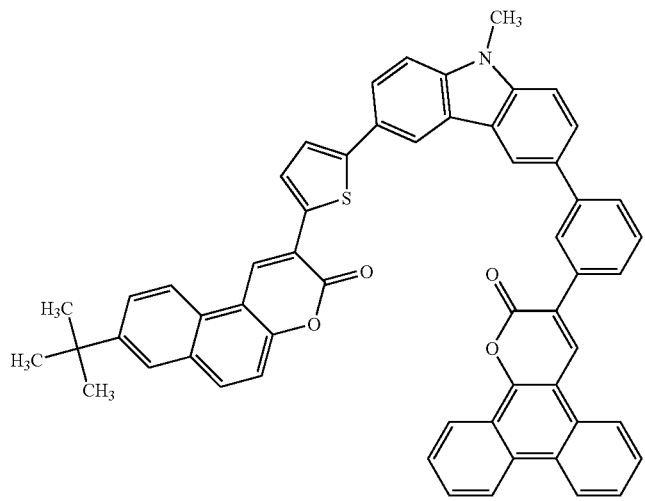
Chemical Formula 358:
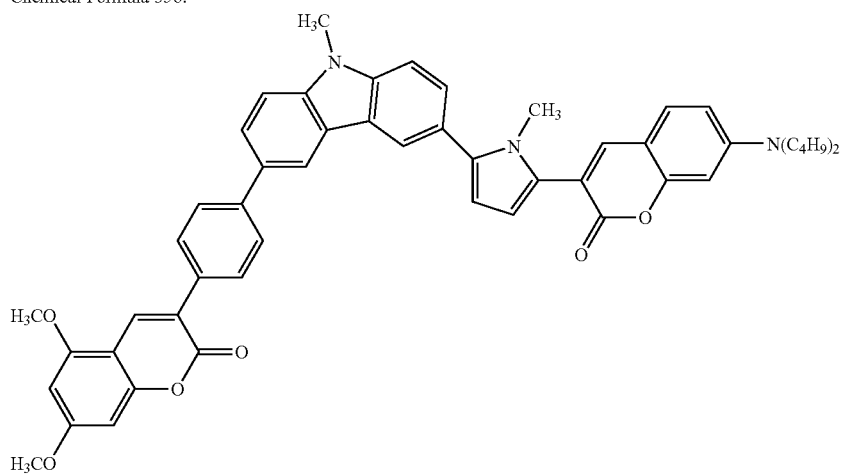
Chemical Formula 359:
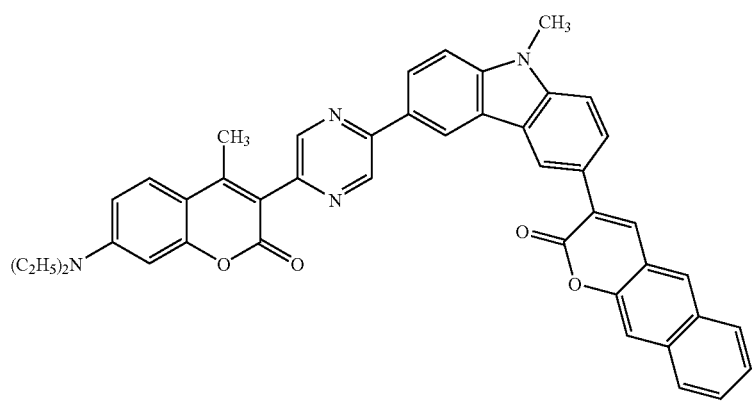

Chemical Formula 360:
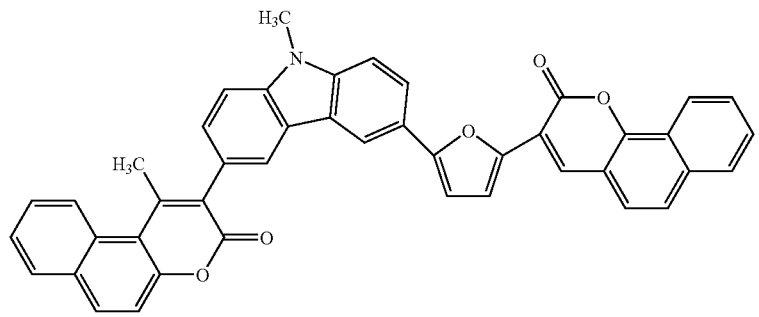
Chemical Formula 361:
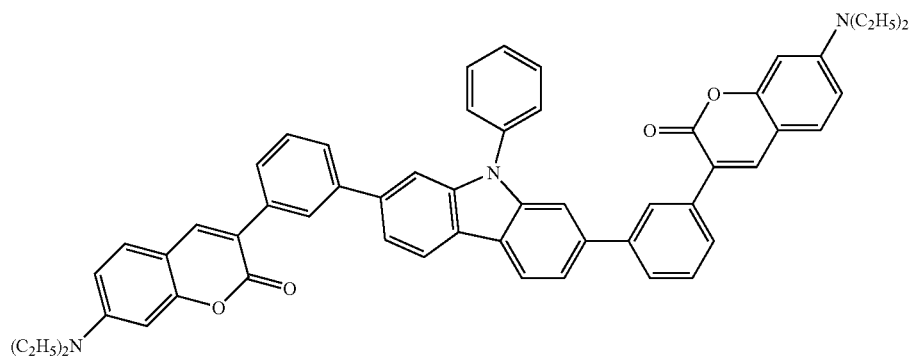
Chemical Formula 362:
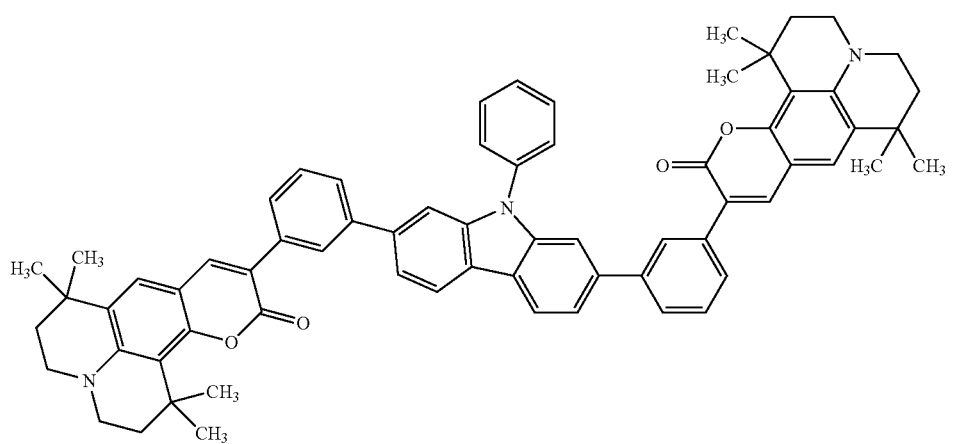

-continued
Chemical Formula 363:
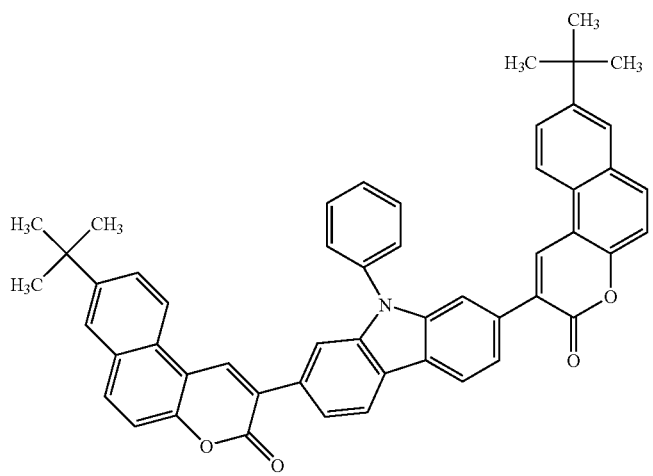
Chemical Formula 364:
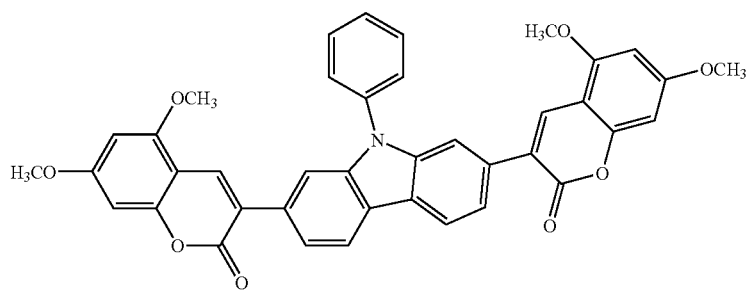
Chemical Formula 365:
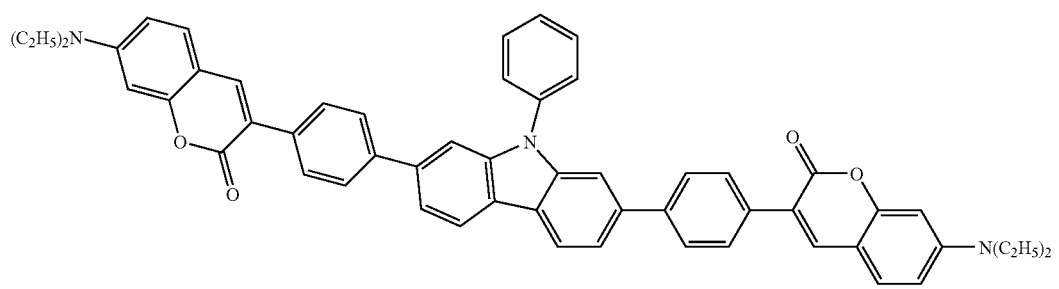
Chemical Formula 366:
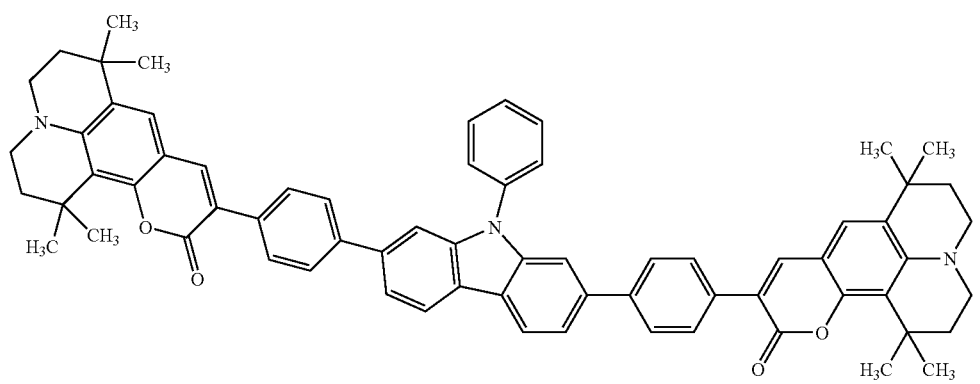

-continued
Chemical Formula 367:
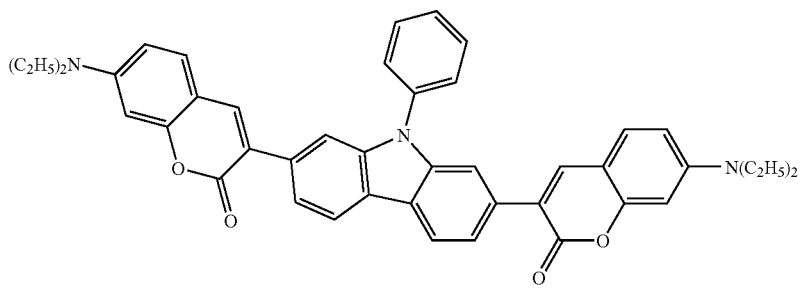
Chemical Formula 368:
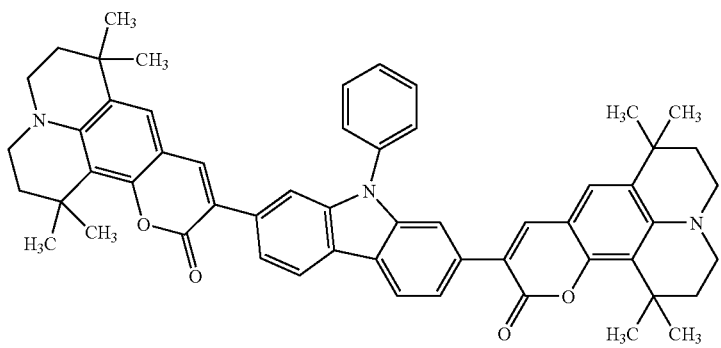
Chemical Formula 369:
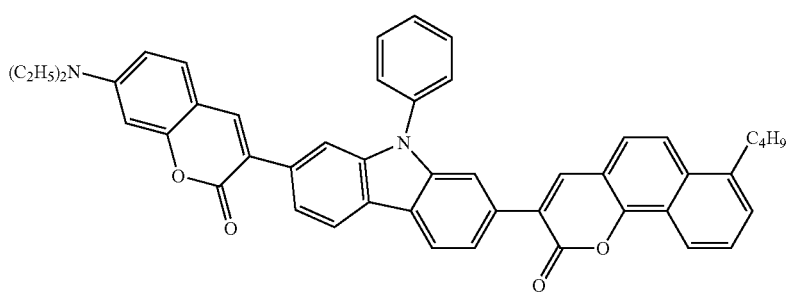
Chemical Formula 370:
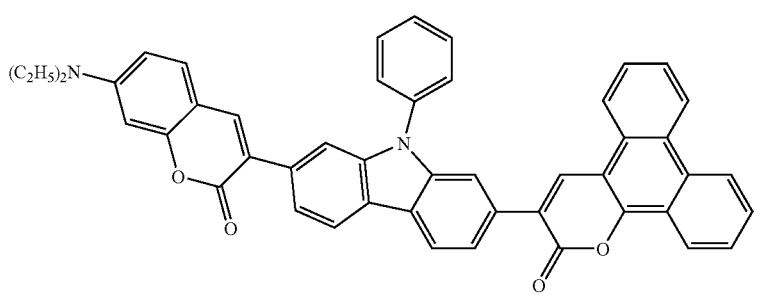
Chemical Formula 371:
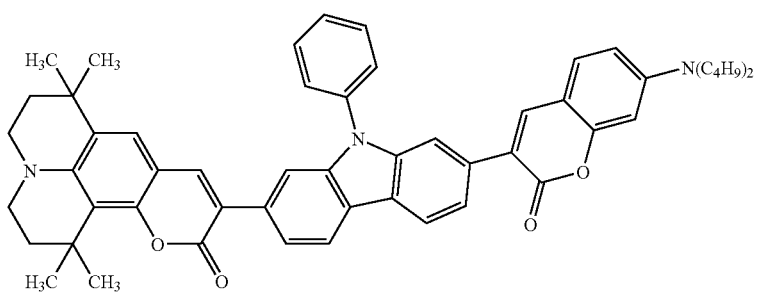

Chemical Formula 372:
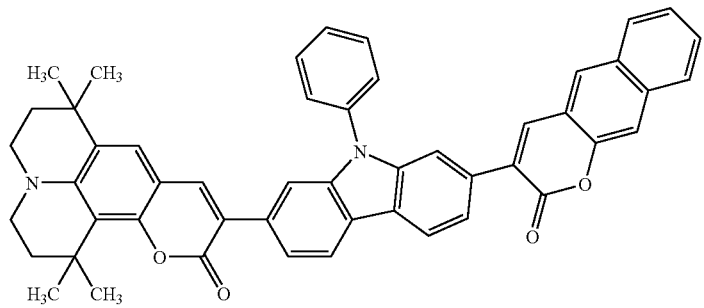
Chemical Formula 373:
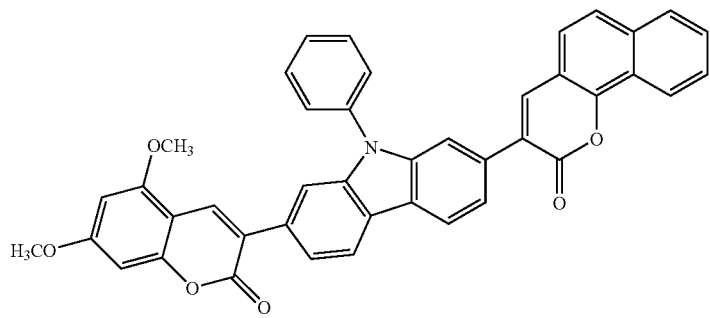
Chemical Formula 374:
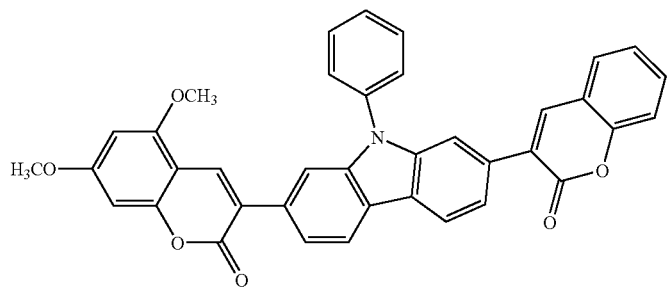
Chemical Formula 375:
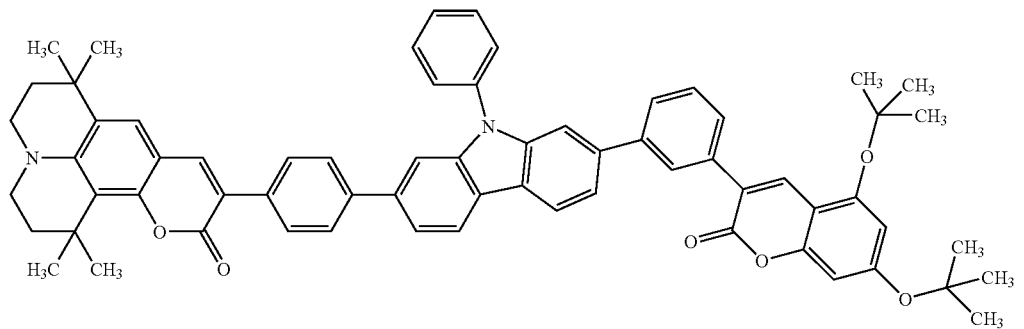

Chemical Formula 376:
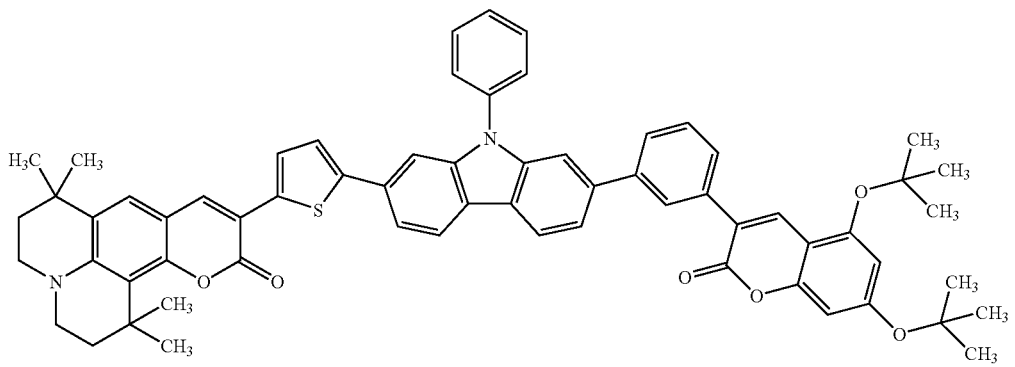
Chemical Formula 377:
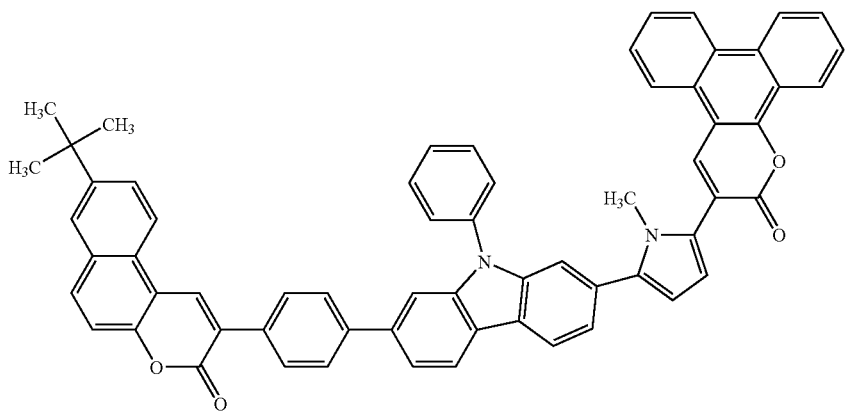
Chemical Formula 378:
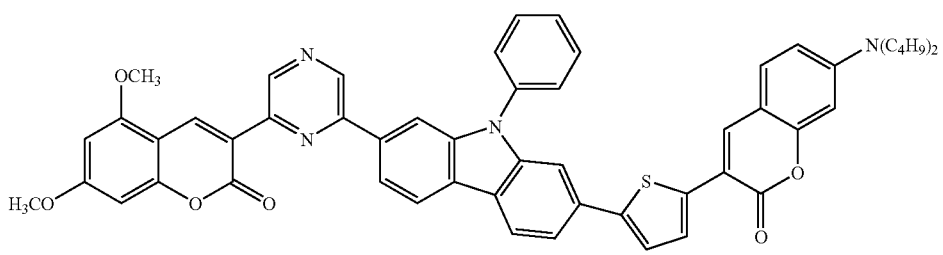
Chemical Formula 379:
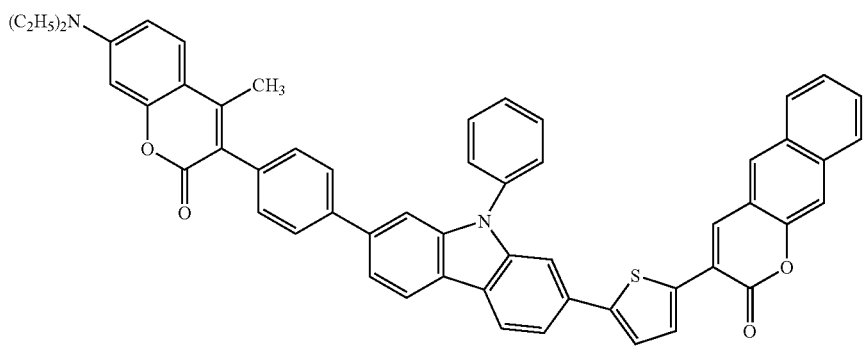

-continued
Chemical Formula 380:
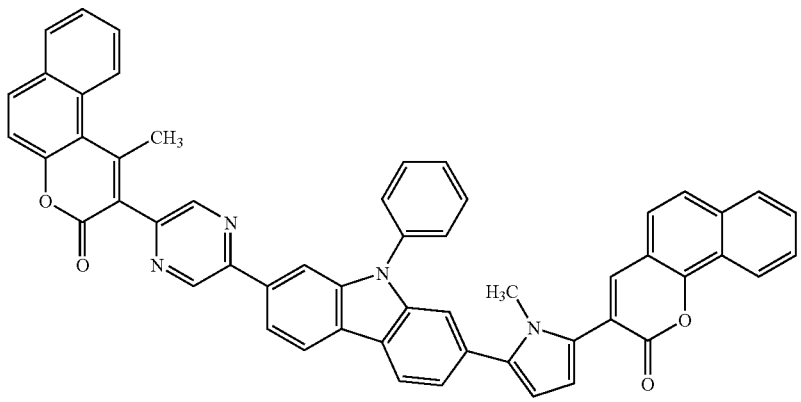
Chemical Formula 381:
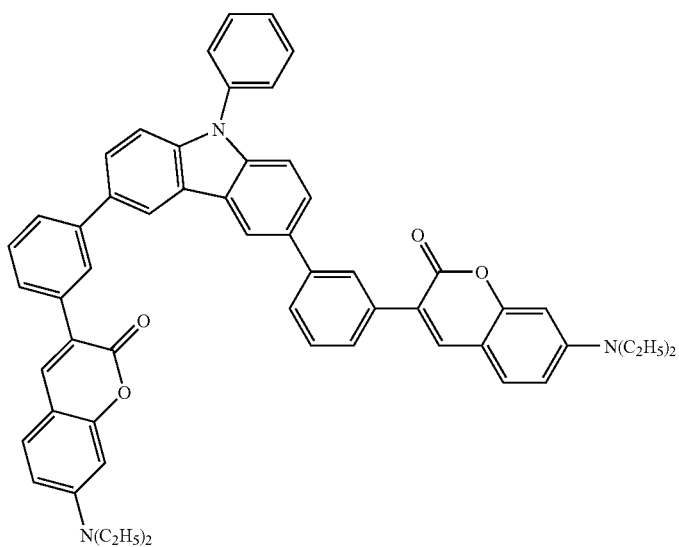
Chemical Formula 382:
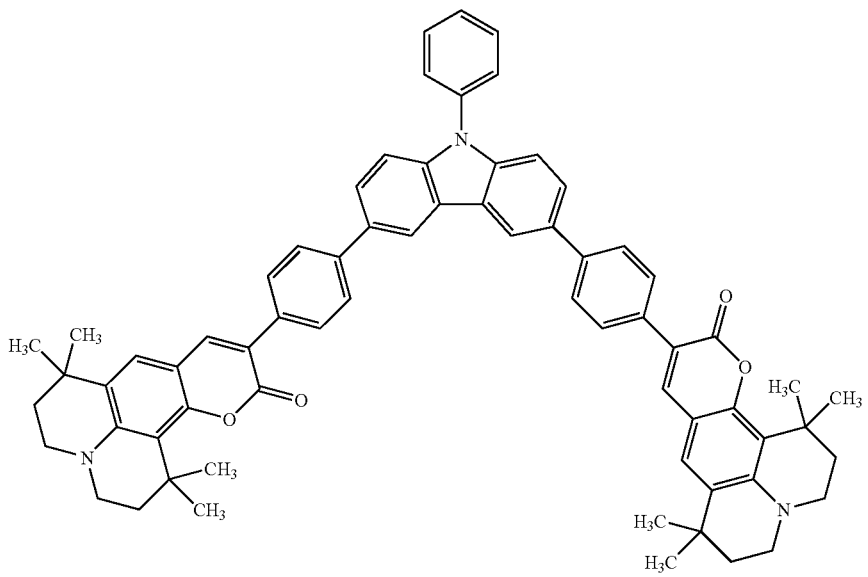

-continued
Chemical Formula 383:
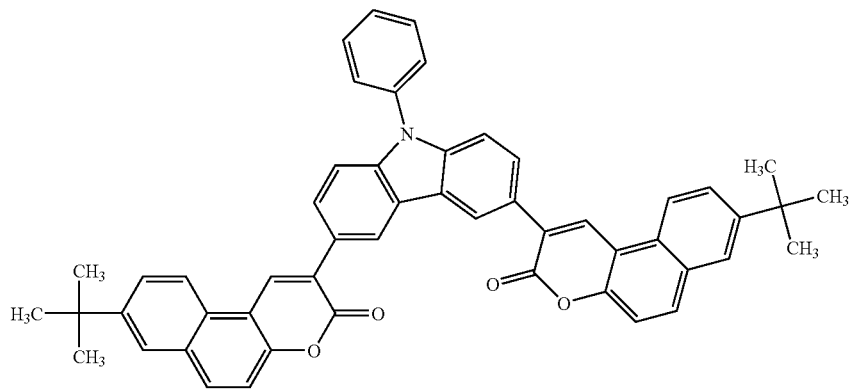
Chemical Formula 384:
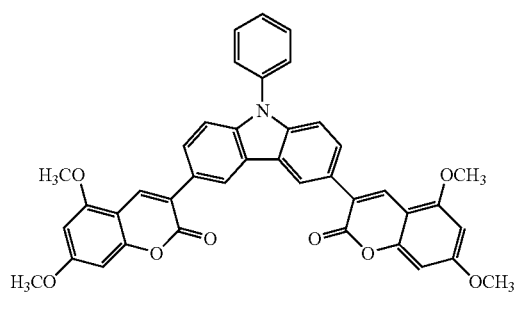
Chemical Formula 385:
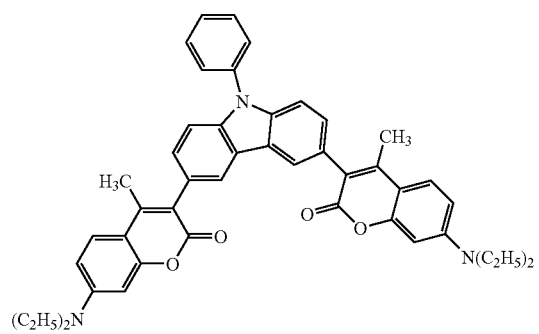
Chemical Formula 386:
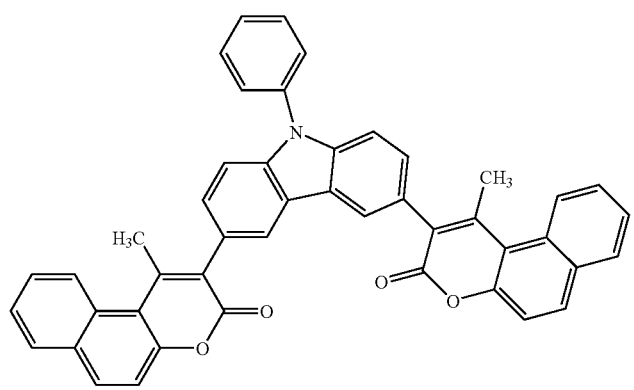
Chemical Formula 387:
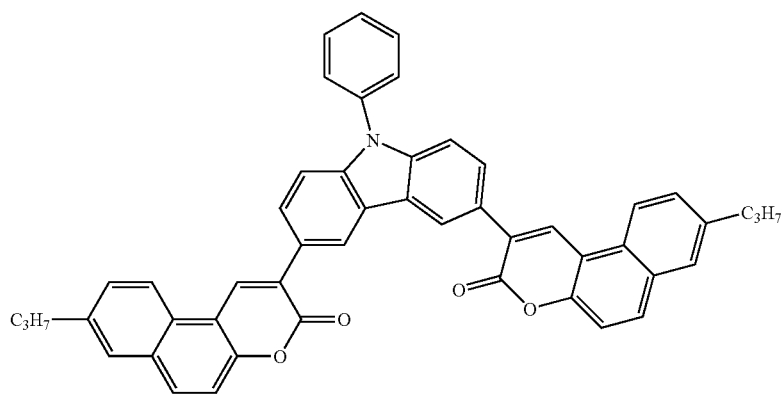

Chemical Formula 388:
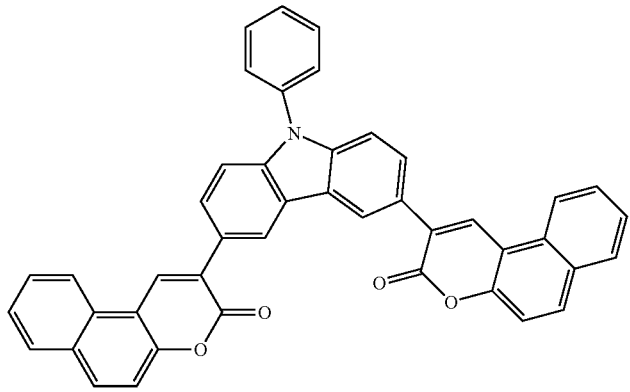
Chemical Formula 389:
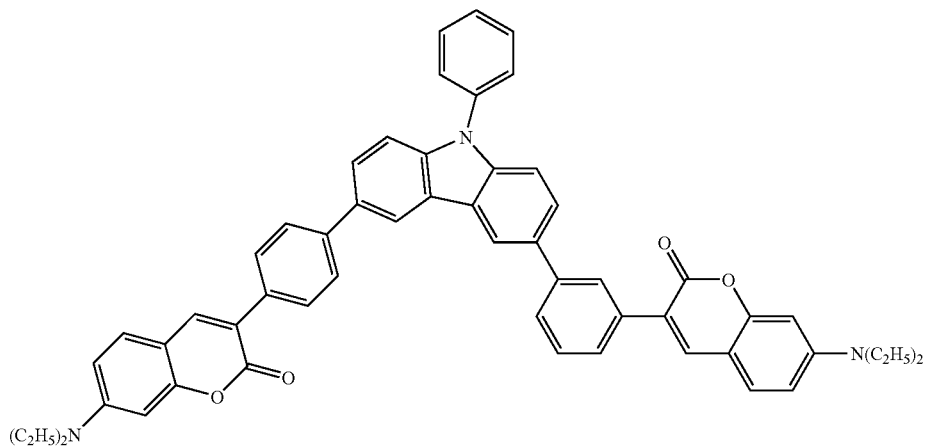
Chemical Formula 390:
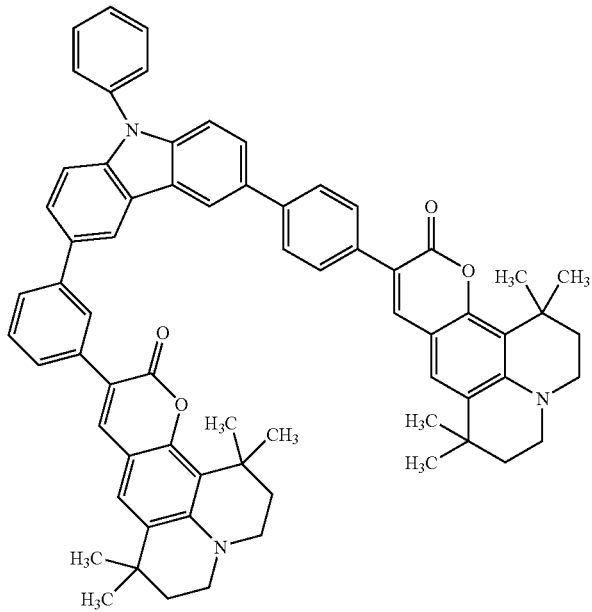

Chemical Formula 391:
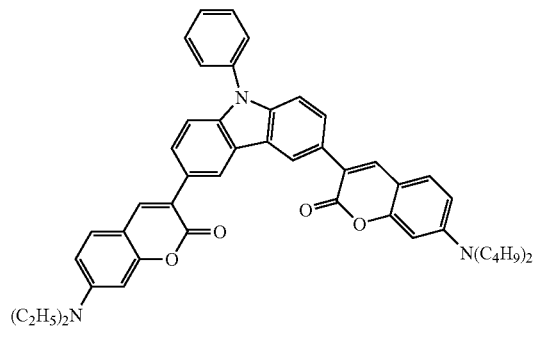
Chemical Formula 392:
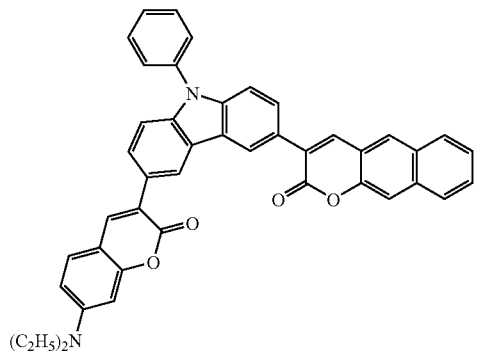
Chemical Formula 393:
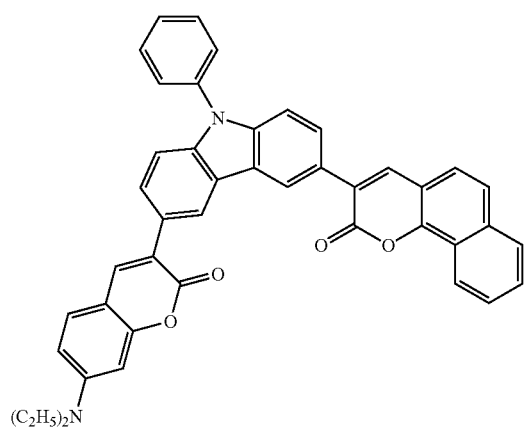
Chemical Formula 394:
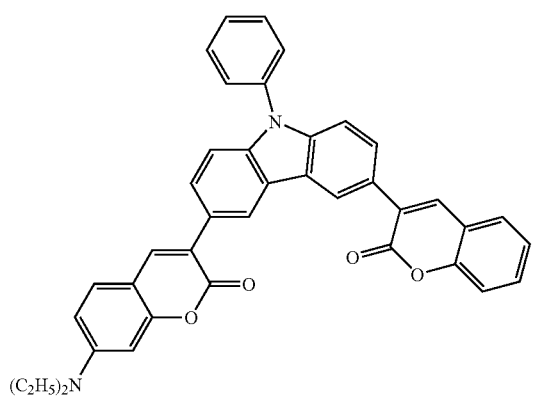
Chemical Formula 395:
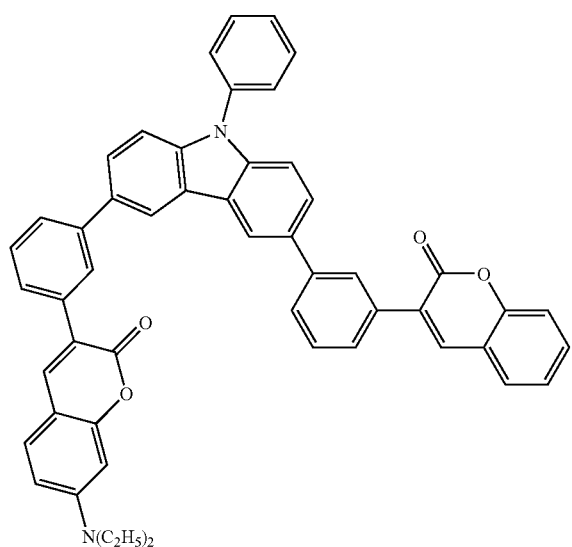

Chemical Formula 396:
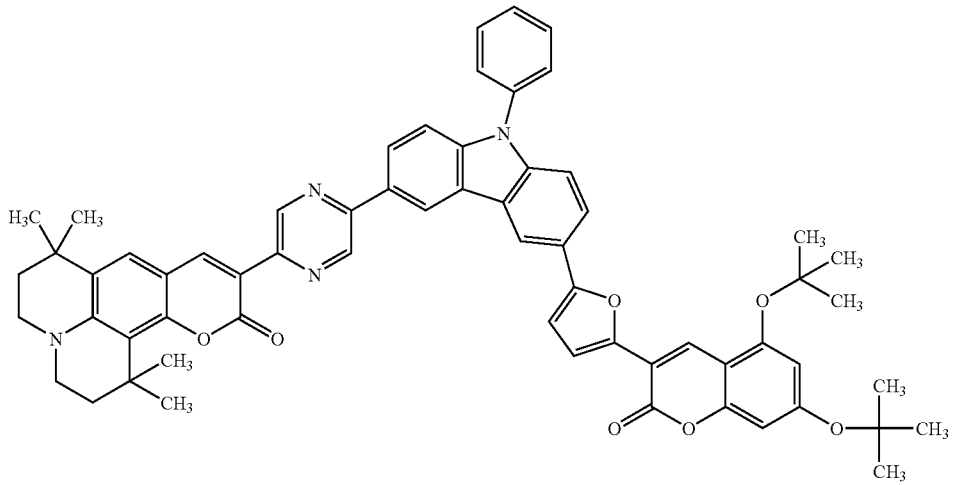
Chemical Formula 397:
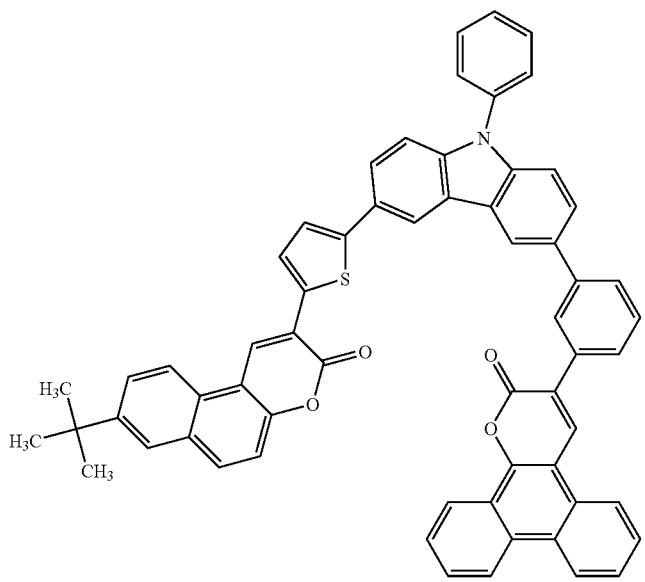
Chemical Formula 398:
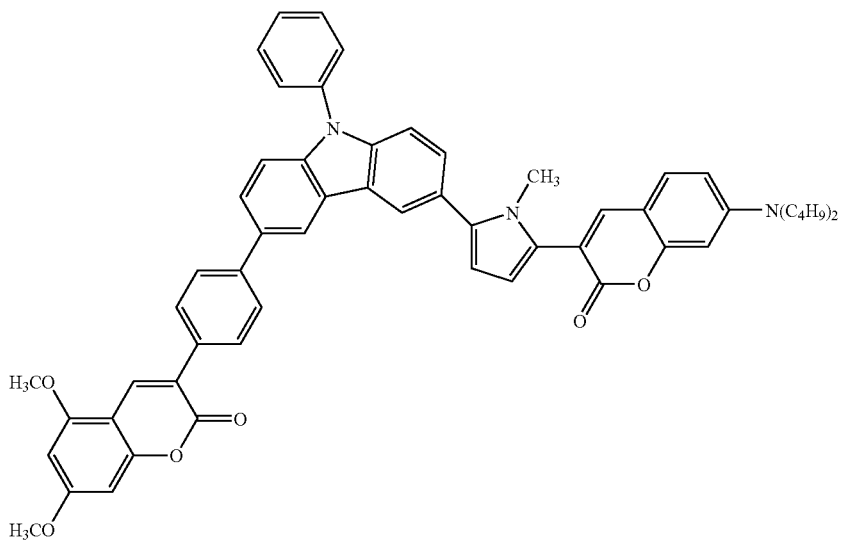

-continued
Chemical Formula 399:
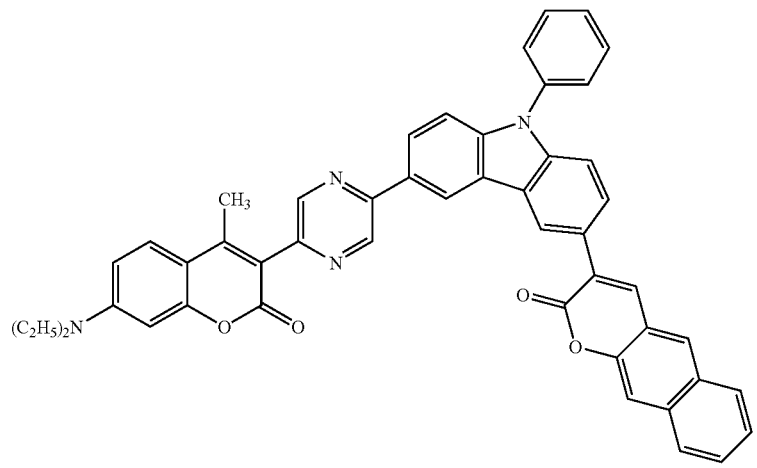
Chemical Formula 400:
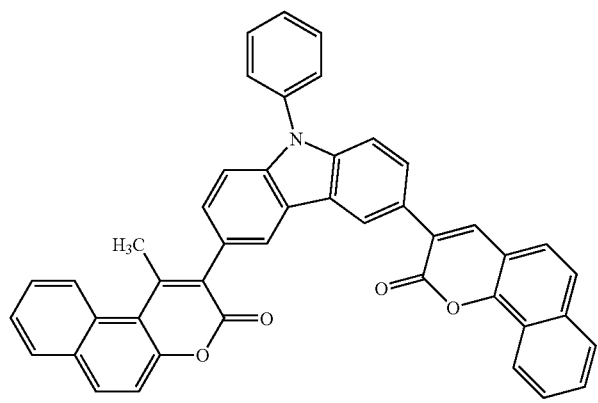
Chemical Formula 401:
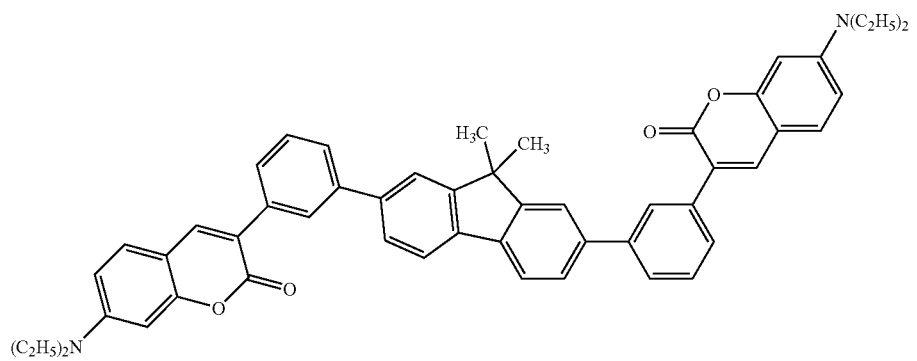

-continued
Chemical Formula 402:
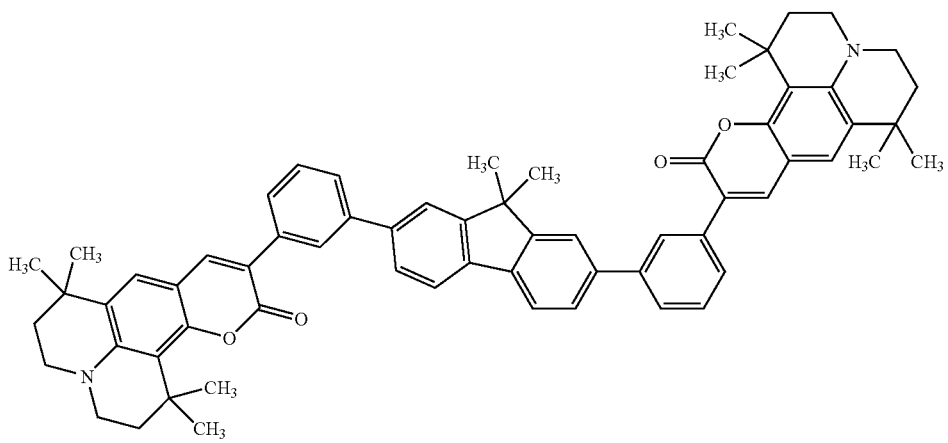
Chemical Formula 403:
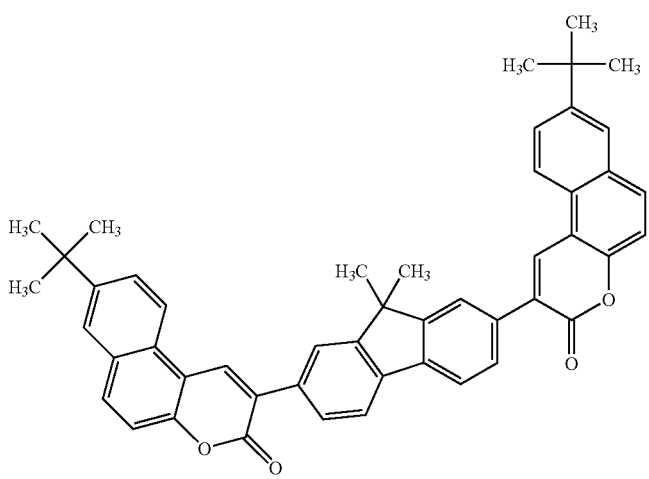
Chemical Formula 404:
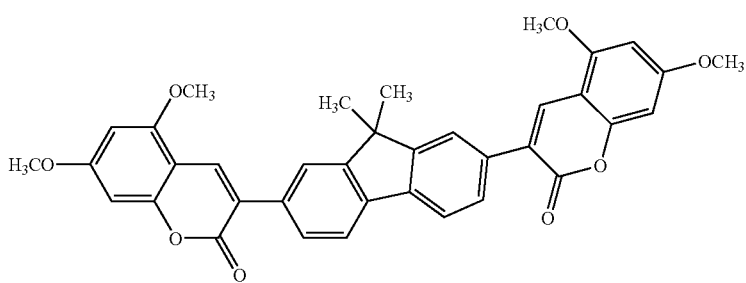
Chemical Formula 405:
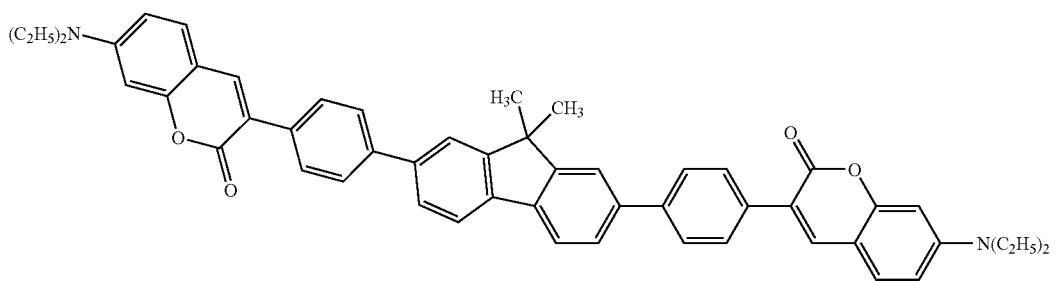

-continued
Chemical Formula 406:
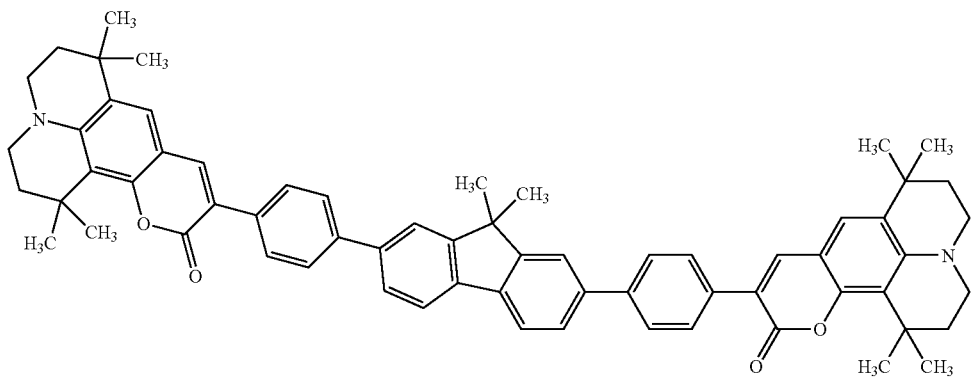
Chemical Formula 407:
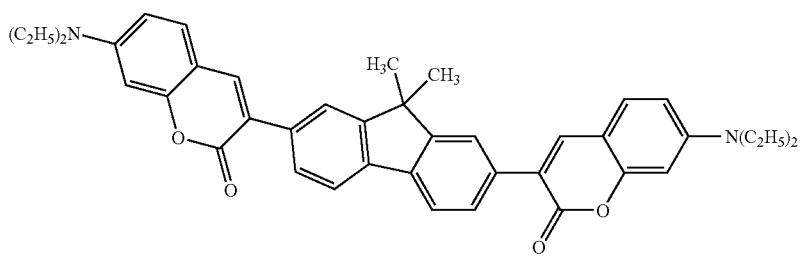
Chemical Formula 408:
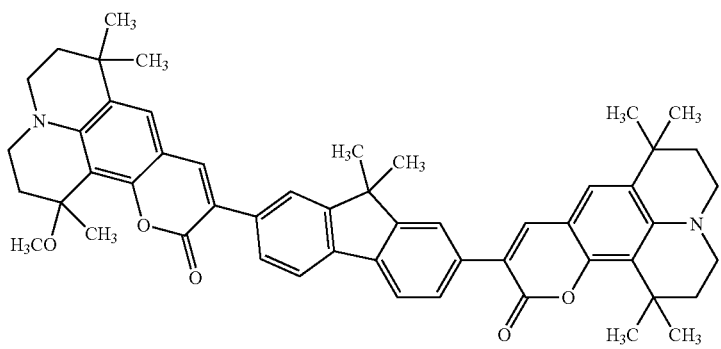
Chemical Formula 409:
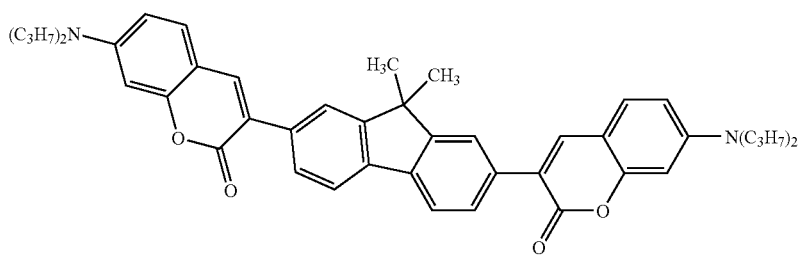
Chemical Formula 410:
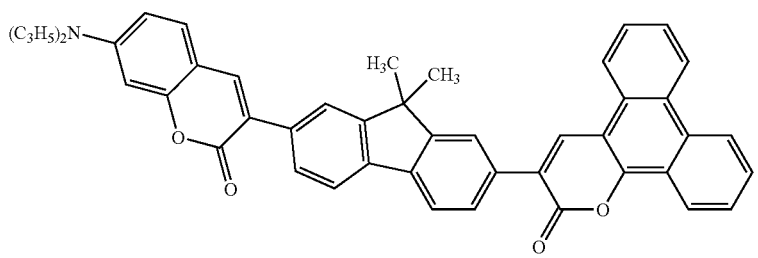

-continued
Chemical Formula 411:
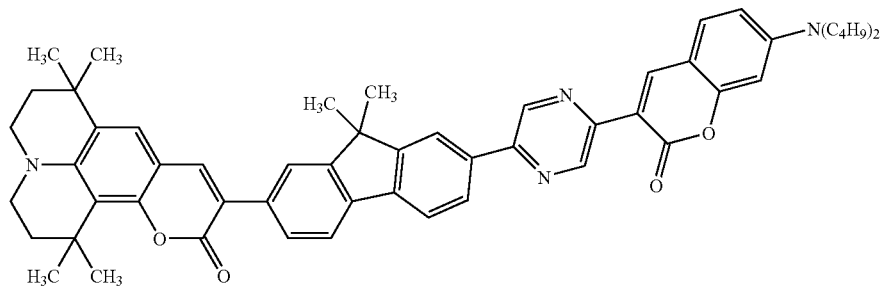
Chemical Formula 412:
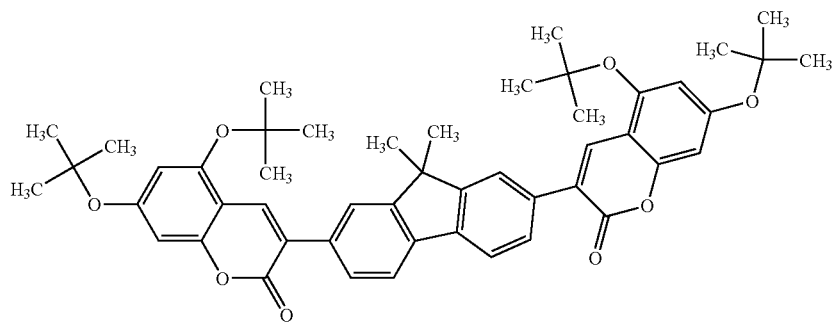
Chemical Formula 413:
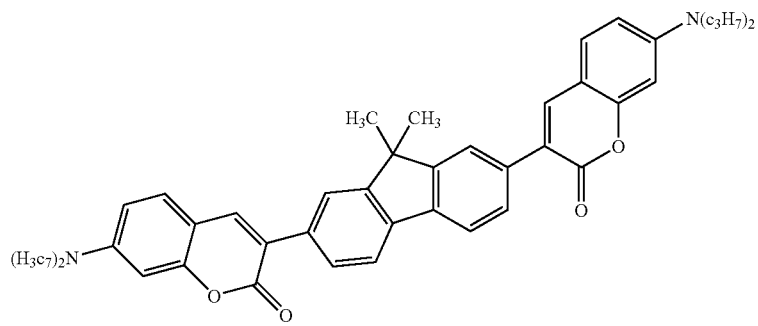
Chemical Formula 414:
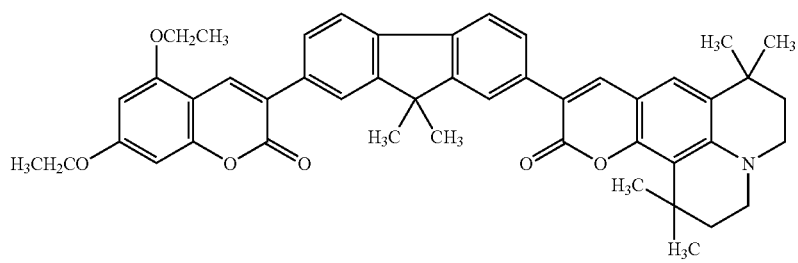
Chemical Formula 415:
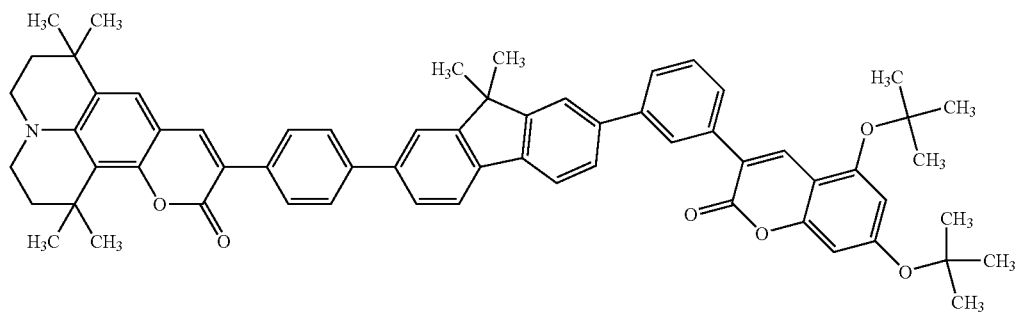

Chemical Formula 416:
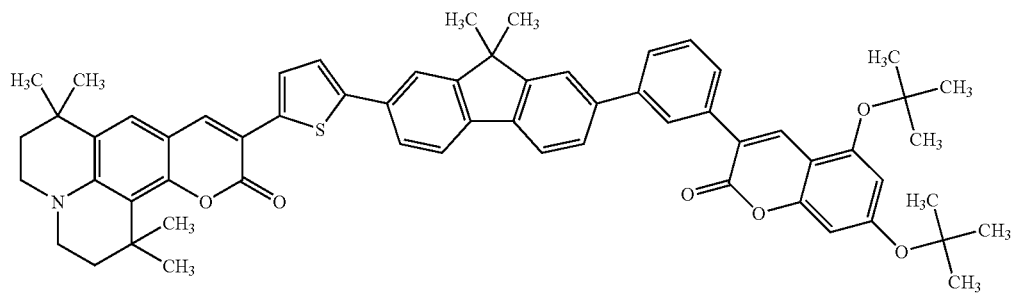
Chemical Formula 417:
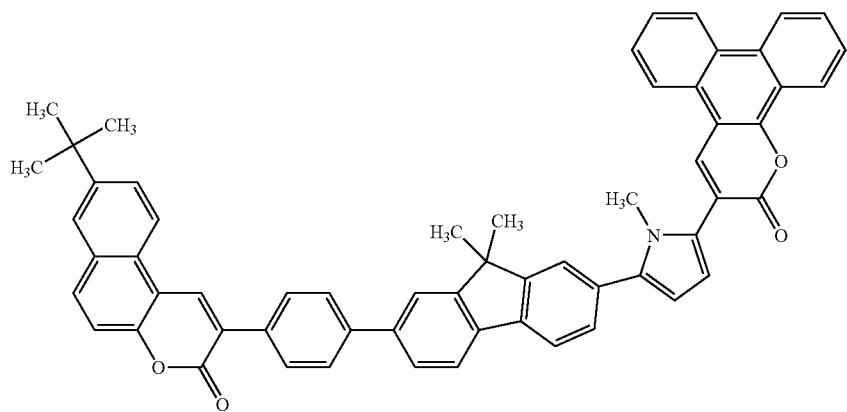
Chemical Formula 418:
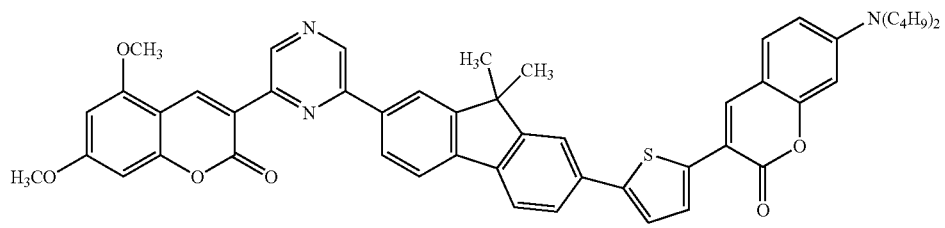
Chemical Formula 419:
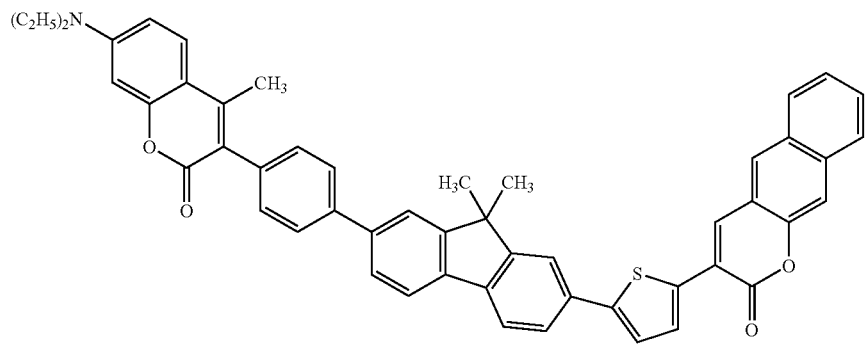

Chemical Formula 420:
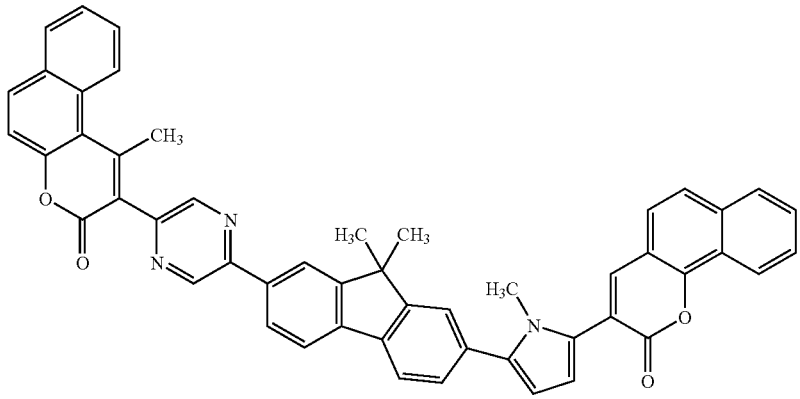
Chemical Formula 421:
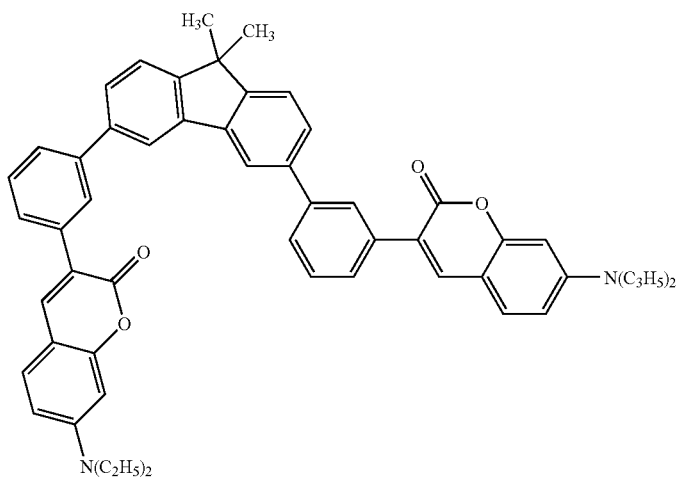
Chemical Formula 422:
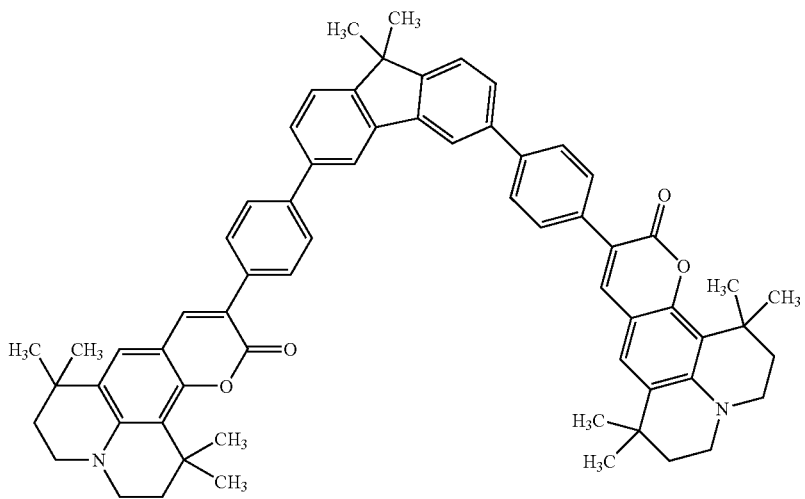

Chemical Formula 423:
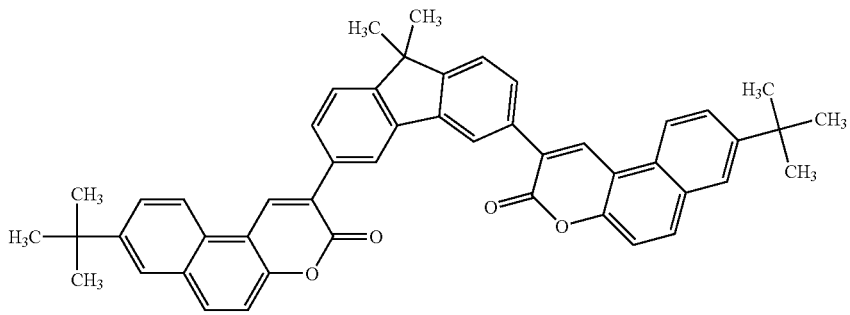
Chemical Formula 424:
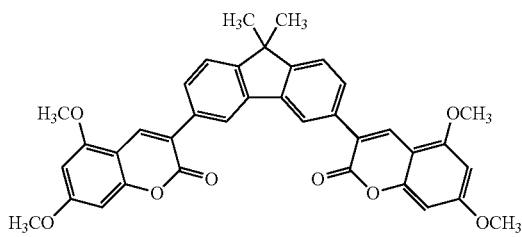
Chemical Formula 425:
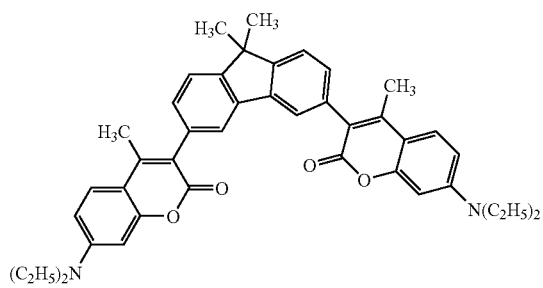
Chemical Formula 426:
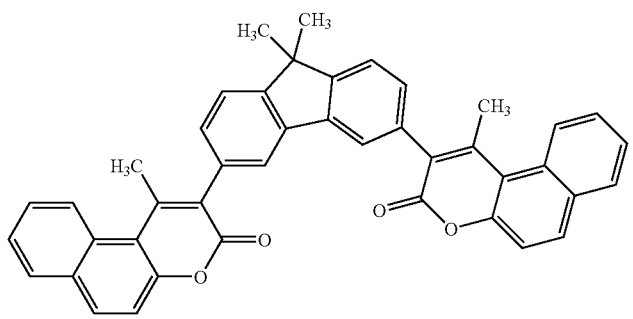
Chemical Formula 427:
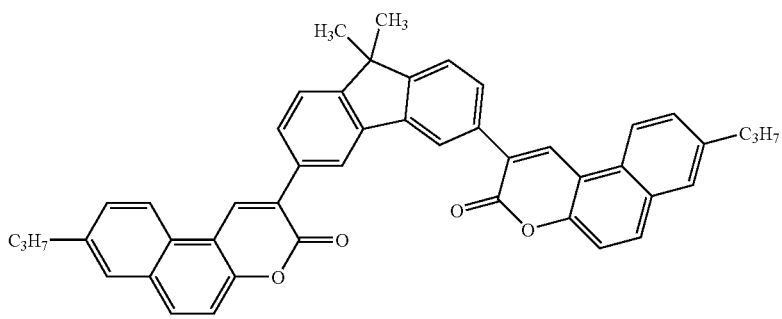
Chemical Formula 428:
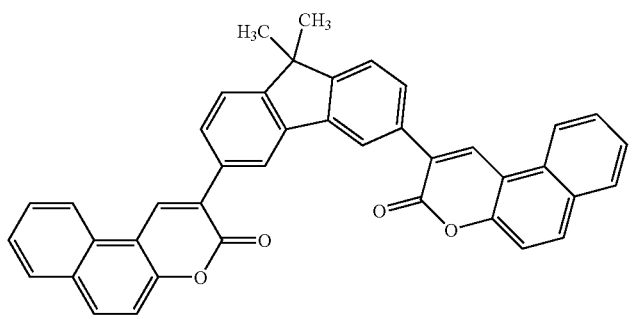

Chemical Formula 429:
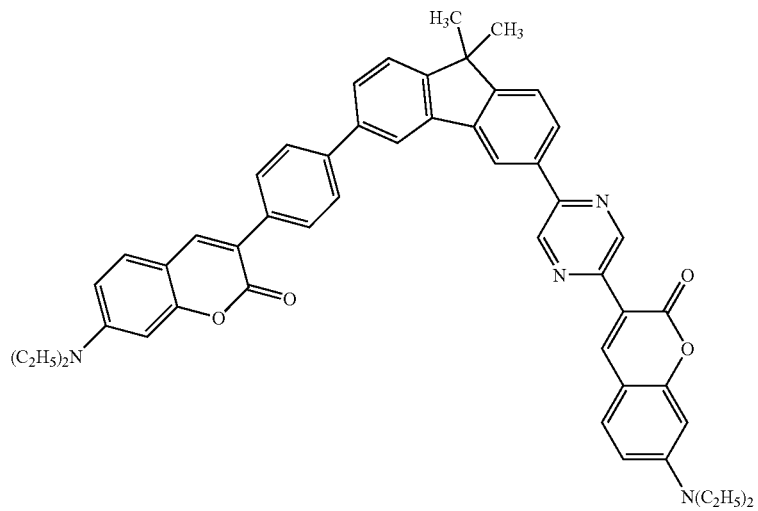
Chemical Formula 430:
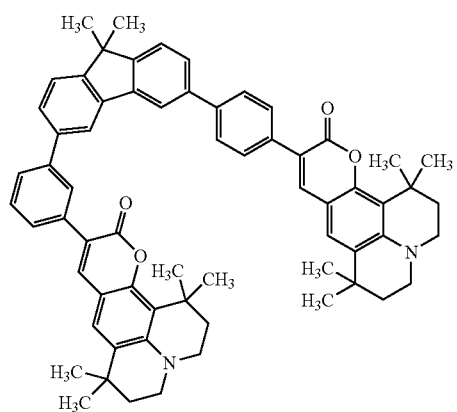
Chemical Formula 431:
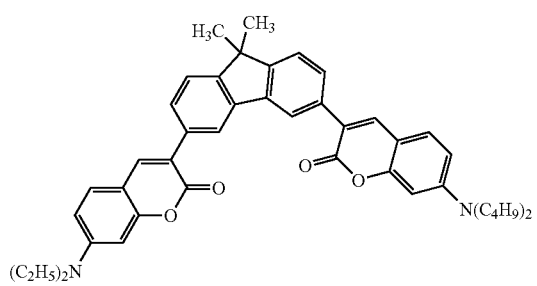
Chemical Formula 432:
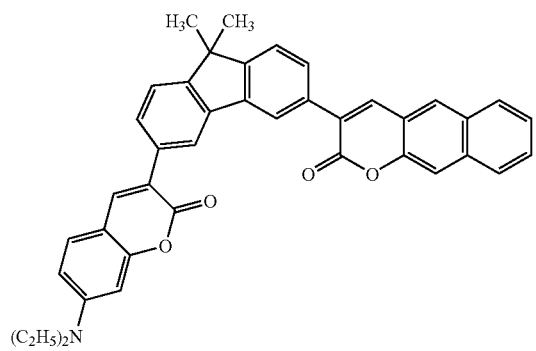
Chemical Formula 433:
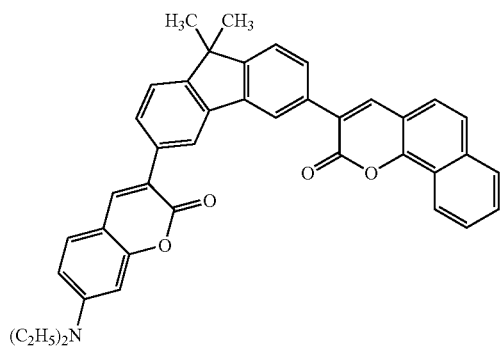

Chemical Formula 434:
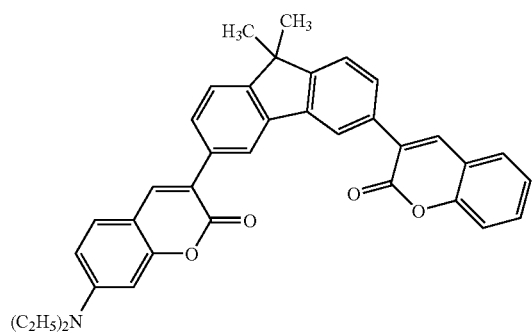
Chemical Formula 435:
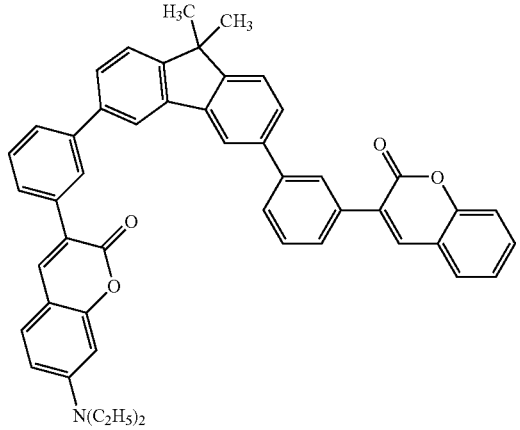
Chemical Formula 436:
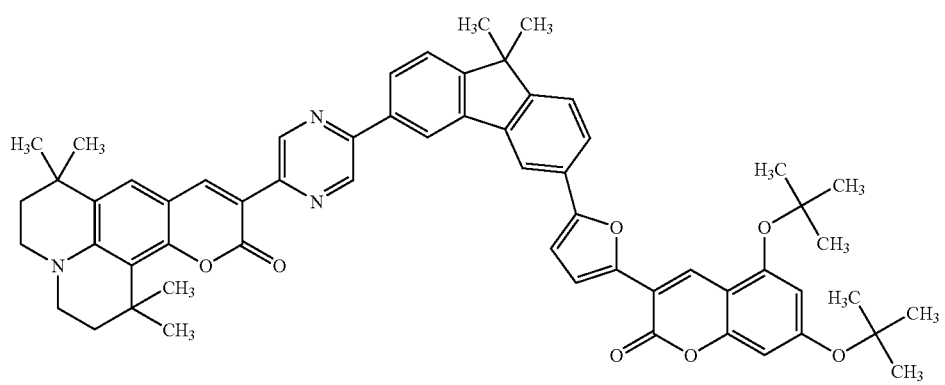
Chemical Formula 437:
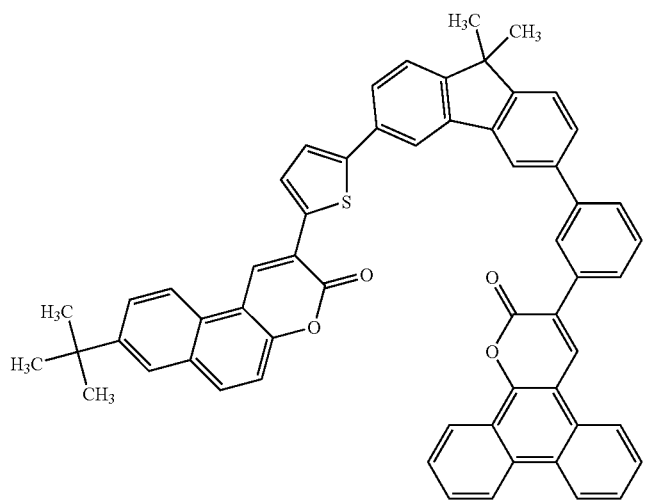

Chemical Formula 438:
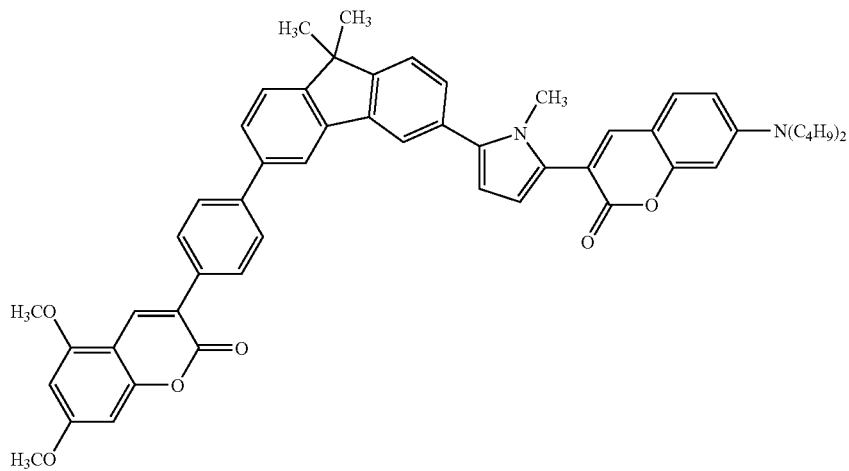
Chemical Formula 439:
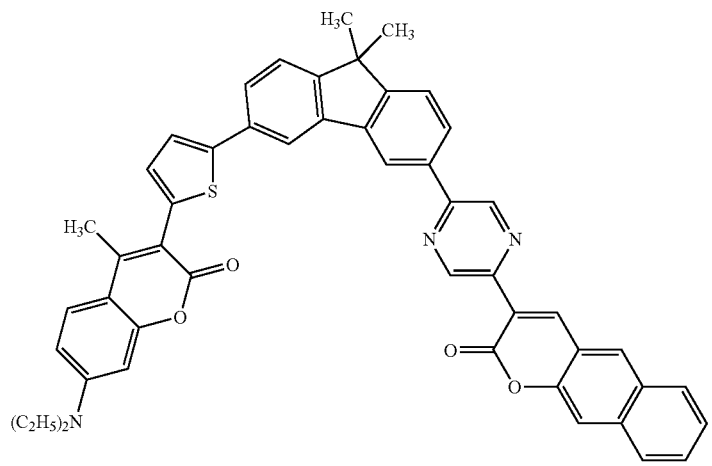
Chemical Formula 440:
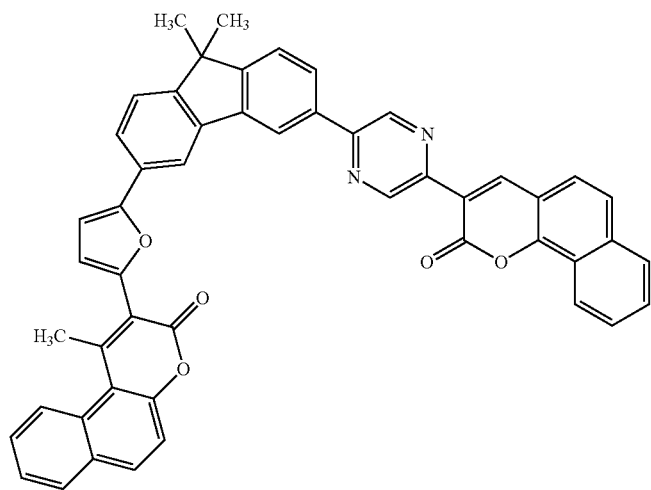

-continued
Chemical Formula 441:
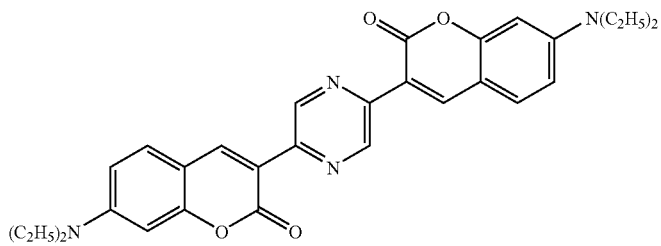
Chemical Formula 442:
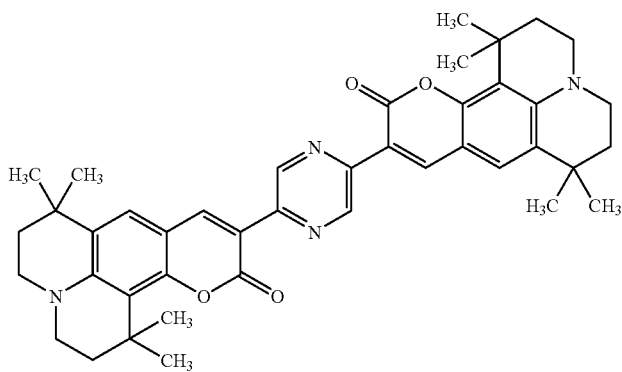
Chemical Formula 443:
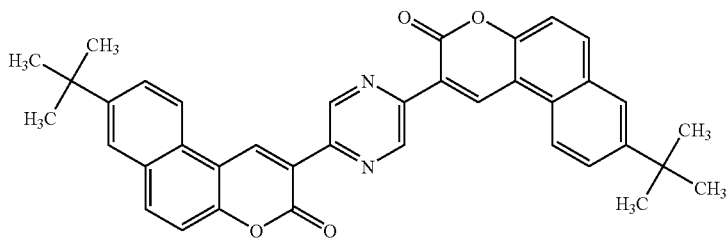
Chemical Formula 444:                         Chemical Formula 445:
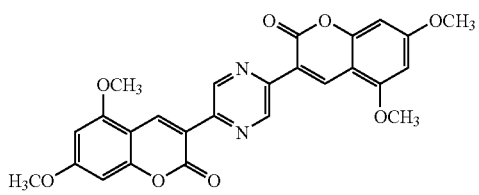              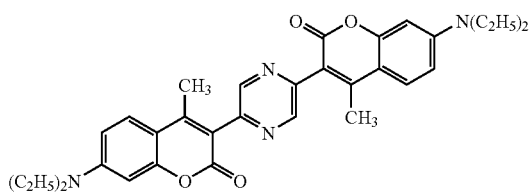
Chemical Formula 446:                         Chemical Formula 447:
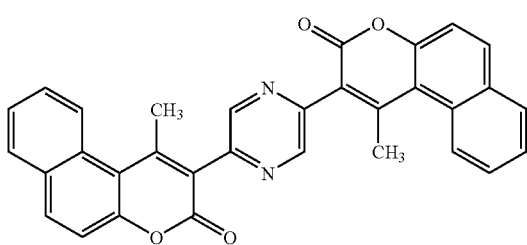              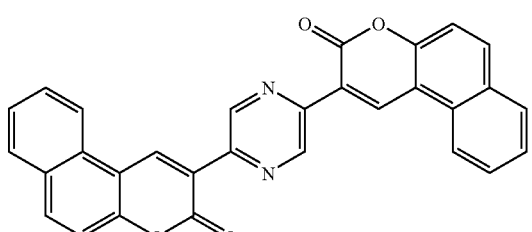
Chemical Formula 448:
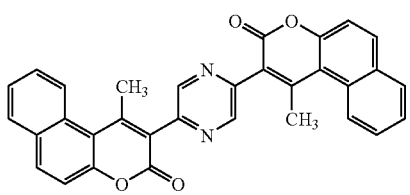

-continued
Chemical Formula 450:
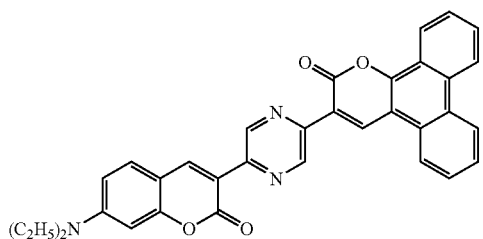
Chemical Formula 451:
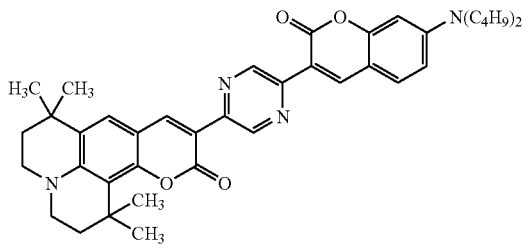
Chemical Formula 452:
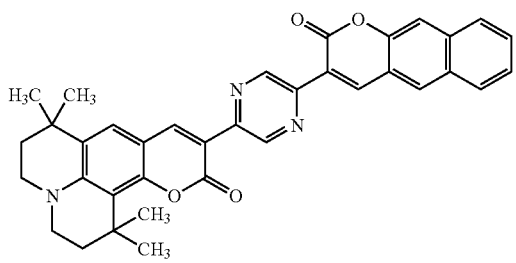
Chemical Formula 453:
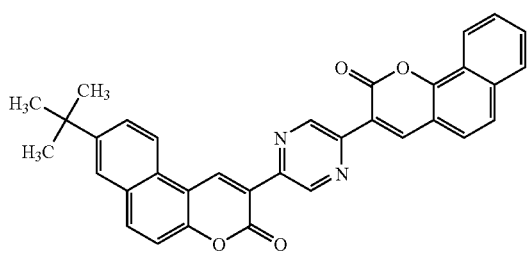
Chemical Formula 454:
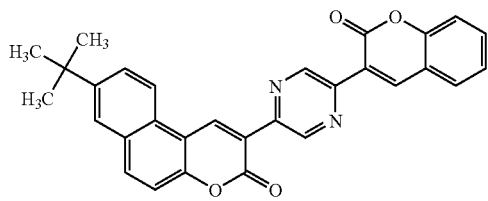
Chemical Formula 455:
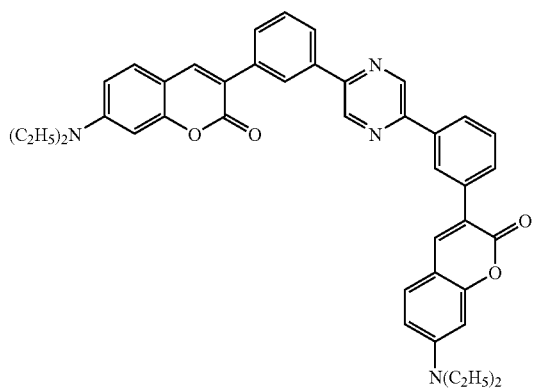
Chemical Formula 456:
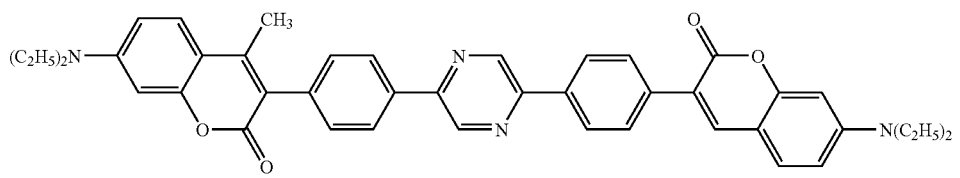
Chemical Formula 457:
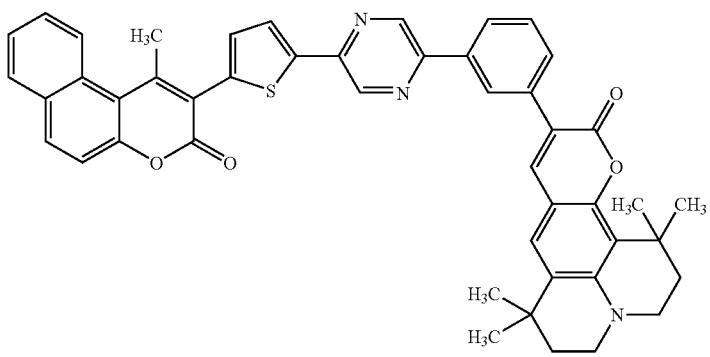

-continued
Chemical Formula 458:
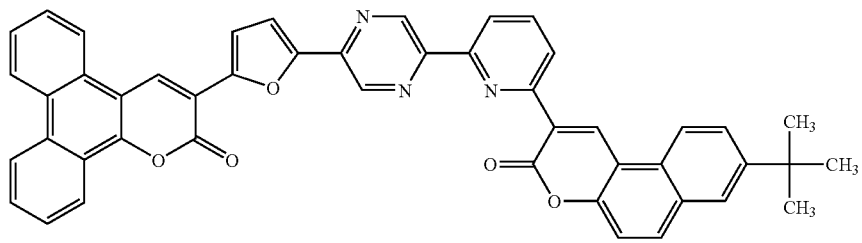
Chemical Formula 459:
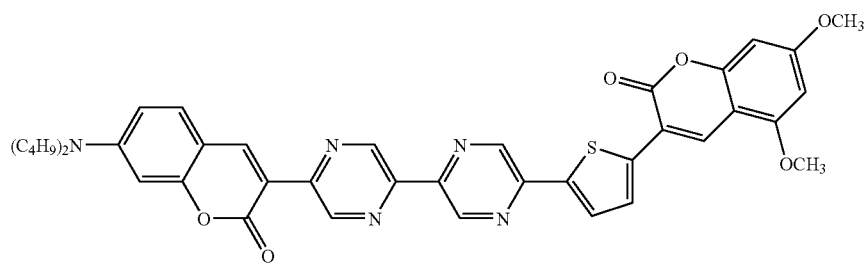
Chemical Formula 460:
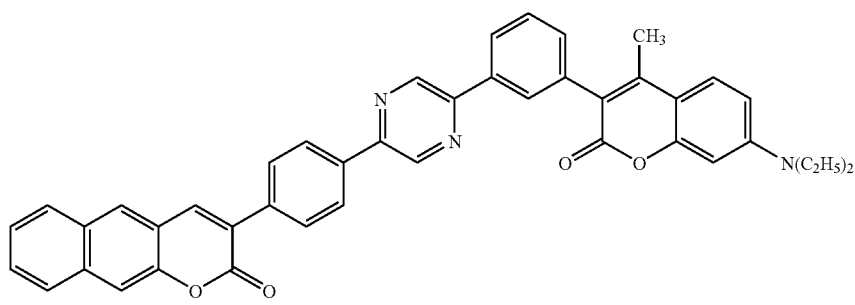
Chemical Formula 461:
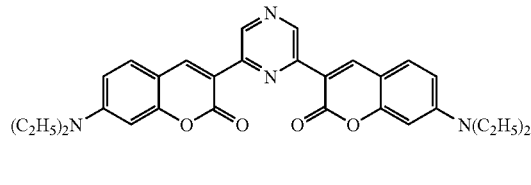
Chemical Formula 462:
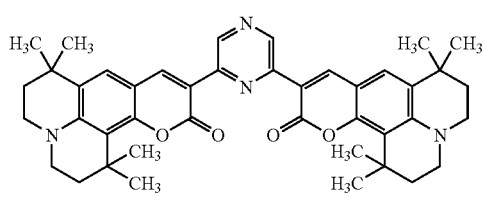
Chemical Formula 463:
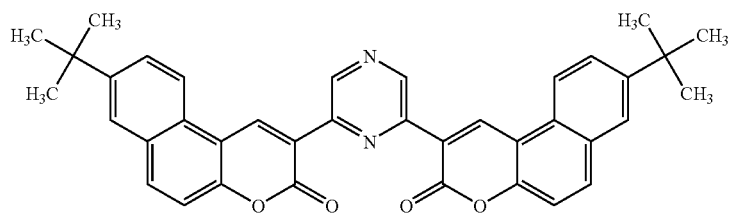
Chemical Formula 464:
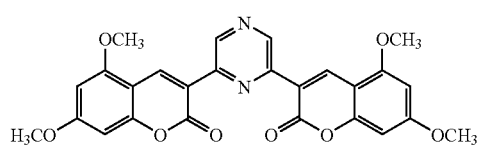
Chemical Formula 465:
Chemical Formula 466:
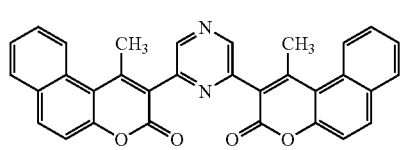
Chemical Formula 467:
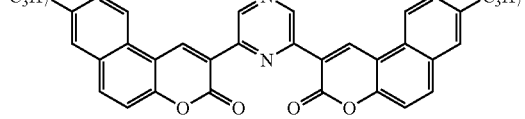

Chemical Formula 468:
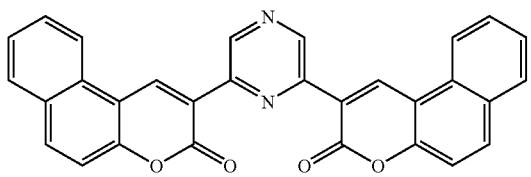
Chemical Formula 469:
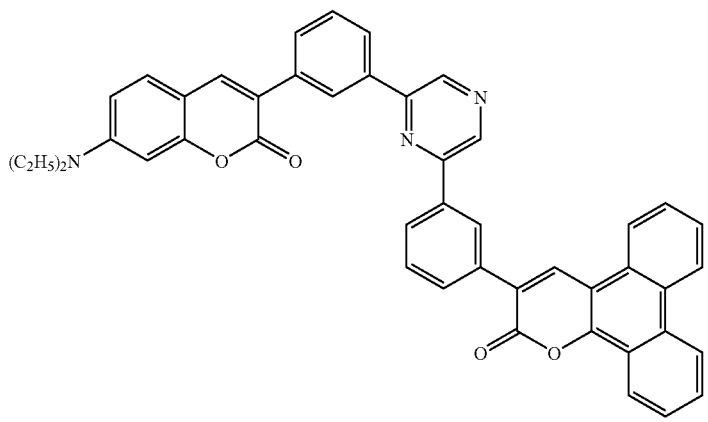
Chemical Formula 470:
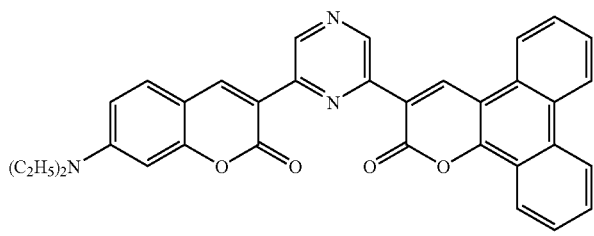
Chemical Formula 471:
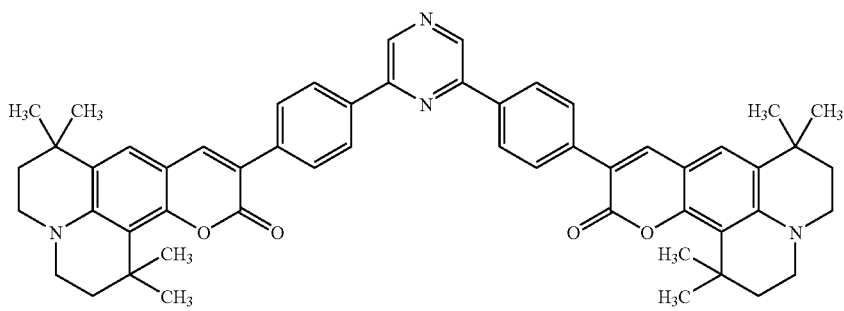
Chemical Formula 472:
Chemical Formula 473:
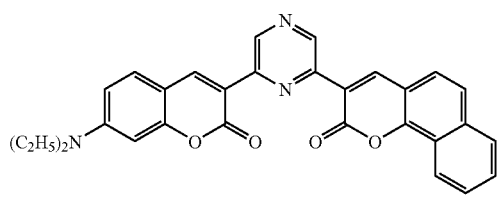

Chemical Formula 474:

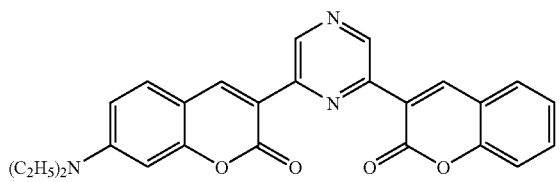

Although the coumarin compounds of the present invention can be prepared by various methods, they are preferably prepared by using the dehydration and condensation reaction method of an aldehyde group and an activated methylene group, when their production costs should not be neglected. According to the reaction method, the coumarin compound of the present invention can be produced in a satisfactory yield by reacting a compound represented by Formula 3 having ø corresponding to that in Formula 1 with a compound represented by Formula 4 having the groups of $R^1$ to $R^5$ corresponding to those in Formula 1, where m is an integer similarly as in Formula 3.

Formula 3:

Formula 4:

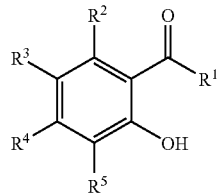

In general, the coumarin derivatives can be prepared by providing appropriate amounts of compounds represented by Formulae 3 and 4, dissolved in an appropriate solvent, for example, basic compounds such as sodium hydroxide, potassium hydroxide, sodium carbonate, potassium carbonate, sodium hydrogen carbonate, sodium carbonate, ammonia, triethylamine, piperidine, pyridine, pyrrolidine, aniline, N,N-dimethylaniline, and N,N-diethylaniline; acid compounds such as hydrochloric acid, sulfuric acid, nitric acid, acetic acid, acetic anhydride, trifluoroacetate, p-toluene sulfonate, methane sulfonate, trifluoromethane, p-toluene sulfonate, methane sulfonate, and trifluoromethane sulfonate; Lewis acid compounds such aluminum chloride, zinc chloride, tin chloride, and titanium tetrachloride; and reacting the mixture at ambient temperature or over under heating and stirring conditions while heat refluxing.

Examples of such an appropriate solvent include hydrocarbons such as pentane, cyclohexane, octane, benzene, toluene, and xylene; halogen compounds such as carbon tetrachloride, chloroform, 1,2-dichlorobenzene, 1,2-dibromobenzene, trichloroethylene, tetrachloroethylene, chlorobenzene, bromobenzene, and α-dichlorobenzene; alcohols and phenols such as methanol, ethanol, 1-propanol, 2-propanol, 1-butanol, 2-butanol, isobutyl alcohol, isopentyl alcohol, cyclohexanol, ethylene glycol, propylene glycol, 2-methoxyethanol, 2-ethoxyethanol, phenol, benzyl alcohol, cresol, diethylene glycol, triethylene glycol, and glycerine; ethers such as diethyl ether, diisopropyl ether, tetrahydrofuran, tetrahydropyran, 1,4-dioxane, anisole, 1,2-dimethoxyethane, diethylene glycol dimethyl ether, dicyclohexyl-18-crown-6, methyl carbitol, ethyl carbitol; acids and their derivatives such as acetic acid, acetic anhydride, trichloroacetate, trifluoroacetate, propionic acid anhydride, ethyl acetate, butyl carbonate, ethylene carbonate, propylene carbonate, formamide, N-methylformamide, N,N-dimethylformamide, N-methylacetamide, N,N-dimethylacetamide, hexamethylphosphoric triamide, and trimethyl phosphate; nitriles such as acetonitrile, propionitrile, succinonitrile, and benzonitrile; nitro compounds such as nitromethane and nitrobenzene; sulfur-atom-containing compounds such as dimethylsulfoxide and sulfolane; and water. Depending on use, these solvents can be used in an appropriate combination.

In the case of using the above solvents, the more the amount of the solvents used, the lower the reaction efficiency becomes, while the lower the amount of the solvents used, the more the homogeneous heating and stirring of the reaction mixtures becomes difficult or the more the formation of by-products tends to easily occur. Because of this, the amount of the solvents is preferably set to 100 times or lower, usually, 5 to 50 times of the total amount of the material compounds used. Varying depending on the kind of the material compounds and the reaction conditions used, the reaction should preferably be completed within 10 hours, usually, 0.5 to 5 hours. The reaction procedure can be monitored, for example, by conventional methods such as thin layer chromatography, gas chromatography, and high performance liquid chromatography. The coumarin compounds of the present invention are produced in a desired amount by the above method or in accordance therewith. The compounds represented by Formulae 3 and 4 can be prepared by conventional methods for producing their related compounds, and in case of commercialized products of such compounds being available, they can be appropriately purified before use, if necessary.

Depending on use, the coumarin compounds thus obtained can be used intact, however, they are usually used after purified by the methods generally used in their related compounds such as dissolution, separation, decantation, filtration, extraction, concentration, thin-layer chromatography, gas chromatography, high-performance liquid chromatography, distillation, sublimation, and crystallization; and if necessary these methods can be used in an appropriate combination. When used, for example, as a luminous agent for organic EL elements or a laser-active substances for dye lasers, which requires a high purity luminous organic compounds, the coumarin compounds should preferably be highly purified, for example, by distillation, crystallization and/or sublimation before use.

Among the above methods, sublimation is particularly advantageous because it facilitates to prepare a high purity crystal in a single step and in a lesser loss of the material coumarin compounds during its handling without incorporating the solvent used into the final crystal. The sublimation applicable to the present invention can be any of those conducted under normal or reduced pressure, however, the latter is preferably employed. To sublimate the coumarin compounds of the present invention by sublimation under reduced pressure, for example, an appropriate amount of any of the coumarin compounds is placed in a sublimation apparatus and heated at a temperature below their melting points as low as possible so as not to decompose them while keeping the inner pressure at a level of below $10^{-2}$ Torr, preferably, $10^{-3}$ Torr or lower. When the coumarin compounds subjected to sublimation purification have a relatively low purity, the levels of reducing pressure and heating temperature are controlled to prevent contamination of impurities, but, when the compounds do not easily sublimate, their sublimation can be accelerated by supplying rare or inactivated gasses to the inner space of the sublimation apparatus. The size of crystals obtained by such sublimation can be controlled by regulating the condensed surface in the sublimation apparatus, i.e., a relatively large-sized crystal can be obtained by keeping the temperature of the condensed surface at a slightly higher temperature than the heating temperature to gradually grow the forming crystal.

Explaining the use of the coumarin compounds of the present invention, as mentioned above, since the compounds have an absorption maximum in the visible region and a relatively large molecular absorption coefficient, they have various uses as materials for polymerizing polymeric compounds by irradiating visible light, sensitizing solar cells, modifying the color degree of optical filters, and for dyes to dye clothes. Particularly, most of the coumarin compounds of the present invention have an absorption maximum at around the wavelengths of conventional visible lasers, that emit light at a wavelength of around 500 nm, particularly, 450 to 550 nm, such as argon-ion-lasers, and krypton-ion-lasers; semiconductor lasers such as CdS lasers; and solid lasers such as distributed feedback lasers, and because of this the coumarin compounds can be quite advantageously used in the fields of information recordings such as facsimiles, copying machines, and printers; printings such as flexographies and gravure printings; printing circuits such as photoresists; and other fields of optical recording materials, optical materials, and holographies.

If necessary, in combination with one or more other light absorbers capable of absorbing light in the visible and/or infrared regions, the coumarin compounds of the present invention can be used in clothes in general and others including, for example, building/bedding/decorating products such as a drape, lace, casement, print, casement cloth, roll screen, shutter, shop curtain, blanket, thick bedquilt including comforter, peripheral material for the thick bedquilt, cover for the thick bedquilt, bed sheet, Japanese-style cushion, pillow, pillow cover, cushion, mat, carpet, sleeping bag, interior finish for car, and window glasses including car window glass; sanitary and health goods such as a paper diaper, diaper cover, eyeglasses, monocle, and lorgnette; internal base sheets, linings, and materials for shoes; wrappers; materials for umbrellas; parasols; stuffed toys; lighting devices; filters, panels and screens for information displaying devices which use cathode-ray tubes, liquid crystal displays, and plasma displays; sunglasses; sun visors; sunroofs; and peeping windows of ovens including electric ones. When used as wrapping materials, injection materials, and vessels for enclosing the above products, the coumarin compounds of the present invention prevent living bodies and the products from troubles and discomforts caused by environmental light such as natural and artificial light or reduce the troubles and discomforts, and furthermore they can advantageously modify the color, tint, and appearance and control the light reflected by or passed through the products to the desired color balance.

Since the coumarin compounds of the present invention, which have a luminescent maximum such as a fluorescent maximum in the visible region, emit a relatively short wavelength of visible light, they can be also advantageously used as those which require organic compounds with the above properties, for example, laser-active substances in dye lasers. When used in dye lasers, similarly as in constructing conventional dye laser oscillating apparatuses, the coumarin compounds of the present invention are purified and dissolved in an appropriate solvent, and after optionally adjusted to the desired pH level, the resulting solution is injected and sealed in a dye cell in a laser oscillating apparatus. Compared with conventional related compounds, the coumarin compounds of the present invention attain a satisfactory amplified gain over a distinctively wide range of wavelength in the visible region, have a relatively high thermal and light tolerance, and have a feature that they are hardly deteriorated even when used for a relatively long period of time. Examples of the other uses to which the coumarin compound of the present invention are applicable include uses as luminous agents for labelling enzymes, substrates, antigens, antibodies, soluble receptors, proteins, glycolipids, and nucleic acids general used in qualitative and quantitative analyses using specific reactions between substances derived from living bodies, such as an enzymatic reaction, antigen-antibody reaction, intra-/extra-cellular signal transmission, complex formation of proteins, and hybridization between protein and nucleic acid or between nucleic acids. The resulting biosubstances labelled with the coumarin compounds are distinctly useful in the fields of researches and diagnoses.

As mentioned above, most of the coumarin compounds of the present invention have a luminescent maximum such as a fluorescent maximum at a wavelength of shorter than 550 nm, usually, at a wavelength of 420 to 520 nm; emit a visible light ranging from the violet region to the green region when excited; form a stable thin membrane in a glassy state, and have a relatively high thermal tolerance. Because of these, by using alone or in combination with other luminous compounds, the coumarin compounds can be quite advantageously used as luminous agents for organic EL elements to emit visible light ranging from the violet region to the green region. The term "organic EL element(s)" as referred to as in the present invention means electroluminescent elements in general using the coumarin compounds of the present invention, particularly, it has an important applicability to mono- and multi-layer organic EL elements, which comprise an anode energized with positive voltage, a cathode energized with negative voltage, a luminous layer for allowing to emit light by rebinding the positive hole and the negative hole, and optionally a positive hole injection/transportation layer for injecting and transporting positive holes from the cathode, an electron injection/transportation layer for injecting and transporting electrons from the anode, and a positive hole block for regulating the transportation of positive holes from the luminous layer to the electron injection/transportation layer.

As it is well known that the actuation of organic EL elements comprise intrinsically the steps of injecting electrons and positive holes from a cathode, allowing the electrons and the positive holes to move though solids, rebinding the electrons and the positive holes to form a singlet exciton or a triplet exciton, emitting the excitons. The above steps are not intrinsically different independently of mono- and multi-layer organic EL elements. However, in mono-layer organic EL elements, the above fours steps can be improved by only modifying the molecular structure of a luminous compound, while in multi-layer organic EL elements, the functions required in each step can be distributed to a plurality of materials which can be optimized independently. Because of this, the desired function is generally more easily attained by constructing into a mono-layer form than into a multi-layer form.

Explaining the organic EL element of the present invention with reference to those in a multi-layer form, FIG. 1 is a brief figure of an example of the organic EL element of the present invention. In FIG. 1, the numeral 1 is a substrate which is generally prepared by forming the following material for such a substrate into a plate, sheet, or film form which can be optionally multilayered for use in an appropriate manner; glasses such as those of aluminosilicate, aluminoborosilicate, quarts, soda-lime, bariumsilicate, bariumborosilicate, and borosilicate; plastics such as aramide, polyacrylate, polyarylate, polyimide, polyurethane, polyether ketone, polyethersulfone, polyester, polyethylene, poly(ethylene terephthalate), polyolefin, polycarbonate, polysulfon, poly(vinyl chloride), polypropylene, polymethacrylate, epoxy resin, phenolic resin, fluorescein, and melamine resin; and ceramics of alumina, silicon, quartz, silicon carbide, etc. Preferable materials for substrate are, for example, photo-masking glasses with a lesser alkaline content and thermal expansion coefficient, plain surface free of scratch, and easiness of grinding; and others with a satisfactory assimilability to an adjacent electroconductive membrane and insubstantial moisture penetration, for example, plastics such as those of aramide, epoxy, phenol, polyarylate, polyimide, polyester, aromatic polyether, polyolefin, melamine, and fluorine. Opaque ceramic materials such as silicon can be used in combination with transparent materials for electrode. When the luminous coloration degree should be regulated, for example, means for regulating the luminous coloration degree such as filter membranes, membranes for altering coloration degree, and refractive membranes of dielectrics.

The numeral 2 is a cathode which is prepared by closely placing one or more metallic or electroconductive compounds, having an electrically low resistivity and a higher light transmittance, on either surface of a substrate 1 by the methods such as vacuum deposition, spattering, chemical vapor deposition (CVD), atomic layer epitaxy (ALE), applying, and soaking to form a mono- or multi-layer having a thickness of 10 to 1,000 nm, preferably, 50 to 500 nm and to give a resistivity of 1 k$\Omega$/□ or lower, preferably, 5 to 50 k$\Omega$/□. The electroconductive materials for the cathode 2 are, for example, metal such as gold, silver, aluminum, and nickel; metal oxides such as zinc oxide, tin oxide, indium oxide, and a mixture system of zinc oxide and indium oxide (abbreviated as "ITO" hereinafter); and electroconductive oligomers and polymers composed of a repeating unit of aniline, thiophene or pyrrole. Among these, ITO has a character that it facilitates to provide the cathode 2 with a lesser resistivity and to form a minute pattern by means of etching with acids, etc.

The numeral 3 is a positive hole injection/transportation layer and usually formed similarly as in the preparation of the cathode 2 in such a manner of closely attaching a material for the positive hole injection/transportation layer to make the material into a membrane having a thickness of 1 to 1,000 nm. Preferable examples of the material for the positive hole injection/transportation layer include those which has a lower ionization potential and a positive hole mobility of at least $10^{-6}$ cm$^2$/V·sec in an electric field, for example, of $10^4$ to $10^6$ V/cm or lower, in order to facilitate to inject and transport the positive holes from the cathode 2. Examples of the materials for positive hole injection/transportation layer include those which are used in organic EL elements, such as allylamine derivatives, imidazole derivatives, oxadiazole derivatives, oxazole derivatives, triazole derivatives, chalcone (benzylideneacetophenone) derivatives, styrylanthracene derivatives, stilbene derivatives, tetraallylethene derivatives, phthalocyanine derivatives, fluorenone derivatives, hydrazone derivatives, N-vinylcarbazole derivatives, pyrazoline derivatives, pyrazolone derivatives, phenylanthracene derivatives, phenylenediamine derivatives, polyarylalkane derivatives, polysilane derivatives, poly(phenylene vinylene) derivatives, and porphyrin derivatives, which are optionally used in an appropriate combination. Among these, aromatic tertiary amines, for example, monomers and polymers of allylamines such as monoallylamines, diallylamines, triallylamine, and tetraallylamines are most preferably used.

The numeral 4 is a luminous layer which is usually formed by, similarly as in the preparation of the anode 2, closely attaching to the positive hole injection/transportation layer one or more of the coumarin compounds of the present invention to form a membrane having a thickness of 10 to 1,000 nm, preferably, 10 to 200 nm. Since the coumarin compounds of the present invention easily form excitons such as a singlet and triplet excitons, emit light such as fluorescence and phosphorescence with a satisfactory energy level, and do not substantially induce "concentration quenching" of luminescence from the material of luminous layer per se, the luminescent brightness of luminescence from organic EL elements can be improved by increasing the ratio of the coumarin compounds in the luminous layer. In the case of using the coumarin compounds of the present invention and conventional host compounds in combination, the luminous layer 4 is formed by using the coumarin compound(s) in a molar ratio of up to equimolar, usually, 0.1 to 10 mol %, preferably, 0.5 to 5 mol % to the conventional host compound(s), and allowing them to form mono- or multi-layers having a thickness of 1 to 1,000 nm, preferably, 10 to 200 nm.

In the case of using the coumarin compounds of the present invention as guest compounds, examples of other luminous compounds usable in combination with the coumarin compound, i.e., host compounds, include quinolinol metal complexes conventionally used in organic EL elements; fused polycyclic aromatic hydrocarbons and derivatives thereof such as anthracene, chrysene, coronene, triphenylene, naphthacene, naphthalene, phenanthrene, picene, pyrene, fluorene, perylene, and benzopyrene; ring assembly hydrocarbons and derivatives thereof such as quarter phenyl, distyrylarylene, 1,4-diphenylbutadiene, stilbene, terphenyl, tetraphenylbutadiene, and biphenyl; heterocyclic compounds and derivatives thereof such as oxadiazole, carbazole, pyridazine, benzimidazole, benzooxazole, and benzothiazole; quinacridone, rubrene, and derivatives thereof; styryl polymethine dyes; and adamantane.

A group of the above host compounds, which are suitably used in organic EL elements that emit light in the blue region, are adamantane derivatives; examples of such are those represented by Formula 5.

Formula 5:

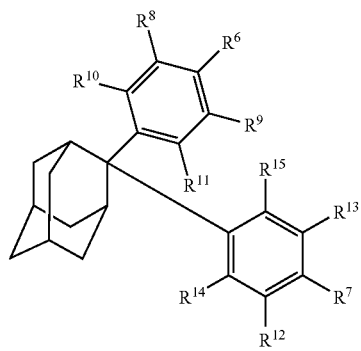

In Formula 5, $R^6$ and $R^7$ are the same or a different aromatic ring. Examples of such an aromatic ring include an azulene ring, acenaphthylene ring, anthracene ring, chrysene ring, triphenylene ring, naphthacene ring, naphthalene ring, picene ring, pyrene ring, phenanthrene ring, phenalene ring, perylene ring, benzene ring, biphenyl ring, terphenyl ring, and combinations thereof Among the adamantane derivatives represented by Formula 5, preferably used are fused polycyclic aromatic rings which have a fundamental structure of benzene ring, naphthalene ring, or phenanthrene ring such as chrysene ring, naphthalene ring, picene ring, pyrene ring, or perylene ring, and which have both a satisfactory luminous ability, a positive hole injection/transportation ability, and/or an electron injection/transportation ability.

The above aromatic rings may have one or more substituents; aliphatic hydrocarbon groups such as methyl, ethyl, propyl, isopropyl, isopropenyl, 1-propenyl, 2-propenyl, 2-propynyl, butyl, isobutyl, sec-butyl, tert-butyl, 2-butenyl, 1,3-butadienyl, pentyl, isopentyl, neopentyl, tert-pentyl, 1-methylpentyl, 2-methylpentyl, 2-pentenyl, 2-pentene-4-ynyl, hexyl, isohexyl, heptyl, octyl, nonyl, decyl, undecyl, dodecyl, and octadecyl groups; alicyclic hydrocarbon groups such as cyclopropyl, cyclobutyl, cyclopentyl, cyclohexyl, cyclohexenyl, and cycloheptyl groups; aromatic hydrocarbon groups such as phenyl, o-tolyl, m-tolyl, p-tolyl, xylyl, mesityl, o-cumenyl, m-cumenyl, p-cumenyl, and biphenylyl groups; heterocycles such as furyl, thienyl, piperidino, and quinolyl groups; ether groups such as methoxy, ethoxy, propoxy, isopropoxy, butoxy, isobutoxy, sec-butoxy, tert-butoxy, pentyloxy, phenoxy, and benzyloxy groups; ester groups such as methoxycarbonyl, ethoxycarbonyl, propoxycarbonyl, acetoxycarbonyl, acetoxy, and benzoyloxy; amino groups such as methylamino, dimethylamino, ethylamino, diethylamino, propylamino, dipropylamino, butylamino, dibutylamino, isobutylamino, diisobutylamino, sec-butylamino, tert-butylamino, pentylamino, and dipentylamino; halogen groups such as fluoro, chloro, bromo, and iodo groups; carbamoyl groups such as carbamoyl, methylcarbamoyl, dimethylcarbamoyl, ethylcarbamoyl, and diethylcarbamoyl; oxo group; thiooxo group, hydroxy group; mercapto group; formyloxy group; thioformyl group; carboxy group; thiocarboxy group; dithiocarboxy group; sulfo group; sulfino group; cyano group; isocyano group; cyanate group; isocyanate group; thiocyanate group; isothiocyanate group; nitro group; imino group; hydrazino group; and combinations thereof $R^8$ to $R^{15}$ in Formula 5 independently represent hydrogen or a substituent similarly as in $R^6$ and $R^7$. Examples of the adamantane derivatives include those disclosed in Japanese Patent Kokai No. 2001-110572.

While, it can be mentioned quinolinol metal complexes as a representative example of host compounds used preferably in organic EL elements which emit light in the green region. The term "quinolinol metal complexes" as referred to as in the present invention generally means complexes which comprise, as ligands, quinolinols such as 8-quinolinols, benzoquinoline-10-ols, etc., which have a pyridine residue and hydroxyl group intramolecularly; and metals or oxides thereof as a central atom usually belonging to the 1, 2, 12, and 13 groups in the periodic law table, for example, monovalent, divalent or trivalent elements such as lithium, sodium, calcium, beryllium, magnesium, calcium, zinc, boron, aluminum, gallium, and indium, which receive electron pairs from the nitrogen atom in the pyridine residue in each of the above quinolinols. When 8-quinolinols or benzoquinoline-10-ols are used as ligands, they may have one or more substituents and do not exclude the binding of the following substitutes to their carbon atoms other than C-8 or C-10 bound with hydroxy group; halogen groups such as fluoro, chloro, bromo, and iodo groups; aliphatic hydrocarbons such as methyl, ethyl, propyl, isopropyl, butyl, isobutyl, sec-butyl, tert-butyl, pentyl, isopentyl, neopentyl, and tert-pentyl groups; ether groups such as methoxy, ethoxy, propoxy, isopropoxy, butoxy, isobutoxy, sec-butoxy, tert-butoxy, pentyloxy, isopentyloxy, hexyloxy, phenoxy, benzyloxy groups; ester groups such as acetoxy, benzoyloxy, methoxycarbonyl, ethoxycarbonyl, and propoxycarbonyl groups; cyano, nitro, sulfo; and combinations thereof. When the quinolinol metal complexes have at least two ligands intramolecularly, the ligands may be the same or different each other.

Examples of the quinolinol metal complexes include aluminum complexes such as tris(8-quinolinolato)aluminum, tris(3,4-dimethyl-8-quinolinolato)aluminum, tris(4-methyl-quinolinolato)aluminum, tris(4-methoxy-8-quinolinolato) aluminum, tris(4,5-dimethyl-8-quinolinolato)aluminum, tris(4,6-dimethyl-8-quinolinolato)aluminum, tris(5-chloro-8-quinolinolato)aluminum, tris(5-bromo-8-quinolinolato) aluminum, tris(5,7-dichloro-8-quinolinolato)aluminum, tris(5-cyano-8-quinolinolato)aluminum, tris(5-sulfonyl-8-quinolinolato)aluminum, tris(5-propyl-8-quinolinolato) aluminum, bis(2-methyl-8-quinolinolato)aluminum, tris(5-bromo-8-quinolinolato)aluminum oxide; zinc complexes such as bis(8-quinolinolato)zinc, bis(2-methyl-8-quinolinolato)zinc, bis(2,4-dimethyl-8-quinolinolato)zinc, bis(2-methyl-5-chloro-8-quinolinolato)zinc, bis(2-methyl-5-cyano-8-quinolinolato)zinc, bis(3,4-dimethyl-8-quinolinolato)zinc, bis(4,6-dimethyl-8-quinolinolato)zinc, bis(5-chloro-8-quinolinolato)zinc, and bis(5,7-dichloro-8-quinolinolato) zinc; beryllium complexes such as bis(8-quinolinolato)beryllium, bis(2-methyl-8-quinolinolato)beryllium, bis(2,4-dimethyl-8-quinolinolato)beryllium, bis(2-methyl-5-chloro-8-quinolinolato)beryllium, bis(2-methyl-5-cyano-8-quinolinolato)beryllium, bis(3,4-dimethyl-8-quinolinolato) beryllium, bis(4,6-dimethyl-8-quinolinolato)beryllium, bis (5-chloro-8-quinolinolato)beryllium, bis(4,6-dimethyl-8-quinolinolato)beryllium; bis(10-hydroxybenzo[h] quinolinolato)beryllium; magnesium complexes such as bis (8-quinolinolato)magnesium, bis(2-methyl-8-quinolinolato) magnesium, bis(2,4-dimethyl-8-quinolinolato)magnesium, bis(2-methyl-5-chloro-8-quinolinolato)magnesium, bis(2-methyl-5-cyano-8-quinolinolato)magnesium, bis(3,4-dimethyl-8-quinolinolato)magnesium, bis(4,6-dimethyl-8-quinolinolato)magnesium, bis(5-chloro-8-quinolinolato) magnesium, and bis(5,7-dichloro-8-quinolinolato) magnesium; indium complexes such as bis(8-quinolinolato) indium; gallium complexes such as tris(5-chloro-8-quinolinolato)gallium; and calcium complexes such as bis(5- chloro-8-quinolinolato)calcium, which can be used in an appropriate combination. Since the above host compounds are just exemplified, the present invention are never restricted thereby.

The numeral 5 is an electron injection/transportation layer and usually formed by a method similarly as in the anode 2 in such a manner of forming a membrane having a thickness of 10 to 500 nm to be closely attached to the luminous layer 4 by using one or more organic compounds with a higher electron affinity, anthraquinodimethane derivatives, anthrone derivatives, oxadiazole derivatives, carbodiimides, distyrylpyradine derivatives, diphenylquinone derivatives, silazane derivatives, thiopyrazineoxide derivatives, triazole derivatives, tetracarboxylic acid derivatives of heterocyclic compounds, phthalocyanine derivatives, fluorenone derivatives, quinolinol metal complexes similarly as in the luminous slayer 4, and electroconductive oligomers/polymers having aniline, thiophene, pyrrole, etc., as a repeating unit. In the case of using a plurality of materials for electron injection/transportation layer, they can be formed into a single layer after mixed to homogeneity or respectively formed into layers for forming multi-layers adjacent each other. In the case of providing a positive hole block layer, prior to the formation of the electron injection/transportation layer 5, such a positive hole block layer is formed by a method similarly as used in the anode 2 into a thin membrane to be closely attached to the luminous layer 4, for example, using materials for positive hole block layer, such as oxadiazole compounds including 2-biphenyl-4-yl-5-(4-tert-butyl phenyl)-[1,3,4]oxadiazole, 2,2-bis[5-(4-biphenyl)-1,3,4-oxadiazole-2-yl-1,4-phenylene]hexafluoropropane, and 1,3,5-tris-(2-naphthalene-1-yl-[1,3,4]oxadiazole-5-yl)benzene. The thickness of the positive hole injection layer is set to a level of 1 to 100 nm, usually, 5 to 50 nm, depending on the thickness of the electron injection/transportation 5 and the operation property of the aimed organic EL devices.

The numeral 6 is a cathode which is usually formed to be closely attached to the electron injection/transportation layer 5 by depositing on the electron injection/transportation layer any of or an appropriate combination of metals, alloys, metal oxides and electroconductive compounds such as lithium, magnesium, calcium, sodium, potassium, silver, copper, aluminum, indium and ytterbium, which have a low work function, i.e., usually at most 5 eV, than those of the compounds used in the electron injection/transportation layer 5. The thickness of the cathode 6 should not be restricted to a specific one, and it is usually set to a level of at least 10 nm, preferably, 50 to 500 nm to give a resistivity of 1 k$\Omega$/□ or lower, depending on the electroconductivity, production cost, overall thickness, and light transmissivity of the aimed element. To improve the adhesion, an interface layer, which comprises any of compounds such as aromatic diamine compounds, quinacridone compounds, naphthacene compounds, organic silicone compounds, and organic phosphorous compounds, can be optionally installed between the cathode 6 and the electron injection/transportation layer 5 comprising an organic compound. To facilitate the transportation of electrons from the cathode 6 to the electron injection/transportation layer 5, for example, an alkaline metal compound or an alkaline earth metal compound such as lithium fluoride or lithium oxide can be formed into a thin membrane with a thickness of 0.1 to 2 nm on the side of the cathode 6 to be contacted with the electron injection/transportation layer 5 by using a similar method as used in the anode 2.

As described above, the organic EL element of the present invention is prepared by systemically forming on a substrate an anode layer and a cathode layer, while optionally closely attaching each other a positive hole injection/transportation layer, an electron injection/transportation layer, and/or a positive hole block layer on the substrate. In forming these layers, it is preferable to perform their processings under a highly reduced pressure, particularly, at a pressure of $10^{-5}$ Torr or lower to minimize the oxidation and the decomposition of the organic compounds used, as well as the adsorption of oxygen and moisture as low as possible. In forming the luminous layer, the composition ratio of the guest and host compounds in the luminous layer can be controlled by previously mixing the compounds in a prescribed ratio, or by independently regulating the deposition rate of the compounds during their deposition in vacuo. The organic EL element thus constructed is preferably sealed partly or wholly, for example, with a sealing glass or metal cap, covered with a protective membrane, or coated with a protective membrane of ultraviolet hardening resins. Varying depending on the structure of the organic EL element, in order to effectively extract light from the luminous layer to the outside of the element any of or an appropriate combination of diffraction means, which alter the angle of incidence of the light against the light-extracting surface in the element, such as zoneplates or one- or two-dimensional reflection- or transmission-type diffraction gratings can be installed in an appropriate position of the element to regulate the total reflection of the interface between the light-extracting surface and the atmosphere.

Explaining the use of the organic EL element of the present invention, it is operated by intermittent energization with a relatively high voltage of pulse voltage or by continuous energization with a relatively low voltage of non-pulse voltage, usually, 2 to 50 V The organic EL element emits light only when the anode has a higher voltage than that of the cathode. Any dc or ac voltage with an appropriate voltage wave form and cycle can be applied to the organic EL element. When energized with ac voltage, the organic EL element of the present invention will theoretically repeat the increase or the decrease of brightness or repeat flashing depending on the wave form and cycle of the energized current. In the case of the organic EL element shown in FIG. 1, when voltage is energized between the anode 2 and the cathode 6, positive holes injected from the anode 2 move to the luminous layer 4 through the positive hole injection/transportation layer 3, and electrons injected from the cathode 6 move to the luminous layer 4 through the electron injection/transportation layer 5. As a result, the positive holes and the electrons rebind in the luminous layer 4 to excite a coumarin compound, followed by emitting the desired light from the excited coumarin compound through the anode 2 and the substrate 1. Depending on the structure and the composition ratio of the coumarin compound and the host compound used in combination, the organic EL element of the present invention has a luminescent maximum such as a fluorescent maximum in the visible region at wavelengths of around 470 nm, usually, in the violet region to the green region at wavelengths of 420 to 520 nm. The luminescence usually has x of 0.1 to 0.4 and y of 0.1 to 0.7 on the Commission International de l'Eclairage's (CIE) x-y chromaticity diagram. Since the organic EL element of the present invention easily increases in brightness due to its advantageous durability and high luminescent efficiency, and thus it has a various uses in both luminous materials and information displaying apparatuses for visually displaying information. Since the luminous materials, comprising the organic EL element of the present invention as a light source, are low in consumption wattage and easily constructed into a lightweight panel form, it is advantageously used as a light source in general, as well as energy- and space-saving lightweight source or information displaying element such as in liquid elements, copying machines, printers, electrophotographic machines, computers including their application appliances, industrial regulators, electric measurement apparatuses, analyzers, instruments in general, communication devices, medical electric measurements, and electric apparatuses in general for home uses and business uses; and others such as apparatuses in general which are used in automobiles, ships, airplanes, and space ships; apparatuses for controlling airplanes; interiors; displaying panels; and signs. In the case of using the organic EL element, for example, as a displaying means for use in meters for automobiles, ships, airplanes, and space ships; computer termini, television receivers, recorders, gaming machines, clocks, calculators, telephones, communication apparatuses, car navigation systems, oscilloscopes, radars, sonars, displaying panels, and signs, it can be used alone or optionally used in combination with other organic EL element(s) which emits a visible light in the blue, green and/or red regions or with appropriate filters for modifying the color degree and color tone of luminescence by operating with a simple matrix or active matrix operation circuit.

As described above, since the coumarin derivatives of the present invention have an absorption maximum in the region with wavelengths of shorter than 550 nm, more particularly, in the region with wavelengths ranging from about 350 nm to about 500 nm, and have a high molecular absorption coefficient of $1\times10^4$ or over, preferably, $3\times10^4$ or over, they can be also advantageously used as materials for regulating color degree to regulate the color degree of the light emitted from organic EL elements to a desired level. Thus, the term "organic EL element(s)" as referred to as in the present invention includes those which comprise a specific coumarin compound as a material for luminous layer, and others in general which comprise a specific coumarin compound, which is provided alone in a part other than luminous layer, for regulating the color. degree of electrolytic luminescence by luminous compounds; and optionally one or more other light-absorptive compounds.

The following examples explain the preferred embodiments of the present invention:

EXAMPLE 1

Coumarin Compound

An adequate amount of xylene was placed in a reaction vessel, followed by dispersing therein 3.86 g of N,N-diethylaminosalicylaldehyde and 1.56 g of m-phenylenediacetonitrile. Adequate amounts of acetic acid and pyridine were added to the above mixture under stirring conditions and dissolved by heating, followed by reacting the mixture for two hours under heat refluxing conditions. Thereafter, the reaction mixture was cooled to ambient temperature and admixed with an adequate amount of methanol, followed by collecting the formed crystals and recrystallizing them in a mixture solution of chloroform and methanol to yield 3.73 g of a pale yellow needle-like crystal of the coumarin compound, represented by Chemical Formula 1, according to the present invention.

A portion of the crystal was. sampled and measured for visible light absorption spectrum and fluorescent spectrum in methylene chloride in a usual manner, revealing to have an absorption maximum at a wavelength of around 410 nm ($\epsilon=7.24\times10^4$) and a fluorescent maximum at a wavelength of around 465 nm. When measured for melting point, glass transition point, and decomposition point on conventional DSC analysis, the coumarin compound of this example had a melting point of 220 to 227° C., a glass transition point of about 88° C., and a decomposition point of about 422° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.23 (12H, t), 3.43 (8H, q), 6.54 (2H, d), 6.60 (2H, dd), 7.33 (2H, d), 7.42-7.48 (1H, m), 7.67-7.70 (2H, m), 7.77 (2H, s), and 7.98 (1H, m).

The coumarin compound, having an improved thermostability and an absorption- and fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 2

Coumarin Compound

Except for replacing N,N-diethylaminosalicylaldehyde with 3.65 g of 4,6-dimethoxysalicylaldehyde, the reaction of Example 1 was similarly proceeded, resulting in a yield of 0.5 g of a pale yellow needle-like crystal of the coumarin compound, represented by Chemical Formula 4, according to the present invention.

A portion of the crystal was sampled and measured for visible light absorption spectrum and fluorescent spectrum in methylene chloride in a usual manner, revealing to have an absorption maximum at a wavelength of around 354 nm ($\epsilon=4.63\times10^4$) and a fluorescent maximum at a wavelength of around 436 nm. When measured for melting point, glass transition point, and decomposition point on conventional DSC analysis, the coumarin compound of this example had a melting point of 307 to 312° C., a glass transition point of about 116° C., and a decomposition point of about 412° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 3.88 (6H, s), 3.92 (6H, s), 6.31 (2H, d), 6.47 (2H, d), 7.48-7.51 (1H, m), 7.71-7.74 (2H, m), 7.99 (1H, m), and 7.17 (2H, s).

The coumarin compound, having an improved thermostability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 3

Coumarin Compound

Except for replacing m-phenylenediacetonitrile with p-phenylenediacetonitrile, the reaction of Example 1 was similarly proceeded, resulting in a yield of 2.0 g of a yellow crystal of the coumarin compound, represented by Chemical Formula 21, according to the present invention.

A portion of the crystal was sampled and measured for visible light absorption spectrum and fluorescent spectrum in methylene chloride in a usual manner, revealing to have an absorption maximum at a wavelength of around 425 nm ($\epsilon=7.68\times10^4$) and a fluorescent maximum at a wavelength of around 495 nm. When measured for melting point, glass transition point, and decomposition point on conventional DSC analysis, the coumarin compound of this example had a melting point of 297 to 310° C. and a decomposition point of about 419° C., but had no glass transition point. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.23 (12H, t), 3.44 (8H, q), 6.54 (2H, d), 6.60 (2H, dd), 7.33 (2H, d), 7.73 (2H, s), and 7.76 (4H, s).

The coumarin compound, having an improved thermostability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 4

Coumarin Compound

Except for replacing N,N-diethylaminosalicylaldehyde and m-phenylenediacetonitrile with 3.65 g of 4,6-dimethoxysalicylaldehyde and 1.56 g of p-phenylenediacetonitrile, the reaction of Example 1 was similarly proceeded, resulting in a yield of 0.56 g of a pale yellow crystal of the coumarin compound, represented by Chemical Formula 24, according to the present invention.

A portion of the crystal was sampled and measured for visible light absorption spectrum and fluorescent spectrum in methylene chloride in a usual manner, revealing to have an absorption maximum at a wavelength of around 377 nm ($\epsilon=5.03\times10^4$) and a fluorescent maximum at a wavelength of around 466 nm. When measured for melting point, glass transition point, and decomposition point on conventional DSC analysis, the coumarin compound of this example had a melting point of 320 to 325° C. and a decomposition point of about 409° C., but had no glass transition point. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 3.88 (6H, s), 3.93 (6H, s), 6.32 (2H, d), 6.47 (2H, d), 7.79 (4H, s), and 8.17 (2H, s).

The coumarin compound, having an improved thermostability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 5

Coumarin Compound

Except for replacing N,N-diethylaminosalicylaldehyde and m-phenylenediacetonitrile with 5.5 g of 1,1,7,7-tetramethyl-8-hydroxy-9-formyl julolidine and 1.56 g of p-phenylenediacetonitrile, the reaction of Example 1 was similarly proceeded, resulting in a yield of 1.5 g of a yellow powdery crystal of the coumarin compound, represented by Chemical Formula 22, according to the present invention.

A portion of the crystal was sampled and measured for visible light absorption spectrum and fluorescent spectrum in methylene chloride in a usual manner, revealing to have an absorption maximum at a wavelength of around 442 nm ($\epsilon=7.34\times10^4$) and a fluorescent maximum at a wavelength of around 508 nm. When measured for melting point, glass transition point, and decomposition point on conventional DSC analysis, the coumarin compound of this example had a melting point of 369 to 375° C., a glass transition point of about 181° C., and a decomposition point of about 429° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.32 (12H, s), 1.60 (12H, s), 1.75-1.83 (8H, m), 3.23-3.32 (8H, m), 7.26 (2H, s), 7.70 (2H, s), and 7.78 (4H, s).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 6

Coumarin Compound

Except for replacing m-phenylenediacetonitrile with 1.3 g of 1,3,5-benzenetriacetonitrile, the reaction of Example 1 was similarly proceeded, resulting in a yield of 2.6 g of a yellow crystal of the coumarin compound, represented by Chemical Formula 209, according to the present invention.

A portion of the crystal was sampled and measured for visible light absorption spectrum and fluorescent spectrum in methylene chloride in a usual manner, revealing to have an absorption maximum at a wavelength of around 412 nm ($\epsilon=1.16\times10^5$) and a fluorescent maximum at a wavelength of around 466 nm. When measured for melting point, glass transition point, and decomposition point on conventional DSC analysis, the coumarin compound of this example had a melting point of 202 to 211° C., a glass transition point of about 142° C., and a decomposition point of about 427° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.24 (18H, t), 3.44 (12H, q), 6.54 (3H, d), 6.61 (3H, dd), 7.36 (3H, d), 7.86 (3H, s), and 8.03 (3H, s).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 7

Coumarin Compound

Except for replacing N,N-diethylaminosalicylaldehyde and m-phenylenediacetonitrile with 5.5 g of 1,1,7,7-tetramethyl-8-hydroxy-9-formyljulolidine and 1.3 g of 1,3,5-benzenetriacetonitrile, the reaction of Example 1 was similarly proceeded, resulting in a yield of 0.33 g of a yellow powdery crystal of the coumarin compound, represented by Chemical Formula 210, according to the present invention.

A portion of the crystal was sampled and measured for visible light absorption spectrum and fluorescent spectrum in methylene chloride in a usual manner, revealing to have an absorption maximum at a wavelength of around 426 nm ($\epsilon=1.15\times10^5$) and a fluorescent maximum at a wavelength of around 480 nm. When measured for melting point, glass transition point, and decomposition point on conventional DSC analysis, the coumarin compound of this example had a melting point of 413 to 417° C., a glass transition point of about 233° C., and a decomposition point of about 456° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.32 (18H, s), 1.61 (18H, s), 1.77-1.85 (12H, m), 3.22-3.32 (12H, m), 7.21 (3H, s), 7.90 (3H, s), and 8.21 (3H, s).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 8

Coumarin Compound

Except for replacing m-phenylenediacetonitrile with 2.32 g of 3,3'-biphenylacetonitrile, the reaction of Example 1 was similarly proceeded, resulting in a yield of 1.5 g of a pale yellow powdery crystal of the coumarin compound, represented by Chemical Formula 41, according to the present invention.

A portion of the crystal was sampled and measured for visible light absorption spectrum and fluorescent spectrum in methylene chloride in a usual manner, revealing to have an absorption maximum at a wavelength of around 404 nm ($\epsilon=7.41\times10^4$) and a fluorescent maximum at a wavelength of around 466 nm. When measured for melting point, glass transition point, and decomposition point on conventional DSC analysis, the coumarin compound of this example had a melting point of 183 to 193° C., a glass transition point of about 99° C., and a decomposition point of about 436° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.23 (12H, t), 3.43 (8H, q), 6.55 (2H, d), 6.60 (2H, dd), 7.33 (2H, d), 7.46-7.51 (2H, m), 7.59-7.61 (2H, m), 7.71-7.73 (2H, m), 7.76 (2H, s), and 7.89-7.90 (2H, m).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 9

Coumarin Compound

Except for m-phenylenediacetonitrile with 2.32 g of 4,4'-biphenyldiacetonitrile, the reaction of Example 1 was similarly proceeded, resulting in a yield of 2.6 g of a bright pale yellow crystal of the coumarin compound, represented by Chemical Formula 61, according to the present invention.

A portion of the crystal was sampled and measured for visible light absorption spectrum and fluorescent spectrum in methylene chloride in a usual manner, revealing to have an absorption maximum at a wavelength of around 420 nm ($\epsilon=9.23\times10^4$) and a fluorescent maximum at a wavelength of around 478 nm. When measured for melting point, glass transition point, and decomposition point on conventional DSC analysis, the coumarin compound of this example had a melting point of 366 to 369° C. and a decomposition point of about 435° C., but had no glass transition point. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.24 (12H, t), 3.44 (8H, q), 6.56 (2H, d), 6.61 (2H, dd), and 7.60-7.82 (12H, m).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 10

Coumarin Compound

Except for replacing N,N-diethylaminosalicylaldehyde and m-phenylenediacetonitrile with 3.65 g of 4,6-dimethoxysalicylaldehyde and 2.32 g of 4,4'-biphenylacetonitrile, the reaction of Example 1 was similarly proceeded, resulting in a yield of 0.33 g of a yellow powdery crystal of the coumarin compound, represented by Chemical Formula 64, according to the present invention.

A portion of the crystal was sampled and measured for visible light absorption spectrum and fluorescent spectrum in methylene chloride in a usual manner, revealing to have an absorption maximum at a wavelength of around 371 nm ($\epsilon=6.16\times10^4$) and a fluorescent maximum at a wavelength of around 460 nm. When measured for melting point, glass transition point, and decomposition point on conventional DSC analysis, the coumarin compound of this example had a melting point of 335 to 343° C. and a decomposition point of about 434° C., but had no glass transition point. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 3.89 (6H, s), 3.93 (6H, s), 6.33 (2H, d), 6.48 (2H, d), 7.69 (4H, d), 7.83 (4H, d), and 8.19 (2H, s).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 11

Coumarin Compound

Except for replacing N,N-diethylaminosalicylaldehyde with 3.4 g of 6-tert-butyl-2-hydroxynaphthoaldehyde, the reaction of Example 1 was similarly proceeded, resulting in a yield of 0.69 g of a yellow powdery crystal of the coumarin compound, represented by Chemical Formula 3, according to the present invention.

A portion of the crystal was sampled and measured for visible light absorption spectrum and fluorescent spectrum in methylene chloride in a usual manner, revealing to have an absorption maximum at a wavelength of around 373 nm ($\epsilon=3.52\times10^4$) and a fluorescent maximum at a wavelength of around 442 nm. When measured for melting point, glass transition point, and decomposition point on conventional DSC analysis, the coumarin compound of this example had a melting point of 203 to 208° C., a decomposition point of about 446° C., and a glass transition point of about 151° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.44 (18H, s), 7.47-8.29 (14H, m), and 8.67 (2H, s).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits visible light in the blue region when excited and has an improved heat tolerance, is useful as materials for luminous layers and agents for regulating color degree used in organic EL elements.

EXAMPLE 12

Coumarin Compound

Except for replacing N,N-diethylaminosalicylaldehyde and m-phenylenediacetonitrile with 7.0 g of 6-tert-butyl-2-hydroxynaphthoaldehyde and 2.0 g of p-phenylenediacetonitrile, the reaction of Example 1 was similarly proceeded, resulting in a yield of 1.43 g of a pale yellow crystal of the coumarin compound, represented by Chemical Formula 27, according to the present invention.

A portion of the crystal was sampled and measured for visible light absorption spectrum and fluorescent spectrum in methylene chloride in a usual manner, revealing to have an absorption maximum at a wavelength of around 390 nm ($\epsilon=4.20\times10^4$) and a fluorescent maximum at a wavelength of around 451 nm. When measured for melting point, glass transition point, and decomposition point on conventional DSC analysis, the coumarin compound of this example had a melting point of 339 to 341° C., a decomposition point of about 459° C., and a glass transition point of about 163° C. According to conventional manner, the coumarin compound was measured for $^1$H-nuclear magnetic resonance spectrum (hereinafter abbreviated as "$^1$H-NMR") in a chloroform deuteride solution, and revealed to have a cheffffical shift δ (ppm, TMS) at peaks of 1.46 (18H, s), 7.50 (2H, d), 7.81-8.00 (10H, m), 8.51 (2H, d), and 8.66 (2H, s).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 13

Coumarin Compound

Except for replacing m-phenylenediacetonitrile with 3.1 g of 3,3"-dicyanomethyl-p-terphenyl, the reaction of Example 1 was similarly proceeded, resulting in a yield of 2.1 g of a pale yellow crystal of the coumarin compound, represented by Chemical Formula 29, according to the present invention.

A portion of the crystal was sampled and measured for visible light absorption spectrum and fluorescent spectrum in methylene chloride in a usual manner, revealing to have an absorption maximum at a wavelength of around 401 nm ($\epsilon=7.85\times10^4$) and a fluorescent maximum at a wavelength of around 466 nm. When measured for melting point, glass transition point, and decomposition point on conventional DSC analysis, the coumarin compound of this example had a melting point of 283 to 288° C., a decomposition point of about 455° C., and a glass transition point of about 117° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.23 (12H, t), 3.44 (8H, q), 6.56 (2H, s), 6.61 (2H, d), 7.34 (2H, d), 7.50 (2H, t), 7.62 (2H, d), 7.63-7.78 (8H, m), and 7.94 (2H, s).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 14

Coumarin Compound

Except for replacing m-phenylenediacetonitrile with 3.8 g of 3"-cyanomethyl-4-(3-cyanomethylphenyl)-p-terphenyl, the reaction of Example 1 was similarly proceeded, resulting in a yield of 1.6 g of a pale yellow crystal of the coumarin compound, represented by Chemical Formula 75, according to the present invention.

A portion of the crystal was sampled and measured for visible light absorption spectrum and fluorescent spectrum in methylene chloride in a usual manner, revealing to have an absorption maximum at a wavelength of around 402 nm ($\epsilon=7.90\times10^4$) and a fluorescent maximum at a wavelength of around 466 nm. When measured for melting point, glass transition point, and decomposition point on conventional DSC analysis, the coumarin compound of this example had a melting point of 310 to 316° C., a decomposition point of about 456° C., and a glass transition point of about 129° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.24 (12H, t), 3.45 (8H, q), 6.57 (2H, s), 6.62 (2H, d), 7.34 (2H, d), 7.51 (2H, t), 7.61-7.64 (2H, m), 7.71-7.78 (12H, m), and 7.95 (2H, s).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 15

Coumarin Compound

Except for replacing m-phenylenediacetonitrile with 3.1 g of 3,3"-dicyanomethyl-m-terphenyl, the reaction of Example 1 was similarly proceeded, resulting in a yield of 2.2 g of a pale yellow crystal of the coumarin compound, represented by Chemical Formula 60, according to the present invention.

A portion of the crystal was sampled and measured for visible light absorption spectrum and fluorescent spectrum in methylene chloride in a usual manner, revealing to have an absorption maximum at a wavelength of around 401 nm ($\epsilon=7.59\times10^4$) and a fluorescent maximum at a wavelength of around 467 nm. When measured for melting point, glass transition point, and decomposition point on conventional DSC analysis, the coumarin compound of this example had a melting point of 195 to 202° C., a decomposition point of about 450° C., and a glass transition point of about 108° C., According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.23 (12H, t), 3.43 (8H, q), 6.54 (2H, d), 6.58 (1H, d), 6.61 (1H, d), 7.33 (2H, d), 7.52 (3H, m), 7.61 (2H, m), 7.63 (2H, m), 7.73 (1H, m), 7.75 (1H, m), 7.77 (2H, s), 7.87 (1H, m), and 7.92 (1H, m).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 16

Coumarin Compound

Except for replacing m-phenylenediacetonitrile with 3.9 g of 2,6-dimethyl-1,5-bis(3-cyanomethylphenyl)naphthalene, the reaction of Example 1 was similarly proceeded, resulting in a yield of 1.2 g of a pale yellow crystal of the coumarin compound, represented by Chemical Formula 81, according to the present invention.

A portion of the crystal was sampled and measured for visible light absorption spectrum and fluorescent spectrum in methylene chloride in a usual manner, revealing to have an absorption maximum at a wavelength of around 401 nm ($\epsilon=7.67\times10^4$) and a fluorescent maximum at a wavelength of around 467 nm. When measured for melting point, glass transition point, and decomposition point on conventional DSC analysis, the coumarin compound of this example had a melting point of 295 to 300° C., a decomposition point of about 441° C., and a glass transition point of about 143° C., According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.22 (12H, t), 2.26 (6H, s), 3.43 (8H, q), 6.55-6.59 (4H, m), 7.27-7.30 (6H, m), 7.45 (2H, d), 7.54-7.59 (4H, m), 7.74 (2H, s), and 7.90 (2H, d).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 17

Coumarin Compound

Except for replacing m-phenylenediacetonitrile with 4.1 g of 9,10-bis(3-cyanomethylphenyl)anthracene, the reaction of Example 1 was similarly proceeded, resulting in a yield of 1.7 g of a pale yellow crystal of the coumarin compound, represented by Chemical Formula 101, according to the present invention.

A portion of the crystal was sampled and measured for visible light absorption spectrum and fluorescent spectrum in methylene chloride in a usual manner, revealing to have an absorption maximum at a wavelength of around 406 nm ($\epsilon=8.48\times10^4$) and a fluorescent maximum at a wavelength of around 472 nm. When measured for melting point, glass transition point, and decomposition point on conventional DSC analysis, the coumarin compound of this example had a melting point of 384 to 389° C., a decomposition point of about 446° C., and a glass transition point of about 156° C., According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.22 (12H, t), 3.42 (8H, q), 6.56 (2H, m), 7.35-7.82 (20H, m), and 7.92 (2H, d).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 18

Coumarin Compound

Except for replacing N,N-diethylaminosalicylaldehyde and m-phenylenediacetonitrile with 5.5 g of 1, 1,7,7-tetramethyl-8-hydroxy-9-formyljulolidine and 1.6 g of 4,4'-biphenylacetonitrile, respectively, the reaction of Example 1 was similarly proceeded, resulting in a yield of 1.5 g of a yellow crystal of the coumarin compound, represented by Chemical Formula 62, according to the present invention.

A portion of the crystal was sampled and measured for visible light absorption spectrum and fluorescent spectrum in methylene chloride in a usual manner, revealing to have an absorption maximum at a wavelength of around 434 nm ($\epsilon=8.40\times10^4$) and a fluorescent maximum at a wavelength of around 497 nm. When measured for melting point, glass transition point, and decomposition point on conventional DSC analysis, the coumarin compound of this example had a melting point of 393 to 398° C., a decomposition point of about 447° C., and a glass transition point of about 188° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.37 (12H, s), 1.61 (12H, s), 1.78 (4H, t), 1.84 (4H, t), 3.23 (4H, t), 3.31 (4H, t), 7.26 (2H, s), 7.67-7.72 (6H, m), and 7.72-7.84 (4H, m).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 19

Coumarin Compound

Except for replacing N,N-diethylaminosalicylaldehyde and m-phenylenediacetonitrile with 5.5 g of 1, 1,7,7-tetramethyl-8-hydroxy-9-formyljulolidine and 3.3 g of 5,5"-dicyanomethyl-[2,2';5',2"]-terthiophene, the reaction of Example 1 was similarly proceeded, resulting in a yield of 0.9 g of a dark red crystal of the coumarin compound, represented by Chemical Formula 137, according to the present invention.

A portion of the crystal was sampled and measured for visible light absorption spectrum and fluorescent spectrum in methylene chloride in a usual manner, revealing to have an absorption maximum at a wavelength of around 505 nm ($\epsilon=1.01\times10^5$) and a fluorescent maximum at a wavelength of around 571 nm. When measured for melting point, glass transition point, and decomposition point on conventional DSC analysis, the coumarin compound of this example had a melting point of 345 to 351° C., a decomposition point of about 432° C., and a glass transition point of about 176° C. According to conventional manner, the coumarin compound was measured for $^1$H-nuclear magnetic resonance spectrum (hereinafter abbreviated as "$^1$H-NMR") in a chloroform deuteride solution, and revealed to have a chemical shift δ (ppm, TMS) at peaks of 1.32 (12H, s), 1.58 (12H, s), 1.77 (4H, t), 1.81 (4H, t), 3.24 (4H, t), 3.31 (4H, t), 7.14 (6H, m), 7.58 (2H, d), and 7.83 (2H, s).

The coumarin compound, having an improved thermal stability and an absorption- and a fluorescent-maxima in the visible region, can be advantageously used as a light absorbent or a luminous agent in the fields of photochemical polymerization, solar cells, optical filters, dyes, dye lasers, analyses, etc. Particularly, the coumarin compound of this example, which emits a visible light in the blue region when excited and has an improved heat tolerance, is useful as materials for luminous layers and agents for regulating color degree used in organic EL elements.

EXAMPLE 20

Coumarin Compound

Any of 19 coumarin compounds obtained by the method in Examples 1 to 19 was placed in a water-cooled sublimation purification apparatus, and in a usual manner heated for sublimation and purification while keeping the inner pressure at a reduced level.

All the coumarin compounds can be arbitrarily used in various fields which require relatively high purity organic EL compounds having both a satisfactory light absorption ability and a luminous ability.

Although the coumarin compounds of the present invention may somewhat differ in production conditions and yields depending on their structures, they, including those represented by Chemical Formulae 1 to 763, can be prepared in a desired amount by the methods in Examples 1 to 20 or in accordance therewith.

As regards related compounds represented by Chemical Formulae 764 and 765, they were measured for visible light absorption spectrum, fluorescent spectrum, melting point, and decomposition point similarly as above, revealing that they exhibited absorption maxima at wavelengths of 398 to 412 nm and fluorescent maxima in the wavelengths of 462 to 479 nm. However, the above related compounds had decomposition points of 318 and 308° C., respectively, which were distinctly lower than those of the coumarin compounds of the present invention. The fact shows that the coumarin compounds of the present invention, which comprise a plurality of coumarin residues are bound together via an aromatic ring or a heterocycle, have an improved thermostability without losing the desired light properties of conventional coumarin compounds comprising a coumarin residue(s).

Chemical Formula 764:

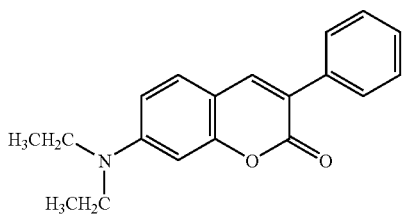

Chemical Formula 765:

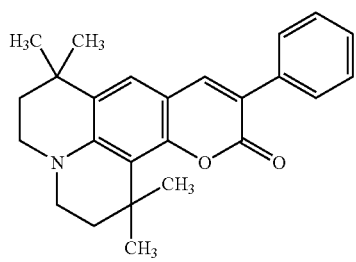

EXAMPLE 21

Organic EL Element

Using a luminous agent for organic EL element according to the present invention, a multi-layer type organic EL element in FIG. 1 was prepared. According to a usual manner, a glass substrate comprising a transparent ITO electrode, having a thickness of 160 nm, patternized with hydrobromic acid, was ultrasonically washed sequentially with an organic alkaline detergent, high-purity water, acetone, and ethanol; dried; treated with ultraviolet ozone to remove organic compounds on the surface of the ITO electrode, and transferred to a pretreatment chamber of a vacuum deposition apparatus. After the pretreatment chamber was reduced to a pressure of $1 \times 10^{-6}$ Torr and introduced with a mixture gas of argon and oxygen to give a pressure of $1 \times 10^{-2}$ Torr, the surface of ITO electrode was treated with plasma to obtain a clean substrate 1 having an ITO electrode as electrode 2.

A positive hole injection/transportation layer 3 was formed by transferring the substrate 1 to an organic decomposition chamber of the vacuum deposition apparatus, which had been reduced to a pressure of $5 \times 10^{-7}$ Torr; installing a mask for forming organic membrane in the ITO electrode as substrate 2; and heating a carbon crucible to deposit triphenylamine tetramer, represented by Chemical Formula 766 (abbreviated as "TPT" hereinafter), as a positive hole injection/transportation layer, on the side with ITO electrode of the substrate 1 to give a thickness of 60 nm. Then, an electron injection/transportation layer 5, attached closely to the luminous layer 4, was formed by depositing together any one of the coumarin compounds of the present invention, shown in Table 1, as a material for luminous layer, and an adamantane compound, represented by Chemical Formula 767 (abbreviated as "PY-AD" hereinafter) in a weight ratio of 0.5:100 to 1.5:100 to give a thickness of 20 nm; and depositing tris(8-quinolinolato)aluminum (abbreviated as "AlQ$_3$" hereinafter) to give a thickness of 40 nm. Chemical Formula 766:

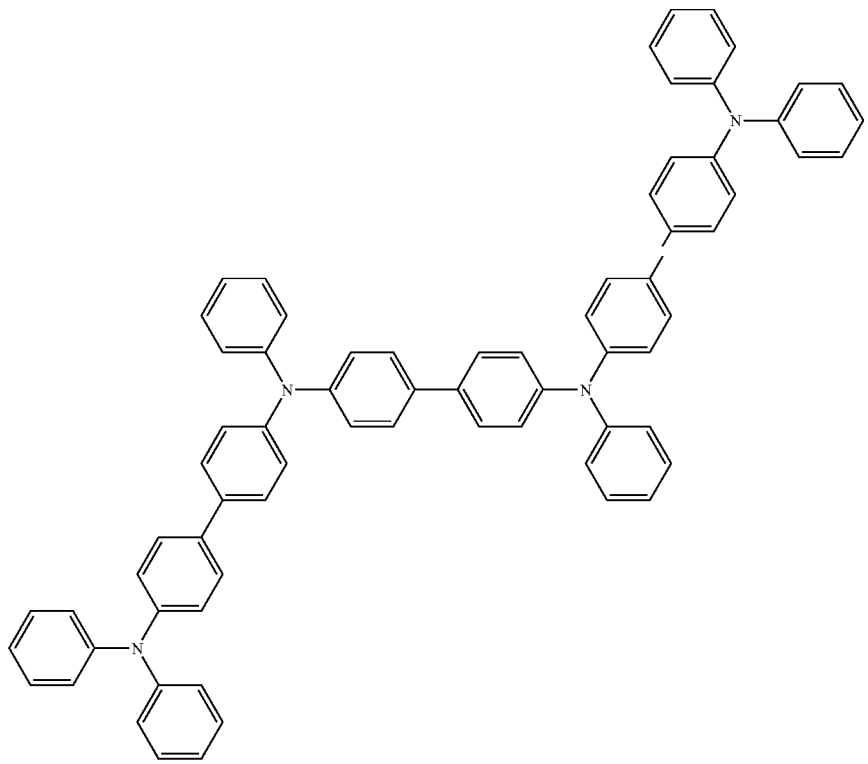

Chemical Formula 767:

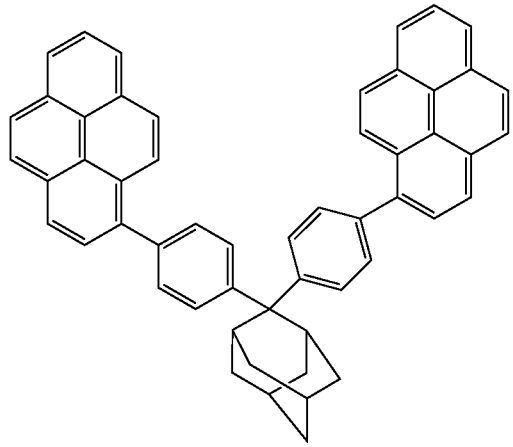

Thereafter, an organic EL element was obtained by transferring the substrate 1 thus obtained to a metal deposition chamber of the vacuum deposition apparatus; sequentially depositing lithium fluoride and aluminum on the substrate 1 to give a thickness of 0.5 nm and 150 nm, respectively, to form a cathode 6 attached closely to the electron injection/transportation layer 5; and sealing the whole of the aimed element with a glass plate and an ultraviolet hardening resin. The organic EL element thus obtained was determined for electroluminescent property and lifetime, i.e., operation time until the initial brightness was halved, respectively. The lifetime of the organic EL element was determined by setting its initial brightness to 3,100 cd/m² at ambient temperature. While, as a reference, an organic EL element for constructing a luminous layer was prepared using PY-AD alone without using any of the coumarin compounds of the present invention, and used as a control. The results were in Table 1.

When energized with a dc voltage, the organic EL elements initiated to emit light at about 3 V, and the brightness reached over 10,000 cd/m² at 10 V and it reached the maximum of 20,000 cd/m² at about 14 V As found in the column of "Brightness" in Table 1, when operated with a constant current at a current density of 11 mA/cm², the organic EL elements of the present invention gave a brightness as high as 300 to 1,360 cd/m² at ambient temperature, and their power efficiency and outer quantum (%) were the same level of those of the control or over. The organic EL elements comprising the coumarin compounds, represented by Chemical Formula 21, 22 and 61, gave a distinctively high power efficiency of 6.21, 6.51 and 4.1 lm/W, respectively, and had an outer quantum (%) of over 3%.

The organic EL elements of the present invention stably and constantly emit light, and most of which had a lifetime of at least 10 hours even when operated at a high brightness of 3,100 cd/M² and showed no non-luminous part such as a dark spot from the beginning of the initiation of their operation until the time at which their initial brightness was halved. The organic EL elements, comprising the coumarin compounds represented by Chemical Formulae 22 and 210, had an outstandingly long lifetime and were determined to have a lifetime of 67 to 300 hours when operated at an initial brightness of 3,100 cd/m². When operated at an actual brightness of 300 cd/m², the above organic EL elements gave a lifetime as long as 2,000 to 10,000 hours. While the organic EL element as a control was determined to have a lifetime of 0.62 hour, when operated at an initial brightness of 3,100 cd/m², which was significantly lower than those of the organic EL elements in this example.

These results indicate that the combination use of the coumarin compound of the present invention and an appropriate host compound will realize organic EL elements which emit light in the blue region and have a satisfactory long lifetime and an improved brightness and efficiency.

TABLE 1

| Coumarin compound | Wavelength of luminescent maximum (nm) | Chromaticity diagram (x, y) | A | B | C | D | E | F | Remarks |
|---|---|---|---|---|---|---|---|---|---|
| Chemical Formula 21 | 507 | (0.265, 0.555) | 1357 | 6.2 | 6.2 | 4.0 | 40 | 213 | Present invention |
| Chemical Formula 24 | 490 | (0.256, 0.375) | 301 | 4.5 | 1.9 | 1.1 | 14 | 196 | Present invention |
| Chemical Formula 22 | 521 | (0.308, 0.559) | 1211 | 5.3 | 6.5 | 3.2 | 300 | 241 | Present invention |
| Chemical Formula 210 | 490 | (0.236, 0.442) | 645 | 4.9 | 3.8 | 2.3 | 67 | 275 | Present invention |
| Chemical Formula 61 | 489 | (0.217, 0.447) | 894 | 6.2 | 4.1 | 3.2 | 10 | 241 | Present invention |
| Chemical Formula 64 | 479 | (0.240, 0.337) | 335 | 4.8 | 2.0 | 1.4 | 5 | 203 | Present invention |
| — | 460 | (0.175, 0.210) | 386 | 5.0 | 2.2 | 1.9 | 0.62 | — | Control |

Note:
The symbols "A", "B", "C", "D", "E", and "F" mean "Brightness (cd/m²)", "Voltage (V)", "Power efficiency (lm/W)", "Outer quantum (%)", "Lifetime (hour)", and "Sublimation temperature (° C.)", respectively.

As shown in Table 1, the organic EL elements in this example and the control had luminescent maxima at wavelengths ranging from 470 to 520 nm in the blue region to the green region. In terms of CIE x-y chromaticity diagram of these organic EL elements, the one of the control had x of 0.175 and y of 0.210, belonging to the blue region, while those of the present invention had x of 0.217 to 0.308 and y of 0.337 to 0.559, meaning to have had shifted to the blue region or to the green region with a slightly longer wavelength.

EXAMPLE 22

Organic EL Element

A positive hole injection/transportation layer 3 was formed by placing a substrate 1, which had been prepared similarly as in Example 21, in an organic deposition chamber of a vacuum deposition apparatus controlled to a reduced pressure of $1\times10^{-6}$ Torr; installing a mask for forming an organic membrane in an ITO electrode as an anode 2, heating a carbon crucible; and sequentially depositing copper phthalocyanine, represented by Chemical Formula 768 (abbreviated as "CuPc" hereinafter), and TPTE, as materials for positive hole injection/transportation layer, on the side with the ITO electrode of the substrate 1 to give a thickness of 10 nm and 30 nm, respectively. Then, a luminous layer 4 was formed by co-depositing any one of the coumarin compounds of the present invention and PY-AD in a weight ratio of 0.5:100 to 2:100 to form a layer with a thickness of 40 nm to be closely attached to the positive hole injection/transportation layer 3, and an electron injection/transportation layer 5 with a thickness of 40 nm was formed by depositing $AlO^3$ to be closely attached to the luminous layer 4 by means of vacuum deposition. After a cathode 6 was formed similarly as in Example 21, the whole of the aimed elements were respectively sealed with a glass plate and an ultraviolet hardening resin to obtain seven types of organic EL elements.

Chemical Formula 768:

Chemical Formula 768:

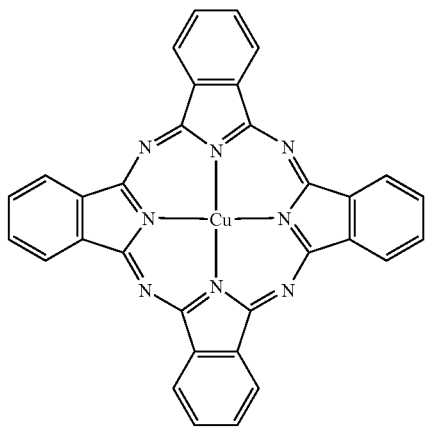

The organic EL elements thus obtained were determined on electroluminescent property and lifetime similarly as in Example 21. In determining the lifetime at ambient temperature and at 85° C., the initial brightness of the testing elements were respectively set to 2,400 cd/m$^2$ and 400 cd/m$^2$. For comparison, as a control, it was prepared an organic EL element comprising an luminous layer consisted of PY-AD without using any of the coumarin compounds of the present invention. The results are in Table 2.

TABLE 2

| Coumarin compound | Wavelength of luminescent maximum (nm) | Chromaticity diagram (x, y) | A | B | C | D | E AT | E 85° C. | Remarks |
|---|---|---|---|---|---|---|---|---|---|
| Chemical Formula 1 | 459 | (0.164, 0.153) | 537 | 8.3 | 1.8 | 4.1 | 8.9 | 32.5 | Present invention |
| Chemical Formula 209 | 466 | (0.171, 0.253) | 535 | 7.5 | 2.0 | 3.1 | 7.1 | 31.6 | Present invention |
| Chemical Formula 41 | 456 | (0.164, 0.251) | 716 | 7.7 | 2.7 | 3.7 | 17.7 | ND | Present invention |
| Chemical Formula 29 | 456 | (0.163, 0.159) | 558 | 7.5 | 2.1 | 3.0 | 9.3 | ND | Present invention |
| Chemical Formula 75 | 459 | (0.176, 0.196) | 466 | 6.9 | 1.9 | 2.6 | 14.6 | ND | Present invention |
| Chemical Formula 81 | 466 | (0.161, 0.191) | 915 | 9.5 | 2.8 | 4.3 | 6.7 | ND | Present invention |
| Chemical Formula 101 | 466 | (0.163, 0.206) | 670 | 6.8 | 2.8 | 3.0 | 23.3 | ND | Present invention |
| — | 449 | (0.180, 0.194) | 335 | 7.7 | 1.3 | 2.1 | 5.0 | 8.9 | Control |

Note:
The symbols "A", "B", "C", "D", "E", "AT", and "ND" mean "Brightness (cd/m$^2$)", "Voltage (V)", "Power efficiency (lm/W)", "Outer quantum (%)", "Lifetime (hour)", "Ambient temperature", and "Not done", respectively.

As evident from the results in Table 2, all the organic EL elements of this example and the control had luminescent maxima at wavelengths of about 450 nm to about 470 nm in the blue region to the green region. In terms of CIE x-y chromaticity diagram of these organic EL elements, the one of the control had x of 0.180 and y of 0.194, belonging to the blue region slightly colored with white, while those of the present invention had x of 0.161 to 0.176 and y of 0.153 to 0.253, belonging to the blue region or to the green region slightly colored with blue. Particularly, the organic EL elements, comprising the coumarin compounds represented by Chemical Formulae 1, 29, 75 and 81, had x and y of below 0.2 on CIE x-y chromaticity diagram and had an especially advantageous color purity as a blue luminescence.

When energized with a dc voltage, the organic EL elements initiated to emit at about 3 V, and the brightness reached over 10,000 cd/m$^2$ at 10 V and it reached the maximum of 20,000 cd/m$^2$ at about 14 V. As found in the column of "Brightness" in Table 2, when operated with a constant current at a current density of 11 mA/cm$^2$, the organic EL elements. of the present invention gave a brightness as high as 400 to 900 cd/m$^2$ at ambient temperature, and their power efficiency and outer quantum (%) significantly exceeded those of the control. The organic EL elements comprising the coumarin compounds, represented by Chemical Formulae 1, 29 and 81, had a satisfactory color purity and gave distinctively high power efficiencies of 1.8 to 2.8 lm/W, respectively, and had an outer quantum (%) of over 3.0 to 4.3% as compared with the control.

The organic EL elements in this experiment stably and constantly emitted light, and most of which had a lifetime of at least five hours even when operated at a high brightness of 2,400 cd/m$^2$ and showed no non-luminous part such as a dark spot from the beginning of the initiation of their operation to the time at which their initial brightness was halved. When operated at 85° C., the organic EL elements, comprising the coumarin compounds represented by Chemical Formulae 1 and 209, had a particularly long lifetime as long as about 32 hours, i.e., over three times longer than that of the control.

These results indicate that the combination use of the coumarin compound of the present invention and an appropriate host compound will realize organic EL elements which emit light in the blue region and have a satisfactory long lifetime and an improved brightness and efficiency.

EXAMPLE 23

Organic EL Element

A positive hole injection/transportation layer 3 was formed by placing a substrate 1, which had been prepared similarly as in Example 21, in an organic deposition chamber of a vacuum deposition apparatus with a reduced pressure of $1\times10^{-6}$ Torr; installing a mask for forming an organic membrane in an ITO electrode as an anode 2, heating a carbon crucible; and sequentially depositing copper phthalocyanine, represented by Chemical Formula 768 (abbreviated as "CuPc" hereinafter), and TPTE, as materials for positive hole injection/transportation layer, on the side with the ITO electrode of the substrate 1 to give a thickness of 10 nm and 50 nm, respectively. Then, a luminous layer 4 was formed by co-depositing any one of the coumarin compounds of the present invention and $AlQ_3$ in a weight ratio of 1:100 to form a layer with a thickness of 20 nm to be closely attached to the positive hole injection/transportation layer 3, and an electron injection/transportation layer 5 with a thickness of 40 nm was formed by depositing $AlO_3$ to be closely attached to the luminous layer 4 by means of vacuum deposition. After a cathode 6 was formed similarly as in Example 21, the whole of the aimed elements were respectively sealed with a stainless steel and an ultraviolet hardening resin to obtain two types of organic EL elements.

The organic EL elements thus obtained were determined for electroluminescent property and lifetime similarly as in Example 21. In determining the lifetime at ambient temperature and at 85° C., the initial brightness of the testing elements were respectively set to 4,000 $cd/m^2$ and 2,400 $cd/m^2$. For comparison, as a control, it was prepared an organic EL element comprising an luminous layer using N,N'-dimethylquinacridone, as a conventional green luminescent agent, in place of the coumarin compound of the present invention. The results are in Table 3.

maxima at wavelengths of 500 nm to 550 nm in the blue region to the green region. In terms of CIE x-y chromaticity diagram of these organic EL elements, the one of the control had x of 0.371 and y of 0.598, belonging to the blue region slightly colored with yellow, while those of the present invention had x of 0.298 to 0.301 and y of 0.585 to 0.624, which were more close to the x and y values of the pure blue region. It is said that EBU-type color televisions have primary colors of x of 0.29 and y of 0.60 in terms of CIE x-y chromaticity diagram.

When energized with a dc voltage, the organic EL elements initiated to emit at about 3 V, and the brightness reached over 10,000 $cd/m^2$ at 10 V and it reached the maximum of 100,000 $cd/m^2$ at about 15 V. As found in the column of "Brightness" in Table 3, when operated with a constant current at a current density of 11 $mA/cm^2$, the organic EL elements of the present invention gave a brightness of over 1,000 $cd/m^2$ at ambient temperature, and their power efficiency and outer quantum (%) significantly exceeded those of the control. The organic EL elements comprising the coumarin compounds, represented by Chemical Formula 22, exhibited about two-times higher power efficiency and outer quantum (%) than those of the control, respectively.

The organic EL elements in this experiment stably and constantly emitted light and gave a lifetime exceeding that of the control even when operated at ambient temperature or at a temperature of 5° C., and showed no non-luminous part such as a dark spot from the beginning of the initiation of their operation to the time at which their initial brightness was halved. The organic EL element represented by Chemical Formula 22 had a particularly longer lifetime, i.e., a two-times longer lifetime as that of the control, and the life-expectancy was estimated to be 3,000 hours when operated at a brightness of 300 $cd/m^2$ on an actual use, meaning that the element can be actually used with no crucial problem.

These results indicate that the combination use of the coumarin compound of the present invention and an appropriate host compound will realize organic EL elements which emit light in the blue region and have a satisfactory long lifetime and an improved brightness and efficiency.

EXAMPLE 24

Organic EL Element

A positive hole injection/transportation layer 3 was formed by placing a substrate 1, which had been prepared similarly as in Example 21, in an organic deposition chamber of a vacuum deposition apparatus with a reduced pressure of $1\times10^{-6}$ Torr;

TABLE 3

| Coumarin compound | Wavelength of luminescent maximum (nm) | Chromaticity diagram (x, y) | E | | | | | | Remarks |
|---|---|---|---|---|---|---|---|---|---|
| | | | A | B | C | D | AT | 85° C. | |
| Chemical Formula 21 | 514 | (0.298, 0.585) | 1027 | 6.8 | 4.3 | 2.8 | 300 | 80 | Present invention |
| Chemical Formula 22 | 527 | (0.301, 0.624) | 1619 | 6.8 | 6.8 | 4.1 | 600 | 85 | Present invention |
| — | 543 | (0.371, 0.598) | 791 | 6.3 | 3.6 | 1.9 | 250 | 70 | Control |

Note:
The symbols "A", "B", "C", "D", "E" and "AT" mean "Brightness ($cd/m^2$)", "Voltage (V)", "Power efficiency (lm/W)", "Outer quantum (%)", "Lifetime (hour)", and "Ambient temperature", respectively.

As evident from the results in Table 3, all the organic EL elements of this example and the control had luminescent installing a mask for forming an organic membrane in an ITO electrode as an anode 2, heating a carbon crucible; and sequentially depositing TPTE, as a material for positive hole injection/transportation layer, on the side with the ITO electrode of the substrate 1 to give a thickness of 40 nm. Then, a luminous layer 4 was formed by co-depositing any one of the coumarin compounds of the present invention and TPTE in a weight ratio of 1:100 to form a layer with a thickness of 20 nm to be closely attached to the positive hole injection/transportation layer 3, and an electron injection/transportation layer 5 with a thickness of 40 nm was formed by sequentially depositing 2,9-dimethyl-4,7-diphenyl-1,10-phenanthroline and $AlO_3$ to form 20 nm and 40 nm layers, respectively, attached closely to the luminous layer 4 by means of vacuum deposition. After a cathode 6 was formed similarly as in Example 21, the whole of the aimed elements were respectively sealed with a glass plate and an ultraviolet hardening resin to obtain three types of organic EL elements.

The organic EL elements thus obtained were determined for electroluminescent property and lifetime similarly as in Example 21. The test on lifetime was conducted at ambient temperature under an initial brightness of 300 cd/m². For comparison, as a control, it was prepared an organic EL element comprising an luminous layer consisted of TPTE without any of the coumarin compounds of the present invention. The results are in Table 4.

EXAMPLE 25

Displaying Panel

Figure 2:
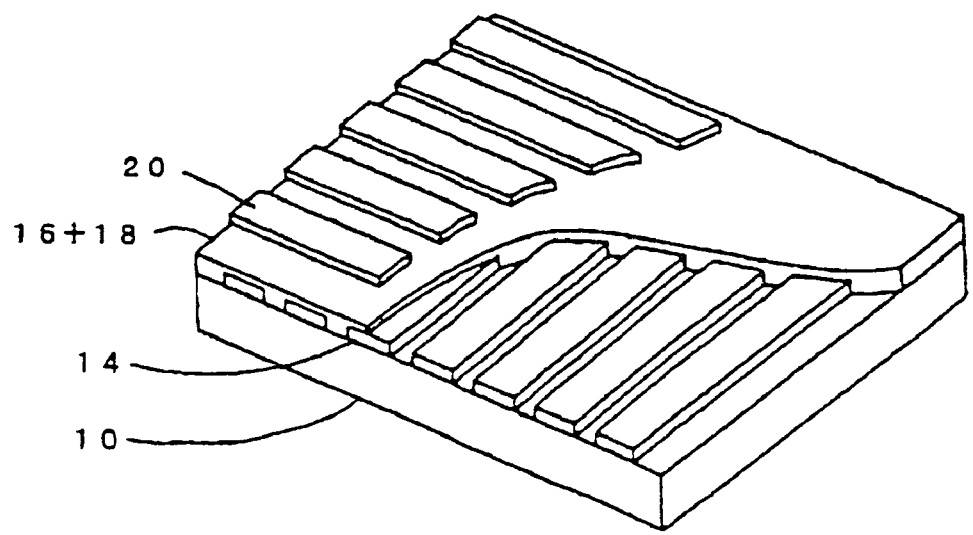
FIG. 2 is a brief drawing of the displaying panel according to the present invention.

FIG. 2 briefly explains an example of a simple matrix displaying panel, which is mainly composed of the organic EL element of the present invention and has 20 electrode lines in the horizontal direction and 30 electrode lines in the longitudinal direction. The displaying panel can be prepared by the following method:

In accordance with the method in Example 21, an anode 14 made of transparent ITO electrode was formed on either surface of a glass substrate 10, and processed into a stripe form by the wet etching method. Then, in accordance with the method in Example 21, the anode 14 was sequentially processed by forming a positive hole injection/transportation layer 16, a luminous layer 18, etc.; forming a cathode 20 into a stripe form using a mechanical mask; and sealing the aimed organic EL element using both a glass plate, not shown, and a ultraviolet hardening resin. In the displaying panel of this example, a radiator means such as a radiator in a plate form or a cooling fan can be optionally installed in the backside of the cathode 20 to inhibit the increase of temperature during operation.

TABLE 4

| Coumarin compound | Wavelength of luminescent maximum (nm) | Chromaticity diagram (x, y) | A | B | C | D | E | Remarks |
|---|---|---|---|---|---|---|---|---|
| Chemical Formula 21 | 490 | (0.215, 0.438) | 350.9 | 5.0 | 2.0 | 1.26 | 5.2 | Present invention |
| Chemical Formula 22 | 503 | (0.241, 0.510) | 356.6 | 4.6 | 2.2 | 1.13 | 5.3 | Present invention |
| Chemical Formula 41 | 451 | (0.166, 0.177) | 85.4 | 5.9 | 0.41 | 0.56 | 1.4 | Present invention |
| — | 426 | (0.176, 0.171) | 24.8 | 4.4 | 0.16 | 0.18 | 0.89 | Control |

Note:
The symbols "A", "B", "C", "D", "E" and "AT" mean "Brightness (cd/m²)", "Voltage (V)", "Power efficiency (lm/W)", "Outer quantum (%)", and "Lifetime (hour) at ambient temperature", respectively.

As evident from the results in Table 4, the organic EL elements of the control had a luminescent maximum at a wavelength of 426 nm, while all the organic EL elements of the present invention had a luminescent maximum at a wavelength of about 450 nm to about 500 nm in the blue region to the green region. Since the coumarin compounds represented by Chemical Formulae 21, 22 and 41 have fluorescent maxima at wavelengths of 495, 508 and 466 nm, respectively, the luminescence of the organic EL elements in this example would be characteristic of the coumarin compounds per se.

When operated with a constant current with a current density of 11 mA/cm², the organic EL elements in this example gave a brightness exceeding 80 cd/m² and up to 350 cd/m² at ambient temperature, and their power efficiency and outer quantum (%) significantly exceeded those of the control. Particularly, the organic EL elements comprising the coumarin compounds, represented by Chemical Formulae 21 and 22, exhibited a power efficiency of 2.0 to 2.21 m/W and an outer quantum (%) of 1.13 to 1.26%, far exceeding those of the control.

These results indicate that the coumarin compounds of the present invention can be actually made into organic EL elements which emit light in the blue region and the green region and have a relatively high brightness and efficiency even when used in combination with those, which have not been usually used as materials for luminous layer, such as TPTE.

EXAMPLE 26

Information Displaying Apparatus

Figure 3:
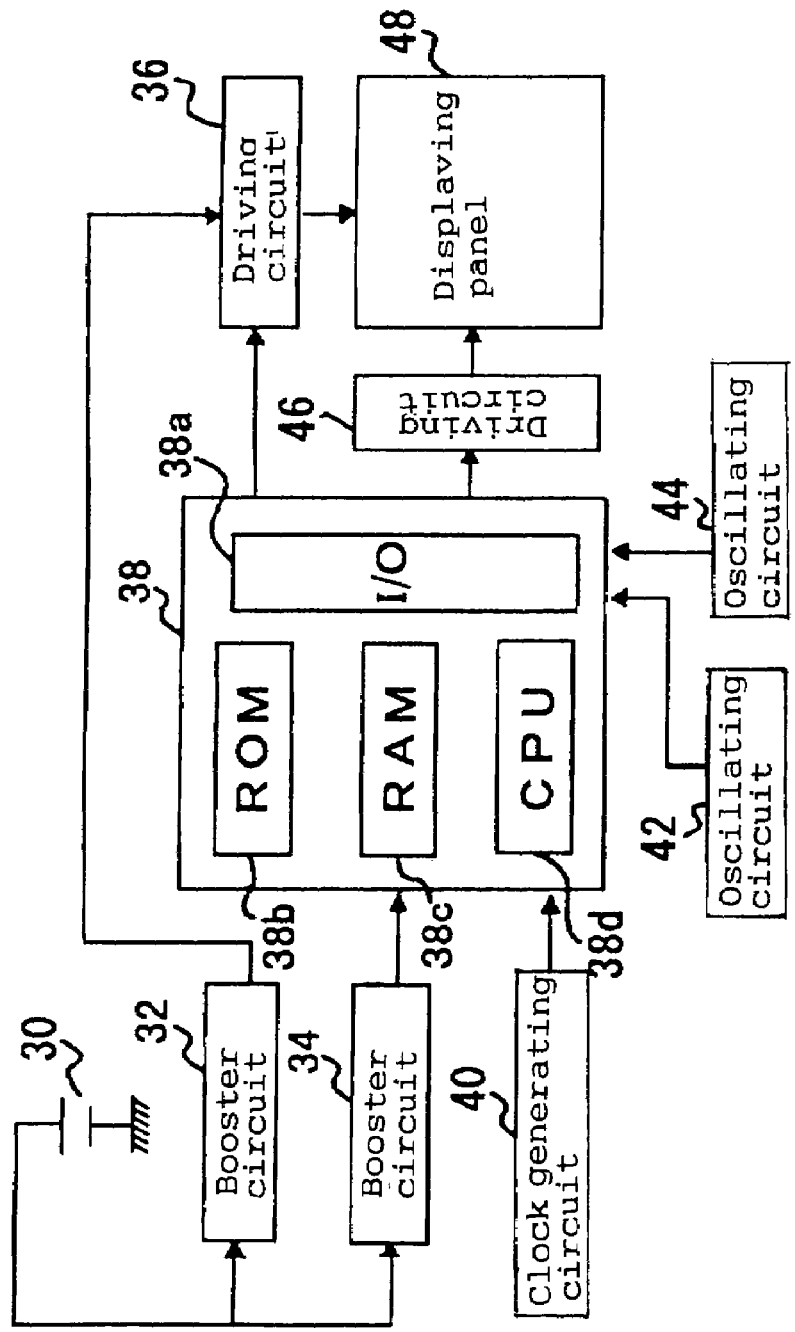
FIG. 3 is a block diagram of the information displaying apparatus according to the present invention.

The block diagram of FIG. 3 is an example of an information displaying apparatus using a displaying panel prepared by the method in Example 25. In FIG. 3, the numeral 30 means a dc power source with an output voltage of 4.5 V, and to the output terminus of which two booster circuits 32 and 34 are connected. The booster circuit 32 can supply a dc voltage of 5 to 12 V, and the output terminus is connected to a driving circuit 36. Another booster circuit 34 is for supplying a constant voltage of 5 V to a microcomputer 38.

The microcomputer 38, which comprises an I/O interface 38a for communicating signals with others, ROM38b for recording programs, etc., RAM38c for recording data, and CPU38d for processing operations, is connected with a clock generating circuit 40 for supplying an 8 MHz clock signal to the microcomputer 38, two oscillating circuits 42 and 44 for supplying a signal of 5 to 50 Hz to regulate the information displaying speed and a signal of 0.2 to 2 kHz to regulate scanning frequency.

The numeral 48 means a displaying panel, comprising mainly the organic EL element of the present invention, connected to the microcomputer 38 through the driving circuits 36 and 46. The driving circuit 36 is a circuit for regulating the supply of a dc voltage from the booster circuit 32 to the displaying panel 48, which comprises a plurality of transistors respectively connected to the electrode lines in the longitudinal direction of the displaying panel 48. Because of this, when any one of the transistors in the driving circuit 36 is "on", the voltage from the booster circuit 32 will be supplied to the electrode lines in the longitudinal direction, connected to the above transistor. While the driving circuit 46 comprises a plurality of transistors respectively connected to the electrode lines in the horizontal direction of the displaying panel 48, and when any one of the transistors in the driving circuit 36 is "on", the electrode lines in the longitudinal direction, which are connected to the above transistor, will be grounded.

Since the information displaying apparatus in this example is composed as described above, when any of the transistors in the driving circuits 36 and 44 is "on" according to the signal of the microcomputer 38, a prescribed voltage will be supplied between the electrodes corresponding to those in the longitudinal direction and in the horizontal direction of the displaying panel 48, followed by emitting light from an organic EL element that is positioned in the intersection. Thus, when the transistors connected to electrode lines in the longitudinal direction are sequentially switched on by appropriately regulating the driving circuit 36 while an electrode line in the horizontal direction is being selected by appropriately regulating the driving circuit 46 and allowing the selected electrode line to be grounded, the selected whole electrode lines in the horizontal direction are scanned in the horizontal direction and the desired scanning spots are displayed. By sequentially repeating such scanning in the vertical direction, one screenful of lines can be displayed. Since the driving circuit 36 in this example has a data register for one electrode line, it is preferable to operate transistors based on the recorded data.

Information to be displayed can be externally supplied as signals by synchronizing the displaying speed and frequency, or those which are, for example, patternized information such as textual information can be used as data that have been previously recorded in ROM38b. In the case of displaying the information of NTSC television broadcasting, received signals are first separated into horizontal synchronizing signals and vertical synchronizing signals according to the horizontal frequency adjustment and the vertical frequency adjustment based the broadcasting standard, and received picture signals are converted into digital signals which correspond to the pixels of the displaying panel 48. By appropriately synchronizing these signals for supplying to the microcomputer 38, the received television broadcasting can be displayed on the displaying panel 48.

POSSIBILITY OF INDUSTRIAL APPLICABILITY

As described above, the present invention was made based on the creation of novel coumarin compounds. Since the coumarin compounds have an absorption- and a luminous-maxima in the visible regions and have a satisfactory thermo-stability, they have various uses as light absorbing agents or luminous agents in the fields of photochemical polymerization, solar cells, optical filters, dyings, dye lasers, analyses, etc. Particularly, the coumarin compounds are quite advantageously used as luminous agents for organic EL elements because they have a luminous maximum in the visible region, emit light when excited, form a stable membrane in a glass state, and have a relatively high thermostability. Also, they are advantageously used as materials for regulating the color degree of luminescence of organic EL elements because they have an absorption maximum in the visible region and have a relatively high molecular absorption coefficient. Since the coumarin compounds are relatively high in luminescent efficiency and durability, they can be quite advantageously used as luminous bodies in luminaries in general and the others, for example, different types of information displaying apparatuses which visually display information such as pictures and textual information.

The coumarin compounds with such usefulness are obtainable by a step of reacting a compound having an aldehyde group with a compound having an activated methylene group.

The present invention with such outstanding functions and effects is a significant invention that greatly contributes to this art.

The invention claimed is:

1. A coumarin compound represented by Formula 1:

$$\emptyset(Z)_m \qquad \text{Formula 1}$$

wherein in Formula 1, Ø is an aromatic ring or heterocycle selected from the group consisting of thiophene, triazine, furan, benzene, pyrazine, pyridine, naphthalene, anthracene, thieno[3,2-b]thiophene, phenanthrene, fluorene, furo[3,2-b]furan, terphenyl, biphenyl, bithiophene, bifuran, acridine, isoquinoline, indole, carbazole, carboline, quinoline, dibenzofuran, cinnoline, thionaphthene, 1,10-phenanthroline, phenothiazine, purine, and benzofuran rings, and combinations thereof, which may optionally have a substituent; each Z is the same or different coumarin group represented by Formula 1, with the proviso that each coumarin group may optionally have a substituent; and m is an integer of two or more; with the proviso that (i), when o contains any of triazine, furan, benzene, pyrazine, naphthalene, indole, and phenanthrene, each of said furan, naphthalene, pyrazine, indole, and phenanthrene is bonded with the same or different aromatic ring or heterocycle as identified above, said triazine is bonded with Z with m being three said bonding being directly or via any one of the above-identified thiophene, furan, benzene, pyrazine, pyridine, naphthalene, and fluorene; (ii) when Ø contains benzene, said benzene is bonded with Z with m being three or more; and (iii) when o contains pyridine, said pyridine is bonded with another pyridine;

Formula 2:

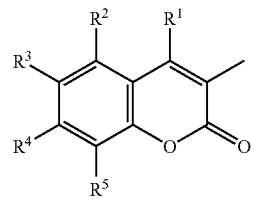

wherein in Formula 2, $R^1$ to $R^5$ independently represent hydrogen or a substituent selected from the group consisting of aliphatic hydrocarbon groups, alicyclic hydrocarbon groups, aromatic hydrocarbon groups, heterocyclic groups, amino groups, halogen groups, and combinations thereof; $R^3$ and $R^4$ may form a cyclic structure together with the carbon atoms linked to $R^2$, $R^3$, $R^4$ and/or $R^5$, and in this case, $R^2$, $R^3$, $R^4$ and/or $R^5$ do not independently exist.

2. The coumarin compound of claim 1, which has a decomposition point of over 330° C.

3. A method for producing a coumarin compound represented by Formula 1, which comprises reacting a compound, represented by Formula 3, having Ø corresponding to that in Formula 1 with a compound, represented by Formula 4, having $R^1$ to $R^5$ corresponding to those in Formula 2:

$Ø(Z)_m$      Formula 1

Formula 2:

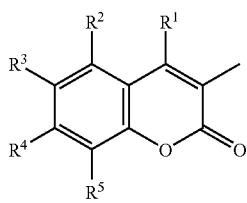

wherein in Formula 1, Ø is an aromatic ring or heterocycle selected from the group consisting of thiophene, triazine, furan, benzene, pyrazine, pyridine, naphthalene, anthracene, thieno[3,2-b]thiophene, phenanthrene, fluorene, furo[3,2-b]furan, terphenyl, biphenyl, bithiophene, bifuran, acridine, isoquinoline, indole, carbazole, carboline, quinoline, dibenzofuran, cinnoline, thionaphthene, 1,10-phenanthroline, phenothiazine, purine, and benzofuran rings, and combinations thereof, which may optionally have a substituent; each Z is the same or different coumarin group represented by Formula 1, with the proviso that each coumarin group may optionally have a substituent; and m is an integer of two or more; with the proviso that (i), when Ø contains any of triazine, furan, benzene, pyrazine, naphthalene, indole, and phenanthrene, each of said furan, naphthalene, pyrazine, indole, and phenanthrene is bonded with the same or different aromatic ring or heterocycle as identified above, said triazine being bonded with Z with m being three said bonding being directly or via any one of the above-identified thiophene, furan, benzene, pyrazine, pyridine, naphthalene, and fluorene; (ii) when Ø contains benzene, said benzene is bonded with Z with m being three or more; and (iii) when o contains pyridine, said pyridine is bonded with another pyridine;

Formula 2:

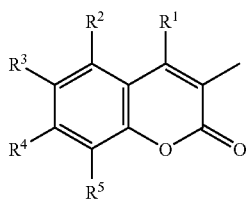

wherein in Formula 2, $R^1$ to $R^5$ independently represent hydrogen or a substituent selected from the group consisting of aliphatic hydrocarbon groups, alicyclic hydrocarbon groups, aromatic hydrocarbon groups, heterocyclic groups, amino groups, halogen groups, and combinations thereof; with the proviso that when o is biphenyl group, $R^4$ is neither an alkoxy group nor a phosphoester group; $R^3$ and $R^4$ may form a cyclic structure together with the carbon atoms linked to $R^2$, $R^3$, $R^4$ and/or $R^5$, and in this case, $R^2$, $R^3$, $R^4$ and/or $R^5$ do not independently exist;

Formula 3:

$Ø(CH_2CN)_m$

Formula 4:

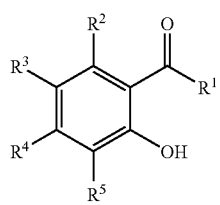

wherein in Formula 3, m is an integer as in Formula 1.

4. An organic EL element, which comprises a coumarin compound represented by Formula 1:

$Ø(Z)_m$      Formula 1 wherein in Formula 1, Ø an aromatic ring or heterocycle selected from the group consisting of thiophene, triazine, furan, benzene, pyrazine, pyridine, naphthalene, anthracene, thieno[3,2-b]thiophene, phenanthrene, fluorene, furo[3,2-b]furan, terphenyl, biphenyl, bithiophene, bifuran, acridine, isoquinoline, indole, carbazole, carboline, quinoline, dibenzofuran, cinnoline, thionaphthene, 1,10-phenanthroline, phenothiazine, purine, and benzofuran rings, and combinations thereof, which may optionally have a substituent; each Z is the same or different coumarin group represented by Formula 1, with the proviso that each coumarin group may optionally have a substituent; and m is an integer of two or more; with the proviso that (i), when Ø contains any of triazine, furan, benzene, pyrazine, naphthalene, indole, and phenanthrene, each of said furan, naphthalene, pyrazine, indole, and phenanthrene is bonded with the same or different aromatic ring or heterocycle as identified above, said triazine being bonded with Z with m being three said bonding being directly or via any one of the above-identified thiophene, furan, benzene, pyrazine, pyridine, naphthalene, and fluorene; (ii) when z contains benzene, said benzene is bonded with Z with m being three or more; and (iii) when o contains pyridine, said pyridine is bonded with another pyridine;

Formula 2:

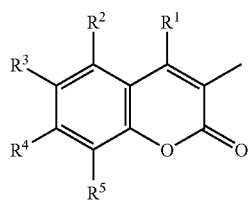

wherein in Formula 2, $R^1$ to $R^5$ independently represent hydrogen or a substituent selected from the group consisting of aliphatic hydrocarbon groups, alicyclic hydrocarbon groups, aromatic hydrocarbon groups, heterocyclic groups; amino groups, halogen groups, and combinations thereof; $R^3$ and $R^4$ may form a cyclic structure together with the carbon atoms linked to $R^2$, $R^3$, $R^4$ and/or $R^5$, and in this case, $R^2$, $R^3$, $R^4$ and/or $R^5$ do not independently exist.

5. A displaying panel, which comprises the organic EL element of claim 4.

6. An information displaying apparatus, which comprises the organic EL element of claim 4.

7. A luminous agent for organic EL elements, which comprises any one of the coumarin compound of claim 1 or 2.

* * * * *